US009376715B2

(12) United States Patent
Brophy et al.

(10) Patent No.: US 9,376,715 B2
(45) Date of Patent: Jun. 28, 2016

(54) METHODS FOR DETECTING MUTATIONS IN THE CATALYTIC SUBUNIT OF THE PHOSPHOINOSITOL-3 KINASE (PIK3CA) GENE

(71) Applicants: Victoria Brophy, Martinez, CA (US); Neil Jones, Therwil (CH); Astrid Kiermaier, Loerrach (DE); Jayantha Ratnayake, Bedford (GB)

(72) Inventors: Victoria Brophy, Martinez, CA (US); Neil Jones, Therwil (CH); Astrid Kiermaier, Loerrach (DE); Jayantha Ratnayake, Bedford (GB)

(73) Assignee: ROCHE MOLECULAR SYSTEMS, INC, Pleasanton, CA (US)

( * ) Notice: Subject to any disclaimer, the term of this patent is extended or adjusted under 35 U.S.C. 154(b) by 0 days.

(21) Appl. No.: 14/363,982

(22) PCT Filed: Dec. 7, 2012

(86) PCT No.: PCT/EP2012/074857
§ 371 (c)(1),
(2) Date: Jun. 9, 2014

(87) PCT Pub. No.: WO2013/083810
PCT Pub. Date: Jun. 13, 2013

(65) Prior Publication Data

US 2015/0079076 A1 Mar. 19, 2015

Related U.S. Application Data

(60) Provisional application No. 61/569,178, filed on Dec. 9, 2011, provisional application No. 61/570,102, filed on Dec. 13, 2011.

(30) Foreign Application Priority Data

Dec. 9, 2011 (EP) .................................... 11192861

(51) Int. Cl.
*C12Q 1/68* (2006.01)
*C07H 21/02* (2006.01)
*C07H 21/04* (2006.01)

(52) U.S. Cl.
CPC ............ *C12Q 1/6827* (2013.01); *C12Q 1/6886* (2013.01); *C12Q 2600/106* (2013.01); *C12Q 2600/156* (2013.01)

(58) Field of Classification Search
None
See application file for complete search history.

(56) References Cited

FOREIGN PATENT DOCUMENTS

| | | | |
|---|---|---|---|
| EP | 1980626 | A1 | 4/2007 |
| WO | WO-2007/050465 | A2 * | 5/2007 |
| WO | 2010014920 | A1 | 2/2010 |
| WO | 2011070499 | A1 | 6/2011 |

OTHER PUBLICATIONS

Chang, Jenny C. HER2 Inhibition: From Discovery to Clinical Practice. (Clin. Clancer Res. 13(1): 1-3, Jan. 1, 2007).*

Spector et al. Small molecule HER-2 tyrosine kinase inhibitors. (Breast Cancer Research 9: 1-8, Mar. 2, 2007).*

Lee et al Oncogene. 2005. 24: 1477-1480.*

NCBI Database. National Center for Biotechnology Information (Bethesda, MD, USA). Refernece SNP Cluster Report for rs104886003, printed on Sep. 8, 2015, available via url: <ncbi.nlm.nih.gov/projects/SNP/snp_ref.cgi?rs=104886003>.*

Board et al Clinical Chemistry. 2008. 54(4): 757-760.*

Chakrabarty, Anindita PhD, et al., 2010, "H1047R phosphatidylinositol 3-kinase mutant enhances HER2-mediated transformation via heregulin production and activation of HER3", Oncogene, 29(37):5193-5203.

Berns, Katrien, et al., 2007, "A Functional Genetic Approach Identifies the PI3K Pathway as a Major Determinant of Trastuzumab Resistance in Breast Cancer", 12(4):395-402.

Dave, Bhuvanesh, et al., 2011, "Loss of Phosphatase and Tensin Homolog or Phosphoinositol-3 Kinase Activation and Response to Trastuzumab or Lapatinib in Human Epidermal Growth Factor Receptor 2-Overexpressing Locally Advanced Breast Cancers", Journal of Clinical Oncology, 29(2):166-173.

Eichhorn, Pieter J. A., et al., 2008, "Phosphatidylinositol 3-Kinase Hyperactivation Results in Lapatinib Resistance that is Reversed by the mTOR/Phosphatidylinositol 3-Kinase Inhibitor NVP-BEZ235", 68(22):9221-9230.

Kataoka, Y., et al., 2010, "Association between gain-of-function mutations in PIK3CA and resistance to HER2-targeted agents in HER2-amplified breast cancer cell lines", Annals of Oncology, 21:255-262.

Serra, Violeta, et al., 2008, "NVP-BEZ235, a Dual PI3K/mTOR Inhibitor, Prevents PI3K Signaling and Inhibits the Growth of Cancer Cells with Activating PI3K Mutations", Cancer Research, 68(19):8022-8030.

Razis, E., et al., 2011, "Evaluation of the association of PIK3CA mutations and PTEN loss with efficacy of trastuzumab therapy in metastatic breast cancer", Breast Cancer Research Treatment, 128(2):447-456.

Rexer, BN, et al, 2009, "Exon 9 and exon 20 mutations in PIK3CA confer resistance to HER2 inhibitors in HER2-overexpressing breast cancer cells", Cancer Research, 60(2)(S1):1-2.

Vorkas, Panagiotis A., et al., 2010, "PIK3CA Hotspot Mutation Scanning by a Novel and Highly Sensitive High-Resolution Small Amplicon Melting Analysis Method", Journal of Molecular Diagnostics, 12(5):697-704.

Vorkas, P., et al., 2009, "PI3K Pathway Activity and Response to First Line Chemotherapy in Combination with Trastuzumab in Patients with HER2-Positive Metastatic Breast Cancer," Cancer Research, 69(24)(S3).

* cited by examiner

*Primary Examiner* — Carla Myers
(74) *Attorney, Agent, or Firm* — Carol Johns; Olga Kay

(57) ABSTRACT

The present invention relates to means and methods for the identification of non-responders to a HER2 inhibitor, whereby one or more mutations in exon 9 of Phosphoinositol-3 kinase (PIK3CA) indicate non-responsiveness.

10 Claims, 19 Drawing Sheets

Figure 2.

Variable Light

```
                   10        20          30         40
2C4       DTVMTQSHKIMSTSVGDRVSITC [KASQDVSIGVA] WYQQRP
           **    **** *      *                     *
574       DIQMTQSPSSLSASVGDRVTITC [KASQDVSIGVA] WYQQKP
                                   *   ** ***
hum κI    DIQMTQSPSSLSASVGDRVTITC [RASQSISNYLA] WYQQKP

                     50          60        70         80
2C4       GQSPKLLIY [SASYRYT] GVPDRFTGSGSGTDFTFTISSVQA
           **                    *  *            *    * *
574       GKAPKLLIY [SASYRYT] GVPSRFSGSGSGTDFTLTISSLQP
                     * *****
hum κI    GKAPKLLIY [AASSLES] GVPSRFSGSGSGTDFTLTISSLQP

                    90          100
2C4       EDLAVYYC [QQYYIYPYT] FGGGTKLEIK (SEQ ID NO:5)
            * *                  *   *
574       EDFATYYC [QQYYIYPYT] FGQGTKVEIK (SEQ ID NO:7)
                       *** *
hum κI    EDFATYYC [QQYNSLPWT] FGQGTKVEIK (SEQ ID NO:9)
```

FIG. 2A

Variable Heavy

```
                   10        20          30        40
2C4       EVQLQQSGPELVKPGTSVKISCKAS [GFTFTDYTMD] WVKQS
              **  **  *  * ***   *                *  *
574       EVQLVESGGGLVQPGGSLRLSCAAS [GFTFTDYTMD] WVRQA
                                         ** * *
hum III   EVQLVESGGGLVQPGGSLRLSCAAS [GFTFSSYAMS] WVRQA

                    50  a        60           70      80
2C4       HGKSLEWIG [DVNPNSGGSIYNQRFKG] KASLTVDRSSRIVYM
          *  *   **                     *** *    **** *
574       PGKGLEWVA [DVNPNSGGSIYNQRFKG] RFTLSVDRSKNTLYL
                     ****** *** ****       * * *
hum III   PGKGLEWVA [VISGDGGSTYYADSVKG] RFTISRDNSKNTLYL

             abc        90          100ab          110
2C4       ELRSLTFEDTAVYYCAR [NLGPSFYFDY] WGQGTTLTVSS (SEQ ID NO:6)
          ***  **                             **
574       QMNSLRAEDTAVYYCAR [NLGPSFYFDY] WGQGTLVTVSS (SEQ ID NO:8)
                             ********
hum III   QMNSLRAEDTAVYYCAR [GRVGYSLYDY] WGQGTLVTVSS (SEQ ID NO:10)
```

Amino Acid Sequence for Pertuzumab Light Chain

1 10 20 30 40 50 60
DIQMTQSPSSLSASVGDRVTITCKASQDVSIGVAWYQQKPGKAPKLLIYSASYRYTGVPS 70 80 90 100 110 120
RFSGSGSGTDFTLTISSLQPEDFATYYCQQYYIYPYTFGQGTKVEIKRTVAAPSVFIFPP 130 140 150 160 170 180
SDEQLKSGTASVVCLLNNFYPREAKVQWKVDNALQSGNSQESVTEQDSKDSTYSLSSTLT 190 200 210
LSKADYEKHKVYACEVTHQGLSSPVTKSFNRGEC

FIG. 3A

Amino Acid Sequence for Pertuzumab Heavy Chain

1 10 20 30 40 50 60
EVQLVESGGGLVQPGGSLRLSCAASGFTFTDYTMDWVRQAPGKGLEWVADVNPNSGGSIY

70 80 90 100 110 120
NQRFKGRFTLSVDRSKNTLYLQMNSLRAEDTAVYYCARNLGPSFYFDYWGQGTLVTVSSA 130 140 150 160 170 180
STKGPSVFPLAPSSKSTSGGTAALGCLVKDYFPEPVTVSWNSGALTSGVHTFPAVLQSSG 190 200 210 220 230 240
LYSLSSVVTVPSSSLGTQTYICNVNHKPSNTKVDKKVEPKSCDKTHTCPPCPAPELLGGP 250 260 270 280 290 300
SVFLFPPKPKDTLMISRTPEVTCVVVDVSHEDPEVKFNWYVDGVEVHNAKTKPREEQYNS 310 320 330 340 350 360
TYRVVSVLTVLHQDWLNGKEYKCKVSNKALPAPIEKTISKAKGQPREPQVYTLPPSREEM 370 380 390 400 410 420
TKNQVSLTCLVKGFYPSDIAVEWESNGQPENNYKTTPPVLDSDGSFFLYSKLTVDKSRWQ 430 440 448
QGNVFSCSVMHEALHNHYTQKSLSLSPG

Light Chain

```
1                                         15                                        30                                        45
D I Q M T Q S P S S L S A S V G D R V T I T C R A S Q D V N T A V A W Y Q Q K P G K A P K
46                                        60                                        75                                        90
L L I Y S A S F L Y S G V P S R F S G S R S G T D F T L T I S S L Q P E D F A T Y Y C Q Q
91                                        105                                       120                                       135
H Y T T P P T F G Q G T K V E I K R T V A A P S V F I F P P S D E Q L K S G T A S V V C L
136                                       150                                       165                                       180
L N N F Y P R E A K V Q W K V D N A L Q S G N S Q E S V T E Q D S K D S T Y S L S S T L T
181                                       195                                       210         214
L S K A D Y E K H K V Y A C E V T H Q G L S S P V T K S F N R G E C
```

Heavy Chain

```
1                                          15                                         30                                         45
E V Q L V E S G G G L V Q P G G S L R L S C A A S G F N I K D T Y I H W V R Q A P G K G L
46                                         60                                         75                                         90
E W V A R I Y P T N G Y T R Y A D S V K G R F T I S A D T S K N T A Y L Q M N S L R A E D
91                                         105                                        120                                        135
T A V Y Y C S R W G G D G F Y A M D Y W G Q G T L V T V S S|A S T K G P S V F P L A P S S
136                                        150                                        165                                        180
K S T S G G T A A L G C L V K D Y F P E P V T V S W N S G A L T S G V H T F P A V L Q S S
181                                        195                                        210                                        225
G L Y S L S S V V T V P S S S L G T Q T Y I C N V N H K P S N T K V D K K V E P K S C D K
236                                        240                                        255                                        270
T H T C P P C P A P E L L G G P S V F L F P P K P K D T L M I S R T P E V T C V V V D V S
271                                        285                                        300                                        315
H E D P E V K F N W Y V D G V E V H N A K T K P R E E Q Y N S T Y R V V S V L T V L H Q D
316                                        330                                        345                                        360
W L N G K E Y K C K V S N K A L P A P I E K T I S K A K G Q P R E P Q V Y T L P P S R E E
361                                        375                                        390                                        405
M T K N Q V S L T C L V K G F Y P S D I A V E W E S N G Q P E N N Y K T T P P V L D S D G
406                                        420                                        435                                      449
S F F L Y S K L T V D K S R W Q Q G N V F S C S V M H E A L H N H Y T Q K S L S L S P G
```

```
1                                         15                                         30                                         45
V H S D I Q M T Q S P S S L S A S V G D R V T I T C K A S Q D V S I G V A W Y Q Q K P G K
46                                        60                                         75                                         90
A P K L L I Y S A S Y R Y T G V P S R F S G S G S G T D F T L T I S S L Q P E D F A T Y Y
91                                        105                                        120                                        135
C Q Q Y Y I Y P Y T F G Q G T K V E I K R T V A A P S V F I F P P S D E Q L K S G T A S V
136                                       150                                        165                                        180
V C L L N N F Y P R E A K V Q W K V D N A L Q S G N S Q E S V T E Q D S K D S T Y S L S S
181                                       195                                        210                 217
T L T L S K A D Y E K H K V Y A C E V T H Q G L S S P V T K S F N R G E C
```

```
1                                         15                                            30                                            45
E V Q L V E S G G G L V Q P G G S L R L S C A A S G F T F T D Y T M D W V R Q A P G K G L
46                                        60                                            75                                            90
E W V A D V N P N S G G S I Y N Q R F K G R F T L S V D R S K N T L Y L Q M N S L R A E D
91                                        105                                           120                                           135
T A V Y Y C A R N L G P S F Y F D Y W G Q G T L V T V S S A S T K G P S V F P L A P S S K
136                                       150                                           165                                           180
S T S G G T A A L G C L V K D Y F P E P V T V S W N S G A L T S G V H T F P A V L Q S S G
181                                       195                                           210                                           225
L Y S L S S V V T V P S S S L G T Q T Y I C N V N H K P S N T K V D K K V E P K S C D K T
226                                       240                                           255                                           270
H T C P P C P A P E L L G G P S V F L F P P K P K D T L M I S R T P E V T C V V V D V S H
271                                       285                                           300                                           315
E D P E V K F N W Y V D G V E V H N A K T K P R E E Q Y N S T Y R V V S V L T V L H Q D W
316                                       330                                           345                                           360
L N G K E Y K C K V S N K A L P A P I E K T I S K A K G Q P R E P Q V Y T L P P S R E E M
361                                       375                                           390                                           405
T K N Q V S L T C L V K G F Y P S D I A V E W E S N G Q P E N N Y K T T P P V L D S D G S
406                                       420                                           435                                       449
F F L Y S K L T V D K S R W Q Q G N V F S C S V M H E A L H N H Y T Q K S L S L S P G K
```

| Mutation | TH | | THP | | HP | | THP | |
|---|---|---|---|---|---|---|---|---|
| | non-pCR | pCR | non-pCR | pCR | non-pCR | pCR | non-pCR | pCR |
| Exon 7 | 2 | 0 | 1 | 0 | 1 | 0 | 0 | 0 |
| Exon 9* | 8 | 0 | 4 | 1 | 5 | 0 | 9 | 1 |
| Exon 20 | 13 | 7 | 8 | 7 | 15 | 2 | 11 | 3 |
| | 23/67 (34.3%) | 7/29 (24.1%) | 13/51 (25.4%) | 8/41 (19.5%) | 21/82 (25.6%) | 2/18 (11%) | 20/62 (32.2%) | 4/23 (17%) |

Figure 7.

```
tctccctcggcgccgccgccgccgcccgcggggctgggacccgatgcggttagagccgcg
         10        20        30        40        50        60
----:----|----:----|----:----|----:----|----:----|----:----|
agagggagccgcggcggcggcggcgggcgccccgaccctgggctacgccaatctcggcgc

----:----|----:----|----:----|----:----|----:----|----:----|

gagcctggaagagccccgagcgtttctgctttgggacaaccatacatctaattccttaaa
         70        80        90       100       110       120
----:----|----:----|----:----|----:----|----:----|----:----|
ctcggaccttctcggggctcgcaaagacgaaaccctgttggtatgtagattaaggaattt

----:----|----:----|----:----|----:----|----:----|----:----|

gtagttttatatgtaaaacttgcaaagaatcagaacaatgcctccacgaccatcatcagg
        130       140       150       160       170       180
----:----|----:----|----:----|----:----|----:----|----:----|
catcaaaatatacattttgaacgtttcttagtcttgttacggaggtgctggtagtagtcc

                                     M  P  P  R  P  S  S  G  8
----:----|----:----|----:----|----:----|----:----|----:----|

tgaactgtggggcatccacttgatgcccccaagaatcctagtagaatgtttactaccaaa
        190       200       210       220       230       240
----:----|----:----|----:----|----:----|----:----|----:----|
acttgacaccccgtaggtgaactacgggggttcttaggatcatcttacaaatgatggttt

 E  L  W  G  I  H  L  M  P  P  R  I  L  V  E  C  L  L  P  N  28
----:----|----:----|----:----|----:----|----:----|----:----|

tggaatgatagtgactttagaatgcctccgtgaggctacattaataaccataaagcatga
        250       260       270       280       290       300
----:----|----:----|----:----|----:----|----:----|----:----|
accttactatcactgaaatcttacggaggcactccgatgtaattattggtatttcgtact

 G  M  I  V  T  L  E  C  L  R  E  A  T  L  I  T  I  K  H  E  48
----:----|----:----|----:----|----:----|----:----|----:----|
```

Figure 7 (cont.).

```
actatttaaagaagcaagaaaataccccctccatcaacttcttcaagatgaatcttctta
         310       320       330       340       350       360
----:----|----:----|----:----|----:----|----:----|----:----|
tgataaatttcttcgttcttttatgggggaggtagttgaagaagttctacttagaagaat

 L  F  K  E  A  R  K  Y  P  L  H  Q  L  L  Q  D  E  S  S  Y  68
----:----|----:----|----:----|----:----|----:----|----:----|

cattttcgtaagtgttactcaagaagcagaaagggaagaattttttgatgaaacaagacg
         370       380       390       400       410       420
----:----|----:----|----:----|----:----|----:----|----:----|
gtaaaagcattcacaatgagttcttcgtctttcccttcttaaaaaactactttgttctgc

 I  F  V  S  V  T  Q  E  A  E  R  E  E  F  F  D  E  T  R  R  88
----:----|----:----|----:----|----:----|----:----|----:----|

actttgtgaccttcggctttttcaaccctttttaaaagtaattgaaccagtaggcaaccg
         430       440       450       460       470       480
----:----|----:----|----:----|----:----|----:----|----:----|
tgaaacactggaagccgaaaaagttgggaaaaattttcattaacttggtcatccgttggc

 L  C  D  L  R  L  F  Q  P  F  L  K  V  I  E  P  V  G  N  R  108
----:----|----:----|----:----|----:----|----:----|----:----|

tgaagaaaagatcctcaatcgagaaattggttttgctatcggcatgccagtgtgtgaatt
         490       500       510       520       530       540
----:----|----:----|----:----|----:----|----:----|----:----|
acttcttttctaggagttagctctttaaccaaaacgatagccgtacggtcacacacttaa

 E  E  K  I  L  N  R  E  I  G  F  A  I  G  M  P  V  C  E  F  128
----:----|----:----|----:----|----:----|----:----|----:----|

tgatatggttaaagatccagaagtacaggacttccgaagaaatattctgaacgtttgtaa
         550       560       570       580       590       600
----:----|----:----|----:----|----:----|----:----|----:----|
actataccaatttctaggtcttcatgtcctgaaggcttctttataagacttgcaaacatt

 D  M  V  K  D  P  E  V  Q  D  F  R  R  N  I  L  N  V  C  K  148
----:----|----:----|----:----|----:----|----:----|----:----|

agaagctgtggatcttagggacctcaattcacctcatagtagagcaatgtatgtctatcc
         610       620       630       640       650       660
----:----|----:----|----:----|----:----|----:----|----:----|
tcttcgacacctagaatccctggagttaagtggagtatcatctcgttacatacagatagg
```

Figure 7 (cont.).

```
 E  A  V  D  L  R  D  L  N  S  P  H  S  R  A  M  Y  V  Y  P  168
----:----|----:----|----:----|----:----|----:----|----:----|

tccaaatgtagaatcttcaccagaattgccaaagcacatatataataaattagataaagg
         670       680       690       700       710       720
----:----|----:----|----:----|----:----|----:----|----:----|
aggtttacatcttagaagtggtcttaacggtttcgtgtatatattatttaatctatttcc

 P  N  V  E  S  S  P  E  L  P  K  H  I  Y  N  K  L  D  K  G  188
----:----|----:----|----:----|----:----|----:----|----:----|

gcaaataatagtggtgatctgggtaatagtttctccaaataatgacaagcagaagtatac
         730       740       750       760       770       780
----:----|----:----|----:----|----:----|----:----|----:----|
cgtttattatcaccactagacccattatcaaagaggtttattactgttcgtcttcatatg

 Q  I  I  V  V  I  W  V  I  V  S  P  N  N  D  K  Q  K  Y  T  208
----:----|----:----|----:----|----:----|----:----|----:----|

tctgaaaatcaaccatgactgtgtaccagaacaagtaattgctgaagcaatcaggaaaaa
         790       800       810       820       830       840
----:----|----:----|----:----|----:----|----:----|----:----|
agacttttagttggtactgacacatggtcttgttcattaacgacttcgttagtcctttttt

 L  K  I  N  H  D  C  V  P  E  Q  V  I  A  E  A  I  R  K  K  228
----:----|----:----|----:----|----:----|----:----|----:----|

aactcgaagtatgttgctatcctctgaacaactaaaactctgtgttttagaatatcaggg
         850       860       870       880       890       900
----:----|----:----|----:----|----:----|----:----|----:----|
ttgagcttcatacaacgataggagacttgttgattttgagacacaaaatcttatagtccc

 T  R  S  M  L  L  S  S  E  Q  L  K  L  C  V  L  E  Y  Q  G  248
----:----|----:----|----:----|----:----|----:----|----:----|

caagtatattttaaaagtgtgtggatgtgatgaatacttcctagaaaaatatcctctgag
         910       920       930       940       950       960
----:----|----:----|----:----|----:----|----:----|----:----|
gttcatataaaattttcacacacctacactacttatgaaggatctttttataggagactc

 K  Y  I  L  K  V  C  G  C  D  E  Y  F  L  E  K  Y  P  L  S  268
----:----|----:----|----:----|----:----|----:----|----:----|
```

Figure 7 (cont.).

```
tcagtataagtatataagaagctgtataatgcttgggaggatgcccaatttgatgttgat
         970       980       990      1000      1010      1020
----:----|----:----|----:----|----:----|----:----|----:----|
agtcatattcatatattcttcgacatattacgaaccctcctacgggttaaactacaacta

 Q  Y  K  Y  I  R  S  C  I  M  L  G  R  M  P  N  L  M  L  M  288
----:----|----:----|----:----|----:----|----:----|----:----|

ggctaaagaaagcctttattctcaactgccaatggactgttttacaatgccatcttattc
         1030      1040      1050      1060      1070      1080
----:----|----:----|----:----|----:----|----:----|----:----|
ccgatttctttcggaaataagagttgacggttacctgacaaaatgttacggtagaataag

 A  K  E  S  L  Y  S  Q  L  P  M  D  C  F  T  M  P  S  Y  S  308
----:----|----:----|----:----|----:----|----:----|----:----|

cagacgcatttccacagctacaccatatatgaatggagaaacatctacaaaatccctttg
         1090      1100      1110      1120      1130      1140
----:----|----:----|----:----|----:----|----:----|----:----|
gtctgcgtaaaggtgtcgatgtggtatatacttacctctttgtagatgttttagggaaac

 R  R  I  S  T  A  T  P  Y  M  N  G  E  T  S  T  K  S  L  W  328
----:----|----:----|----:----|----:----|----:----|----:----|

ggttataaatagtgcactcagaataaaaattctttgtgcaacctacgtgaatgtaaatat
         1150      1160      1170      1180      1190      1200
----:----|----:----|----:----|----:----|----:----|----:----|
ccaatatttatcacgtgagtcttatttttaagaaacacgttggatgcacttacatttata

 V  I  N  S  A  L  R  I  K  I  L  C  A  T  Y  V  N  V  N  I  348
----:----|----:----|----:----|----:----|----:----|----:----|

tcgagacattgataagatctatgttcgaacaggtatctaccatggaggagaacccttatg
         1210      1220      1230      1240      1250      1260
----:----|----:----|----:----|----:----|----:----|----:----|
agctctgtaactattctagatacaagcttgtccatagatggtacctcctcttgggaatac

 R  D  I  D  K  I  Y  V  R  T  G  I  Y  H  G  G  E  P  L  C  268
----:----|----:----|----:----|----:----|----:----|----:----|

tgacaatgtgaacactcaaagagtaccttgttccaatcccaggtggaatgaatggctgaa
         1270      1280      1290      1300      1310      1320
----:----|----:----|----:----|----:----|----:----|----:----|
actgttacacttgtgagtttctcatggaacaaggttagggtccaccttacttaccgactt

 D  N  V  N  T  Q  R  V  P  C  S  N  P  R  W  N  E  W  L  N  388
----:----|----:----|----:----|----:----|----:----|----:----|
```

Figure 7 (cont.).

```
ttatgatatatacattcctgatcttcctcgtgctgctcgactttgcctttccatttgctc
          1330      1340      1350      1360      1370      1380
----:----|----:----|----:----|----:----|----:----|----:----|
aatactatatatgtaaggactagaaggagcacgacgagctgaaacggaaaggtaaacgag

 Y  D  I  Y  I  P  D  L  P  R  A  A  R  L  C  L  S  I  C  S  408
----:----|----:----|----:----|----:----|----:----|----:----|

tgttaaaggccgaaagggtgctaaagaggaacactgtccattggcatggggaaatataaa
          1390      1400      1410      1420      1430      1440
----:----|----:----|----:----|----:----|----:----|----:----|
acaatttccggctttcccacgatttctccttgtgacaggtaaccgtacccctttatattt

 V  K  G  R  K  G  A  K  E  E  H  C  P  L  A  W  G  N  I  N  428
----:----|----:----|----:----|----:----|----:----|----:----|

cttgtttgattacacagacactctagtatctggaaaaatggctttgaatctttggccagt
          1450      1460      1470      1480      1490      1500
----:----|----:----|----:----|----:----|----:----|----:----|
gaacaaactaatgtgtctgtgagatcatagacctttttaccgaaacttagaaaccggtca

 L  F  D  Y  T  D  T  L  V  S  G  K  M  A  L  N  L  W  P  V  448
----:----|----:----|----:----|----:----|----:----|----:----|

acctcatggattagaagatttgctgaaccctattggtgttactggatcaaatccaaataa
          1510      1520      1530      1540      1550      1560
----:----|----:----|----:----|----:----|----:----|----:----|
tggagtacctaatcttctaaacgacttgggataaccacaatgacctagtttaggtttatt

 P  H  G  L  E  D  L  L  N  P  I  G  V  T  G  S  N  P  N  K  468
----:----|----:----|----:----|----:----|----:----|----:----|

agaaactccatgcttagagttggagtttgactggttcagcagtgtggtaaagttcccaga
          1570      1580      1590      1600      1610      1620
----:----|----:----|----:----|----:----|----:----|----:----|
tctttgaggtacgaatctcaacctcaaactgaccaagtcgtcacaccatttcaagggtct

 E  T  P  C  L  E  L  E  F  D  W  F  S  S  V  V  K  F  P  D  488
----:----|----:----|----:----|----:----|----:----|----:----|

tatgtcagtgattgaagagcatgccaattggtctgtatcccgagaagcaggatttagcta
          1630      1640      1650      1660      1670      1680
----:----|----:----|----:----|----:----|----:----|----:----|
atacagtcactaacttctcgtacggttaaccagacatagggctcttcgtcctaaatcgat
```

```
            M  S  V  I  E  E  H  A  N  W  S  V  S  R  E  A  G  F  S  Y  508
         ----:----|----:----|----:----|----:----|----:----|----:----|

                         ********************************************
exon9
         ttcccacgcaggactgagtaacagactagctagagacaatgaattaagggaaaatgacaa
                  1690      1700      1710      1720      1730      1740
         ----:----|----:----|----:----|----:----|----:----|----:----|
         aagggtgcgtcctgactcattgtctgatcgatctctgttacttaattcccttttactgtt

            S  H  A  G  L  S  N  R  L  A  R  D  N  E  L  R  E  N  D  K  528
         ----:----|----:----|----:----|----:----|----:----|----:----|

         ************************************************************
exon9
         agaacagctcaaagcaatttctacacgagatcctctctctgaaatcactgagcaggagaa
                  1750      1760      1770      1780      1790      1800
         ----:----|----:----|----:----|----:----|----:----|----:----|
         tcttgtcgagtttcgttaaagatgtgctctaggagagagactttagtgactcgtcctctt

            E  Q  L  K  A  I  S  T  R  D  P  L  S  E  I  T  E  Q  E  K  548
         ----:----|----:----|----:----|----:----|----:----|----:----|

         *********************
         agatttctatggagtcacagacactattgtgtaactatccccgaaattctacccaaatt
                  1810      1820      1830      1840      1850      1860
         ----:----|----:----|----:----|----:----|----:----|----:----|
         tctaaaagatacctcagtgtctgtgataacacattgataggggctttaagatgggtttaa

            D  F  L  W  S  H  R  H  Y  C  V  T  I  P  E  I  L  P  K  L  568
         ----:----|----:----|----:----|----:----|----:----|----:----|

         gcttctgtctgttaaatggaattctagagatgaagtagcccagatgtattgcttggtaaa
                  1870      1880      1890      1900      1910      1920
         ----:----|----:----|----:----|----:----|----:----|----:----|
         cgaagacagacaatttaccttaagatctctacttcatcgggtctacataacgaaccattt

            L  L  S  V  K  W  N  S  R  D  E  V  A  Q  M  Y  C  L  V  K  588
         ----:----|----:----|----:----|----:----|----:----|----:----|

         agattggcctccaatcaaacctgaacaggctatggaacttctggactgtaattacccaga
                  1930      1940      1950      1960      1970      1980
         ----:----|----:----|----:----|----:----|----:----|----:----|
         tctaaccggaggttagtttggacttgtccgataccttgaagacctgacattaatgggtct

            D  W  P  P  I  K  P  E  Q  A  M  E  L  L  D  C  N  Y  P  D  608
         ----:----|----:----|----:----|----:----|----:----|----:----|
```

Figure 7 (cont.).

```
tcctatggttcgaggttttgctgttcggtgcttggaaaaatatttaacagatgacaaact
         1990      2000      2010      2020      2030      2040
----:----|----:----|----:----|----:----|----:----|----:----|
aggataccaagctccaaaacgacaagccacgaacctttttataaattgtctactgtttga

 P  M  V  R  G  F  A  V  R  C  L  E  K  Y  L  T  D  D  K  L  628
----:----|----:----|----:----|----:----|----:----|----:----|

ttctcagtatttaattcagctagtacaggtcctaaaatatgaacaatatttggataactt
         2050      2060      2070      2080      2090      2100
----:----|----:----|----:----|----:----|----:----|----:----|
aagagtcataaattaagtcgatcatgtccaggattttatacttgttataaacctattgaa

 S  Q  Y  L  I  Q  L  V  Q  V  L  K  Y  E  Q  Y  L  D  N  L  648
----:----|----:----|----:----|----:----|----:----|----:----|

gcttgtgagatttttactgaagaaagcattgactaatcaaaggattgggcactttttctt
         2110      2120      2130      2140      2150      2160
----:----|----:----|----:----|----:----|----:----|----:----|
cgaacactctaaaaatgacttctttcgtaactgattagtttcctaacccgtgaaaaagaa

 L  V  R  F  L  L  K  K  A  L  T  N  Q  R  I  G  H  F  F  F  668
----:----|----:----|----:----|----:----|----:----|----:----|

ttggcatttaaaatctgagatgcacaataaaacagttagccagaggtttggcctgctttt
         2170      2180      2190      2200      2210      2220
----:----|----:----|----:----|----:----|----:----|----:----|
aaccgtaaattttagactctacgtgttattttgtcaatcggtctccaaaccggacgaaaa

 W  H  L  K  S  E  M  H  N  K  T  V  S  Q  R  F  G  L  L  L  688
----:----|----:----|----:----|----:----|----:----|----:----|

ggagtcctattgtcgtgcatgtgggatgtatttgaagcacctgaataggcaagtcgaggc
         2230      2240      2250      2260      2270      2280
----:----|----:----|----:----|----:----|----:----|----:----|
cctcaggataacagcacgtacaccctacataaacttcgtggacttatccgttcagctccg

 E  S  Y  C  R  A  C  G  M  Y  L  K  H  L  N  R  Q  V  E  A  708
----:----|----:----|----:----|----:----|----:----|----:----|

aatggaaaagctcattaacttaactgacattctcaaacaggagaagaaggatgaaacaca
         2290      2300      2310      2320      2330      2340
----:----|----:----|----:----|----:----|----:----|----:----|
ttaccttttcgagtaattgaattgactgtaagagtttgtcctcttcttcctactttgtgt
```

Figure 7 (cont.).

```
 M  E  K  L  I  N  L  T  D  I  L  K  Q  E  K  K  D  E  T  Q  728
----:----|----:----|----:----|----:----|----:----|----:----|

aaaggtacagatgaagtttttagttgagcaaatgaggcgaccagatttcatggatgctct
         2350      2360      2370      2380      2390      2400
----:----|----:----|----:----|----:----|----:----|----:----|
tttccatgtctacttcaaaaatcaactcgtttactccgctggtctaaagtacctacgaga

 K  V  Q  M  K  F  L  V  E  Q  M  R  R  P  D  F  M  D  A  L  748
----:----|----:----|----:----|----:----|----:----|----:----|

acagggctttctgtctcctctaaaccctgctcatcaactaggaaacctcaggcttgaaga
         2410      2420      2430      2440      2450      2460
----:----|----:----|----:----|----:----|----:----|----:----|
tgtcccgaaagacagaggagatttgggacgagtagttgatcctttggagtccgaacttct

 Q  G  F  L  S  P  L  N  P  A  H  Q  L  G  N  L  R  L  E  E  768
----:----|----:----|----:----|----:----|----:----|----:----|

gtgtcgaattatgtcctctgcaaaaaggccactgtggttgaattgggagaacccagacat
         2470      2480      2490      2500      2510      2520
----:----|----:----|----:----|----:----|----:----|----:----|
cacagcttaatacaggagacgtttttccggtgacaccaacttaacccctcttgggtctgta

 C  R  I  M  S  S  A  K  R  P  L  W  L  N  W  E  N  P  D  I  788
----:----|----:----|----:----|----:----|----:----|----:----|

catgtcagagttactgtttcagaacaatgagatcatctttaaaaatggggatgatttacg
         2530      2540      2550      2560      2570      2580
----:----|----:----|----:----|----:----|----:----|----:----|
gtacagtctcaatgacaaagtcttgttactctagtagaaatttttacccctactaaatgc

 M  S  E  L  L  F  Q  N  N  E  I  I  F  K  N  G  D  D  L  R  808
----:----|----:----|----:----|----:----|----:----|----:----|

gcaagatatgctaacacttcaaattattcgtattatggaaaatatctggcaaaatcaagg
         2590      2600      2610      2620      2630      2640
----:----|----:----|----:----|----:----|----:----|----:----|
cgttctatacgattgtgaagtttaataagcataataccttttatagaccgttttagttcc

 Q  D  M  L  T  L  Q  I  I  R  I  M  E  N  I  W  Q  N  Q  G  828
----:----|----:----|----:----|----:----|----:----|----:----|
```

Figure 7 (cont.).

```
tcttgatcttcgaatgttaccttatggttgtctgtcaatcggtgactgtgtgggacttat
         2650      2660      2670      2680      2690      2700
----:----|----:----|----:----|----:----|----:----|----:----|
agaactagaagcttacaatggaataccaacagacagttagccactgacacaccctgaata

 L  D  L  R  M  L  P  Y  G  C  L  S  I  G  D  C  V  G  L  I  848
----:----|----:----|----:----|----:----|----:----|----:----|

tgaggtggtgcgaaattctcacactattatgcaaattcagtgcaaaggcggcttgaaagg
         2710      2720      2730      2740      2750      2760
----:----|----:----|----:----|----:----|----:----|----:----|
actccaccacgctttaagagtgtgataatacgtttaagtcacgtttccgccgaactttcc

 E  V  V  R  N  S  H  T  I  M  Q  I  Q  C  K  G  G  L  K  G  868
----:----|----:----|----:----|----:----|----:----|----:----|

tgcactgcagttcaacagccacacactacatcagtggctcaaagacaagaacaaaggaga
         2770      2780      2790      2800      2810      2820
----:----|----:----|----:----|----:----|----:----|----:----|
acgtgacgtcaagttgtcggtgtgtgatgtagtcaccgagtttctgttcttgtttcctct

 A  L  Q  F  N  S  H  T  L  H  Q  W  L  K  D  K  N  K  G  E  888
----:----|----:----|----:----|----:----|----:----|----:----|

aatatatgatgcagccattgacctgtttacacgttcatgtgctggatactgtgtagctac
         2830      2840      2850      2860      2870      2880
----:----|----:----|----:----|----:----|----:----|----:----|
ttatatactacgtcggtaactggacaaatgtgcaagtacacgacctatgacacatcgatg

 I  Y  D  A  A  I  D  L  F  T  R  S  C  A  G  Y  C  V  A  T  908
----:----|----:----|----:----|----:----|----:----|----:----|

cttcattttgggaattggagatcgtcacaatagtaacatcatggtgaaagacgatggaca
         2890      2900      2910      2920      2930      2940
----:----|----:----|----:----|----:----|----:----|----:----|
gaagtaaaacccttaacctctagcagtgttatcattgtagtaccactttctgctacctgt

 F  I  L  G  T  G  D  R  H  N  S  N  I  M  V  K  D  D  G  Q  928
----:----|----:----|----:----|----:----|----:----|----:----|

actgtttcatatagattttggacactttttggatcacaagaagaaaaaatttggttataa
         2950      2960      2970      2980      2990      3000
----:----|----:----|----:----|----:----|----:----|----:----|
tgacaaagtatatctaaaacctgtgaaaaacctagtgttcttctttttttaaaccaatatt

 L  F  H  I  D  F  G  H  F  L  D  H  K  K  K  K  F  G  Y  K  948
----:----|----:----|----:----|----:----|----:----|----:----|
```

Figure 7 (cont.).

```
acgagaacgtgtgccatttgttttgacacaggatttcttaatagtgattagtaaaggagc
         3010      3020      3030      3040      3050      3060
----:----|----:----|----:----|----:----|----:----|----:----|
tgctcttgcacacggtaaacaaaactgtgtcctaaagaattatcactaatcatttcctcg

 R  E  R  V  P  F  V  L  T  Q  D  F  L  I  V  I  S  K  G  A  968
----:----|----:----|----:----|----:----|----:----|----:----|

ccaagaatgcacaaagacaagagaatttgagaggtttcaggagatgtgttacaaggctta
         3070      3080      3090      3100      3110      3120
----:----|----:----|----:----|----:----|----:----|----:----|
ggttcttacgtgtttctgttctcttaaactctccaaagtcctctacacaatgttccgaat

 Q  E  C  T  K  T  R  E  F  E  R  F  Q  E  M  C  Y  K  A  Y  988
----:----|----:----|----:----|----:----|----:----|----:----|

tctagctattcgacagcatgccaatctcttcataaatcttttctcaatgatgcttggctc
         3130      3140      3150      3160      3170      3180
----:----|----:----|----:----|----:----|----:----|----:----|
agatcgataagctgtcgtacggttagagaagtatttagaaaagagttactacgaaccgag

 L  A  I  R  Q  H  A  N  L  F  I  N  L  F  S  M  M  L  G  S 1008
----:----|----:----|----:----|----:----|----:----|----:----|

tggaatgccagaactacaatcttttgatgacattgcatacattcgaaagaccctagcctt
         3190      3200      3210      3220      3230      3240
----:----|----:----|----:----|----:----|----:----|----:----|
accttacggtcttgatgttagaaaactactgtaacgtatgtaagctttctgggatcggaa

 G  M  P  E  L  Q  S  F  D  D  I  A  Y  I  R  K  T  L  A  L 1028
----:----|----:----|----:----|----:----|----:----|----:----|

agataaaactgagcaagaggctttggagtatttcatgaaacaaatgaatgatgcacatca
         3250      3260      3270      3280      3290      3300
----:----|----:----|----:----|----:----|----:----|----:----|
tctattttgactcgttctccgaaacctcataaagtactttgtttacttactacgtgtagt

 D  K  T  E  Q  E  A  L  E  Y  F  M  K  Q  M  N  D  A  H  H 1048
----:----|----:----|----:----|----:----|----:----|----:----|

tggtggctggacaacaaaaatggattggatcttccacacaattaaacagcatgcattgaa
         3310      3320      3330      3340      3350      3360
----:----|----:----|----:----|----:----|----:----|----:----|
accaccgacctgttgtttttacctaacctagaaggtgtgttaatttgtcgtacgtaactt

 G  G  W  T  T  K  M  D  W  I  F  H  T  I  K  Q  H  A  L  N 1068
----:----|----:----|----:----|----:----|----:----|----:----|
```

Figure 7 (cont.).

```
ctgaaaagataactgagaaaatgaaagctcactctggattccacactgcactgttaataa
          3370      3380      3390      3400      3410      3420
----:----|----:----|----:----|----:----|----:----|----:----|
gacttttctattgactcttttactttcgagtgagacctaaggtgtgacgtgacaattatt

 *
----:----|----:----|----:----|----:----|----:----|----:----|


ctctcagcaggcaaagaccgattgcataggaattgcacaatccatgaacagcattagaat
          3430      3440      3450      3460      3470      3480
----:----|----:----|----:----|----:----|----:----|----:----|
gagagtcgtccgtttctggctaacgtatccttaacgtgttaggtacttgtcgtaatctta

----:----|----:----|----:----|----:----|----:----|----:----|


ttacagcaagaacagaaataaaatactatataatttaaataatgtaaacgcaaacagggt
          3490      3500      3510      3520      3530      3540
----:----|----:----|----:----|----:----|----:----|----:----|
aatgtcgttcttgtctttattttatgatatattaaatttattacatttgcgtttgtccca

----:----|----:----|----:----|----:----|----:----|----:----|


ttgatagcacttaaactagttcatttcaaaattaagctttagaataatgcgcaatttcat
          3550      3560      3570      3580      3590      3600
----:----|----:----|----:----|----:----|----:----|----:----|
aactatcgtgaatttgatcaagtaaagttttaattcgaaatcttattacgcgttaaagta

 ----:----|----:----|----:----|----:----|----:----|----:----|


gttatgccttaagtccaaaaaggtaaactttgaagattgtttgtatctttttttaaaaaa
          3610      3620      3630      3640      3650      3660
----:----|----:----|----:----|----:----|----:----|----:----|
caatacggaattcaggtttttccatttgaaacttctaacaaacatagaaaaaaatttttt

 ----:----|----:----|----:----|----:----|----:----|----:----|


caaaacaaaacaaaaatccccaaaatatatagaaatgatggagaaggaaaaaaaaaaaaa
          3670      3680      3690      3700      3710      3720
----:----|----:----|----:----|----:----|----:----|----:----|
gttttgttttgtttttaggggttttatatatctttactacctcttccttttttttttttt

 ----:----|----:----|----:----|----:----|----:----|----:----|


aaaa

----
tttt

----
```

METHODS FOR DETECTING MUTATIONS IN THE CATALYTIC SUBUNIT OF THE PHOSPHOINOSITOL-3 KINASE (PIK3CA) GENE

The present invention relates to means and methods for the identification of non-responders to a HER2 inhibitor, whereby one or more mutations (mutational SNPs) in exon 9 of Phosphoinositol-3 kinase (PIK3CA) indicate non-responsiveness.

The HER family of receptor tyrosine kinases are important mediators of cell growth, differentiation and survival. The receptor family includes four distinct members including epidermal growth factor receptor (EGFR, ErbB1, or HER1), HER2 (ErbB2 or p185$^{neu}$), HER3 (ErbB3) and HER4 (ErbB4 or tyro2).

EGFR, encoded by the erbB1 gene, has been causally implicated in human malignancy. In particular, increased expression of EGFR has been observed in breast, bladder, lung, head, neck and stomach cancer as well as glioblastomas. Increased EGFR receptor expression is often associated with increased production of the EGFR ligand, transforming growth factor alpha (TGF-α), by the same tumor cells resulting in receptor activation by an autocrine stimulatory pathway. Baselga and Mendelsohn *Pharmac. Ther.* 64:127-154 (1994). Monoclonal antibodies directed against the EGFR or its ligands, TGF-α and EGF, have been evaluated as therapeutic agents in the treatment of such malignancies. See, e.g., Baselga and Mendelsohn., supra; Masui et al. *Cancer Research* 44:1002-1007 (1984); and Wu et al. *J. Clin. Invest.* 95:1897-1905 (1995).

The second member of the HER family, p185$^{neu}$, was originally identified as the product of the transforming gene from neuroblastomas of chemically treated rats. The activated form of the neu proto-oncogene results from a point mutation (valine to glutamic acid) in the transmembrane region of the encoded protein. Amplification of the human homolog of neu is observed in breast and ovarian cancers and correlates with a poor prognosis (Slamon et al., *Science,* 235:177-182 (1987); Slamon et al., *Science,* 244:707-712 (1989); and U.S. Pat. No. 4,968,603). To date, no point mutation analogous to that in the neu proto-oncogene has been reported for human tumors. Overexpression of HER2 (frequently but not uniformly due to gene amplification) has also been observed in other carcinomas including carcinomas of the stomach, endometrium, salivary gland, lung, kidney, colon, thyroid, pancreas and bladder. See, among others, King et al., *Science,* 229:974 (1985); Yokota et al., *Lancet:* 1:765-767 (1986); Fukushige et al., *Mol Cell Biol.,* 6:955-958 (1986); Guerin et al., *Oncogene Res.,* 3:21-31 (1988); Cohen et al., *Oncogene,* 4:81-88 (1989); Yonemura et al., *Cancer Res.,* 51:1034 (1991); Borst et al., *Gynecol. Oncol.,* 38:364 (1990); Weiner et al., *Cancer Res.,* 50:421-425 (1990); Kern et al., *Cancer Res.,* 50:5184 (1990); Park et al., *Cancer Res.,* 49:6605 (1989); Zhau et al., *Mol. Carcinog.,* 3:254-257 (1990); Aasland et al. *Br. J. Cancer* 57:358-363 (1988); Williams et al. *Pathobiology* 59:46-52 (1991); and McCann et al., *Cancer,* 65:88-92 (1990). HER2 may be overexpressed in prostate cancer (Gu et al. *Cancer Lett.* 99:185-9 (1996); Ross et al. *Hum. Pathol.* 28:827-33 (1997); Ross et al. *Cancer* 79:2162-70 (1997); and Sadasivan et al. *J. Urol.* 150:126-31 (1993)).

Antibodies directed against the rat p185$^{neu}$ and human HER2 protein products have been described. Drebin and colleagues have raised antibodies against the rat neu gene product, p185$^{neu}$ See, for example, Drebin et al., *Cell* 41:695-706 (1985); Myers et al., *Meth. Enzym.* 198:277-290 (1991); and WO94/22478. Drebin et al. *Oncogene* 2:273-277 (1988) report that mixtures of antibodies reactive with two distinct regions of p185$^{neu}$ result in synergistic anti-tumor effects on neu-transformed NIH-3T3 cells implanted into nude mice. See also U.S. Pat. No. 5,824,311 issued Oct. 20, 1998.

Hudziak et al., *Mol. Cell. Biol.* 9(3):1165-1172 (1989) describe the generation of a panel of HER2 antibodies which were characterized using the human breast tumor cell line SK-BR-3. Relative cell proliferation of the SK-BR-3 cells following exposure to the antibodies was determined by crystal violet staining of the monolayers after 72 hours. Using this assay, maximum inhibition was obtained with the antibody called 4D5 which inhibited cellular proliferation by 56%. Other antibodies in the panel reduced cellular proliferation to a lesser extent in this assay. The antibody 4D5 was further found to sensitize HER2-overexpressing breast tumor cell lines to the cytotoxic effects of TNF-α. See also U.S. Pat. No. 5,677,171 issued Oct. 14, 1997. The HER2 antibodies discussed in Hudziak et al. are further characterized in Fendly et al. *Cancer Research* 50:1550-1558 (1990); Kotts et al. *In Vitro* 26(3):59A (1990); Sarup et al. *Growth Regulation* 1:72-82 (1991); Shepard et al. *J. Clin. Immunol.* 11(3):117-127 (1991); Kumar et al. *Mol. Cell. Biol.* 11(2):979-986 (1991); Lewis et al. *Cancer Immunol. Immunother.* 37:255-263 (1993); Pietras et al. *Oncogene* 9:1829-1838 (1994); Vitetta et al. *Cancer Research* 54:5301-5309 (1994); Sliwkowski et al. *J. Biol. Chem.* 269(20):14661-14665 (1994); Scott et al. *J. Biol. Chem.* 266:14300-5 (1991); D'souza et al. *Proc. Natl. Acad. Sci.* 91:7202-7206 (1994); Lewis et al. *Cancer Research* 56:1457-1465 (1996); and Schaefer et al. *Oncogene* 15:1385-1394 (1997).

A recombinant humanized version of the murine HER2 antibody 4D5 (huMAb4D5-8, rhuMAb HER2, Trastuzumab or Herceptin™; U.S. Pat. No. 5,821,337) is clinically active in patients with HER2-overexpressing metastatic breast cancers that have received extensive prior anti-cancer therapy (Baselga et al., *J. Clin. Oncol.* 14:737-744 (1996)). Trastuzumab received marketing approval from the Food and Drug Administration Sep. 25, 1998 for the treatment of patients with metastatic breast cancer whose tumors overexpress the HER2 protein.

Other HER2 antibodies with various properties have been described in Tagliabue et al. *Int. J. Cancer* 47:933-937 (1991); McKenzie et al. *Oncogene* 4:543-548 (1989); Maier et al. *Cancer Res.* 51:5361-5369 (1991); Bacus et al. *Molecular Carcinogenesis* 3:350-362 (1990); Stancovski et al. *PNAS (USA)* 88:8691-8695 (1991); Bacus et al. *Cancer Research* 52:2580-2589 (1992); Xu et al. *Int. J. Cancer* 53:401-408 (1993); WO94/00136; Kasprzyk et al. *Cancer Research* 52:2771-2776 (1992); Hancock et al. *Cancer Res.* 51:4575-4580 (1991); Shawver et al. *Cancer Res.* 54:1367-1373 (1994); Arteaga et al. *Cancer Res.* 54:3758-3765 (1994); Harwerth et al. *J. Biol. Chem.* 267:15160-15167 (1992); U.S. Pat. No. 5,783,186; and Klapper et al. *Oncogene* 14:2099-2109 (1997).

Homology screening has resulted in the identification of two other HER receptor family members; HER3 (U.S. Pat. Nos. 5,183,884 and 5,480,968 as well as Kraus et al. *PNAS (USA)* 86:9193-9197 (1989)) and HER4 (EP Pat. Appln. No 599,274; Plowman et al., *Proc. Natl. Acad. Sci. USA,* 90:1746-1750 (1993); and Plowman et al., *Nature,* 366:473-475 (1993)). Both of these receptors display increased expression on at least some breast cancer cell lines.

The HER receptors are generally found in various combinations in cells and heterodimerization is thought to increase the diversity of cellular responses to a variety of HER ligands (Earp et al. *Breast Cancer Research and Treatment* 35: 115-132 (1995)). EGFR is bound by six different ligands; epidermal growth factor (EGF), transforming growth factor alpha (TGF-α), amphiregulin, heparin binding epidermal growth factor (HB-EGF), betacellulin and epiregulin (Groenen et al. *Growth Factors* 11:235-257 (1994)). A family of heregulin proteins resulting from alternative splicing of a single gene are ligands for HER3 and HER4. The heregulin family includes alpha, beta and gamma heregulins (Holmes et al., *Science,* 256:1205-1210 (1992); U.S. Pat. No. 5,641,869; and Schaefer et al. *Oncogene* 15:1385-1394 (1997)); neu differentiation factors (NDFs), glial growth factors (GGFs); acetylcholine receptor inducing activity (ARIA); and sensory and motor neuron derived factor (SMDF). For a review, see Groenen et al. *Growth Factors* 11:235-257 (1994); Lemke, G. *Molec. & Cell. Neurosci.* 7:247-262 (1996) and Lee et al. *Pharm. Rev.* 47:51-85 (1995). Recently three additional HER ligands were identified; neuregulin-2 (NRG-2) which is reported to bind either HER3 or HER4 (Chang et al. *Nature* 387 509-512 (1997); and Carraway et at *Nature* 387:512-516 (1997)); neuregulin-3 which binds HER4 (Zhang et al. *PNAS* (USA) 94(18):9562-7 (1997)); and neuregulin-4 which binds HER4 (Harari et al. *Oncogene* 18:2681-89 (1999)) HB-EGF, betacellulin and epiregulin also bind to HER4.

While EGF and TGFα do not bind HER2, EGF stimulates EGFR and HER2 to form a heterodimer, which activates EGFR and results in transphosphorylation of HER2 in the heterodimer. Dimerization and/or transphosphorylation appears to activate the HER2 tyrosine kinase. See Earp et al., supra. Likewise, when HER3 is co-expressed with HER2, an active signaling complex is formed and antibodies directed against HER2 are capable of disrupting this complex (Sliwkowski et al., *J. Biol. Chem.,* 269(20):14661-14665 (1994)). Additionally, the affinity of HER3 for heregulin (HRG) is increased to a higher affinity state when co-expressed with HER2. See also, Levi et al., *Journal of Neuroscience* 15: 1329-1340 (1995); Morrissey et al., *Proc. Natl. Acad. Sci. USA* 92: 1431-1435 (1995); and Lewis et al., *Cancer Res.,* 56:1457-1465 (1996) with respect to the HER2-HER3 protein complex. HER4, like HER3, forms an active signaling complex with HER2 (Carraway and Cantley, *Cell* 78:5-8 (1994)).

To target the HER signaling pathway, rhuMAb 2C4 (Pertuzumab) was developed as a humanized antibody that inhibits the dimerization of HER2 with other HER receptors, thereby inhibiting ligand-driven phosphorylation and activation, and downstream activation of the RAS and AKT pathways. In a phase I trial of Pertuzumab as a single agent for treating solid tumors, 3 subjects with advanced ovarian cancer were treated with pertuzumab. One had a durable partial response, and an additional subject had stable disease for 15 weeks. Agus et al. *Proc Am Soc Clin Oncol* 22: 192, Abstract 771 (2003).

Also antibody variant compositions are described in the art. U.S. Pat. No. 6,339,142 describes a HER2 antibody composition comprising a mixture of anti-HER2 antibody and one or more acidic variants thereof, wherein the amount of the acidic variant(s) is less than about 25%. Trastuzumab is the exemplified HER2 antibody. Reid et al. Poster presented at Well Characterized Biotech Pharmaceuticals conference (January, 2003) "Effects of Cell Culture Process Changes on Humanized Antibody Characteristics" describes an unnamed, humanized IgG1 antibody composition with N-terminal heterogeneities due to combinations of VHS signal peptide, N-terminal glutamine, and pyroglutamic acid on the heavy chain thereof. Harris et al. "The Ideal Chromatographic Antibody Characterization Method" talk presented at the IBC Antibody Production Conference (February, 2002) reports a VHS extension on the heavy chain of E25, a humanized anti-IgE antibody. Rouse et al. Poster presented at WCBP "Glycoprotein Characterization by High Resolution Mass Spectrometry and Its Application to Biopharmaceutical Development" (Jan. 6-9, 2004) describes a monoclonal antibody composition with N-terminal heterogeneity resulting from AHS or HS signal peptide residues on the light chain thereof. In a presentation at IBC Meeting (September, 2000) "Strategic Use of Comparability Studies and Assays for Well Characterized Biologicals," Jill Porter discussed a late-eluting form of ZENAPAX™ with three extra amino acid residues on the heavy chain thereof. US2006/0018899 describes a composition comprising a main species pertuzumab antibody and an amino-terminal leader extension variant, as well as other variant forms of the pertuzumab antibody.

Patent publications related to HER antibodies include: U.S. Pat. No. 5,677,171, U.S. Pat. No. 5,720,937, U.S. Pat. No. 5,720,954, U.S. Pat. No. 5,725,856, U.S. Pat. No. 5,770,195, U.S. Pat. No. 5,772,997, U.S. Pat. No. 6,165,464, U.S. Pat. No. 6,387,371, U.S. Pat. No. 6,399,063, US2002/0192211A1, U.S. Pat. No. 6,015,567, U.S. Pat. No. 6,333,169, U.S. Pat. No. 4,968,603, U.S. Pat. No. 5,821,337, U.S. Pat. No. 6,054,297, U.S. Pat. No. 6,407,213, U.S. Pat. No. 6,719,971, U.S. Pat. No. 6,800,738, US2004/0236078A1, U.S. Pat. No. 5,648,237, U.S. Pat. No. 6,267,958, U.S. Pat. No. 6,685,940, U.S. Pat. No. 6,821,515, WO98/17797, U.S. Pat. No. 6,127,526, U.S. Pat. No. 6,333,398, U.S. Pat. No. 6,797,814, U.S. Pat. No. 6,339,142, U.S. Pat. No. 6,417,335, U.S. Pat. No. 6,489,447, WO99/31140, US2003/0147884A1, US2003/0170234A1, US2005/0002928A1, U.S. Pat. No. 6,573,043, US2003/0152987A1, WO99/48527, US2002/0141993A1, WO01/00245, US2003/0086924, US2004/0013667A1, WO00/69460, WO01/00238, WO01/15730, U.S. Pat. No. 6,627,196B1, U.S. Pat. No. 6,632,979B1, WO01/00244, US2002/0090662A1, WO01/89566, US2002/0064785, US2003/0134344, WO 04/24866, US2004/0082047, US2003/0175845A1, WO03/087131, US2003/0228663, WO2004/008099A2, US2004/0106161, WO2004/048525, US2004/0258685A1, U.S. Pat. No. 5,985,553, U.S. Pat. No. 5,747,261, U.S. Pat. No. 4,935,341, U.S. Pat. No. 5,401,638, U.S. Pat. No. 5,604,107, WO 87/07646, WO 89/10412, WO 91/05264, EP 412,116 B1, EP 494,135 B1, U.S. Pat. No. 5,824,311, EP 444,181 B1, EP 1,006,194 A2, US 2002/0155527A1, WO 91/02062, U.S. Pat. No. 5,571,894, U.S. Pat. No. 5,939,531, EP 502,812 B1, WO 93/03741, EP 554,441 B1, EP 656,367 A1, U.S. Pat. No. 5,288,477, U.S. Pat. No. 5,514,554, U.S. Pat. No. 5,587,458, WO 93/12220, WO 93/16185, U.S. Pat. No. 5,877,305, WO 93/21319, WO 93/21232, U.S. Pat. No. 5,856,089, WO 94/22478, U.S. Pat. No. 5,910,486, U.S. Pat. No. 6,028,059, WO 96/07321, U.S. Pat. No. 5,804,396, U.S. Pat. No. 5,846,749, EP 711,565, WO 96/16673, U.S. Pat. No. 5,783,404, U.S. Pat. No. 5,977,322, U.S. Pat. No. 6,512,097, WO 97/00271, U.S. Pat. No. 6,270,765, U.S. Pat. No. 6,395,272, U.S. Pat. No. 5,837,243, WO 96/40789, U.S. Pat. No. 5,783,186, U.S. Pat. No. 6,458,356, WO 97/20858, WO 97/38731, U.S. Pat. No. 6,214,388, U.S. Pat. No. 5,925,519, WO 98/02463, U.S. Pat. No. 5,922,845, WO 98/18489, WO 98/33914, U.S. Pat. No. 5,994,071, WO 98/45479, U.S. Pat. No. 6,358,682 B1, US 2003/0059790, WO 99/55367, WO 01/20033, US 2002/0076695 A1, WO 00/78347, WO 01/09187, WO 01/21192, WO 01/32155, WO 01/53354, WO 01/56604, WO 01/76630, WO02/05791, WO 02/11677, U.S. Pat. No. 6,582,919, US2002/0192652A1, US 2003/0211530A1, WO 02/44413, US 2002/0142328, U.S. Pat. No. 6,602,670 B2, WO 02/45653, WO 02/055106, US 2003/0152572, US 2003/0165840, WO 02/087619, WO 03/006509, WO03/012072, WO 03/028638, US 2003/0068318, WO 03/041736, EP 1,357,132, US 2003/0202973, US 2004/0138160, U.S. Pat. No. 5,705,157, U.S. Pat. No. 6,123,939, EP 616,812 B1, US 2003/0103973, US 2003/0108545, U.S. Pat. No. 6,403,630 B1, WO 00/61145, WO 00/61185, U.S. Pat. No. 6,333,348 B1, WO 01/05425, WO 01/64246, US 2003/0022918, US 2002/0051785 A1, U.S. Pat. No. 6,767,541, WO 01/76586, US 2003/0144252, WO 01/87336, US 2002/0031515 A1, WO 01/87334, WO 02/05791, WO 02/09754, US 2003/0157097, US 2002/0076408, WO 02/055106, WO 02/070008, WO 02/089842 and WO 03/86467.

Patients treated with the HER2 antibody Trastuzumab/Herceptin™ are selected for therapy based on HER2 protein overexpression/gene amplification; see, for example, WO99/31140 (Paton et al.), US2003/0170234A1 (Hellmann, S.), and US2003/0147884 (Paton et al.); as well as WO01/89566, US2002/0064785, and US2003/0134344 (Mass et al.). See, also, US2003/0152987, Cohen et al., concerning immunohistochemistry (IHC) and fluorescence in situ hybridization (FISH) for detecting HER2 overexpression and amplification. WO2004/053497 and US2004/024815A1 (Bacus et al.), as well as US 2003/0190689 (Crosby and Smith), refer to determining or predicting response to Trastuzumab therapy. US2004/013297A1 (Bacus et al.) concerns determining or predicting response to ABX0303 EGFR antibody therapy. WO2004/000094 (Bacus et al.) is directed to determining response to GW572016, a small molecule, EGFR-HER2 tyrosine kinase inhibitor. WO2004/063709, Amler et al., refers to biomarkers and methods for determining sensitivity to EGFR inhibitor, erlotinib HCl. US2004/0209290, Cobleigh et al., concerns gene expression markers for breast cancer prognosis.

Patients treated with pertuzumab (a HER2 dimerisation inhibitor described herein below in more detail) can be selected for therapy based on HER activation or dimerization. Patent publications concerning pertuzumab and selection of patients for therapy therewith include: WO01/00245 (Adams et al.); US2003/0086924 (Sliwkowski, M.); US2004/0013667A1 (Sliwkowski, M.); as well as WO2004/008099A2, and US2004/0106161 (Bossenmaier et al.).

Herceptin™/Trastuzumab is indicated in the art for the treatment of patients with metastatic breast cancer whose tumors overexpress HER2 protein or have HER 2 gene amplification:

a) As monotherapy for the treatment of those patients who have received at least two chemotherapy regimens for their metastatic disease. Prior chemotherapy must have included at least an anthracycline and a taxane unless patients are unsuitable for these treatments. Hormone receptor positive patients must also have received hormonal therapy, unless patients are unsuitable for these treatments, b) In combination with paclitaxel for the treatment of those patients who have not received chemotherapy for their metastatic disease and for whom an anthracycline is not suitable and c) In combination with docetaxel for the treatment of those patients who have not received chemotherapy for their metastatic disease.

Herceptin™/Trastuzumab can also be used as adjuvant treatment in early breast cancer. Herceptin™/Trastuzumab is also approved for the treatment of patients with HER2-positive early breast cancer following surgery, chemotherapy (neoadjuvant (i.e. before surgery) or adjuvant), and radiotherapy (if applicable). In addition Herceptin in combination with capecitabine or 5-fluorouracil and cisplatin is indicated for the treatment of patients with HER2 positive locally advance or metastatic adenocarcinoma of the stomach or gastroesophageal junction who have not received prior anticancer treatment for their metastatic disease.

In the art, the treatment of breast cancer patients with Herceptin™/Trastuzumab is, for example, recommended and routine for patients having HER2-positive cancer. HER2-positive cancer is present if a high HER2 (protein) expression level detected by immunohistochemical methods (e.g. HER2 (+++)) or HER2 gene amplification detected by in-situ-hybridization (e.g. ISH positive, like a HER2 gene copy number higher than 4 copies of the HER2 gene per tumor cell or ratio of ≥2.0 for the number of HER2 gene copies to the number of signals for CEP17.) or both is found in samples obtained from the patients such as breast tissue biopsies or breast tissue resections or in tissue derived from metastatic sites.

The NEOSPHERE study (Neoadjuvant Study of Pertuzumab and Herceptin in an Early Regimen Evaluation) is a randomized multicentre, international Phase II study that was conducted in 78 centres worldwide (except the USA) in 417 women with newly diagnosed HER2-positive early, inflammatory or locally advanced breast cancer who had never received Herceptin. Prior to surgery (neoadjuvant treatment) these women were randomized to four study arms. The primary endpoint was complete tumour disappearance at time of surgery (pathological complete response, pCR) and the results were:

pCR of 29.0 percent for Herceptin and docetaxel pCR of 45.8 percent for Herceptin, pertuzumab and docetaxel pCR of 16.8 percent for Herceptin and pertuzumab pCR of 24.0 percent for pertuzumab and docetaxel The data shows that the two antibodies plus docetaxel given in the neoadjuvant setting prior to surgery significantly improved the rate of complete tumour disappearance (pathological complete response rate, pCR, of 45.8 percent) in the breast by more than half compared to Herceptin plus docetaxel (pCR of 29.0 percent), p=0.014. The study is described in detail e.g. in Lancet Oncol. 2012 January; 13(1):25-32. doi: 10.1016/S1470-2045(11)70336-9. Epub 2011 Dec. 6, which is incorporated by reference herein in its entirety. Core biopsies (tumor tissue) from 387 patients were used for biomarker analyses.

However, not all patients having HER2-positive cancer or cancer cells respond to treatment with a HER2 inhibitor. Therefore, efforts have been made in the art to identify non-responding patients that may be excluded from treatment. Barbereschi (Clin Cancer Res 2007, 13:6064-6069) investigated the association of phosphoinositide-3-kinase, catalytic, alpha polypeptide (PIK3CA) mutations on exon 9 and 20 with pathologic features and clinical outcome in breast cancer patients treated with chemotherapy and/or hormone therapy. Berns (Cancer Cell (2007) 12, 395-402) describes that the presence of PIK3CA mutations (inter alia in exon 9 and 20) was associated with poor prognosis after trastuzumab therapy. Also Razis (Breast Cancer Res Treat (DOI 10.1007/s10549-011-1572-5) investigates the association of PIK3CA mutations (in exon 9 and 20) with efficacy of trastuzumab therapy and describes that these mutations were associated with shorter median time to progression. Dave (2011, J Clinical Oncology 29, 166) also find that activating mutations in the PIK3CA conferred resistance to Trastuzumab.

Thus, the technical problem underlying the present invention is the provision of means and methods for identifying a patient or a group of patients with HER2-positive cancer who are non-responsive to a treatment with a HER2 inhibitor, in particular to a treatment with a HER2 antibody such as Trastuzumab or Pertuzumab.

The technical problem is solved by provision of the embodiments characterized in the claims.

Accordingly, the present invention relates to a method for identifying a non-responder to a HER2-inhibitor, said method comprising evaluating the presence of one or more mutations in exon 9 of the catalytic subunit of Phosphoinositol-3 kinase (PIK3CA or p110α) in a sample from a patient with HER2-positive cancer; and whereby the presence of one or more mutations in exon 9 indicates non-responsiveness of said patient to said HER2 inhibitor.

In the present invention, it was surprisingly found that mutations in exon 9 of Phosphoinositol-3 kinase (PIK3CA) are indicative for non-responsiveness of a patient with HER2-positive cancer to a HER2 inhibitor, such as Trastuzumab and, in particular Pertuzumab. In contrast, as found herein, mutations in exon 20 were not predictive for non-responsiveness. In other words, it was unexpectedly found that the evaluation only of mutations in exon 9 of Phosphoinositol-3 kinase (PIK3CA) is sufficient for a highly reliable determination of non-responders to treatment with HER2 inhibitors, in particular anti-HER2 antibodies. Therefore, exon 9 mutations are, preferably, the only PIK3CA mutations evaluated in the methods of the present invention. In accordance with the invention, solely the presence of mutations in exon 9 of PIK3CA is determined/evaluated/measured, i.e. the presence of mutations in other parts (e.g. like exon 20) of the PIK3CA gene or coding sequence are not evaluated or determined. The invention is, thus, based on the surprising finding that the determination/evaluation of solely (only) mutations (like mutational SNPs) in exon 9 of PIK3CA is enough for a reliable read-out whether a patient will or will not respond to treatment with a HER2 inhibitor. The evaluation of such mutations and/or SNPs is described herein below in more detail and exemplified in the examples. None of the documents discussed above discloses or proposes the use of only (solely) PIK3CA mutations (or mutational SNPs) in exon 9 for identifying non-responders to therapy with HER2 inhibitors.

Exemplary mutations/SNPs in exon 9 of PIK3CA that can be determined/evaluated in the herein provided method for identification of non-responders to HER2-inhibitors are those where the mutation results in a change in the amino acid sequence at position 542 and 545 of the full length protein sequence of PIK3CA as shown in SEQ ID NO: 2. In the wild-type protein sequence of PIK3CA the amino acid at position 542 and 545 is "E". In the mutant forms of PIK3CA to be determined herein, the wild type "E" at these positions is replaced by the amino acid "K" ("E542K" or "E545K"), amino acid "A" ("E545A") or amino acid "G" ("E545G"). These changes at amino acid level are also reflected in mutations at the nucleic acid level (like mutational SNPs) and corresponding mutated triplets (codons) to be determined/detected/evaluated are given herein further below.

The non-responders identified by the herein provided means and methods may be subject to other treatments than treatment with a HER2 inhibitor; for example, they may advantageously be treated with compounds other than HER2 inhibitors. The term "non-responder" as used herein can refer to an individual/patient/subject that is less likely to respond to a treatment using a HER2 inhibitor (like pertuzumab or trastuzumab). "Less likely to respond" as used herein refers to a decreased likeliness that a pathological complete response (pcR) will occur in a patient treated with a HER2 inhibitor. In cases where (with the methods of the present invention) it was assessed that the subject is a "non-responder" or is "less likely to respond", said subject is to receive phosphoinositol-3 kinase-targeted agents. Such agents are known in the art and comprise, but are not limited to fused pyrimidine derivatives as disclosed in U.S. Pat. No. 8,022,205 B2 or fused pyrrolopyrimidine derivatives as disclosed in WO2009/099163.

The sample to be evaluated can be obtained from a patient with HER2-positive cancer. The HER2-positive cancer may assessed be breast cancer, such as early-stage breast cancer. However, the method of identifying non-responders provided herein can be applied to a wide range of HER2-positive cancers, like gastric cancer, colon cancer, lung cancer and the like. In a preferred embodiment, the HER2 inhibitor is an anti-HER2 antibody, like pertuzumab or trastuzumab. Preferably, the patient is a human.

Accordingly, this invention relates to a method for identifying a non-responder to a HER2-inhibitor, said method comprising detecting/measuring the presence of one or more mutations in exon 9 of the catalytic subunit of Phosphoinositol-3 kinase (PIK3CA or p110α) in a sample from a patient with HER2-positive cancer; and whereby the presence of one or more mutations in exon 9 indicates non-responsiveness of said patient to said HER2 inhibitor.

The present invention relates to a method for identifying a non-responder to a HER2-inhibitor, said method comprising the steps (a) obtaining a sample from a patient with HER2-positive cancer;

(b) evaluating the presence of one or more mutations in exon 9 of the catalytic subunit of Phosphoinositol-3 kinase (PIK3CA or p110α) in said sample;

whereby the presence of one or more mutations in exon 9 of the catalytic subunit of Phosphoinositol-3 kinase (PIK3CA or p110α) indicates non-responsiveness of said patient to said HER2 inhibitor.

As mentioned, it has been found herein that the presence of one or more mutations in exon 9 of the catalytic subunit of PI3K i.e. PIK3CA indicates non-responsiveness to a HER2 inhibitor. The following provides some background information on PIK3CA and the family of Phosphatidylinositol 3-kinase to which it belongs; the mutations in exon 9 of the catalytic subunit of PI3K are explained in more detail further below. The mutation may be the replacement or exchange (substitution) of one or more amino acids as compared to the wild-type sequence of exon 9 of Phosphoinositol-3 kinase catalytic subunit (PIK3CA).

Corresponding nucleic acid sequences and amino acid sequences of wild-type PIK3CA are shown in SEQ ID NO. 1 and SEQ ID NO: 2, respectively, and in FIG. 7. As used herein, the term "PIK3CA" refers to the catalytic subunit of Phosphoinositol-3 kinase (PI3K), isoform alpha, also referred to as p110alpha. The terms "PIK3CA", "catalytic subunit of Phosphoinositol-3 kinase isoform alpha" or, short, "p110alpha"/"p110α" are used interchangeably herein. "PIK3CA" is the term recommended and commonly used in the art; however, the entire protein is also known as PI3K. Phosphatidylinositol 3-kinase (PI3K) is composed of an 85 kDa regulatory subunit and a 110 kDa catalytic subunit. The protein encoded by the PIK3CA gene represents the catalytic subunit of PI3K, which uses ATP to phosphorylate PtdIns, PtdIns4P and PtdIns(4,5)P2 (i.e. this catalytic subunit is "PIK3CA" as defined and used herein). This gene has been found to be oncogenic and has been implicated in a variety of cancers.

Phosphoinositol-3 kinase belongs to the family of Phosphatidylinositol 3-kinases (PI 3-kinases or "PI3Ks"). This is a family of enzymes involved in cellular functions such as cell growth, proliferation, differentiation, motility, survival and intracellular trafficking, which in turn are involved in cancer. In response to lipopolysaccharide, PI3Ks phosphorylate p65, inducing anandamide synthesis to inhibit NF-κB activation. This is under the control of FAAH limiting the ability of LPS to increase AEA levels and is also inhibited by wortmannin and cannabidiol, one of the only natural compounds to inhibit FAAH. The phosphoinositol-3-kinase family is divided into three different classes: Class I, Class II, and Class III. The classifications are based on primary structure, regulation, and in vitro lipid substrate specificity.

The following table provides an overview of the human genes/proteins of Phosphatidylinositol 3-kinases family members. PIK3CA is highlighted in bold.

| group | gene | protein | synonyms |
|---|---|---|---|
| class 2 | PIK3C2A | PI3K, class 2, alpha polypeptide | PI3K-C2α |
| | PIK3C2B | PI3K, class 2, beta polypeptide | PI3K-C2β |
| | PIK3C2G | PI3K, class 2, gamma polypeptide | PI3K-C2γ |
| class 3 | PIK3C3 | PI3K, class 3 | Vps34 |
| class 1 | PIK3CA | PI3K, catalytic, alpha polypeptide | p110-α |
| catalytic | PIK3CB | PI3K, catalytic, beta polypeptide | p110-β |
| | PIK3CG | PI3K, catalytic, gamma polypeptide | p110-γ |
| | PIK3CD | PI3K, catalytic, delta polypeptide | p110-γ |
| class 1 | PIK3R1 | PI3K, regulatory subunit 1 (alpha) | p85-α |
| regulatory | PIK1R2 | PI3K, regulatory subunit 2 (beta) | p85β |
| | PIK3R3 | PI3K, regulatory subunit 3 (gamma) | p55-γ |
| | PIK3R4 | PI3K, regulatory subunit 4 | p150 |
| | PIK3R5 | PI3K, regulatory subunit 5 | p101 |
| | PIK3R5 | PI3K, regulatory subunit 6 | p87 |

PIK3CA and its genetic variants to be used in the herein provided methods for identifying non-responders to HER2-inhibitors and their use in screening methods for responsiveness to treatment with a compound are described, for example, in WO 2011/031861, WO 2005/091849 and WO 2011/060380.

In context of the present invention, the mutation (mutational SNP) to be determined/assessed in accordance with the present invention may be a mutation in the codon encoding an amino acid at position 542 and/or 545 of the full-length amino acid sequence of Phosphatidylinositol-3 kinase (PIK3CA) (see e.g. SEQ ID NO. 2 of FIG. 7). The mutation may comprise one or more of the mutations E542K, E545K, E545A and E545G (i.e. mutations/SNP in exon 9 encoding the amino acid K, A or G at position 542 or 545 of the amino acid sequence of Phosphatidylinositol-3 kinase (PIK3CA) instead of wildtype E. The term E542K, E545K, E545A and E545G as used herein refer to amino acid substitutions at a given position of the amino acid sequence of wild type PIK3CA. Corresponding nucleic acid sequences (codons/triplets) encoding the amino acid at positions 542 and 545 in wild type and mutant PIK3CA genes/coding sequences are described below. In accordance with internationally accepted nomenclature, the term "E542K" refers to a substitution/replacement of amino acid "E" at position 542 of the amino acid sequence of wild type PIK3CA by amino acid "K". The same explanation applies, mutatis mutandis, to "E545K", "E545A" and "E545G". These mutations are well known in the art and corresponding mutated sequences can be retrieved from the respective databases like Uniprot. Based on the herein provided teaching, the presence of these mutations can readily be determined by a person skilled in the art. Preferably, the mutation is determined on a nucleic acid level as described below and exemplified in the examples. The mutations E542K E545K, E545A and E545G are also illustrated in the herein described sequences. For example, nucleic acid and amino acid sequences of mutation (mutational SNP) E542K are shown in SEQ ID NO. 17 and SEQ ID NO. 18, respectively; nucleic acid and amino acid sequences of mutation E545K are shown in SEQ ID NO: 19 and SEQ ID NO. 20, respectively; nucleic acid and amino acid sequences of mutation E545A are shown in SEQ ID NO: 21 and SEQ ID NO. 22, respectively, and nucleic acid and amino acid sequences of mutation E545G are shown in SEQ ID NO: 23 and SEQ ID NO. 24, respectively.

Methods for the determining/evaluation assessed/measured of the presence of the mutations are described herein and provided in the examples. Exemplary, non-limiting methods to be used are methods for sequencing of nucleic acids (e.g. Sanger di-deoxy sequencing), "next generation" sequencing methods, single molecule sequencing, methods enabling detection variant alleles/mutations, such as Real-time PCR, PCR-RFLP assay (see Cancer Research 59 (1999), 5169-5175), mass-spectrometric genotyping (e.g. MALDI-TOF), HPLC, enzymatic methods and SSPC (single strand conformation polymorphism analysis; see Pathol Int (1996) 46, 801-804).

Such methods may include enzymatic amplification of DNA or cDNA fragments using oligonucleotides specifically hybridizing to exon 9 (or parts thereof) of the PIK3CA gene by PCR. Given that mutations in exon 9 of the PIK3CA gene are to be evaluated, such amplifications may be carried out in one or two reactions when employing RNA or genomic DNA. The resulting PCR products may be subjected to either conventional Sanger-based dideoxy nucleotide sequencing methods or employing parallel sequencing methods ("next generation sequencing") such as those marketed by Roche (454 technology), Illumina (Solexa technology) or ABI (Solid technology). Mutations may be identified from sequence reads by comparison with publicly available gene sequence data bases. Alternatively, mutations may be identified by incorporation of allele-specific probes that can either be detected using enzymatic detection reactions, fluorescence, mass spectrometry or others; see Vogeser (2007) Dtsch Arztebl 104 (31-32), A2194-200.

Paraffin-embedded clinical material as well as fresh frozen tissue may be used in the detection of these mutations. Detection may comprise a histolopathology review of the sample to be tested to see whether tumour tissue is present. The following table shows exemplary nucleic acid sequences of the mutations (mutational SNPs) to be determined in accordance with the present invention; any other point mutation(s) that result in an amino acid change at position 542 and/or 545 (or position 546, like the E545D mutation having the sequence "gat"/"T" mutation") of full-length the amino acid sequence of PIK3CA can be included in the assessment in accordance with the present invention.

| | |
|---|---|
| gaa | codonitripiet encoding wild type E542 |
| gag | codon/tripiet encoding wild type E545 |
| aaa | codonitripiet encoding mutant E542K ((E >> K) |
| aag | codon/tripiet encoding mutant E545K (E >> K), |
| gcg | codon/triplet encoding mutant E545A (E >> A), |
| ggg | I codon/triplet encoding mutant E545G(E >> G), |

Accordingly, the term "mutation E542K in exon 9 of Phosphoinositol-3 kinase (PIK3CA)" as used herein may refer to a codon/triplet (like aaa) encoding amino acid K at position 542 of the full-length amino acid sequence of PIK3CA (the wild-type sequence thereof is shown in FIG. 7 and SEQ ID NO: 2). The term "mutation E545K in exon 9 of Phosphoinositol-3 kinase (PIK3CA)" as used herein may refer to a codon/triplet (like aag) encoding amino acid K at position 545 of the full-length amino acid sequence of PIK3CA (the wild-type sequence thereof is shown in FIG. 7 and SEQ ID NO: 2).

The term "mutation E545A in exon 9 of Phosphoinositol-3 kinase (PIK3CA)" as used herein may refer to a codon/triplet (like gcg) encoding amino acid A at position 545 of the full-length amino acid sequence of PIK3CA (the wild-type sequence thereof is shown in FIG. 7 and SEQ ID NO: 2). The term "mutation E545G in exon 9 of Phosphoinositol-3 kinase (PIK3CA)" as used herein may refer to a codon/triplet (like ggg) encoding amino acid G at position 545 of the full-length amino acid sequence of PIK3CA (the wild-type sequence thereof is shown in FIG. 7 and SEQ ID NO: 2).

The following exemplary test may be used.

The PCR amplification of isolated DNA and mutation detection procedures for the PIK3CA mutation detection test are summarized below.

Each standard 50-4 amplification reaction targeting one of the Exons 7, 9 or 20 included 100 ng genomic DNA, dNTPs (including dUTP), 0.05 U/μL Z05, DNA polymerase, 0.04 U/μL uracil-DNA glycosylase (UNG), and 200-400 nM forward and reverse primer (Table 1), 75-200 nM mutant and wild-type specific probes (Table 2). Amplification was performed in the Cobas® 4800 analyzer using the following temperature profile: 5 min at 50° C. followed by 55 cycles of 95° C. for 10 sec and 63° C. for 50 sec, followed by a single round of 40° C. for 2 min and 25° C. for 10 sec (melting curve analysis). Fluorescence data was collected during each amplification cycle and during the final melting curve analysis.

The following exemplary primers/primer pair may be used in the method for identifying a non-responder to a HER2-inhibitor provided herein, wherein the non-responder has a mutation in exon 9 of PIK3CA.

TABLE 1

Primer Sequences for the PIK3CA Mutation Detection Test

| Primer | Sequence 5' to 3' |
|---|---|
| 542/545 Forward primer PIK3CA-9F13 | UAAAAUUUAUUGAGAAUGUAUUUG CTTTTTC (SEQ ID NO: 25) |
| 542/545 Reverse primer PIK3CA-9R01 | TCCATTTTAGCACTTACCTGTGAC (SEQ ID NO: 26) |

Key:
U = 5-propynyl dU

The following exemplary probes may be used in the method for identifying a non-responder to a HER2-inhibitor provided herein, wherein the non-responder has a mutation in exon 9 of PIK3 CA.

TABLE 2

Probe Sequences for the PIK3CA Mutation Detection Test

| Probe | Sequence 5' to 3' |
|---|---|
| 542 WT Probe | FTTTCAQAGAGAGGAUEUEGUGUAGAAAUUGEP (SEQ ID NO: 27) |
| 542 542K Mutation Probe | LATTTTQGAGAGAGGAUEUEGUGUAGAAAUUGEUUP (SEQ ID NO: 28) |
| 545 WT Probe | OCTGCTCAGTQAUUUIAGAGAGAGGATCTCGTGTP (SEQ ID NO: 29) |
| 545 545K Mutation Probe | JAATCACTAAGQAGGAGAAAGAUUUUEUAUGGAGUEP (SEQ ID NO: 30) |
| 545 545A Mutation Probe | FCTGCGCQGGAGAAAGAUUUUEUAUGGAGUEAP (SEQ ID NO: 31) |
| 545 545G Mutation Probe | LCCTGCCCQGTGAUUUIAGAGAGAGGATCTCGP (SEQ ID NO: 32) |

Key:
F = FAM Reporter Dye , J = JA270 Reporter Dye, 0 = CY5.5 Reporter Dye, L = HEX Reporter Dye, U = 5-propynyl dU, E = 5-methyl dC,, I = deoxyinosine, Z = 7-deaza dG, Q = BHQ2 Quencher Dye, P = 3' Phosphate In accordance with the present invention, the presence of one or more mutations in exon 9 of PIK3CA may be evaluated/determined/measured in the herein provided method for identifying a non-responder to HER2 inhibitors (the terms "evaluating", "determining" and "measuring" can be used interchangeably in context of the present invention). In one embodiment, the presence of only one of the mutations is evaluated/determined. Accordingly, the presence of only one of the E542K, E545K, E545A and E545G mutations of PIK3CA (i.e. the nucleic acids in exon 9 of PIK3CA encoding the amino acid at these positions in the full length amino acid sequence of PIK3CA) may be evaluated, i.e. only E542K, only E545K, only E545A or only E545G. The methods of the present invention may also comprise the subsequent evaluation of the presence of two or more of these mutations in any order. For example, the evaluation of the presence of E542K may be followed by the evaluation of E545K (or vice versa) which may be followed by the evaluation of the presence of E545A, which may be followed by the evaluation of the presence of E545G. Other possible orders of evaluation are easily conceivable by a person skilled in the art and contemplated herein.

The mutations may be evaluated in combination/simultaneously. Again, any combination is envisaged. For example, the presence of E542K and E545K is evaluated; or the presence of E542K and E545A; or the presence of E542K and E545G is evaluated. Other combinations are easily conceivable. The evaluation of a combination of these mutations may be followed or preceded by the evaluation of the presence of one other mutation or a combination of other mutations.

As mentioned, the present invention provides for means to determine whether an individual/patient with HER2-positive cancer (i.e. suffering from, suspected to suffer from or being prone to suffer from HER2-positive cancer) will respond to treatment with a HER2 inhibitor or will not respond to treatment to a HER2 inhibitor. This assessment may be advantageously done before the start of treatment with the HER2 inhibitor. Even if a patient has been treated with a HER2 inhibitor, a person skilled in the art can determine whether a person showed no response after the treatment with the HER2 inhibitor. For example, a non-response to an inhibitor may be reflected in an increased suffering from cancer, such as an increased growth of a cancer/tumor and/or increase in the size of a tumor, the (increase in) the formation of metastases or a increase in the number or size of metastases. A non-response may also be the development of a tumor or metastases, for example after resection of a tumor, in the shortening of time to disease progression, or in the increase in the size of (a) tumor(s) and/or (a) metastases, for example in neoadjuvant therapy.

In accordance with the methods provided in the present invention a patient group can be identified that does not respond to treatment with HER2 inhibitors, like Pertuzumab or Trastuzumab. It has been found herein that some individuals with HER2 positive cancer or cancer cells do not adequately respond to treatment with a HER2 inhibitor, if the patients have mutations in exon 9 of PIK3CA. In one embodiment of the present invention, at least 80%, 90%, 95% or more of the patient group identified by the herein provided method do not respond to treatment with a HER2 inhibitor. That means that at least 80% of the identified individuals having the herein described mutation(s) in exon 9 of PIK3CA will not respond to the treatment with the herein defined HER2 inhibitors, like Pertuzumab or Trastuzumab.

As the skilled artisan fully appreciates a positive test for one or more mutations in exon 9 of PIK3CA in a sample of a patient with HER2-positive cancer does not indicate that the patient will not respond to treatment with absolute certainty. However, by the herein provided methods sub-groups of patients are identified that have a lower chance of response (=show a lower response rate) to a treatment with a HER2 inhibitor like pertuzumab or trastuzumab as compared to the sub-groups of patients not having these mutations in exon 9 of PIK3CA. With other words the determination of a presence of one or more mutations in exon 9 of PIK3CA indicates (=is indicative for) that the patient has a lower chance (=probability, likelihood) to respond to treatment with a HER2 inhibitor, as compared to a patient having no mutation in exon 9 of PIK3CA (wild type PIK3CA). Preferably, the response is pathologic complete response (pCR). The term "pCR" as used herein refers to the absence of invasive cancer cells in tissue like breast tissue or absence of invasive tumor cells in tissue like breast tissue and/or lymph nodes. pCR is commonly used as an endpoint in neoadjuvant treatment such as in breast cancer treatment.

The term "HER2-positive cancer" as used herein refers to a cancer/tumorous tissue etc. which comprises cancer cells which have higher than normal levels of HER2. Examples of HER2-positive cancer include HER2-positive breast cancer and HER2-positive gastric cancer. For the purpose of the present invention, "HER2-positive cancer" has an immunohistochemistry (IHC) score of at least 2+ and/or an in situ hybridization (ISH) amplification ratio ≥2.0 (i.e. is ISH-positive). Accordingly, HER2-positive cancer is present if a high HER2 (protein) expression level detected e.g. by immunohistochemical methods and/or HER2 gene amplification detected by in-situ-hybridization (ISH positive, like a HER2 gene copy number higher than 4 copies of the HER2 gene per tumor cell or ratio of ≥2.0 for the number of HER2 gene copies to the number of signals for CEP17.) is found in samples obtained from the patients such as breast tissue biopsies or breast tissue resections or in tissue derived from metastatic sites. In one embodiment "HER2-positive cancer" has an immunohistochemistry (IHC) score of HER2(3+) and/or is ISH positive.

The expression level of HER2 may be detected by an immunohistochemical method, whereas said HER2 gene amplification status can be measured with in situ hybridization methods, like fluorescence in situ hybridization techniques (FISH). Corresponding assays and kits are well known in the art, for protein expression assays as well as for the detection of gene amplifications. Alternatively other methods like qRT-PCR might be used to detect levels of HER2 gene expression.

The expression level of HER2 can, inter alia, be detected by an immunohistochemical method. Such methods are well known in the art and corresponding commercial kits are available. Exemplary kits which may be used in accordance with the present invention are, inter alia, HerceptTest™ produced and distributed by the company Dako or the test called Ventana Pathway™. The level of HER2 protein expression may be assessed by using the reagents provided with and following the protocol of the Herceplest™. A skilled person will be aware of further means and methods for determining the expression level of HER2 by immunohistochemical methods; see for example WO 2005/117553. Therefore, the expression level of HER2 can be easily and reproducibly determined by a person skilled in the art without undue burden. However, to ensure accurate and reproducible results, the testing must be performed in a specialized laboratory, which can ensure validation of the testing procedures.

The expression level of HER2 can be classified in a low expression level, an intermediate expression level and a high expression level. It is preferred in context of this invention that HER2-positive disease is defined by a strong expression level of HER2 (e.g. HER2(3+) by IHC), for example determined in a sample of a cancer patient.

The recommended scoring system to evaluate the IHC staining patterns which reflect the expression levels of HER2 designated herein HER2(0), HER2(+), HER2(++) and HER2(+++), is as follows:

| Staining Intensity Score | Staining Pattern | HER2 overexpression assessment |
|---|---|---|
| 0 | No staining is observed or membrane staining is observed in <10% of the tumor cells | negative |
| 1+ | A faint/barely perceptible membrane staining is detected in >10% of the tumor cells. The cells are only stained in part of their membrane. | negative |
| 2+ | A weak to moderate complete staining is detected in >10% of the tumor cells. | weak to moderate overexpression. |
| 3+ | A strong complete membrane staining is detected in >10% of the tumor cells. | strong overexpression. |

The terms HER2(+), HER2(++) and HER2(+++) used herein are equivalent to the terms HER2(1+), HER2(2+) and HER2(3+). A "low protein expression level" used in context of this invention corresponds to a 0 or 1+ score ("negative assessment" according to the table shown herein above), an "weak to moderate protein expression level" corresponds to a 2+ score ("weak to moderate overexpression", see the table above) and a "high protein expression level" corresponds to a 3+ score ("strong overexpression", see the table above). As described herein above in detail, the evaluation of the protein expression level (i.e. the scoring system as shown in the table) is based on results obtained by immunohistochemical methods. As a standard or routinely, the HER-2 status is, accordingly, performed by immunohistochemistry with one of two FDA-approved commercial kits available; namely the Dako Herceptest™ and the Ventana Pathway™. These are semi-quantitative assays which stratify expression levels into 0 (<20,000 receptors per cell, no expression visible by IHC staining), 1+ (~100,000 receptors per cell, partial membrane staining, <10% of cells overexpressing HER-2), 2+ (~500,000 receptors per cell, light to moderate complete membrane staining, >10% of cells overexpressing HER-2), and 3+ (~2,000,000 receptors per cell, strong complete membrane staining, >10% of cells overexpressing HER-2).

Alternatively, further methods for the evaluation of the protein expression level of HER2 may be used, e.g. Western Blots, ELISA-based detection systems and so on.

A HER2-positive cancer may also be diagnosed by assessing the gene amplification status of HER2. HER2-positive cancer is, accordingly, diagnosed if this assessment by ISH is positive. In accordance with this assessment, a HER2-positive cancer may, inter alia, relate to an average HER2 gene copy number higher than 4 copies of the HER2 gene per tumor cell (for those test systems without an internal centromere control probe) or to a HER2/CEP17 ratio of >=2.0 (for those test systems using an internal chromosome 17 centromere control probe). In other words, the HER2-positive cancer may, inter alia, relate to a HER2 gene copy number greater than 4. The amplification level of the HER2 gene may easily be identified by in situ hybridization (ISH) like fluorescent in situ hybridization (FISH), chromogenic in situ hybridization (CISH) and silver in situ hybridization (SISH). These methods are known to the skilled artisan. The principles of these methods can be deduced from standard text books. Commercial kits for the determination of the HER2 gene amplification status by in situ hybridization are available.

The HER2-positive cancer may be breast cancer or gastric cancer. Further, the HER2-positive cancer may be ovarian cancer, lung cancer, colorectal cancer, kidney cancer, bone cancer, bone marrow cancer, bladder cancer, skin cancer, prostate cancer, esophagus cancer, salivary gland cancer, pancreas cancer, liver cancer, head and neck cancer, CNS (especially brain) cancer, cervix cancer, cartilage cancer, colon cancer, genitourinary cancer, gastrointestinal tract cancer, pancreas cancer, synovium cancer, testis cancer, thymus cancer, thyroid cancer and uterine cancer. In one embodiment the breast cancer is early-stage breast cancer, as also assessed in the appended example.

The sample to be assessed in accordance with the herein provided methods for identification a non-responder to a HER2 inhibitor may comprise non-diseased cells and/or diseased cells, i.e. non-cancerous cells and/or cancerous cells however the content of cancerous cells among non cancerous cells should be higher than 50%. The sample may also (or even solely) comprise cancer/tumor cell(s), such as breast cancer/tumor cell(s). The term “sample” shall generally mean any biological sample obtained from a patient’s tumor. The sample may be a tissue resection or a tissue biopsy. The sample may also be a metastatic lesion or a section of a metastatic lesion or a blood sample known or suspected to comprise circulating tumor cells. In accordance with the above, the biological sample may comprise cancer cells and to a certain extent i.e. less than 50% non-cancer cells (other cells). The skilled pathologist is able to differentiate cancer cells from normal tissue cells. Methods for obtaining tissue biopsies, tissue resections and body fluids and the like from mammals, such as humans, are well known in the art.

As mentioned, the sample is obtained from a patient with HER2-positive cancer as defined above. For example, the sample may be obtained from a tumorous tissue, (a) tumor(s) and, accordingly, is (a) tumor cell(s) or (a) tumor tissue(s) suspected of being HER2-positive tumour, like a breast tumor and the like. A person skilled in the art is in the position to identify such tumors and/or individuals/patients suffering from corresponding cancer using standard techniques known in the art and methods disclosed herein. Generally, said tumor cell or cancer cell may be obtained from any biological source/organism, particularly any biological source/organism, suffering from the above-mentioned cancer. In context of this invention particular useful cells are, preferably, human cells. These cells can be obtained from e.g. biopsies or from biological samples. The tumor/cancer/tumor cell/cancer cell is a solid tumor/cancer/tumor cell/cancer cell. In accordance with the above, the cancer/tumor cell may be a breast cancer/tumor cell or said sample comprises a cancer/tumor cell, such as a breast cancer/tumor cell. In line with the above, said tumor/cancer may be a breast tumor/cancer.

The method for identifying a non-responder to a HER2-inhibitor provided herein may further comprise obtaining a sample of tissue from a patient with HER2-positive cancer prior to said step of identifying. The tissue may be cancerous tissue. The method may further comprise adjusting the treatment of the patient in response to the presence of said one or more mutations in exon 9.

The identification of non-responders allows for the treatment of patients that do not have the mutations in exon 9 of PIK3CA, as these patients respond well to treatment with HER2 inhibitor(s), such as Pertuzumab. Accordingly, the present invention relates in one embodiment to an inhibitor of HER2 for use in treating a patient with HER2-positive cancer, whereby the cancer has been found to be PIK3CA mutation-negative in Exon 9 of PIK3CA. Also the use of an inhibitor of HER2 for the preparation of a pharmaceutical composition for the treatment of a HER2-positive cancer patient is envisaged, whereby the cancer has been found to be PIK3CA mutation-negative.

Further, the present invention relates to the use of a HER2 inhibitor to treat a HER2-positive cancer patient by administering the HER2 dimerization inhibitor in an amount effective to treat the cancer, provided the cancer has been found to be PIK3CA mutation-negative. Accordingly, a method for the treatment of a HER2-positive cancer patient is provided which comprises administering the HER2 dimerization inhibitor in an amount effective to treat the cancer, provided the cancer has been found to be PIK3CA mutation-negative. The term “PIK3CA mutation-negative” as used herein means that the mutations are not present (absent). As mentioned above, the PIK3CA mutation comprises or consists of preferably one or more mutations in exon 9 of Phosphoatidylinositol-3 kinase (PIK3CA) as defined herein above. Preferably, the patient is a human.

In one embodiment of the present invention, the HER2 inhibitor is to be administered as a single anti-tumor agent. In a further embodiment, the inhibitor may be administered in form of a combination therapy, such as chemotherapy, an anti-hormonal therapy and/or another HER2 targeted agent/another HER2 targeted therapy in addition.

The chemotherapy may be docetaxel, anthracycline/taxane chemotherapy, therapy with an anti-metabolite agents, therapy with an anti-hormonal compound, therapy with an anti-estrogen, therapy with a tyrosine kinase inhibitor, therapy with a raf inhibitor, therapy with a ras inhibitor, therapy with a dual tyrosine kinase inhibitor, therapy with taxol, therapy with taxane, therapy with doxorubicin, therapy with adjuvant (anti-) hormone drugs and/or therapy with cisplatin and the like. In accordance with the present invention, the HER2 inhibitor may be administered by any one of a parenteral route, oral route, intravenous route, subcutaneous route, intranasal route or transdermal route. Further, the HER2 inhibitor may be employed in a neoadjuvant or adjuvant setting. Accordingly, said HER2 inhibitor may be administered to a patient in need of such a treatment and having the herein defined biomarker status before, during or after a surgical intervention/resection of the cancerous tissue. Therefore, the present invention is useful in neoadjuvant therapy, i.e. the treatment with the herein defined HER2 inhibitor (like Pertuzumab or Trastuzumab) given to the herein defined cancer patient group prior to surgery, as well as in adjuvant therapy. Again, the patient group of the present invention to be treated by the means and methods provided herein (in particular with Pertuzumab) are cancer patients without one or more mutations in exon 9 of PIK3CA. The attending physician may modify, change or amend the administration schemes for the HER2 inhibitor in accordance with his/her professional experience.

In one embodiment, the HER2 inhibitor is a HER dimerization/signaling inhibitor or an inhibitor of HER2 shedding. The HER dimerization inhibitor may be a HER2 dimerization inhibitor. HER dimerization inhibitor inhibits HER heterodimerization or HER homodimerization. The HER dimerization inhibitor may be an anti-HER antibody.

The term "antibody" herein is used in the broadest sense and specifically covers intact monoclonal antibodies, polyclonal antibodies, multispecific antibodies (e.g., bispecific antibodies) formed from at least two intact antibodies, and antibody fragments, so long as they exhibit the desired biological activity. Also human and humanized as well as CDR-grafted antibodies are comprised.

The HER antibody may bind to a HER receptor selected from the group consisting of EGFR, HER2 and HER3. Preferably, the antibody binds to HER2. In one embodiment, the anti HER2 antibody may bind to domain II of HER2 extracellular domain. In another embodiment, the antibody may bind to a junction between domains I, II and III of HER2 extracellular domain. Most preferably, the anti HER2 antibody is Pertuzumab.

For the purposes herein, "Pertuzumab" and "rhuMAb 2C4", which are used interchangeably, refer to an antibody comprising the variable light and variable heavy domains (amino acid sequences thereof shown in SEQ ID Nos. 5 and 6, respectively, as depicted in FIG. 2). The variable light and variable heavy domains of variant 574/Pertuzumab are also shown in FIG. 2 (amino acid sequences thereof shown in SEQ ID Nos. 7 and 8, respectively, as depicted in FIG. 2). Where Pertuzumab is an intact antibody, it preferably comprises an IgG1 antibody; in one embodiment comprising the light chain amino acid sequence in it preferably comprises the light chain and heavy chain amino acid sequences in SEQ ID Nos. 11 and 12, respectively, as shown in FIGS. 3A/3B and 5A/5B (FIG. 5A/5B show the light chain and heavy chain amino acid sequences of a variant Pertuzumab, SEQ ID NO:s 15 and 16, respectively). The heavy chain amino acid sequences of Pertuzumab as shown in SEQ ID NO: 12 (FIG. 3B) may optionally comprise an additional amino acid "K" at position 449 at the C-terminus. The antibody is optionally produced by recombinant Chinese Hamster Ovary (CHO) cells. The terms "Pertuzumab" and "rhuMAb 2C4" herein cover biosimilar versions of the drug with the United States Adopted Name (USAN) or International Nonproprietary Name (INN): Pertuzumab. Again, corresponding sequences are shown in FIGS. 2 to 5.

In a further embodiment, the inhibitor of HER shedding is a HER2 shedding inhibitor. The inhibitor of HER shedding may inhibit HER heterodimerization or HER homodimerization. Said inhibitor of HER shedding may be an anti-HER antibody. The anti-HER antibody may bind to a HER receptor selected from the group consisting of EGFR, HER2 and HER3. Preferably, the antibody binds to HER2. In one embodiment, the HER2 antibody binds to sub-domain IV of the HER2 extracellular domain. Preferably, the HER2 antibody is Herceptin™/Trastuzumab.

For the purposes herein, "Trastuzumab" and "rhuMAb4D5-8", which are used interchangeably, refer to an antibody comprising the variable light domains and variable heavy domains (amino acid sequences thereof are shown in FIG. 4 in SEQ ID NO: 13 and 14, respectively; the domain is indicated by arrows). Where Trastuzumab is an intact antibody, it preferably comprises an IgG1 antibody; in one embodiment comprising the light chain amino acid sequence of SEQ ID NO: 13 and the heavy chain amino acid sequence of SEQ ID NO: 14 as shown in FIG. 4. The antibody is optionally produced by Chinese Hamster Ovary (CHO) cells. The terms "Trastuzumab" and "rhuMAb4D5-8" herein cover biosimilar versions of the drug with the United States Adopted Name (USAN) or International Nonproprietary Name (INN): Trastuzumab.

The HER2 positive cancer to be treated may be breast cancer, such early stage breast cancer. The term "early-stage breast cancer" as used herein refers to breast cancer that has not spread beyond the breast or the axilliary lymph nodes. Such cancer is generally treated with neoadjuvant or adjuvant therapy. "Neoadjuvant therapy" refers to systemic therapy given prior to surgery. "Adjuvant therapy" refers to systemic therapy given after surgery. Also other HER2 positive cancer types like gastric cancer can be treated in accordance with the present invention. In one embodiment, the treatment is neoadjuvant or adjuvant therapy of the early-stage breast cancer.

The pharmaceutical composition to be employed in the medical uses of the present invention, will be formulated and dosed in a fashion consistent with good medical practice, taking into account the clinical condition of the individual patient, the site of delivery of the pharmaceutical composition, the method of administration, the scheduling of administration, and other factors known to practitioners. The "effective amount" of the pharmaceutical composition for purposes herein is thus determined by such considerations.

The skilled person knows that the effective amount of pharmaceutical composition administered to an individual will, inter alia, depend on the nature of the compound. For example, if said compound is a (poly)peptide or protein the total pharmaceutically effective amount of pharmaceutical composition administered parenterally per dose will be in the range of about 1 μg protein/kg/day to 10 mg protein/kg/day of patient body weight, although, as noted above, this will be subject to therapeutic discretion. More preferably, this dose is at least 0.01 mg protein/kg/day, and most preferably for humans between about 0.01 and 1 mg protein/kg/day.

The following administration may be employed in respect of Pertuzumab:

A dosing regimen of pertuzumab administered every 3 weeks to patients in Phase II studies (TOC2689g, BO16934) using a fixed 840 mg loading dose (equivalent to 12 mg/kg for a 70 kg patient) for treatment cycle 1 followed by a fixed 420 mg "maintenance" dose (equivalent to 6 mg/kg) for subsequent treatment cycles resulted in steady-state serum trough concentrations of approximately 60 μg/mL by the second treatment cycle. A dose based on body-surface area or weight was not superior to a fixed dose, supporting the continued use of a fixed dose of pertuzumab in female patients with locally advanced, inflammatory or early stage HER2-positive breast cancer, metastatic breast cancer and ovarian cancer.

If given continuously, the pharmaceutical composition is typically administered at a dose rate of about 1 μg/kg/hour to about 50 μg/kg/hour, either by 1-4 injections per day or by continuous subcutaneous infusions, for example, using a mini-pump. An intravenous bag solution may also be employed. The length of treatment needed to observe changes and the interval following treatment for responses to occur appears to vary depending on the desired effect. The particular amounts may be determined by conventional tests which are well known to the person skilled in the art. Pharmaceutical compositions of the invention may be administered orally, rectally, parenterally, intracisternally, intravaginally, intraperitoneally, topically (as by powders, ointments, drops or transdermal patch), bucally, or as an oral or nasal spray.

Pharmaceutical compositions of the invention may comprise a pharmaceutically acceptable carrier. By "pharmaceutically acceptable carrier" is meant a non-toxic solid, semisolid or liquid filler, diluent, encapsulating material or formulation auxiliary of any type. The term "parenteral" as used herein refers to modes of administration which include intravenous, intramuscular, intraperitoneal, intrasternal, subcutaneous and intraarticular injection and infusion.

The pharmaceutical composition is also suitably administered by sustained release systems. Suitable examples of sustained-release compositions include semi-permeable polymer matrices in the form of shaped articles, e.g., films, or microcapsules. Sustained-release matrices include polylactides (U.S. Pat. No. 3,773,919, EP 58,481), copolymers of L-glutamic acid and gamma-ethyl-L-glutamate (Sidman, U. et al., Biopolymers 22:547-556 (1983)), poly(2-hydroxyethyl methacrylate) (R. Langer et al., J. Biomed. Mater. Res. 15:167-277 (1981), and R. Langer, Chem. Tech. 12:98-105 (1982)), ethylene vinyl acetate (R. Langer et al., Id.) or poly-D-(−)-3-hydroxybutyric acid (EP 133,988). Sustained release pharmaceutical composition also include liposomally entrapped compound. Liposomes containing the pharmaceutical composition are prepared by methods known per se: DE 3,218,121; Epstein et al., Proc. Natl. Acad. Sci. (USA) 82:3688-3692 (1985); Hwang et al., Proc. Natl. Acad. Sci. (USA) 77:4030-4034 (1980); EP 52,322; EP 36,676; EP 88,046; EP 143,949; EP 142,641; Japanese Pat. Appl. 83-118008; U.S. Pat. Nos. 4,485,045 and 4,544,545; and EP 102,324. Ordinarily, the liposomes are of the small (about 200-800 Angstroms) unilamellar type in which the lipid content is greater than about 30 mol. percent cholesterol, the selected proportion being adjusted for the optimal therapy.

For parenteral administration, the pharmaceutical composition is formulated generally by mixing it at the desired degree of purity, in a unit dosage injectable form (solution, suspension, or emulsion), with a pharmaceutically acceptable carrier, i.e., one that is non-toxic to recipients at the dosages and concentrations employed and is compatible with other ingredients of the formulation.

Generally, the formulations are prepared by contacting the components of the pharmaceutical composition uniformly and intimately with liquid carriers or finely divided solid carriers or both. Then, if necessary, the product is shaped into the desired formulation. The carrier may be a parenteral carrier, such as a solution that is isotonic with the blood of the recipient. Examples of such carrier vehicles include water, saline, Ringer's solution, and dextrose solution. Non aqueous vehicles such as fixed oils and ethyl oleate are also useful herein, as well as liposomes. The carrier suitably contains minor amounts of additives such as substances that enhance isotonicity and chemical stability. Such materials are non-toxic to recipients at the dosages and concentrations employed, and include buffers such as phosphate, citrate, succinate, acetic acid, and other organic acids or their salts; antioxidants such as ascorbic acid; low molecular weight (less than about ten residues) (poly)peptides, e.g., polyarginine or tripeptides; proteins, such as serum albumin, gelatin, or immunoglobulins; hydrophilic polymers such as polyvinylpyrrolidone; amino acids, such as glycine, glutamic acid, aspartic acid, or arginine; monosaccharides, disaccharides, and other carbohydrates including cellulose or its derivatives, glucose, manose, or dextrins; chelating agents such as EDTA; sugar alcohols such as mannitol or sorbitol; counterions such as sodium; and/or nonionic surfactants such as polysorbates, poloxamers, or PEG.

The components of the pharmaceutical composition to be used for therapeutic administration must be sterile. Sterility is readily accomplished by filtration through sterile filtration membranes (e.g., 0.2 micron membranes). Therapeutic components of the pharmaceutical composition generally are placed into a container having a sterile access port, for example, an intravenous solution bag or vial having a stopper pierceable by a hypodermic injection needle.

The components of the pharmaceutical composition ordinarily will be stored in unit or multi-dose containers, for example, sealed ampoules or vials, as an aqueous solution or as a lyophilized formulation for reconstitution. As an example of a lyophilized formulation, 10-ml vials are filled with 5 ml of sterile-filtered 1% (w/v) aqueous solution, and the resulting mixture is lyophilized. The infusion solution is prepared by reconstituting the lyophilized compound(s) using bacteriostatic Water-for-Injection.

Another embodiment of the present invention relates to the use of a nucleic acid or antibody capable of detecting a mutation in exon 9 of PIK3CA for identifying a non-responder to a HER2-inhibitor in accordance with the herein provided methods. The oligonucleotide(s) may be about 15 to 100 nucleotides in length.

Accordingly, the present invention relates in one embodiment to a forward primer having the sequence 5'-UAAAAUUUAUUGAGAAUGUAUUUGCTTTTTC-3' (SEQ ID NO: 25). This forward primer can be used in amplification of exon 9 or a part thereof encoding the mutant triplet which encodes position 542 and/or 545 of the herein described mutant exon 9 of PIKC3A. In a further embodiment, the present invention relates to a reverse primer having the sequence 5'-TCCATTTTAGCACTTACCTGTGAC-3' (SEQ ID NO: 26). This reverse primer can also be used in amplification of exon 9 or a part thereof encoding the mutant triplet which encodes position 542 and/or 545 of the herein described mutant exon 9 of PIKC3A. The present invention provides a primer pair of the forward primer having the sequence 5'-UAAAAUUUAUUGAGAAUGUAUUUGCTTTTTC-3' (SEQ ID NO: 25) and the reverse primer having the sequence 5'-TCCATTTTAGCACTTACCTGTGAC-3' (SEQ ID NO: 26).

In a further embodiment, the present invention relates to probe(s)/probe sequence(s) for evaluating/determining the presence of one or more mutations in exon 9 of PIK3CA. In one embodiment, the present invention relates to a probe having the sequence 5'-FTTTCAQAGAGAGGAUEUEGUGUAGAAAUUGEP-3' ("542 WT Probe") (SEQ ID NO: 27). In one embodiment, the present invention relates to a probe having the sequence 5'-LATTTTQGAGAGAGGAUEUEGUGUAGAAAUUGEUUP-3' (542K Mutation Probe) (SEQ ID NO: 28). In one embodiment, the present invention relates to a probe having the sequence 5'-OCTGCTCAGTQAUUUIAGAGAGAGGATCTCGTGTP-3' (545 WT Probe) (SEQ ID NO: 29). In one embodiment, the present invention relates to a probe having the sequence 5'-JAATCACTAAGQAGGAGAAAGAUUUUEUAUGGAGUEP-3' (545K Mutation Probe) (SEQ ID NO: 30). In one embodiment, the present invention relates to a probe having the sequence 5'-FCTGCGCQGGAGAAAGAUUUUEUAUGGAGUEAP-3' (545A Mutation Probe) (SEQ ID NO: 31). In one embodiment, the present invention relates to a probe having the sequence 5'-LCCTGCCCQGTGAUUUIAGAGAGAGGATCTCGP-3' (545G Mutation Probe) (SEQ ID NO: 32). In this context, the following abbreviations used: F=FAM Reporter Dye, J=JA270 Reporter Dye, O=CY5.5 Reporter Dye, L=HEX Reporter Dye, U=5-propynyl dU, E=5-methyl dC, I=deoxyinosine, Z=7-deaza dG, Q=BHQ2 Quencher Dye, P=3' Phosphate A person skilled in the art is, based on his general knowledge and the teaching provided herein, in the position to identify and/or prepare further oligo-polynucleotide(s) for use in the present methods. In particular these oligo- or polynucleotides may be used as probe(s) in the detection methods described herein. A skilled person will know, for example, computer programs which may be useful for the identification of corresponding probes to be used herein. For example, the PIK3CA coding sequence (SEQ ID NO: 1) may be used in this context. Exemplary nucleic acid sequences are available on corresponding databases, such as the NCBI database available online at ncbi.nlm.nih.gov/sites/entrez The present invention also relates to a kit useful for carrying out the herein provided methods, the kit comprising a nucleic acid or an antibody capable of detecting a mutation in exon 9 of PIK3CA. Also envisaged herein is the use of the herein described kit for carrying out the herein provided methods.

For example, said kit may comprise (a) compound(s) required for specifically determining the one or more mutations in exon 9 of PIK3CA. Moreover, the present invention also relates to the use of (a) compound(s) required for specifically determining the presence of one or more mutations in exon 9 of PIK3CA for the preparation of a kit for carrying out the methods or uses of this invention.

On the basis of the teaching of this invention, the skilled person knows which compound(s) is (are) required for specifically determining the presence of one or more mutations in exon 9 of PIK3CA. Particularly, such compound(s) may be (a) (nucleotide) probe(s), (a) primer(s) (pair(s)), (an) antibody(ies) and/or (an) aptamer(s) specific to the mutation described herein. The kit (to be prepared in context) of this invention may be a diagnostic kit.

The kit (to be prepared in context) of this invention or the methods and uses of the invention may further comprise or be provided with (an) instruction manual(s). For example, said instruction manual(s) may guide the skilled person (how) to determine one or more mutations in exon 9 of PIK3CA i.e. (how) to diagnose non-responsiveness to a HER2 inhibitor. Particularly, said instruction manual(s) may comprise guidance to use or apply the herein provided methods or uses.

The kit (to be prepared in context) of this invention may further comprise substances/chemicals and/or equipment suitable/required for carrying out the methods and uses of this invention. For example, such substances/chemicals and/or equipment are solvents, diluents and/or buffers for stabilizing and/or storing (a) compound(s) required for specifically determining the presence of a mutation in exon 9 of PIK3CA.

The present invention relates to a method of detecting mutations in the human PI3KCA nucleic acid in a sample comprising:

(a) contacting the nucleic acid in the sample with at least one mutation-specific oligonucleotide from Table 2;

(b) incubating the sample under conditions allowing hybridization of the oligonucleotide to the target sequence within the PI3KCA nucleic acid;

(c) detecting the hybridization thereby detecting the presence of the mutation in the PI3KCA nucleic acid.

TABLE 2

Probe Sequences for the PIK3CA Mutation Detection Test

| Probe | Sequence 5' to 3' |
|---|---|
| 542 WT Probe | FTTTCAQAGAGAGGAUEUEGUGUAGAAA UUGEP (SEQ ID NO: 27) |
| 542 542K Mutation Probe | LATTTTQGAGAGAGGAUEUEGUGUAGAA AUUGEUUP (SEQ ID NO: 28) |
| 545 WT Probe | OCTGCTCAGTQAUUUIAGAGAGAGGATC TCGTGTP (SEQ ID NO: 29) |
| 545 545K Mutation Probe | JAATCACTAAGQAGGAGAAAGAUUUUEU AUGGAGUEP (SEQ ID NO: 30) |
| 545 545A Mutation Probe | FCTGCGCQGGAGAAAGAUUUUEUAUGGA GUEAP (SEQ ID NO: 31) |
| 545 545G Mutation Probe | LCCTGCCCQGTGAUUUIAGAGAGAGGAT CTCGP (SEQ ID NO: 32) |

Key:
F = FAM Reporter Dye,
J = JA270 Reporter Dye,
O = CY5.5 Reporter Dye,
L = HEX Reporter Dye,
U = 5-propynyl dU,
E = 5-methyl dC,,
I = deoxyinosine,
Z = 7-deaza dG,
Q = BHQ2 Quencher Dye,
P = 3' Phosphate The present invention relates to a method of detecting mutations in the human PI3KCA nucleic acid in a sample comprising:

(a) contacting the nucleic acid in the sample with one or more of the following mutation-specific oligonucleotides:

(542 542K Mutation Probe) (SEQ ID NO: 28)
LATTTTQGAGAGAGGAUEUEGUGUAGAAAUUGEUUP;

(545 545K Mutation Probe) (SEQ ID NO: 30)
JAATCACTAAGQAGGAGAAAGAUUUUEUAUGGAGUEP;

(545 545A Mutation Probe) (SEQ ID NO: 31)
FCTGCGCQGGAGAAAGAUUUUEUAUGGAGUEAP;
and/or (545 545G Mutation Probe) (SEQ ID NO: 32)
LCCTGCCCQGTGAUUUIAGAGAGAGGATCTCGP;

(b) incubating the sample under conditions allowing hybridization of the one or more oligonucleotide to the target sequence within the PI3KCA nucleic acid;

(c) detecting the hybridization thereby detecting the presence of the mutation in the PI3KCA nucleic acid.

The method may further comprise, prior to detection in step (c), contacting the nucleic acid in the sample with at least one oligonucleotide from Table 1 and generating an amplification product containing the target sequence within the PI3KCA nucleic acid.

TABLE 1

| Primer Sequences for the PIK3CA Mutation Detection Test | |
|---|---|
| Primer | Sequence 5' to 3' |
| 542/545 Forward primer PIK3CA-9F13 | UAAAAUUUAUUGAGAAUGUAUUUG CTTTTTC (SEQ ID NO: 25) |
| 542/545 Reverse primer PIK3CA-9R01 | TCCATTTTAGCACTTACCTGTGAC (SEQ ID NO: 26) |

Key:
U = 5-propynyl dU

The present invention relates to a method of detecting mutations in the human PI3KCA nucleic acid in a sample comprising:

(a) contacting the nucleic acid in the sample with at least one mutation-specific oligonucleotide from Table 2;

(b) (i) incubating the sample under conditions allowing hybridization of the oligonucleotide to the target sequence within the PI3KCA nucleic acid;

(ii) contacting the nucleic acid in the sample with at least one oligonucleotide from Table 1

(iii) generating an amplification product containing the target sequence within the PI3KCA nucleic acid;

(c) detecting the hybridization thereby detecting the presence of the mutation in the PI3KCA nucleic acid.

In accordance with the above, the present invention provides a method of detecting mutations in the human PI3KCA nucleic acid in a sample comprising:

(a) contacting the nucleic acid in the sample with one or more of the following mutation-specific oligonucleotides:

```
(542 542K Mutation Probe)
                                        (SEQ ID NO: 28)
LATTTTQGAGAGAGGAUEUEGUGUAGAAAUUGEUUP;

(545 545K Mutation Probe)
                                        (SEQ ID NO: 30)
JAATCACTAAGQAGGAGAAAGAUUUUEUAUGGAGUEP;

(545 545A Mutation Probe)
                                        (SEQ ID NO: 31)
FCTGCGCQGGAGAAAGAUUUUEUAUGGAGUEAP;
and/or

(545 545G Mutation Probe)
                                        (SEQ ID NO: 32)
LCCTGCCCQGTGAUUUIAGAGAGAGGATCTCGP;
```

(b) (i) incubating the sample under conditions allowing hybridization of the oligonucleotide to the target sequence within the PI3KCA nucleic acid;

(ii) contacting the nucleic acid in the sample with one or both of the following oligonucleotides:

```
(542/545 Forward primer PIK3CA-9F13)
                                        (SEQ ID NO: 25)
UAAAAUUUAUUGAGAAUGUAUUUGCTTTTTC
and/or

(542/545 Reverse primer PIK3CA-9R01)
                                        (SEQ ID NO: 26)
TCCATTTTAGCACTTACCTGTGAC;
```

(iii) generating an amplification product containing the target sequence within the PI3KCA nucleic acid;

(c) detecting the hybridization thereby detecting the presence of the mutation in the PI3KCA nucleic acid.

The present invention provides a method of determining whether a patient having a malignant tumor is likely to respond to a HER2-inhibitor, comprising:

(a) contacting the nucleic acid in the sample from the patient with the oligonucleotide from Table 2;

(b) incubating the sample under conditions allowing hybridization of the oligonucleotide to the target sequence within the PI3KCA nucleic acid;

(c) detecting the hybridization thereby detecting the presence of the mutation in the PI3KCA nucleic acid, wherein the presence of the mutation indicates that the patient is likely to respond to the HER2 inhibitor.

TABLE 2

| Probe Sequences for the PIK3CA Mutation Detection Test | |
|---|---|
| Probe | Sequence 5' to 3' |
| 542 WT Probe | FTTTCAQAGAGAGGAUEUEGUGUAGAAA UUGEP (SEQ ID NO: 27) |
| 542 542K Mutation Probe | LATTTTQGAGAGAGGAUEUEGUGUAGAA AUUGEUUP (SEQ ID NO: 28) |
| 545 WT Probe | OCTGCTCAGTQAUUUIAGAGAGAGGATC TCGTGTP (SEQ ID NO: 29) |
| 545 545K Mutation Probe | JAATCACTAAGQAGGAGAAAGAUUUUEU AUGGAGUEP (SEQ ID NO: 30) |
| 545 545A Mutation Probe | FCTGCGCQGGAGAAAGAUUUUEUAUGGA GUEAP (SEQ ID NO: 31) |
| 545 545G Mutation Probe | LCCTGCCCQGTGAUUUIAGAGAGAGGAT CTCGP (SEQ ID NO: 32) |

Key:
F = FAM Reporter Dye,
J = JA270 Reporter Dye,
O = CY5.5 Reporter Dye,
L = HEX Reporter Dye,
U = 5-propynyl dU,
E = 5-methyl dC,,
I = deoxyinosine,
Z = 7-deaza dG,
Q = BHQ2 Quencher Dye,
P = 3' Phosphate The method may further comprise, prior to detection in step (c), contacting the nucleic acid in the sample with at least one oligonucleotide from Table 1 and generating an amplification product containing the target sequence within the PI3KCA nucleic acid.

TABLE 1

| Primer Sequences for the PIK3CA Mutation Detection Test | |
|---|---|
| Primer | Sequence 5' to 3' |
| 542/545 Forward primer PIK3CA-9F13 | UAAAAUUUAUUGAGAAUGUAUUU GCTTTTTC (SEQ ID NO: 25) |
| 542/545 Reverse primer PIK3CA-9R01 | TCCATTTTAGCACTTACCTGTGAC (SEQ ID NO: 26) |

Key:
U = 5-propynyl dU

The present invention provides a method of determining whether a patient having a malignant tumor is less likely to respond to a HER2-inhibitor, comprising:

(a) contacting the nucleic acid in the sample from the patient with one or more of the following mutation-specific oligonucleotides:

```
(542 542K Mutation Probe)
                                    (SEQ ID NO: 28)
LATTTTQGAGAGAGGAUEUEGUGUAGAAAUUGEUUP;

(545 545K Mutation Probe)
                                    (SEQ ID NO: 30)
JAATCACTAAGQAGGAGAAAGAUUUUEUAUGGAGUEP;

(545 545A Mutation Probe)
                                    (SEQ ID NO: 31)
FCTGCGCQGGAGAAAGAUUUUEUAUGGAGUEAP;
and/or

(545 545G Mutation Probe)
                                    (SEQ ID NO: 32)
LCCTGCCCQGTGAUUUIAGAGAGAGGATCTCGP;
```

(b) incubating the sample under conditions allowing hybridization of the oligonucleotide to the target sequence within the PI3KCA nucleic acid;

(c) detecting the hybridization thereby detecting the presence of the mutation in the PI3KCA nucleic acid, wherein the presence of the mutation indicates that the patient is less likely to respond to the HER2 inhibitor.

The present invention relates to a method of determining whether a patient having a malignant tumor is less likely to respond to a HER2-inhibitor, comprising:

(a) contacting the nucleic acid in the sample from the patient with one or more of the following mutation-specific oligonucleotides:

```
(542 542K Mutation Probe)
                                    (SEQ ID NO: 28)
LATTTTQGAGAGAGGAUEUEGUGUAGAAAUUGEUUP;

(545 545K Mutation Probe)
                                    (SEQ ID NO: 30)
JAATCACTAAGQAGGAGAAAGAUUUUEUAUGGAGUEP;

(545 545A Mutation Probe)
                                    (SEQ ID NO: 31)
FCTGCGCQGGAGAAAGAUUUUEUAUGGAGUEAP;
and/or

(545 545G Mutation Probe)
                                    (SEQ ID NO: 32)
LCCTGCCCQGTGAUUUIAGAGAGAGGATCTCGP;
```

(b) (i) incubating the sample under conditions allowing hybridization of the oligonucleotide to the target sequence within the PI3KCA nucleic acid;

(ii) contacting the nucleic acid in the sample with one or both of the following oligonucleotides:

```
(542/545 Forward primer PIK3CA-9F13)
                                    (SEQ ID NO: 25)
UAAAAUUUAUUGAGAAUGUAUUUGCTTTTTC
and/or

(542/545 Reverse primer PIK3CA-9R01)
                                    (SEQ ID NO: 26)
TCCATTTTAGCACTTACCTGTGAC;
```

(iii) generating an amplification product containing the target sequence within the PI3KCA nucleic acid;

(c) detecting the hybridization thereby detecting the presence of the mutation in the PI3KCA nucleic acid, wherein the presence of the mutation indicates that the patient is less likely to respond to the HER2 inhibitor.

The present invention provides a method for identifying a non-responder to a HER2-inhibitor, said method comprising a) detecting the presence of one or more mutations in exon 9 of the catalytic subunit of Phosphoinositol-3 kinase (PIK3CA or p110α) nucleic acid in a sample from an individual, (b)) identifying the patient as less likely to respond to a HER2 inhibitor if the presence of one or more mutations in exon 9 of the catalytic subunit of Phosphoinositol-3 kinase (PIK3CA or p110α) nucleic acid is detected.

The present invention provides a method for identifying a non-responder to a HER2-inhibitor, said method comprising detecting the presence of one or more mutations in exon 9 of the catalytic subunit of Phosphoinositol-3 kinase (PIK3CA or p110α) nucleic acid by (a) contacting the nucleic acid in the sample from a patient with HER2-positive cancer with a oligonucleotide comprising a sequence from Table 2;

(b) incubating the sample under conditions allowing hybridization of the oligonucleotide to the target sequence within the PIK3CA nucleic acid;

(c) detecting hybridization (d) identifying the patient as less likely to respond to a HER2 inhibitor if the presence of one or more mutations in exon 9 of the catalytic subunit of Phosphoinositol-3 kinase (PIK3CA or p110α) nucleic acid is detected.

TABLE 2

Probe Sequences for the PIK3CA Mutation Detection Test

| Probe | Sequence 5' to 3' |
|---|---|
| 542 WT Probe | FTTTCAQAGAGAGGAUEUEGUGUAGAAAUUGEP (SEQ ID NO: 27) |
| 542 542K Mutation Probe | LATTTTQGAGAGAGGAUEUEGUGUAGAAAUUGEUUP (SEQ ID NO: 28) |
| 545 WT Probe | OCTGCTCAGTQAUUUIAGAGAGAGGATCTCGTGTP (SEQ ID NO: 29) |
| 545 545K Mutation Probe | JAATCACTAAGQAGGAGAAAGAUUUUEUAUGGAGUEP (SEQ ID NO: 30) |
| 545 545A Mutation Probe | FCTGCGCQGGAGAAAGAUUUUEUAUGGAGUEAP (SEQ ID NO: 31) |
| 545 545G Mutation Probe | LCCTGCCCQGTGAUUUIAGAGAGAGGATCTCGP (SEQ ID NO: 32) |

Key:
F = FAM Reporter Dye,
J = JA270 Reporter Dye,
O = CY5.5 Reporter Dye,
L = HEX Reporter Dye,
U = 5-propynyl dU,
E = 5-methyl dC,,
I = deoxyinosine,
Z = 7-deaza dG,
Q = BHQ2 Quencher Dye,
P = 3' Phosphate The term "non-responder" as used herein can refer to a "patient who is less likely to respond" "Less likely to respond" as used herein refers to a decreased likeliness that a pathological complete response (pcR) will occur in a patient treated with a HER2 inhibitor.

The present invention relates to a method for identifying a non-responder to a HER2-inhibitor, said method comprising detecting the presence of one or more mutations in exon 9 of the catalytic subunit of Phosphoinositol-3 kinase (PIK3CA or p110α) nucleic acid by (a) contacting the nucleic acid in the sample from a patient with HER2-positive cancer with one or more of the following mutation-specific oligonucleotides:

```
(542 542K Mutation Probe)
                                            (SEQ ID NO: 28)
LATTTTQGAGAGAGGAUEUEGUGUAGAAAUUGEUUP;

(545 545K Mutation Probe)
                                            (SEQ ID NO: 30)
JAATCACTAAGQAGGAGAAAGAUUUUEUAUGGAGUEP;

(545 545A Mutation Probe)
                                            (SEQ ID NO: 31)
FCTGCGCQGGAGAAAGAUUUUEUAUGGAGUEAP;
and/or

(545 545G Mutation Probe)
                                            (SEQ ID NO: 32)
LCCTGCCCQGTGAUUUIAGAGAGAGGATCTCGP;
```

(b) incubating the sample under conditions allowing hybridization of the oligonucleotide to the target sequence within the PIK3CA nucleic acid;

(c) detecting hybridization (d) identifying the patient as less likely to respond to a HER2 inhibitor if the presence of one or more mutations in exon 9 of the catalytic subunit of Phosphoinositol-3 kinase (PIK3CA or p110α) nucleic acid is detected.

The method can further comprise, prior to detection in step (c), contacting the nucleic acid in the sample with at least one oligonucleotide from Table 1 and generating an amplification product containing the target sequence within the PI3KCA nucleic acid.

TABLE 1

Primer Sequences for the PIK3CA Mutation Detection Test

| Primer | Sequence 5' to 3' |
|---|---|
| 542/545 Forward primer PIK3CA-9F13 | UAAAAUUUAUUGAGAAUGUAUUUGC TTTTTC (SEQ ID NO: 25) |
| 542/545 Reverse primer PIK3CA-9R01 | TCCATTTTAGCACTTACCTGTGAC (SEQ ID NO: 26) |

Key:
U = 5-propynyl dU

The present invention relates to a method for identifying a non-responder to a HER2-inhibitor, said method comprising detecting the presence of one or more mutations in exon 9 of the catalytic subunit of Phosphoinositol-3 kinase (PIK3CA or p110α) nucleic acid by (a) contacting the nucleic acid in the sample from a patient with HER2-positive cancer with one or more of the following mutation-specific oligonucleotides:

```
                                            (SEQ ID NO: 28)
LATTTTQGAGAGAGGAUEUEGUGUAGAAAUUGEUUP
(542 542K Mutation Probe);

                                            (SEQ ID NO: 30)
JAATCACTAAGQAGGAGAAAGAUUUUEUAUGGAGUEP
(545 545K Mutation Probe);

                                            (SEQ ID NO: 31)
FCTGCGCQGGAGAAAGAUUUUEUAUGGAGUEAP
(545 545A Mutation Probe);
and/or
```

-continued

```
                                            (SEQ ID NO: 32)
LCCTGCCCQGTGAUUUIAGAGAGAGGATCTCGP
(545 545G Mutation Probe);
```

(b) (i) incubating the sample under conditions allowing hybridization of the oligonucleotide to the target sequence within the PI3KCA nucleic acid;

(ii) contacting the nucleic acid in the sample with one or both of the following oligonucleotides:

```
                                            (SEQ ID NO: 25)
UAAAAUUUAUUGAGAAUGUAUUUGCTTTTTC
(542/545 Forward primer PIK3CA-9F13)
and/or

                                            (SEQ ID NO: 26)
TCCATTTTAGCACTTACCTGTGAC
(542/545 Reverse primer PIK3CA-9R01);
```

(iii) generating an amplification product containing the target sequence within the PI3KCA nucleic acid;

(c) detecting hybridization (d) identifying the patient as less likely to respond to a HER2 inhibitor if the presence of one or more mutations in exon 9 of the catalytic subunit of Phosphoinositol-3 kinase (PIK3CA or p110α) nucleic acid is detected.

The present invention is further illustrated by reference to the following non-limiting figures and examples.

BRIEF DESCRIPTION OF THE DRAWINGS

The Figures show:

FIG. 1 provides a schematic of the HER2 protein structure, and amino acid sequences for Domains (SEQ ID Nos. 1-4, respectively) of the extracellular domain thereof.

FIG. 2.

FIGS. 2A and 2B depict alignments of the amino acid sequences of the variable light ($V_L$) (FIG. 2A) and variable heavy ($V_H$) (FIG. 2B) domains of murine monoclonal antibody 2C4 (SEQ ID Nos. 5 and 6, respectively); $V_L$ and $V_H$ domains of variant 574/Pertuzumab (SEQ ID Nos. 7 and 8, respectively), and human $V_L$ and $V_H$ consensus frameworks (hum κ1, light kappa subgroup I; humIII, heavy subgroup III) (SEQ ID Nos. 9 and 10, respectively). Asterisks identify differences between variable domains of Pertuzumab and murine monoclonal antibody 2C4 or between variable domains of Pertuzumab and the human framework. Complementarity Determining Regions (CDRs) are in brackets.

FIG. 3.

FIGS. 3A and 3B show the amino acid sequences of Pertuzumab light chain (FIG. 3A; SEQ ID NO. 11) and heavy chain (FIG. 3B; SEQ ID No. 12). CDRs are shown in bold. Calculated molecular mass of the light chain and heavy chain are 23,526.22 Da and 49,216.56 Da (cysteines in reduced form). The carbohydrate moiety is attached to Asn 299 of the heavy chain.

FIG. 4.

FIGS. 4A and 4B show the amino acid sequences of Trastuzumab light chain (FIG. 4A; SEQ ID NO. 13) and heavy chain (FIG. 4B; SEQ ID NO. 14), respectively. Boundaries of the variable light and variable heavy domains are indicated by arrows.

FIG. 5.

FIGS. 5A and 5B depict a variant Pertuzumab light chain sequence (FIG. 5A; SEQ ID NO. 15) and a variant Pertuzumab heavy chain sequence (FIG. 5B; SEQ ID NO. 16), respectively.

FIG. 6.

FIG. 6 shows Results of PIK3CA mutational analyses. PIK3CA mutations were in general associated with decreased sensitivity to HER2-targeted therapy in NeoSphere (The NeoSphere study is described in detail e.g. in Lancet Oncol. 2012 January; 13(1):25-32. doi: 10.1016/S1470-2045(11) 70336-9. Epub 2011 Dec. 6). Analyses per Exon i.e. Exons 7, 9 and 20 was carried out to explore in more detail the impact of specific mutations. Exon 9 mutations: Out of 28 mutations detected across the 4 arms, 26 were found to be in the non-responder group. Exon 20 mutations had little impact on pCR. Too few exon 7 mutations to draw conclusions. TH=Patients treated with docetaxel (75→100 mg/m$^2$) and trastuzumab (8→6 mg/kg), THP=Patients treated with docetaxel (75→100 mg/m$^2$), trastuzumab (8→6 mg/kg) and pertuzumab (840→420 mg), HP=Patients treated with trastuzumab (8→6 mg/kg) and pertuzumab (840→420 mg), TP=Patients treated with docetaxel (75→4100 mg/m$^2$) and pertuzumab (840→420 mg).

FIG. 7.

FIG. 7 shows the PIK3CA nucleotide (SEQ ID NO:1) and the protein (SEQ ID NO:2) sequences aligned. Exon9 is annotated with ***. The wild-type triplets encoding positions E542 and E545 of the wild-type amino acid sequence are indicated in bold letters.

EXAMPLE

Figure 1:
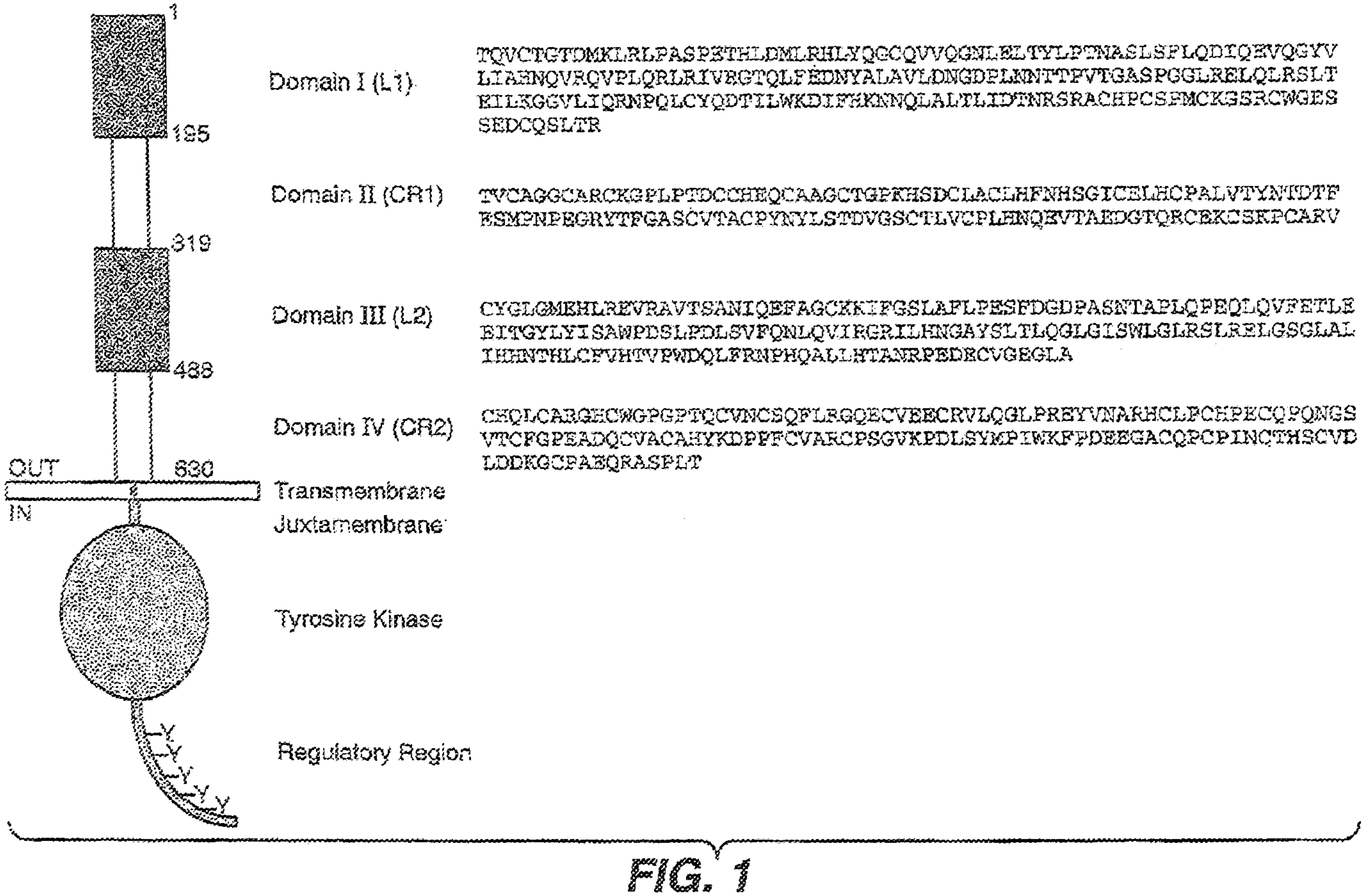
FIG. 1.

Identification of Non-Responders to HER2 Inhibitors by Determining the Presence of Mutations in Exon 9 of PIK3CA Each standard 50-μL amplification reaction targeting one of the Exons 7, 9 or 20 included 100 ng genomic DNA, dNTPs (including dUTP), 0.05 U/μL Z05, DNA polymerase, 0.04 U/μL uracil-DNA glycosylase (UNG), and 200-400 nM forward and reverse primer (Table 1), 75-200 nM mutant and wild-type specific probes (Table 2). Amplification was performed in the Cobas® 4800 analyzer using the following temperature profile: 5 min at 50° C. followed by 55 cycles of 95° C. for 10 sec and 63° C. for 50 sec, followed by a single round of 40° C. for 2 min and 25° C. for 10 sec (melting curve analysis). Fluorescence data was collected during each amplification cycle and during the final melting curve analysis.

TABLE A

Primer Sequences for the PIK3CA Mutation Detection Test

| Primer | Sequence 5' to 3' |
|---|---|
| Codon 420 Forward Primer PIK3CA-7F03 | UUUUGGGGAAGAAAAGUGUUUUGAA (SEQ ID NO: 33) |
| Codon 420 Reverse primer PIK3CA-7R04 | GATTCAAAGCCATTTTTCCAGATACTAGA (SEQ ID NO: 34) |
| Codon 542/545 Forward primer PIK3CA-9F13 | UAAAAUUUAUUGAGAAUGUAUUUGCTTTTTC (SEQ ID NO: 25) |
| Codon 542/545 Reverse primer PIK3CA-9R01 | TCCATTTTAGCACTTACCTGTGAC (SEQ ID NO: 26) |
| Codon 1047 Forward primer PIK3CA-20F01 | GAGGCTTTGGAGTATTTCATGAA (SEQ ID NO: 35) |
| Codon 1047 Reverse primer PIK3CA-20R01 | CCAATCCATTTTTGTTGTCCA (SEQ ID NO: 36) |

Key:
U = 5-propynyl dU

TABLE B

Probe Sequences for the PIK3CA Mutation Detection Test

| Probe | Sequence 5' to 3' |
|---|---|
| Codon 420 WT Probe | JCAATGGACAGQGUUEEUUAAAAAAAEAAAGAAAAAUAUUP (SEQ ID NO: 37) |
| Codon 420 420R Mutation Probe | OGAACACCQTCCAUUGGEAUGGGGAAAUAUAAAP (SEQ ID NO: 38) |
| Codon 542 WT Probe | FTTTCAQAGAGAGGAUEUEGUGUAGAAAUUGEP (SEQ ID NO: 27) |
| Codon 542 542K Mutation Probe | LATTTTQGAGAGAGGAUEUEGUGUAGAAAUUGEUUP (SEQ ID NO: 28) |
| Codon 545 WT Probe | OCTGCTCAGTQAUUUIAGAGAGAGGATCTCGTGTP (SEQ ID NO: 29) |
| Codon 545 545K Mutation Probe | JAATCACTAAGQAGGAGAAAGAUUUUEUAUGGAGUEP (SEQ ID NO: 30) |
| Codon 545 545A Mutation Probe | FCTGCGCQGGAGAAAGAUUUUEUAUGGAGUEAP (SEQ ID NO: 31) |
| Codon 545 545G Mutation Probe | LCCTGCCCQGTGAUUUIAGAGAGAGGATCTCGP (SEQ ID NO: 32) |
| Codon 1047 WT Probe | FTZCACATCQTZZTZZCTZZACAACAAP (SEQ ID NO: 39) |
| Codon 1047 1047R Mutation Probe | LGACGTQCAUEAUUEAUUUGUUUEAUGP (SEQ ID NO: 40) |
| Codon 1047 1047L Mutation Probe | JGCACTTCATGQTGGCTGGACAACAAAAAP (SEQ ID NO: 41) |
| Codon 1047 1047Y Mutation Probe | OACCATGATATQCAUEAUUEAUUUGUUUEP (SEQ ID NO: 42) |

Key:
F = FAM Reporter Dye,
J = JA270 Reporter Dye,
O = CY5.5 Reporter Dye,
L = HEX Reporter Dye,
U = 5-propynyl dU,
E = 5-methyl dC,,
I = deoxyinosine,
Z = 7-deaza dG,
Q = BHQ2 Quencher Dye,
P = 3' Phosphate FIG. 6 shows Results of PIK3CA mutational analyses. PIK3CA mutations were in general associated with decreased sensitivity to HER2-targeted therapy in NeoSphere. Analyses per exon i.e. exons 7, 9 and 20 was carried out to explore in more detail the impact of specific mutations. For exon 9 mutations, out of 28 mutations detected across the 4 arms, 26 were found to be in the non-responder group. Exon 20 mutations had little impact on pCR. There were too few exon 7 mutations to draw conclusions.

While the invention has been described in detail with reference to specific examples, it will be apparent to one skilled in the art that various modifications can be made within the scope of this invention. Thus the scope of the invention should not be limited by the examples described herein, but by the claims presented below.

The present invention refers to the following nucleotide and amino acid sequences:

The sequences provided herein are available in the NCBI database and can be retrieved from the website at ncbi.nlm-.nih.gov/sites/entrez?db=gene. These sequences also relate to annotated and modified sequences. The present invention also provides techniques and methods wherein homologous sequences, and, variants of the concise sequences provided herein are used. Preferably, such "variants" are genetic variants.

SEQ ID No. 1:

Nucleotide sequence encoding homo sapiens phosphoinositide-3-kinase, catalytic, alpha (PIK3CA), (NCBI accession number: NG_012113.1 GI:237858742).

SEQ ID No. 2:

Amino acid sequence of homo sapiens phosphatidylinositol-4,5-bisphosphate 3-kinase catalytic subunit. The sequence can be retrieved from the NCBI database under accession number NP_006209.2 GI:54792082 or from Uniprot database under accession number >sp|P42336|.

Positions 542 and 545 are indicated in bold letters.

SEQ ID No. 4:

Amino acid sequence encoded by exon 9 of homo sapiens phosphoinositide-3-kinase, catalytic, alpha (PIK3CA).

SEQ ID No. 5:

Amino acid sequence of the variable light ($V_L$) (FIG. 2A) domain of murine monoclonal antibody 2C4 (SEQ ID Nos. 5 and 6, respectively) as shown in FIG. 2.

SEQ ID No. 6:

Amino acid sequence of the variable heavy ($V_H$) (FIG. 2B) domain of murine monoclonal antibody 2C4 as shown in FIG. 2.

SEQ ID No. 7:

Amino acid sequence of the variable light ($V_L$) (FIG. 2A) domain of variant 574/Pertuzumab as shown in FIG. 2.

SEQ ID No. 8:

Amino acid sequence of the variable heavy ($V_H$) (FIG. 2B) domain of variant 574/Pertuzumab as shown in FIG. 2.

SEQ ID No. 9:

human $V_L$ consensus frameworks (hum κ1, light kappa subgroup I; humIII, heavy subgroup III) as shown in FIG. 2.

SEQ ID No. 10:

human $V_H$ consensus frameworks (hum id, light kappa subgroup I; humIII, heavy subgroup III) as shown in FIG. 2.

MPPRPSSGELWGIHLMPPRILVECLLPNGMIVTLECLREATLITIKHELFKEARKYPLHQ

LLQDESSYIFVSVTQEAEREEFFDETRRLCDLRLFQPFLKVIEPVGNREEKILNREIGFA

IGMPVCEFDMVKDPEVQDFRRNILNVCKEAVDLRDLNSPHSRAMYVYPPNVESSPELPKH

IYNKLDKGQIIVVIWVIVSPNNDKQKYTLKINHDCVPEQVIAEAIRKKTRSMLLSSEQLK

LCVLEYQGKYILKVCGCDEYFLEKYPLSQYKYIRSCIMLGRMPNLMLMAKESLYSQLPMD

CFTMPSYSRRISTATPYMNGETSTKSLWVINSALRIKILCATYVNVNIRDIDKIYVRTGI

YHGGEPLCDNVNTQRVPCSNPRWNEWLNYDIYIPDLPRAARLCLSICSVKGRKGAKEEHC

PLAWGNINLFDYTDTLVSGKMALNLWPVPHGLEDLLNPIGVTGSNPNKETPCLELEFDWF

SSVVKFPDMSVIEEHANWSVSREAGFSYSHAGLSNRLARDNELRENDKEQLKAISTRDPL

SEITEQEKDFLWSHRHYCVTIPEILPKLLLSVKWNSRDEVAQMYCLVKDWPPIKPEQAME

LLDCNYPDPMVRGFAVRCLEKYLTDDKLSQYLIQLVQVLKYEQYLDNLLVRFLLKKALTN

QRIGHFFFWHLKSEMHNKTVSQRFGLLLESYCRACGMYLKHLNRQVEAMEKLINLTDILK

QEKKDETQKVQMKFLVEQMRRPDFMDALQGFLSPLNPAHQLGNLRLEECRIMSSAKRPLW

LNWENPDIMSELLFQNNEIIFKNGDDLRQDMLTLQIIRIMENIWQNQGLDLRMLPYGCLS

IGDCVGLIEVVRNSHTIMQIQCKGGLKGALQFNSHTLHQWLKDKNKGEIYDAAIDLFTRS

CAGYCVATFILGIGDRHNSNIMVKDDGQLFHIDFGHFLDHKKKKFGYKRERVPFVLTQDF

LIVISKGAQECTKTREFERFQEMCYKAYLAIRQHANLFINLFSMMLGSGMPELQSFDDIA

YIRKTLALDKTEQEALEYFMKQMNDAHHGGWTTKMDWIFHTIKQHALN

SEQ ID No. 3:

Nucleotide sequence encoding exon 9 of homo sapiens phosphoinositide-3-kinase, catalytic, alpha (PIK3CA).

AGTAACAGACTAGCTAGAGACAATGAATTAAGGGAAAATGACAAAGAAC

AGCTCAAAGCAATTTCTACACGATCCTCTCTCTGAAATCACTGAGCAGG

AGAAAGATTTTCTATGGAGTCACAG

SEQ ID No. 11:

Amino acid sequences of Pertuzumab light chain as shown in FIG. 3A.

SEQ ID No. 12:

Amino acid sequences of Pertuzumab heavy chain as shown in FIG. 3B.

SEQ ID No. 13:

Amino acid sequence of Trastuzumab light chain domain as shown in FIG. 4A. Boundaries of the variable light domain are indicated by arrows.

SEQ ID No. 14:

Amino acid sequence of Trastuzumab heavy chain as shown in FIG. 4B. Boundaries of the variable heavy domain are indicated by arrows.

SEQ ID No. 15:

Amino acid sequence of variant Pertuzumab light chain sequence (FIG. 5A).

SEQ ID No. 16:

Amino acid sequence of variant Pertuzumab heavy chain sequence (FIG. 5B).

SEQ ID No. 17:

Nucleotide sequence encoding exon 9 of homo sapiens E542K mutant of phosphoinositide-3-kinase, catalytic, alpha (PIK3CA). The triplet (codon) encoding the mutant amino acid “K” at position 542 of the full-length amino acid sequence of PIKC3CA (see SEQ ID NO: 2 and FIG. 7) is highlighted in bold letters.

AGTAACAGACTAGCTAGAGACAATGAATTAAGGGAAAATGACAAA

GAACAGCTCAAAGCAATTTCTACACGAGATCCTCTCTCTAAAATCACTGAG

CAGGAGAAAGATTTTCTATGGAGTCACAG

SEQ ID No. 18:

Amino acid sequence of homo sapiens E542K mutant of phosphoinositide-3-kinase, catalytic, alpha (PIK3CA). Position 542 is highlighted in bold. The mutant shows an increase in lipid kinase activity; oncogenic in vivo; occurs in the interface between the PIK3CA helical domain and the nSH2 (N-terminal SH2) region of the p85 regulatory subunit and may reduce the inhibitory effect of p85; requires interaction with RAS to induce cellular transformation.

```
MPPRPSSGEL WGIHLMPPRI LVECLLPNGM IVTLECLREA TLITIKHELF KEARKYPLHQ
70         80         90         100        110        120

LLQDESSYIF VSVTQEAERE EFFDETRRLC DLRLFQPFLK VIEPVGNREE KILNREIGFA
130        140        150        160        170        180

IGMPVCEFDM VKDPEVQDFR RNILNVCKEA VDLRDLNSPH SRAMYVYPPN VESSPELPKH
190        200        210        220        230        240

IYNKLDKGQI IVVIWVIVSP NNDKQKYTLK INHDCVPEQV IAEAIRKKTR SMLLSSEQLK
250        260        270        280        290        300

LCVLEYQGKY ILKVCGCDEY FLEKYPLSQY KYIRSCIMLG RMPNLMLMAK ESLYSQLPMD
310        320        330        340        350        360

CFTMPSYSRR ISTATPYMNG ETSTKSLWVI NSALRIKILC ATYVNVNIRD IDKIYVRTGI
370        380        390        400        410        420

YHGGEPLCDN VNTQRVPCSN PRWNEWLNYD IYIPDLPRAA RLCLSICSVK GRKGAKEEHC
430        440        450        460        470        480

PLAWGNINLF DYTDTLVSGK MALNLWPVPH GLEDLLNPIG VTGSNPNKET PCLELEFDWF
490        500        510        520        530        540

SSVVKFPDMS VIEEHANWSV SREAGFSYSH AGLSNRLARD NELRENDKEQ LKAISTRDPL
550        560        570        580        590        600

SKITKQEKDF LWSHRHYCVT IPEILPKLLL SVKWNSRDEV AQMYCLVKDW PPIKPEQAME
610        620        630        640        650        660

LLDCNYPDPM VRGFAVRCLE KYLTDDKLSQ YLIQLVQVLK YEQYLDNLLV RFLLKKALTN
670        680        690        700        710        720

QRIGHFFEWH LKSEMHNKTV SQRFGLLLES YCRACGMYLK HLNRQVEAME KLINLTDILK
730        740        750        760        770        780

QEKKDETQKV QMKFLVEQMR RPDFMDALQG FLSPLNPAHQ LGNLRLEECR IMSSAKRPLW
790        800        810        820        830        840

LNWENPDIMS ELLFQNNEII FKNGDDLRQD MLTLQIIRIM ENIWQNQGLD LRMLPYGCLS
850        860        870        880        890        900

IGDCVGLIEV VRNSHTIMQI QCKGGLKGAL QFNSHTLHQW LKDKNKGEIY DAAIDLFTRS
910        920        930        940        950        960

CAGYCVATFI LGIGDRHNSN IMVKDDGQLF HIDFGHFLDH KKKKFGYKRE RVPFVLTQDF
970        980        990        1000       1010       1020

LIVISKGAQE CTKTREFERF QEMCYKAYLA IRQHANLFIN LFSMMLGSGM PELQSFDDIA
1030       1040       1050       1060

YIRKTLALDK TEQEALEYFM KQMNDAHHGG WTTKMDWIFH TIKQHALN
```

SEQ ID No.19:

Nucleotide sequence encoding exon 9 of homo sapiens E545K mutant of phosphoinositide-3-kinase, catalytic, alpha (PIK3CA). The triplet (codon) encoding the mutant amino acid "K" at position 545 of the full-length amino acid sequence of PIKC3CA (see SEQ ID NO: 2 and FIG. 7) is highlighted in bold letters.

AGTAACAGACTAGCTAGAGACAATGAATTAAGGGAAAATGACAAA

GAACAGCTCAAAGCAATTTCTACACGAGATCCTCTCTCTGAAATCACTAAG

CAGGAGAAAGATTTTCTATGGAGTCACAG

SEQ ID No. 20:

Amino acid sequence of homo sapiens E545K mutant of phosphoinositide-3-kinase, catalytic, alpha (PIK3CA). Position 545 is highlighted in bold. The mutant shows an increase in lipid kinase activity: oncogenic in vivo; occurs in the interface between the PIK3CA helical domain and the nSH2 (N-terminal SH2) region of the p85 regulatory subunit and may reduce the inhibitory effect of p85; requires interaction with RAS to induce cellular transformation; enhances invadopodia-mediated extracellular matrix degradation and invasion in breast cancer cells.

MPPRPSSGEL WGIHLMPPRI LVECLLPNGM IVTLECLREA TLITIKHELF KEARKYPLHQ
70 80 90 100 110 120

LLQDESSYIF VSVTQEAERE EFFDETRRLC DLRLFQPFLK VIEPVGNREE KILNREIGFA
130 140 150 160 170 180

IGMPVCEFDM VKDPEVQDFR RNILNVCKEA VDLRDLNSPH SRAMYVYPPN VESSPELPKH
190 200 210 220 230 240

IYNKLDKGQI IVVIWVIVSP NNDKQKYTLK INHDCVPEQV IAEAIRKKTR SMLLSSEQLK
250 260 270 280 290 300

LCVLEYQGKY ILKVCGCDEY FLEKYPLSQY KYIRSCIMLG RMPNLMLMAK ESLYSQLPMD
310 320 330 340 350 360

CFTMPSYSRR ISTATPYMNG ETSTKSLWVI NSALRIKILC ATYVNVNIRD IDKIYVRTGI
370 380 390 400 410 420

YHGGEPLCDN VNTQRVPCSN PRWNEWLNYD IYIPDLPRAA RLCLSICSVK GRKGAKEEHC
430 440 450 460 470 480

PLAWGNINLF DYTDTLVSGK MALNLWPVPH GLEDLLNPIG VTGSNPNKET PCLELEFDWF
490 500 510 520 530 540

SSVVKFPDMS VIEEHANWSV SREAGFSYSH AGLSNRLARD NELRENDKEQ LKAISTRDPL
550 560 570 580 590 600

SEITKQEKDF LWSHRHYCVT IPEILPKLLL SVKWNSRDEV AQMYCLVKDW PPIKPEQAME
610 620 630 640 650 660

LLDCNYPDPM VRGFAVRCLE KYLTDDKLSQ YLIQLVQVLK YEQYLDNLLV RFLLKKALTN
670 680 690 700 710 720

QRIGHFFFWH LKSEMHNKTV SQRFGLLLES YCRACGMYLK HLNRQVEAME KLINLTDILK
730 740 750 760 770 780

QEKKDETQKV QMKFLVEQMR RPDFMDALQG FLSPLNPAHQ LGNLRLEECR IMSSAKRPLW
790 800 810 820 830 840

LNWENPDIMS ELLFQNNEII FKNGDDLRQD MLTLQIIRIM ENIWQNQGLD LRMLPYGCLS
850 860 870 880 890 900

IGDCVGLIEV VRNSHTIMQI QCKGGLKGAL QFNSHTLHQW LKDKNKGEIY DAAIDLFTRS
910 920 930 940 950 960

CAGYCVATFI LGIGDRHNSN IMVKDDGQLF HIDFGHFLDH KKKKFGYKRE RVPFVLTQDF
970 980 990 1000 1010 1020

LIVISKGAQE CTKTREFERF QEMCYKAYLA IRQHANLFIN LFSMMLGSGM PELQSFDDIA
1030 1040 1050 1060

YIRKTLALDK TEQEALEYFM KQMNDAHHGG WTTKMDWIFH TIKQHALN

SEQ ID No.21:

Nucleotide sequence encoding exon 9 of homo sapiens E545A mutant of phosphoinositide-3-kinase, catalytic, alpha (PIK3CA). The triplet (codon) encoding the mutant amino acid "A" at position 545 of the full-length amino acid sequence of PIKC3CA (see SEQ ID NO: 2 and FIG. 7) is highlighted in bold letters.

AGTAACAGACTAGCTAGAGACAATGAATTAAGGGAAAATGACAAA

GAACAGCTCAAAGCAATTTCTACACGAGATCCTCTCTCTGAAATCACTGCG

CAGGAGAAAGATTTTCTATGGAGTCACAG

SEQ ID No. 22:

Amino acid sequence of homo sapiens E545A mutant of phosphoinositide-3-kinase, catalytic, alpha (PIK3CA). Position 545 is highlighted in bold.

MPPRPSSGEL WGIHLMPPRI LVECLLPNGM IVTLECLREA TLITIKHELF KEARKYPLHQ
70 80 90 100 110 120

LLQDESSYIF VSVTQEAERE EFFDETRRLC DLRLFQPFLK VIEPVGNREE KILNREIGFA
130 140 150 160 170 180

IGMPVCEFDM VKDPEVQDFR RNILNVCKEA VDLRDLNSPH SRAMYVYPPN VESSPELPKH
190 200 210 220 230 240

IYNKLDKGQI IVVIWVIVSP NNDKQKYTLK INHDCVPEQV IAEAIRKKTR SMLLSSEQLK
250 260 270 280 290 300

LCVLEYQGKY ILKVCGCDEY FLEKYPLSQY KYIRSCIMLG RMPNLMLMAK ESLYSQLPMD
310 320 330 340 350 360

CFTMPSYSRR ISTATPYMNG ETSTKSLWVI NSALRIKILC ATYVNVNIRD IDKIYVRTGI
370 380 390 400 410 420

YHGGEPLCDN VNIQRVPCSN PRWNEWLNYD IYIPDLPRAA RLCLSICSVK GRKGAKEEHC
430 440 450 460 470 480

PLAWGNINLF DYTDTLVSGK MALNLWPVPH GLEDLLNPIG VTGSNPNKET PCLELEFDWF
490 500 510 520 530 540

SSVVKFPDMS VIEEHANWSV SREAGFSYSH AGLSNRLARD NELRENDKEQ LKAISTRDPL
550 560 570 580 590 600

SEITAQEKDF LWSHRHYCVT IPEILPKLLL SVKWNSRDEV AQMYCLVKDW PPIKPEQAME
610 620 630 640 650 660

LLDCNYPDPM VRGFAVRCLE KYLTDDKLSQ YLIQLVQVLK YEQYLDNLLV RFLLKKALTN
670 680 690 700 710 720

QRIGHFFFWH LKSEMHNKTV SQRFGLLLES YCRACGMYLK HLNRQVEAME KLINLTDILK
730 740 750 760 770 780

QEKKDETQKV QMKFLVEQMR RPDFMDALQG FLSPLNPAHQ LGNLRLEECR IMSSAKRPLW
790 800 810 820 830 840

LNWENPDIMS ELLFQNNEII FKNGDDLRQD MLTLQIIRIM ENIWQNQGLD LRMLPYGCLS
850 860 870 880 890 900

IGDCVGLIEV VRNSHTIMQI QCKGGLKGAL QFNSHTLHQW LKDKNKGEIY DAAIDLFTRS
910 920 930 940 950 960

CAGYCVATFI LGIGDRHNSN IMVKDDGQLF HIDFGHFLDH KKKKFGYKRE RVPFVLTQDF
970 980 990 1000 1010 1020

LIVISKGAQE CTKTREFERF QEMCYKAYLA IRQHANLFIN LFSMMLGSGM PELQSFDDIA
1030 1040 1050 1060

YIRKTLALDK TEQEALEYFM KQMNDAHHGG WTTKMDWIFH TIKQHALN

SEQ ID No. 23:

Nucleotide sequence encoding exon 9 of homo sapiens E545G mutant of phosphoinositide-3-kinase, catalytic, alpha (PIK3CA). The triplet (codon) encoding the mutant amino acid "G" at position 545 of the full-length amino acid sequence of PIKC3CA (see SEQ ID NO: 2 and FIG. 7) is highlighted in bold letters.

AGTAACAGACTAGCTAGAGACAATGAATTAAGGGAAAATGACAAA

GAACAGCTCAAAGCAATTTCTACACGAGATCCTCTCTCTGAAATCACTGGG

CAGGAGAAAGATTTTCTATGGAGTCACAG

SEQ ID No. 24:

Amino acid sequence of homo sapiens E545G mutant of phosphoinositide-3-kinase, catalytic, alpha (PIK3CA). Position 545 is highlighted in bold.

MPPRPSSGEL WGIHLMPPRI LVECLLPNGM IVTLECLREA TLITIKHELF KEARKYPLHQ
70 80 90 100 110 120

-continued

```
LLQDESSYIF VSVTQEAERE EFFDETRRLC DLRLFQPFLK VIEPVGNREE KILNREIGFA
  130        140        150        160        170        180

IGMPVCEFDM VKDPEVQDFR RNILNVCKEA VDLRDLNSPH SRAMYVYPPN VESSPELPKH
  190        200        210        220        230        240

IYNKLDKGQI IVVIWVIVSP NNDKQKYTLK INHDCVPEQV IAEAIRKKTR SMLLSSEQLK
  250        260        270        280        290        300

LCVLEYQGKY ILKVCGCDEY FLEKYPLSQY KYIRSCIMLG RMPNLMLMAK ESLYSQLPMD
  310        320        330        340        350        360

CFTMPSYSRR ISTATPYMNG ETSTKSLWVI NSALRIKILC ATYVNVNIRD IDKIYVRTGI
  370        380        390        400        410        420

YHGGEPLCDN VNTQRVPCSN PRWNEWLNYD IYIPDLPRAA RLCLSICSVK GRKGAKEEHC
  430        440        450        460        470        480

PLAWGNINLF DYTDTLVSGK MALNLWPVPH GLEDLLNPIG VTGSNPNKET PCLELEFDWF
  490        500        510        520        530        540

SSVVKFPDMS VIEEHANWSV SREAGFSYSH AGLSNRLARD NELRENDKEQ LKAISTRDPL
  550        560        570        580        590        600

SEITGQEKDF LWSHRHYCVT IPEILPKLLL SVKWNSRDEV AQMYCLVKDW PPIKPEQAME
  610        620        630        640        650        660

LLDCNYPDPM VRGFAVRCLE KYLTDDKLSQ YLIQLVQVLK YEQYLDNLLV RFLLKKALTN
  670        680        690        700        710        720

QRIGHFFFWH LKSEMHNKTV SQRFGLLLES YCRACGMYLK HLNRQVEAME KLINLTDILK
  730        740        750        760        770        780

QEKKDETQKV QMKFLVEQMR RPDFMDALQG FLSPLNPAHQ LGNLRLEECR IMSSAKRPLW
  790        800        810        820        830        840

LNWENPDIMS ELLFQNNEII FKNGDDLRQD MLTLQIIRIM ENIWQNQGLD LRMLPYGCLS
  850        860        870        880        890        900

IGDCVGLIEV VRNSHTIMQI QCKGGLKGAL QFNSHTLHQW LKDKNKGEIY DAAIDLFTRS
  910        920        930        940        950        960

CAGYCVATFI LGIGDRHNSN IMVKDDGQLF HIDFGHFLDH KKKKFGYKRE RVPFVLTQDF
  970        980        990       1000       1010       1020

LIVISKGAQE CTKTREFERF QEMCYKAYLA IRQHANLFIN LFSMMLGSGM PELQSFDDIA
  1030       1040       1050       1060

YIRKTLALDK TEQEALEYFM KQMNDAHHGG WTTKMDWIFH TIKQHALN
```

All references cited herein are fully incorporated by reference. Having now fully described the invention, it will be understood by a person skilled in the art that the invention may be practiced within a wide and equivalent range of conditions, parameters and the like, without affecting the spirit or scope of the invention or any embodiment thereof.

The invention claimed is:

1. A method of detecting one or more mutations in exon 9 of the catalytic subunit of Phosphoinositol-3 kinase (PIK3CA or p110α) in a sample comprising nucleic acids, said method comprising (a) contacting the sample with primers comprising SEQ ID NOs:25 and 26;

(b) carrying out an amplification reaction to generate an amplification product comprising a PIK3CA target sequence comprising codons 542 and 545 of PIK3CA if PIK3CA nucleic acid is present in the sample;

(c) contacting the amplification product with at least one labeled oligonucleotide having a nucleotide sequence selected from the group consisting of:

SEQ ID NO: 28, wherein the oligonucleotide comprising SEQ ID NO:28 is modified to have a 5' HEX dye, a BHQ2 quencher between positions 5 and 6, 5-propynyl dU at positions 15, 17, 20, 22, 28, 29, 32, and 33, and 5-methyl dC at positions 16, 18, and 31;

SEQ ID NO: 30, wherein the oligonucleotide comprising SEQ ID NO:30 is modified to have a 5' JA270 dye, a BHQ2 quencher between positions 10 and 11, 5-propynyl dU at positions 21, 22, 23, 24, 26, 28, and 33, and 5-methyl dC at positions 25 and 34;

SEQ ID NO:31, wherein the oligonucleotide comprising SEQ ID NO:31 is modified to have a 5' FAM dye, a BHQ2 quencher between positions 6 and 7, 5-propynyl dU at positions 16, 17, 18, 19, 21, 23, and 28, and 5-methyl dC at positions 20 and 29; and SEQ ID NO: 32, wherein the oligonucleotide comprising SEQ ID NO:32 is modified to have a 5' HEX dye, a BHQ2 quencher between positions 7 and 8, and 5-propynyl dU at positions 12, 13, and 14, under conditions allowing hybridization of the at least one labeled oligonucleotide to the PIK3CA target sequence; and (d) detecting hybridization of the at least one labeled oligonucleotide to the PIK3CA target sequence, wherein said hybridization indicates that one or more mutations in exon 9 of the catalytic subunit of PIK3CA is present, and wherein the one or more mutations in exon 9 is E542K, E545K, E545A, or E545G.

2. The method of claim 1, wherein the sample is selected from the group consisting of breast tissue resection, breast tissue biopsy, metastatic lesion and circulating tumor cells.

3. The method of claim 1, wherein the sample is from a patient with HER-2 positive cancer.

4. The method of claim 3, wherein the cancer is breast cancer.

5. The method of claim 3, wherein the cancer is early-stage breast cancer.

6. The method of claim 1, wherein the amplification reaction is PCR.

7. The method of claim 1, wherein steps (b) and (c) are carried out simultaneously using real-time PCR.

8. The method of claim 1, wherein steps (b) and (c) are carried out sequentially.

9. The method of claim 1, wherein at least two of the labeled oligonucleotides are contacted with the amplification product.

10. The method of claim 1, wherein at least three of the labeled oligonucleotides are contacted with the amplification product.

* * * * *

SEQUENCE LISTING

```
<160> NUMBER OF SEQ ID NOS: 47

<210> SEQ ID NO 1
<211> LENGTH: 93190
<212> TYPE: DNA
<213> ORGANISM: Homo sapiens

<400> SEQUENCE: 1

tttcgccctg ttgcccaggt tggtctcaaa ctgctgggct caagtgatcc acccacctca      60

gcctcccaaa gtgctgggat tacaggcgtg agccaacaca cctggctgaa aatagtcttt     120

tacgaatttc aaagctttga tttctccata agtgcactcc tggtaacttg agaacattac     180

acatttgtct cctttctgtg gccagaattg ttttgtattt caagtatgga aaggagcttt     240

gccagaatcc tcccgtgcta agtgtaagta gagcagttag actttaacat ggttgtgtga     300

tagtaatgac attcatatct gactctaggc aaggcatggc tggaatgaaa aacattgact     360
```

-continued

```
gttaagtgtt ttaaggtgaa cttctcagat actagatctc ttagctcaca tagtggaatt    420
ttgaggaaag tacagggttt gctcttcatc tcctaagaaa tgcaatgatg attctttaaa    480
gtactgatgg gtcagggagg ggagaaaacc attaaccgag aattgtataa tcagctaaaa    540
tattttgcag aaatgaaggc aaaagtaaaa tattctcaaa tgaaggaaaa tgaagggaat    600
ttgtcacaag cagactttct ctaaaaagaa tgttaaaatt cttcaggata aagggaaatt    660
ataccagaag gaaaaatgga ttttcaggaa tgaagcaaaa cataaatgta aatggatacg    720
taaatataaa agattatttt tcctcttgag ttctatatga ctgttgaaag caaaaattat    780
aaaaacatct gatggggctt ccatatatat aaatgtaata catatgccaa ctaatgacat    840
aaaggtcagg gagtggggta ggagacagtg gtaaatctac acggttgcaa ggcttctttc    900
tacattttac ttgaagtggt gtaatagtaa tactaagtag accgcaaaac tttaggtatg    960
tatattataa tccatagaat taccaaaaaa ttaccaagaa atatattaaa actacaatat   1020
agaaattaaa atggaatatt aaaaattttt caaataatcc acaagaaagc aggaaagtag   1080
aaacataaaa acaaaagtat agaggaaaaa cagaaaacaa ataataaaat ggcaagccta   1140
aatccatata attacattaa atgtaaatta aacacagcaa ttaaaacaca gaaattgtca   1200
gattggaatt tttaaaaaga gatctaatac gtgttgtcta cgagtaactc actttaaata   1260
taaaaataga tataaaaaag atgggaaaaa ataccatgga aaaattaatc aaaaaaagct   1320
ggactggctg tattaatatc agacaaagta gatttcagaa caaagatatt actaggaata   1380
aagagagata gtacagattg attaaaaaga gtcaatgtat caaaacacaa gagttctaaa   1440
tgtgtataca tctaacaaca aagcttcaaa acacacaaag taaaaataca cagaagtgaa   1500
atgagaaata aagaaatcca caattatatt ttgaaacatc aatgctaaca aaatcatcaa   1560
cttggtaaga aactacattc tgcccaacaa tagcaaacaa aatattcttt cataagtgca   1620
catgggacat tcaccaagat attctggggc aacacaaatc ttaacttgaa aagaactgaa   1680
atcttaaaag tacgtgtgtg tatgtgtgtg tgggtgtatg gttttttttt ttttaagatg   1740
gagtctcggt caggcgtggt ggctcacacc tgtaatctca gcactttggg aggccaaggc   1800
gggcggatca tgaggtcagg agttcaagac cagcctgacc aatatggtga aaccccgtct   1860
ctactaaaaa tacaaaaatt agccgggcgt ggtggcacgt gcctgtagtc ccagctactc   1920
ggaaggctga ggcaggagaa tcacttgaac ctgggaggca gaggttgcag tgagccaaga   1980
tcgcgccact gcactccagc ctgggtgaca gagcgagact ccatctcaaa aaaaaaaaaa   2040
aaaaaaaaaa aacagtgcta catggtaact catatcgtta tctcttggtg tgtttttatt   2100
gtttgacttg gcaattttat acatctaaag tatactgcta cataatcaac ttgactctta   2160
tttacaaagg acttcaaagc ttagtagtga cttaagcgct attagagaat gtttcggtgc   2220
atatttgagt atcagttatg attttcaatg gaaataaacc caaaaggcaa gtaactgtca   2280
ttataattct gattattaga atagaacaat agctacatac tggacatttc acctcccgtc   2340
tttagaaccc ttaggatgca attatttaat tttgaagtat accatttttt gtttcattta   2400
cagcctgaga atcattattt ttttaaaacc ttctttcagc tcctaatcct tgagtgatga   2460
gtttggtcat atagatgctt atatcataca gatattttta tatcatatag atattttaaa   2520
cactgaataa cattgcaaaa acctttgaaa gcaagatgac acctaagacc aatggcttac   2580
atataaggca aacattatca accgtgaatt gaatagtaaa tgctactcct gtaccaatga   2640
atggtgtcat gcattcaagt accaggtatg gctttttctg ctatgacaca caacttctta   2700
ggggcagata atcacataac aaaaaacata ttatgtaatt agcattttct tattaaaaaa   2760
```

-continued

```
taaattttag gctgggcatg tcggctgaag tctgtaatcc caacactttg ggaggccgag   2820
gtagatgaat ctcttgagcc caggagttgg agaccagtct gggcaacgaa gcaagaccct   2880
gtctttacaa aaaataaaac atttttaaaa atcacaaata ggccaggtgc ggtggcttac   2940
gcctgtaatc ctagcactct gggaagtcga ggggggtgga tcacctgaag tcagaagttt   3000
gagaccagcc tgaccaacat ggtgaaaccc cgtctctact aagaaataca aaaattagct   3060
ggcatgttgg ctggtgcctg taatcccagc tactcgggag gctgaggcag aagaatcgct   3120
tgaacccggg aggcagaggc tgcagtgagc cgagactgca ccgctgaact ccagcctggg   3180
ctacagagtg agactctggc tcaaaaaaat aataataata aataaataat aaattttata   3240
aggaaaaata tccctagtat atttttcccc accaaggtct acctattaat atctcatata   3300
actctgtgct tgaaacacaa tttgggatat attgccttaa aatttacttt gactagcaat   3360
tcagtgttcc tttttaaaa aaatctgtac tctggagtaa cagtgttcta aaactgttga   3420
agaacattgg ttcgagaaaa acatttagaa acacaaaccc ctggaatgtg agatgaaaat   3480
ccgagctaaa gggagaaaaa ggacgaaaga aagaaaacac agaaaagaaa gaaatacagt   3540
caagtgaaac tacgaccaca aagaggaaca gatccatctc atttaccatt ggggtatgga   3600
cggacgtgcg gtgttcgaga agactgttat tggtcagagt tttgctctag aggacaagta   3660
ggactgtaac atctctagga tgggtcactt cccaagccct ctattactta aaaattcaag   3720
gaggaaccga tgctggagta cttgtatctc agacttctaa tcactgctcc tacgcttttc   3780
caatattaca acaaaagacc agtaggggga gaaaaacgca cagtaccgaa cccttatcag   3840
tagtaatctc aaaagtcaac agattgattt actctcaagc aaacagactt ctaaggtacg   3900
cagcaccaag acactacctt gaatcaaatc tatagcctat atgacatttc tgaagtctct   3960
gttggcatta cgcgaaaaat cccccacgtc ttctgaatag ttagaattga atcctacaag   4020
ctgcttcgaa tcagaattcg atttaaaaaa aaaaatgagg gcatagcaaa aggtctccac   4080
gaagtgagtc aaaggactgc agagggctgt gacagtgcat tccgccttcg ggatggtata   4140
caacttaaac catgtcggca gaagaacgca cagcaacgct ttgtaaaaag cattctttct   4200
attatagaat ccataaccac gctggttagc cactgacagc ggcggttagc caccgcacct   4260
cctctcaccc ccgaactaat ctcgtttcct ctatgggtgt aaaagtgaaa taacccactt   4320
gctcccaata ttcctttcta tatctctacc ccagctcgcc tgctgctcgt agaaacaaat   4380
atactacacg tacgctgtcc taggatgaca caacaccctc actactgcag aagacggatc   4440
attaaacaaa cgtcagaaga gcagccccaa ctgtacataa acttcgggcg gaaaagcaag   4500
acgcaggcgc agtagcacat attgttaccc tatttgccca ctccctgctc ctcctcgcct   4560
caatttcgct tccgcttctt tgcgcatctg cttccggggg attgtaggct ctgcccctcc   4620
tcagctctta ccctcttctg ccggaggagg gggggggccg agggggtggg gaagagttcg   4680
ttgtttgttt acacgatgtg agcggaaaaa gagaccaata aagtttattc tggaaacaaa   4740
aggaaaaaaa aacaggggcg acggagaaag gagtcggggg cgggggcgtg tggcgggggc   4800
tagcgaggag agggagcgag aagtagaaag cggcagttcc ggtgccgccg ctgcggccgc   4860
tgaggtgtcg ggctgctgct gccgcggccg ctgggactgg ggctggggcc gccggcgagg   4920
cagggctcgg gcccggccgg gcagctccgg agcggcgggg gagaggggcc gggaggcggg   4980
ggccgtgccg cccgctctcc tctccctcgg cgccgccgcc gccgcccgcg gggctgggac   5040
ccgatgcggt tagagccgcg gagcctggaa gagccccgag cgtgagtaga gcgcggactg   5100
```

-continued gccggtagcg ggtgcggtgg gaatggggac cgggtgggtg ccggagactc ccgggcgcgc 5160
ccgccgtgtt gggcggaggc tacgggctgg tcgtctccca gcgtcggccc gcggcggagt 5220
tcgcctgcga tcgccgcacc ctctccctcg cctgcctctg gcctctccta gctgcagagg 5280
cgagggctcg ccgctccctc tcctttctct ctggctgccg cctcgctctt cctttgcttc 5340
tactcccagt tttggggacg gggcggctgg aggttgagga agtgcgccca gggccgccgc 5400
cccggccgcg gtggctctgt ctcccgcgcc ctgcacgccc acccagcccg cgggtggagg 5460
ggctgccgcg aggactgcgg ctcaagggac gcgggcgcga aaccgcgagc ttttcttgag 5520
gggctgtcac gcccgaggac tccggccccg ccagcctggc ggccctgcgt ttgcctctta 5580
ctgggtttaa atcgcccggc aggggtatgg aaggaacacc gctcccctca cccccgccag 5640
ctcccctccc acccttcctt tcgaggttgt tttttccttt tagctgagac aaacgcttag 5700
atctttcatt catagacctg agacactgac tcatgtgact tgtctcttta ctaagtgtat 5760
tatgtgatgc ctgttccatg gctcttaagt ggctcggaaa ggtagggtag ggcccgggat 5820
tgggctatgt aaacaccaga cgttcagccg gcgtgttttt gacctcggct cgaggggttt 5880
attttaggat gctaaaggaa tagtgatggt ggccaaccgt gttaccagac ttgggaatcg 5940
aaagctattt ttttatgtca ataattgaga ctgtttacat ggttaaataa agggtagggt 6000
aaagggagcg caacaagagg gtctttctag aaaacagtct gcatattctt taatgaatta 6060
gagttgtgat ttcatcttgg tgaagcttcc tcattccagc actgcgcctt tgtgcacatg 6120
caggacctgg gttttcggaa cgatgttttg aatcatagtt tgtgtggccg gggagaaccc 6180
cttagaatac ttgggtaggt aaattccagg ttatctcagg ggattatttc tactgcgact 6240
tttgaaccac tgagggcaat attggtcata tgttatcctg cttagaaatt gaatttttct 6300
gagtatttgc ttacattgca ccgtacaaaa tttgtttatg tgctggattg cgtgttttaa 6360
gaaaacttct ggaaaatact caaaataccg tgttgctaag ttagtttgga taaatcaaaa 6420
cactttgctt tcaaagcaac tacagtctta acaatttaac gtgtctttgt attcaggttt 6480
taagtttttg gtgttttttt tttttccttt taactgaagc actgaggtcc gattgacagc 6540
atagatctcc atctaaacat cacatgttct ggaaattttt aattatcaga ttaactgttc 6600
tgcagtgtca tcagccaaaa ttatctgaag aggactgtgt gtgtttacgt gtgtgtgtgt 6660
gtgtgtgtgt gtgtgtgtgt tggtattttg cttaagtttt ttcatctcac attttgggac 6720
aaaataaaac ttcatagctt ttttcaaaag tttcttgtgc tttttcaaac tagagtactt 6780
tcctattaaa atcacaaaat agtttattta aaaatgatag catatcgtaa taatagcatc 6840
atgggggaaa taacaagaaa gtaaaggaat attaatattg catgattgtg cgtataaagt 6900
tttaaagaca ttcctgtcag ttttaaataa ttaaaaatga aacacctgta aatatagaag 6960
agtgttttta tttaaggtta aaaaaattta actaaattgg ttatagcatt aaagagatgt 7020
tactaaatac aaatattgta cttaaactga aaaatggctt catggaagtg taaattgtca 7080
tgggccttga tatatttaaa agggagacta aaagtgcagt ggttttgctt gctctgtgcg 7140
tggaacagcc tttctggtgg cagagcttcc ttcctgtcag gataaggtcc tctccatccc 7200
aaatcagtat ccccttaaaa aaccaaagaa aaaacccaaa cttataaata atgcacaaca 7260
taaagtagac tgtaataact ttttctctaa accagtttac tttgtgtgcc gcttcttata 7320
agtacccttt actgaataaa gagttttaaa cagttacgat taccatttaa agggcacttg 7380
ctctgttgat ctgtttattt gaagagaggt aacttaatcc catttgatct cttgagcagc 7440
tacagtagca ttaaaaggat cagttctcta ttttgttatt ttatatcttg aattccaaga 7500

-continued

```
taggggtgat tctttaaatg aagtgtttct taagcattat aaaatatttc atctccagtg   7560
aaagtattta caatcttaaa aattattcag ctttagaagt atatgtctta gaatatcatg   7620
gtttacattt tattagcaca gttatcaaat agtttttctt aagtattacc ttgagctata   7680
ttaacagtgc cgtagacaga gtggtattac tatccctaag aaatggtatt ctaatctgaa   7740
gtcagttggc aggtgacaga ctcattgaca aaaccaacat tttccgactc ctttcactgt   7800
atcatgctgc gtctaatctc cagcctgttt tttaatagaa ctgaagaaat tagggcccaa   7860
ggaggcttaa ttactgaaga tctccatttc ctatatttgc agtaatatct ttatttaatt   7920
tcctttacat catgaacagt ggttttcaat cctggctaca cattagaata atctagggag   7980
ctttttaaaa gtactctggt ctcatcccca gagatgctca tttaattggt ctgagatgga   8040
tcccagttat ctgtgttttg ttttgtttgt tttgaagttc accaggaaat gctaatagaa   8100
aaggatgtaa agccctggct gtcaaggacc tgtatatttg gtccttgctt ctttctctag   8160
gtttatttct cctccctact cctgcagctc ccttggtctt ttcatactct cctgtgcaaa   8220
tacagtttgt acttcctgag acatttgaac actccattct tctttaactg gttgactcct   8280
actcatcttt cacatcacct cctttgaaaa gtctagcttg agttaggtat ccctgcttcc   8340
tgttcccata gcatcgtgta ctcccactgt catagcatta acctcactgc attgtaattg   8400
cctatttctt tgtccatatc ctctaccagg ctgtaaattc catgaggata gggactccta   8460
tcttatatac tgtacagtag tattcttatt gccaagcaca gtagcctgta cattacagca   8520
cttgactaaa caaataaata tagtagagac agacttcttt aaaacatgta gtgattcata   8580
agcaccagtt tttattcttg ccaatttcat ttaatatttt tggtcactaa aaatgtacaa   8640
ccctgaaatt gccacacata cgaatttcat ttggggacag ttgagatgtt ataaattgta   8700
tagagtggca ttccacctca gacatataca cacacacgca aaaaatgaag attattatca   8760
tatatagtac tgcactggaa ataaggagac ttgaattctt acccctgttt caccacaaac   8820
atttgggcac gtctcaatct ctttgggtgt catgtataat acagagggat tgtacgaggt   8880
gctctacatg gttctcagtg atctagcctt aaaattctgt gagtatcaac agtattggct   8940
ttggaatttg aggcaccatg gttcaaaacc tagttcttaa acttactggc aggattactt   9000
tggacagatt ttcttatctg taatgggggt gattactatt caacagagtt gttgaattaa   9060
atgagataat gtagatccaa gagagttctt gccctggatc aggtgcttaa taaatgttca   9120
tttcctttct ccttaggaag tgttagatct catgagtgga cttatctgag ataacagaag   9180
gacacagttt atgtaataaa tcctattttc cactttgctg actgttagca ctgcaggtgt   9240
gattagggac caaaaaacac tgtgacattt ggtttcagtc tctcagaacc ccattccact   9300
gtcaaacacc caggtgttag tcaacctgct tgggaaataa ttatgcctgg aagtttcaac   9360
caagagagaa tagcaagtgc caaactattc acacatatat aataatatgc aggagggtac   9420
agtctaaact gatgaactta cactgtctcc aaagataagt aaaatcagac ttcatcattc   9480
taaaaaaagg aaacaaaatt aaggatgatt tataaaagaa aatccaaaga ttttggtgaa   9540
gtctctgttc accaaacctt aaaattcagg agccattatt tagtaatttt caggtgatat   9600
aagaaatata ggaaaaattg gtcttctggt caggactaat tccagaacat aggcacaaat   9660
aatgttttca atttcagatt agcggttaca gatatcagca gactgaagtt attgatacct   9720
ttctctactt gggaactgtg ttttaaaatt taatattgtg ttatatatat cacctttatt   9780
tatttggtaa tattgaaagt aaacttacac agaatgtaat acaggttgga catccctaat   9840
```

-continued

```
ctgaaaattt gaaattttat atgctccaaa atctgaaact tcttgagtgc caacatacgg   9900
ccataagtgg aaaattctac acctggcatg tttgctttct ggtggtcaaa ggtacacaaa   9960
ctttgtttca tgcatataat tatttaaaat actgtattaa attaccttca acctgtgtgt  10020
ataaggtgta tgtgaaacat aaatgaattt tatgtttaga cttgggtccc tagtatgtct  10080
cattatgtat atgcaaatat tccaaaatct gaaatctgaa atctccagtg ttttggataa  10140
gggatactca aaacattgct ctgcagaagt ttcttgttac cagtcttatt tttgtataaa  10200
tcaaatttgc ttgcctgagt tttcctttaa gtttatgtga aagtgaattt tataagtaac  10260
ttattcgaaa gaaatactgt aataaaaatt aaaaactgtg gatgggggaa actgaagtgt  10320
taggatataa aagataaata tgaggcaata tatagttaaa gtctgaggat tcagcttcaa  10380
ggctagagat ttccatcatt caaaaagatt attcagctat tggatatact aatattttat  10440
cactgtatac cttattcaca tttaattatt atgtgaatca gttgatcctg gttaaggact  10500
ttttaggtgt tctttctttc cctctctacc tatacagttt agggagtttt aagttaaaat  10560
attccaataa aaagtttgta agtttgtaat aaaagtggtg gcttagagct atctttttct  10620
tcaaatagtt cttaaagtga aactgtgtct aatacgtatt agagagctct ggtttagatg  10680
cctaaaacgg gtcctcctgg ccagcagacc cagtacctgt ccctggcctg ttaggaaccg  10740
ggctgcacag ctggaggtga gcagtggggc cagcattacc acatgtgctc tgcctgttgt  10800
cggagcagca gcggcactag attctcatag aaggaccaac cctattgtga actgcacatg  10860
caagggatct aggttgcctg ctcctaatga gaatctaatg cctgatgatc tgaggtggaa  10920
cagtttcatc cccaaaccat cgcccccaca cttccccaat ccatggaaaa attgtcttcc  10980
acgaaactgc tccctggtgc caaaaaagtt ggggaccact ggcctaaggg actaaattcc  11040
ccttcggact gctactttgt atatgtatat ggtgggggac agattgtaac acatttttgt  11100
gtctttttct atattgatac aataggaatt gtaatgtgtt gcttgctaag taacataatg  11160
agataattca aataatcaca agttgcataa aactaggaaa aaatgtgcac atactaatta  11220
ttattttaaa tttatattta acagaagcat aatattttat atttggcctg acaatgtact  11280
catttctcaa gcatcacttt ggtagttagc ttgataattt aaattgtact catttataag  11340
aggttgtgtt ttagcaactt ttgtacatta ttgcgattgt tacaaagggg tctttatgat  11400
ggctagcatt gccatttgaa ataaattagg gatttttaaa aatctataag aattcttaca  11460
gactatgctt gtcaggtaca cttcggattt taagtatttg tatagtaaag ccaaggaaat  11520
cagtgttgtg atgtgaagaa aaaaactgta tagggataga atcattttgc tctaatcata  11580
actctcctaa ctcaccagga gttagcaagg cttagtggac gaatatgtct tataagtaca  11640
acaaaaatat aaggcactat tatgaagagg attttaggca tatgtttttg aacaggagga  11700
gacaatgttg tgtttattgt atcctcagca catactgtag tgtccaaatg taggtgatca  11760
gtaagcactg atctttgtga catagaatca tatttagaaa taaaaatact ttcttatatt  11820
tctatcagga gccatacgct ttatctgaaa agcaggtaaa ttgctgtgtg ccagtcttat  11880
ttgatcattt attgagcaca gatttggccc tttgtattcg tgggttttgc ctccatgggt  11940
tccacttacc atggattgaa aatattagga aaaaaaagga tagttatttc tgtactatgc  12000
atatacagat tttttttggt cattattccc taaacaaaac agtagaacaa ctatttacat  12060
aacatttaca ttgtattaag tattaaaagt aatctagaga tgatttaaaa tatacaggag  12120
taggttatat gcatctgcta ccccatttta tataagggac ttgaacctct atggattctg  12180
gtatccacag gggtcctaga cccaatctcc aattttccat agataccaag ggataactgt  12240
```

-continued

```
atataagaaa cacttttgta taagttatta actagttgcc tatttctatt gatatttgga  12300
gacattttgg caaagattgt taggttacag agaggctgtg tgctgtggtg aaaaaaaatt  12360
cgatcacgaa tcagaaaaca cggtttttcc attcatctat taactagctg tttggcctaa  12420
gatcttggcc tttcagagct tgtttcttca cctgcaaaat ttctaataca actcccaaat  12480
gctgagattc ctagtatgtt aaagcctgtt tttttatttc agggaagagt aagtaaatca  12540
ctccctagag agaagacagt ctagctcagt ttgttgtatt ttcagaagct aagatcattt  12600
tgtctgcctg tttataaatt tgcacatatt ttaaaggtcc ttgtgtgaaa ttctgtggca  12660
gagaaaagct gccattggaa aagaatggag tggaaggatt ttcccccctt ttttgaaacc  12720
gttagtgact ttggagaata aattgctaca ggtgtggtca aaattttggt tactggcact  12780
gggagcaatt aaatgactgc cagacattga gagtaggtca tctactgcac accagttgcc  12840
agggttataa aggccagcag acttgtcaca gcacccttaa tagccactgg ccatcatcct  12900
tacttgttaa agacttctag gaaagtatat tccatatttc ccttggtaac tcatccctct  12960
aggtggtttt cagaaaatgt gttctaatct tagaaacata aatctgtagg catggtaagc  13020
ctctttttc taggtctatc ctcagttgtg cagataagta tgtggaaaga taacagaaat  13080
cattgtattt gatcagaaag cagtgatgtt tatgctattg atttattgtt tttttctgtt  13140
aatattcaaa ttaccttcaa cttttgaata ttttttaacc agcacactgc tcaggtaatg  13200
agatattatt tagagttatt ttgaggatgt actcattttt caacaagcta agcatatttc  13260
tgcagcttgt ttttctttga gagttcttgc ttttccaagt tctttttcct gatggactta  13320
tggcaggtct agacctgaaa gtactattgt atttcaaaac aactgactgc ctttagcccc  13380
acagtgactg aactgtattt ttttcttagg aggttaatgt ctttggcaag ctaaacatcc  13440
ttggaatttt ttgctaagtc agccactatt ttgtgaatat agatttatgg agtatatcat  13500
caaattcaaa gcagcattaa tgggaaaatt tgcggaaaaa atattgaaat tagacactac  13560
ttacaaactc caatctgaaa tgaaaccata catgacagca gggaaaggaa agaattacat  13620
tttggaaccc taacttttat gcatataaat atcaatgcat agtaatgtca ttttaaagtt  13680
atatgccttc tgaagctttt cttaaaatct aatggctact attatttgca gttgagacca  13740
tgataggcag catcttatgg tatttatgaa agtgatattt gtgttctttt ttctaactat  13800
ataccaattg taaaagttga acatgacttt ttcaaagcag tttctatact tgataataac  13860
agtggtagta aaactcagaa cagtttaaaa tattagtaat tttacagtgt agagactttt  13920
cttcactaga aatgaccagc tttcagattt cttagtgata ttatgagact ctagatttct  13980
tcaaaatcat tttgagtaaa tctaccagtg tataactgct aaagcacagt taaatgtatc  14040
atgctgtggt ctttttttgtt tgtttgtttg gtataaatat cagacatata tgtttgttta  14100
ctctaaaact aatttttttt accaatcaaa attgaggcac gtaatctgac aatgggacag  14160
gatatttgca gtcaggatag tcttagaaaa gccacaaaat atggtcgatg tacttagact  14220
tctttaattt tccttgcctt ttcctaaata tatctcataa tgattaagag catgttctct  14280
agagtcagac tatcgagatt actagttttg taactttggg aaagttattt aacctgctaa  14340
atattctccg ggtaatacgt atttcttcat ttgtaaatga ggggtaataa ctacctacat  14400
cacaatgttg taatgaggat taaataaata atacttgaaa gcatttagta aagtgtgttg  14460
tacatagtaa gcactcagta agtatctgtg aactccttga gagtaagaac catgttacat  14520
tcatccattt atttgggtgc tttaacatta tgaagtgaat tgaattctgt cccttccaag  14580
```

-continued

```
aatttaccag tggatccgat ttctggatag tgggcaataa ggttgccttc aaacaagttt  14640
agagtagttt tcagttcttt acaatactgc ttgcttttta ttcgttaaaa cttttaaaat  14700
ttcattctag ctctaggaat ctgaatgcta tttcatacct actcctaagg gaagttagca  14760
tatggatatt tagtttaata ggaatgagga attaatggac agaaggtatt aagtaagtga  14820
atgtacaatt ttcacatcta gtctgtgctt cctgtggatt gattttccct gtccattcct  14880
ggaatcttcg aattcccagc acttatctta atagcactct accattgaag cagttttgtt  14940
ttgtgctgtt agatacttcc tttccctgtc ttgtcttttt ttcatgcact aaagacaaga  15000
gttgtgtcgt attgtcacat agtccttata ttacagggct tttaaagaaa tctcacgtcc  15060
tgttttcaag ctgcttgtat cttgtttgtc cattctactt gctatgaagt ctttattgaa  15120
tataatatta aactcttttg catatcattg tttgttacct aggacactca atggacatgt  15180
gtaaacttta caagtcattt atgtaaaaat aaggaaagca accatgtgtt ttaattattt  15240
ccatcagttc aatctctaag tctttgcctt taattaccaa acagctatgt ggtgccactg  15300
atacgagttt ctgtggtatc ggctacctgg ttttagtact gttgttacta ctttatgtaa  15360
atgagactat tcactcatat ttaagtttgt ggaaaatgta tatatgttct tgcgttttag  15420
cagttttggc tagactgctc ttgatggtca tgcagggtaa cttacttttc taaagttgat  15480
gatttcatgg tctgtatttc tcatatacca ggataatagt aaaatctaca cactttaaaa  15540
aactacatat gttgttgtta acatatatgg aggtttcttc agaaattatc tgcgattttt  15600
gttgtaattg ttttcattgt tgtgtgcttt taaagaatga cttttattaa gcatgcttcc  15660
aagctttttt gtacatgaaa aactgcatat aattttgtct cttttagggg gtgatatgta  15720
caatgaaaaa ataacatgac attggattgc cctggggctg accaagagtt tgtttccata  15780
gtaagggatt atgactaatt taggcattga agttaagaat ttattactta tttttaaatg  15840
acatcacgaa gagttacagc tgaaacccat ggaagaagtt ttcttgattt ttctatatgt  15900
acacacaaat gtgtattttg aattcccata aacccaaact ttaatataaa cctgaggagg  15960
gggagcatta tggactttgt atatgctgcc tcccttaatc ctcacaataa cacttctgat  16020
acatgtgtaa tcacttcatt tccatgatta ggaaaatgaa gtcccacatc aaattaatac  16080
agtagaatct cacctcattt attttacatg aaatcaactg tacctactca gtcaaacata  16140
aaaacgtgac aaaaataata cagtcatgtg tagctttaca gtggcaatat gttgtgagaa  16200
atgcatcatt agatgatttc atcattgtgc agacaccaca gagtgtaccg acacaaactt  16260
agatggtata gcttactaaa cacctatgct atctggtaca gcctgttact cctgggctac  16320
aaacctgtac agtatattac tatactgaat accataggaa aatgtaacac agtggtattt  16380
gtatatataa atatatctaa acatagaaaa ggtacagtaa aatacggtgt aaaaaatttt  16440
aaaaatggta tgcatgtata aagccttacc gtaagtgaag cttgcaagac tagaagttac  16500
tctgggtgag ttggtgagtg agtggtgagt gaatgtgaag gcccacgaca ttactacaca  16560
ctaccgtaga cttgatgaac actgcaccct taggctacac tagattttt aaaaagtaaa  16620
gtaattgcgc tacaatgtta tgacagctat gatgtcacta aatgatgaga gtttgtcagc  16680
tccattaatc ttacgggatc actgttgtat atgtagtcca cagttgacca gaacattgtt  16740
atgtagcaca taactaatgt aaatattgca aatcacatct gactactgag cttttgcttc  16800
aaagtagaca cttaaagata agaatttgcc atcctttcag ttggtctcag tgcctaggtc  16860
taggtatgtt acattttgtt gtgttgagtg tgattctgtt attcagacat gtaatgttca  16920
tacaacatgg cctctaatac ccagcctgta gtgcccaacc aaagaaacag cagtttgatc  16980
```

```
cggtgctgga agagaaactg ctgtttgggc ttgctgagca attgtattgg tctccaatgt  17040
ggcctgcaga tatggcaaca agaaactgtc atgtattctc tttgatatac acacgtgtgc  17100
accccacatg taagccttca cccttcttaa ttctatgtat attttatata ttgtgtatat  17160
agttctattg ttttagattg ctatatgtgc attatatctt tgtacaacac acaattttgt  17220
acagtgtggt atacaaaaac cacatacatt atactttatg gatgacttga gatttttcaa  17280
gaaaaatgtc gattctgtac aatcatagac tctgtttgtt tgcacatact catttctaga  17340
acatggcacc ccagaaatac ctctttcagt tactagctac ttagtaccaa cttttcaggc  17400
tcacaaaaca gtagtttgtt caatgttaca tagtaggcaa attactatta tggttctgat  17460
ctagaattat aagcaaacgt gctgtttcat tgcatcagac cttcccttct tcctcggtgt  17520
aagagagatc aagtcttctt ggctcagtag caatgtcttc tgtccagcta gcaagaatgg  17580
cacaggaggc tcagggtaca cttctcatta caaggcctta agggaagtgc tgcttctcca  17640
cacagagcag ataggacaaa aattgggtgt ttgcacaaag ggagcaatga ttccataagg  17700
aggtgaaagt aacacataga tttgtcacct tatttacatt ttctatcttc ttgtctctag  17760
gcaaaggggg taacagaaac ctgcttagtg tttttataaa gtaaattctg cctagtatca  17820
ttgaatttcc tttagcacat ccatagacat acaacagaac agataggaga aagaaacata  17880
aataacagga agtgctgggc gtggtggctc acgcctgtaa ttccagcact ttgggaggcc  17940
gaggcgggca gatcacttga ggtcaggagt ttaagaccac cctggccaac atggcaaaac  18000
cccgtctcta ccaaaaatac aaaaaattag ctgggcgtgg tggcgcgtgc ctgtaatccc  18060
agctatcggg aggcttaggc agcagaatcg cttaaaccca ggagttggag gttgcggtga  18120
gctgagatca cgccactgca ctccagcctg ggtgacagaa tgagactctg tctcaaaaag  18180
tgataataat aaagagataa cagaaagtcc agtggtcaca ggaccagatg ttttgagatg  18240
cttgtaattc caaatgttcc atttccatac tgttctaata tgactcaagt aattcatctg  18300
gggaatgaaa cagattttc aaaagcgcct tcagaatttg ggctgagaaa atatcactat  18360
atgtatattt atattttttt aaaaagctga gtgattaaac attatttcct gtttattcaa  18420
tataccctat aattgacaat gtggtagacc ctgggtatat aatggtaaac aacacaaaca  18480
tactctgtga ttgtacggtc aacgttttcc ttgaaaaatc tctttaatta ctcataaagt  18540
acaatgtata tagtttttat atatcacctt gtacagaaat atacatttta tctctgtata  18600
aaacatacag aaatctgaaa catgatgaag ttatatatgc aatgtatgca atacatgtat  18660
ttaaaagtgt gaatttatgt gtatatatat atgtatcaaa gagaatacac atgcacagat  18720
gatagtttgt tgtggccata ttaagccatc tttgcatttt aaggataatt tctacttgta  18780
gaaattatct acaagtagat aaacacatta tctaaacaca tgttgtagag tcacactctg  18840
ccacacccat ctaatttttc atatttttgg tagagacagg gtttcgccat gttgcccagg  18900
ctggtcttga actcctgggc tcgagcagtc tgcctacctc agtctcccaa agtgttggga  18960
ttacatgcct aagttagact taatatcata cccggcctgg tatgatagga tttcattcct  19020
aggaaaacca agagtcaact gagaaattgt tagaatgaat aagaattcta gagtaaatag  19080
atgtaaggca aatatttaaa aatcaatagt tcttccttat gatagcagta attgtttaga  19140
aaacgggaaa aaaacccatt tagaatagta acagaaaata taaaattata aatgagccaa  19200
tgtgaagaaa cctaaaaatc tacttggatg ttggaggtta cagggaaagg aatatcatgt  19260
ttctgaatgg gaagtccagc aattacagat accagtttc ctcattaaat tacaggttta  19320
```

-continued

```
gcctaattct cttctttaaa aaaaaaaaag tgagaaatta gcaaggtaat ttttaatttt  19380
gtctgagaaa ctataaacag ataaaagtaa ggtatctttt gagtggaaaa tgaaggacag  19440
agcgctaacc ctgtagctta ttagctatca aaatatacaa tacaattaga gtaaatgaaa  19500
gagttgaata ctggcataca cattgatagt aaaattggta aaagggaata gagatcccag  19560
aaacactcta aatatgataa agaagtaatc agaaattagg agaaaaagga aaactaagat  19620
ttgtttttga gagtattaaa tacttaggaa aatagacttt tgaatcttta tttcatctta  19680
cataccaaaa taaagtctag gtaagttgaa gagttaattg gaaaagagta aacttatgcc  19740
tagtgtcatt ttaaaaagac atttatgtga atggggaaat actttccaaa gcttcaagaa  19800
ttgtaagtac tcaaaaggag gaacaatcat tcgttcgact ctcaaataag attggggcat  19860
ggcaatgtgc cccctctagt ccaagctact caggagactg aggcaggaag actgcttgac  19920
ccccggagtt taaatgcagc ctgctagcaa gactccctat ctttaaaaaa acaaaaaaag  19980
aaaaaaatct ctttctctca cctcctctcc ccccaacccc catacaagtg aacaaattaa  20040
aagatgtgca gaccaggatt agagttctgc aaaaattcaa tagatgtttg tctttaaatt  20100
tttactacaa atactttcaa aagcaccatg acccatatgg atgaatgagc aaagaatttg  20160
agaagttggg ctcatttact aaagaggaaa tgcaggtaca agcataaggg acatgttttt  20220
ccctgacagg taattgaaga agtgaaattt taatatgtag tgattttttt ttttttactt  20280
tttgagttag cagaagtatt tttctaatga tgtttttgct ggtgagggtg ccatgcaatg  20340
tgcttgtcca tttatttcca ttgacagtct gaattggttt aaccctttcg aaaagcacgt  20400
gaacaatttg catgccttta aaatcaacat acagtttgac ccaataattc tctttgcagc  20460
attagatata ataatttaca acagcttatg tatttaacaa ctaaactgtt taacatctcc  20520
cgtggaaata ggttgtcata gaaaatgttt atgaagagtt tacaataatt tgcggaaatg  20580
tttttgtagt gaaaaaagat acaaaattat gtatactata tgagtacaag tatacaaaac  20640
tatagaaaac aaagaaataa accaaaaata tccagacaaa actgtaagag aatacataaa  20700
agatgctaat atggtgtctt aggtacgttt tcttttggtt tcatcattca tctgtgcacc  20760
gctatatttc cgatacttac agagcacaat cccaggccca taatagacct ttcagtcagt  20820
gcttaagtga ataaatttct gtaataaaca tgggattcat ttacattgaa agaaatatga  20880
atacactttc catccaagtt aagaaaagga aaaatgtggg aagcactcta gaaaggaaac  20940
tgattaatac cttacaatta gattttgttt tcagaatgtt ttcacatctc tattttatgc  21000
gatccttttc tgttctaatt taataatatc attacttacc taagttagaa atttgtgcta  21060
accggctggg cgtggtgcct catgcctgta atcccagcac tttgggaggc caaggcgggt  21120
ggataacctg aggtcaggag ttcaagacca agcctgacca acatggcaaa accccgtctc  21180
tactaaaaaa tataaaatta gccaggcatg gtggcgcata cctgtaattc cagctactca  21240
gaaggctgag gcagaagaat cacttgaacc caggaggcgg aggtagcagt gagccaagat  21300
tgcgccattg tactccagcc tgggcaacaa gagtgaaact ctgtcttaaa aaaaaaaaga  21360
aaaagaaaaa agaaatttct gctaaccttg attctatccc ttttgacctg ccaaatccaa  21420
ctgattacca aatcttgggt attctttctt agaaatgtct ctggatttta gccccatctt  21480
ttctcataat cactgcctta gtttattcct ttctcatttc actttactgt ccctacctgt  21540
ccttctacct ttctactctc ctcttttact ttccacactg ctgtaaaaat tgtcaggtaa  21600
atagcagaat tttgtgtgtg tgctattata aataggctgt atggaagaga ctggggggag  21660
attaacactg ctttcacact gctattacaa taatcaccct aaaatacaaa attgatctgc  21720
```

ttaaagctta gtaattcctt atgacctata ttgatgcttc tcaaacttgg gttgtataag 21780
atcacccagg agacttgata atgtgcaaat tatccagacc ctagaaattc tggttgagtg 21840
gatccatagt actgggaacc tgaattttat ttttatttta attttttgaa acaagagtct 21900
cactgtgaca cccaggctgg agtgcagtgg ctgatcataa ctcactgcag ccttgaactc 21960
ctgggcttaa gtagtcctcc cacctccacc tcccaaagcc ttaagattgc aggcatgagc 22020
cactgtgttg agcctggaac ctgaatttta ataaggcttc cctctcatga tccttacgca 22080
tatgatccca ggacaagatg ttgaagaaca gaccttggga taacatgcag tctcattaat 22140
ttactgtaat tctcacaatt tggcatcagc cttcttttct gtgctcattt tctacatttt 22200
tttctcatgg acaccttaca gtctagtcac tctgaactgc tacatgctca cctaggttat 22260
tgtggacccc tgttcttgtg ctcatgctgt tctgtggttc acagcctttt ttgctatggc 22320
ttctcctact cagtaacatg ttgatcttgg tacactatct tcagcttata tgtaatctga 22380
gtaaagtatt cccagactca ctctcctaga caaagtctat ctctccctct tctgtatttc 22440
catagcctct attacaacac acatatacta aattacactt cttttcatac cttcctcact 22500
agaccatgaa cctcttgaag tcagggatgc catattttag atcttttatt taatcttaga 22560
gtaaaagcct ggcacaaaat aattgcatgc taaatatttg tcaaatcatt aacaatccaa 22620
taaagaaggc aaggagtaat tagtcccatt ttcagtgagg aaaatgatat cttgagaaat 22680
taagtatttg cttttaatta cccagcttgt aagcgtaggc tcaagactta cacataagaa 22740
atctggcttc ttttctggtt ttggtcttta cagaaaagat agagaataac tgtaaaatta 22800
ccccttccat ttttacccac acggctcaca tgttcattta aattaccccc tccattttct 22860
acccataaag ctcacatatt agtttatgtt ttatcatttt atgggtaaag gtgttttaat 22920
aaacttttac atcatattca cactttataa aaataaaata atgcctattc ctctagggta 22980
tgaacagatt gctggatatt aagccatttg tctctcactt tcacatctaa ccttctttac 23040
tctgctttgt aatgcttatt tatttctctt gcagaaagca tgttatagtg ccttatggga 23100
tgtctacaaa tatttgttta atcaaattga gctaatattt atgtaggaaa cattttattc 23160
tgcaacaatt aaggcaaaca gatatatgtg tgtaagtatt cacatgggtt tccactgtag 23220
ttttgaaagc tcagtttcca aagtttagat gtgtttagcc ttactgtaga cttcactctt 23280
aaggtgttga tggaaatcaa caaccagctg caaaattcag atccagtatg ccataggata 23340
catgtagcca cggtttaaac caaatgttag caatgaaata tttagtagca actgttcttt 23400
taaaagaaac attttagata attagagtcg tcttgtaata tcttataccc agctgtcagc 23460
tttttacttt ttctgccaat atttctggaa ctgaaaccaa gaaaatggaa attagggcac 23520
cacactttga aatgtattaa acacttgaaa aactgttata tcttatagga tttccaaaaa 23580
gagttcttca gtgcctcaga agatttttat aaaaagcaat tatctacaat aaccctcccc 23640
agtattaagc tgaaatatac acataccta gtaaataata ggagcatttg ggaagtggaa 23700
gaattgcctc ttaatagcta ctggacttga agattattaa atttgagcat tctaattcca 23760
tttttgaaag tttctgatat tgtttcttaa ttttgttacc atgtttaatc agtatctcac 23820
tagcctttca ttcatttctt tagcttctgt tactatcttt ctacttttaa gatactcata 23880
tcttcatttt ctgccacatc aactttcagt aatattcctg attcctcact atgttagaca 23940
gtgataatag tgtctcattc ttcctttcaa gtctttccca cccttctaca aaatgttata 24000
tataattact ttttaaattg tcaagtattg ataacatttg cattctgttc tataaccata 24060

-continued

```
tttaaatcct ctttcttttt aactatagat agattgtaat agttgaacct agtactattt  24120
acattaatat tatataaaaa tgtttcactt tacaaccaag tagagtgcta cagttggatt  24180
tctttctctg aatctgtgtc cagcatcatg aactacgcaa tgaatattct ttgcattcag  24240
atcatatggt ttatcttttc atatattcca catactgctc aaaattgtgc tcttttgctt  24300
catttttagc atgatgttat acatttttttg ttttcccta aagtttccaa ttacttttct  24360
tttttctatt gtgaaaacca taaaaacggt attcagcgtg ccattagtgc tgctggactc  24420
ctcagttctt catctgttgc ttcaaacctg ttgtattgtt tttcctgaat actttttact  24480
ctggaattca gatttcatct tcaagtttgg gcatattact ttctgtaatt aaagtttatc  24540
tcaggactgc tttttcttaa tgatttgttt acgttatttg accactggtt cagttccacc  24600
atttctagca tgtggtctct tcctctttct tgacctccac ctttggttgg ctagagtaat  24660
taatcaatta agtgccttag aattggttca ggggaagtaa aactttggaa aactaattgt  24720
ctgaaaagac ttttattttt tctttacaca tgatagtttg ctgagtatag aattcctggt  24780
caaattgttt tccagcattt taattactgc attgtttttt acttgttatt gatgagaata  24840
gcattgccag tcagataatt tttcttttgc agattacttg tttttccatc tctgaaagct  24900
tttaagcttt tatctctatc ttttattgtc tagtatagtt ctttacattt attctgccca  24960
ctggtccctt ttaatctaaa catgtaagtc tctccagctc ccagatgttt ttcttttata  25020
tctttaattt cctttcttcc atttttctct tacctcagaa cttgtgcaat aaggaagtat  25080
tcagttgttg aacctctttg atttattgta tatctttttc acccttgttt cattatgtct  25140
gtctttttgc tctatgttct agcaattttt taaattttgc aaatataggt gaaatgttat  25200
atccttatga ttttattttt atattgtgtt tgttattcta ttaagattca tttcaatata  25260
aggtataaat tggaaaccca ctcttttttc ccaaatgtct agccgtttcc aggtggtctc  25320
ttccctattg atttgaaatg ataccttttat catgtaacac attctgtgtc tattttttta  25380
atttctgggt tttttttcct tttgtctggc tctttatgag ccgtatctta ccattgtgat  25440
tattgtagtt tcataatttt tttttctaga gaagagaagg tttggttaaa cttttgagat  25500
gtttatttat tttcccacgt caacaatcat ggactatcat gttatgttta tgagtggctg  25560
agtcatatct cctgaggaaa acatagcacc attgagtgct acagcatcct atagagaact  25620
tcagtttttg gtcatactgt taagacctct tggtttcaca gccccacaag ccctctttga  25680
agtgacctat ccagtagggc tagacctttc tctccccctg ccttctcccc tcccctaatt  25740
tttctggtct cctgcaattt ttttttaaac attagaatca gcatgcttaa ttctacacac  25800
aaacacaaaa atcctattgg cattttattg ggattacatc atatgtgtag attatctaag  25860
gaagaattga cattttggga attggttgtc ttcctatccg agaatgtgga atgtttttcc  25920
atgtcttcaa tcttttgtgt tacttgggag catttttaaag ttttcttcgt ttattttaaa  25980
gcagttaaaa ttcatttttt ttcagttcac gtgactaatc aattctacca ggaccgtcta  26040
ttaaataatc tgtcctaatt aaggttctgg ggtttttccc tatacaaaat tgcagcaact  26100
attgtactta agtttgtttc tgaactcagt tctgttctct ggatctgcat gggccaatac  26160
tattctattt ttataactaa ggatttaata cctacttagg ctagcccctt ctcattactc  26220
ttctttcaaa cattcagtat attaaaagct gttataatac ttcttactct gttttagagg  26280
tggacataga cattacacac atacaaaaaa actgcaagcc aatctcactt aaagtattag  26340
ttatcttaaa taaaatatta gcagattcag tagtttgtta aaacacacac acataccata  26400
gccaaatggc atttattctg gaaatacaaa ggtcatttta atcttaggaa atctgtaaca  26460
```

-continued

```
gacattaatt ctctctcttt ccctgcctcc cttcctccct ccctcttcct ttctccagca  26520
cagacatgca catgcgcgtg cacacgcgcg cgcgcacaca cacacacaca cacacacgac  26580
cttagtaaaa tagggataga aagctattct ttgacgtact aagtaataga tataccaaac  26640
tagaagcttc agtcaggctt aataatgaaa gactcgcatt gtcattcata ttacgaataa  26700
ttcaagaaac aatcaatagc tatttttttg ccttgctttt gtaagggaaa aaagtaatat  26760
aaaggagaag acatattcgc aaattttaat ttcctgtatc agtttctcct gaccactcac  26820
tcacattctc cccaaagtga agccaatgtt ggtaacggag tgaattctag tgggggacat  26880
tggaggggat atagaaatac gtttgttcat atatgctttt taacacagat ttttaattgt  26940
attagtataa aagtgtgata aacatgcttt cattttaaat atcttctgaa cctataaatt  27000
atattcccct tttaaatttt tgtttaattt ttatcatcaa aataaatgta tcttccagta  27060
aggacagtgt gaggaggttg gatgatttcc ttcttcagaa aacaggcatc aaaatactgg  27120
agtaactgtg ttaatgtcag ccaaaataga ttgtaagaaa aggagtatta ttagagataa  27180
agaggaacat ttcaaaatta tgaagtgaca aatatggcag gaaaatataa aaattctaaa  27240
tgtatatgca cttaagagag gcacaaaatg catgaaacaa agattgatag aactgagaga  27300
tgaaataggc aattcaatat ttagaagagt tggagatttt aatactcttc tctcaacagt  27360
tgataggata agtaaacaga aaacaggata cagaagacag gaataaagca atcagccaac  27420
tcaatctaat tgacatctgc agaataccca acaacagtag aaaacacatt attctaaagt  27480
gcattggtaa cattagccag ggtgaatagt atactggccc acaaaaatga aatgttttaa  27540
taaatatgga agaattgaaa ttatatggta tgttttgcaa ctacaaagga attaaaaatc  27600
atggagagaa ataaggaaga aataagtaaa atccccaaat atgtgcaaat gaatactatt  27660
tctgagtaac ccatgggtga aaaaagaatt cactgggcaa aatagaaaat atttttaact  27720
gagtgaaaat gaacacaaaa tgtaagaaaa tatttggtat gtagctctca ggcagtgcta  27780
agaaagaaat gtttggcttt aaatgcttat gccagaaagg aagaaaggtt aaaaagtcaa  27840
ttatctaagc tactacctta agaagctaga aaagaaagag taaagtgtac caaagtaagt  27900
agaagaaagg gagtaataaa gatcagaaca gaaatcaagg aaatcaaaag ctggttcttt  27960
aaagagttca gtaaatcttt agctaaaatg aacaagaagg gatgtaaatt agaaatactg  28020
agaatgaaag aatgggtatt actacagata ctataaatac taaaaagata aaggaatatt  28080
atgaacaagt ttacaacaac caatttggca acttagatga aatgaacaaa ttctttgaaa  28140
gatactaatt accaaaactg actccaaaag aagtagaaaa tctaaataga cctatataga  28200
gtaaataaat tgaattagta gtttaaaact tccaataaag aaaatctggg ctttaatggc  28260
atagctagta attctgtcag acaccaaagg aagaaaaaaa tacaagtccc aaccacattt  28320
tcagaaaagc aggagggagg agagcatcac aattcatttt atgaggacag tattactaga  28380
taccaaagcc aacacaaagg catcccaaga aaagaaaact agcagccagt attcctcata  28440
aatgtagaca caaaaatcct tagcaaaata ttagcatgtt taattagcaa tattatattt  28500
aaaaggataa tactataatc atggtcaagt aggatttatc ccagcaatgc aaggctcact  28560
taacttagaa atatcaattc tgtgtaatat accatactaa taagatatat ttgaaaaaaa  28620
agtgatcatc tcaatagatg cagaaaagta tttgacaaaa ttcaatacaa attataataa  28680
aaactcttag caagctagga attgaaggca acttcctcaa cctgataaag aatgtctgtg  28740
aaaaaaaaaa tcatacttca tggtgaatga ttttatagtt ttccacttaa gatgaagaac  28800
```

-continued

```
aaggcaagga tgtttgctct tactgctttt attcagcatt atcctggagg tcctagctaa  28860
tgcagtaagg caagaaaaag aaatttaaag gatatttgga atggaaagga agaagtaaaa  28920
ccaaatagat ggcatttata cagaaagttc taaagaatct accaaaaaga aaaaaaaaaa  28980
atactagaac taacaagtga cttaggcaag gctgtagagt aaaagataac aaacaggaat  29040
taattatatt tctaaacact agcaatgaac catccaaaaa tgaaattaaa aaaccattta  29100
cagtagtatt gcatagctaa atacttagta ataagaatag atacacaaac ctgtacactg  29160
aacactacaa aatattgttg atggaagtta aagaagaact aagttaattg agaggtacac  29220
tatattcatg aattggtaca ctatgttcag tgcagtccca gtcaaaatct tgtcagattt  29280
tctcatagaa attgacaggc tggttttaaa atttatatgg aagtgcaaaa aacataacca  29340
cacataaaaa ctataaaatc tgaacactta caagtacctg atttgtactt gctataaagc  29400
tacaataatc aaaatagtac agtattagca taaggataga catatagatg gatgaaagag  29460
atttgaaaat ctagaaagag taattcttaa tatagtaata tttttcaatt aatttcttat  29520
tttggacaat tggtatatcc tatagatctt tttcccgtga tttaatgaaa tgtaacattt  29580
ataataattt tctttttatt gaacattttt gctttgtata ttatatgtta ccttatttgt  29640
taataaaaac acataaataa acttggttag gtattattta tgtggtaact gattttcaac  29700
aaaggtgcca aggtaattca atgggaaaag aatagtcttt tcaaaaaaaa gaaaggccgg  29760
gcgcggtagc tcacgcctgt aatcccagca ctttgggagg ctgaggcggg ttgatcacga  29820
ggtcaggaga tcgagaccat cctggctaac acacagtgaa accccgtctc tgctaaaaat  29880
acaaaaaaaa aaaaaaaaaa aaaaaactta gccaggtgtg gtggcgggcg cctgtagtcc  29940
cagctactcg ggaggctgag gcaggggaat ggcaggaatc cgggaggcgg agcttgcagt  30000
gagcctatat cgtgccactg cactccagcc tgggtgacag agggagactc catctcaaaa  30060
aaaaaagtgc tagaataaca aaaaatttat taaaaatgga ttgatggttc atagacctaa  30120
acttcagttc ttaccccagt aattacctac gtggtgtatt gacaacaaag gaagaaaact  30180
tgtagaggtg ggttttggca gtgttttttt gtttttgttt agaggtggag tttcactctt  30240
gttgcccagg ctagagtgca atggcacaat ctcggcacac tgcaacctcc gcctccctgg  30300
ttcaagtgat tcttctgcct cagcctccca agtagctggg attacaggcc cctgccacca  30360
cacctggcta attttttgta tttttagtag agacagggtt tcgctatatt ggccaggctg  30420
gtctcaaact cctgacctca ggtgatccac ccgcctcggc ctcccgaagt gctgggatta  30480
caggcgtgac ccattgcgcc cggcccggaa gtgttttaaa acttggttgt agtggtggtt  30540
tttacaacta tacattcacc aagactcatc aaactgaatt ttaatttata cctcaggtaa  30600
agctaaaata aagtaataca tgcatattat tttcaaatta caactgaaag gttaataaaa  30660
acatcaggcc gagcatggtg gctcatgcct gtaatcccag cactttggga ggctgaggtg  30720
ggcgggtcat gaggtcagga gttcgagacc agcctggcca acacagcgaa accctgtctc  30780
tactaaaaat acaaaaaaat tagctgggca tggtggcaag cacctgtaat cccagctctc  30840
gggaggctaa ggcaggagaa tagcttgaac ctgggaggcg gaggttgcag tgagccgaga  30900
ttgtgccact gcactctcta gcctgagcag cagagctaga ctccatctca gaaacaaaca  30960
aaacatcagt tcattactgt atctcacttc ccccccattc cctctcacaa ctttgtcttg  31020
tctcatgtca tgcttcagga aaccactttc aactatttaa gctactactt ctggtatttg  31080
ccaccttata ataatggggt atattgctct gtcttggtcc accaatattt gacattattc  31140
attagtttc tcttataatt ttaatgctca tatcttcctt tgccttatct catcatccta  31200
```

tatttaatca ttactggtta aatccacatt tagttatttc attattcaat gaccatatag 31260
taataaagca aatgctacat ggggttatat tttttctgtt acaactttct tgttgttttt 31320
taattaattg cttcatctca gaaatctgct tagttaccat tgtgtctgaa tttgtctttc 31380
catgggcttc aatccatctt tgcaataact ctcacatgtg ataattagtt tggttatttt 31440
cctataatat ccttcataga gccttcagta tttctgattt aatcttgatt gcttgctagg 31500
tctgtttcac agctgttatc tcaagactct tttttgtctt catcctggaa attccctaca 31560
cctgcttcct gtgttgaagc attgattcct cctatgcccc ataccttcat ggttgactac 31620
ctcattctat aggagcttat cctctcgtgg catcttgaag agagataact gggaggtaat 31680
ttttttgaga ttttacatac ctgaatatgt gttattctac tcctacaatt atgtgatatt 31740
ttaagtgagt gtagaatgct agattgaaaa tcatttttac ccagatattg ctctggtatc 31800
ttccagcttt caattttgct agagttctaa gtgccactct gtttcctgat tttttattta 31860
ttcttttttc tctctgtctg gaagtgatta atctcttctc ttcattttat ggtatggtac 31920
cttggtgtgc atcgtttatc tgttgtgctg tgtactccgt aagtccctgc tgcttgcaga 31980
cttacattct tctcggaagt atccttgcct tttttggtag ttccctctcc tttgttttca 32040
ttattctctc tggaactcct actagccaga tactacactt cctagattgt ttttctaaat 32100
ttttaccatt ccctcctctt actcatccct ttctttttat tctgccttct ggaaaattgc 32160
cttaacttta acttcaaaca tttgttgatt tttttttttt ttcagttctt attctctggt 32220
cttattggtt cctctgcata aggatgcagt cttttatctt tacagtttct ttgacatttt 32280
cctctgtccc atcattctct gtttctcacc acttctgttt cattttggtc tcaatcttta 32340
atattggaga cattcctcaa atgcatgaag atcctcagtg gtcatttata tttaaaagat 32400
gtgaaaagct gaccgaaagc tctgggtgtg aagtcagagc tcttgtctat tggtaaacta 32460
tgctgtagga aatcttcata tcacaatttt tctttaggtt agttttgttt tctctagttt 32520
tgaatccttt ccagaggaaa tctatagtct tctctgtggg ggctgcttat gttttagaga 32580
aatactgaag aaagggactt tgggtctctt tagagttgca cataatcttc tggttttagt 32640
catatctact tctgtatcta ttgaagtcca aagcatcttg agtttagttt ttccagaaat 32700
tatgccttct gatttctgca tgattgggaa gtcactgagt acaccaactg gagttggaga 32760
cctggaattc cagtagttcc aggaacctcc tagtcctgaa cttaatgggg tttcatgaga 32820
attgactggc ttctttaggc acttaaattt aacattcctc acctctggtg aggtttttgt 32880
ttgttgtttg tttttctcc ctgtctttgt atattatggt ttagggttac agttttccag 32940
cttcatcaaa aaaagagttt ttctcattct ccttgtttag aaatgattgg tgacacaaag 33000
gtctgtactc tgatatttta agatccgaag tgtattctac cccttttttta taaactattt 33060
tgcagctgtt ccttcacgac tttgctacat cttggagatc ttttcatgtc agtacctaca 33120
agtctatatc attgatatta tcagctatat agtactccat aaaatgcttt attataattt 33180
atgtaatcat cttcctattg atgaagattt tggtggtttc tagtttttgc tttcatgaat 33240
attgttgcaa tgaatattgt ttggcttact tttgggtgaa tttttacaaa gacatccata 33300
taataagttc ccagtagtgg ggttgcctaa tctaagaata agtgtattta aaatttgaat 33360
catattgtca gactgtctcc cagaaagttt acattcctac caacaatctg agagagctgt 33420
ctttgcagtt actaggtttc atcaaacttg tttttttcag tatggtaggt ttaaaaatgg 33480
ggatacattt ttgtttttat ttgcattttt aaatattttc ttaggttagt tggctactta 33540

-continued aatttctttt tctgaaaact ttgtatttat agccttttaa aattcttatt gacttgcctg 33600
aactatttgt aaattacaga aattagccct ttgtcgtatg tgttgcaggt gcttttccag 33660
tttgccagtg gtcattcatt ttggtttatg gtacttttga tagaccagaa tctttgactt 33720
ttatttagtg agatttatcc atctttttct gtgtggcatc ttggtattat agcattaata 33780
ttctcttttc tttttttttt ttttttttga gatggagtct cactctgtcg cccaggctgg 33840
cgtgcagtgg cctggtctcc actcactgca acctccgcct cctcgtttca agtgattctc 33900
ctgcctcagc ctcctgagta gctgggatta caggcatctg ccaccacacc cagctaattt 33960
ttgaattttt agtagagatg gggtttcatc atgttggtca ggctggtctc aaactcctga 34020
tctcaggtga tccgcccgcc ttggcctccc aaagtgctgg aattacaggc atgagccacc 34080
acgcccaggc tatagttttt ctttatctga acaataacta attataaagt atagtggaag 34140
agaaaaaccc attcagaaaa ttaacaaaaa gatcacttat ctagaaataa acttaaacca 34200
tagcagagct tacatgaaga aatcttttaa aactgagcaa ggatttgttg gacaggacac 34260
agcactaatc tcaaaagaaa atttgatgaa taggtcttat tcatagtttt tgctcatcaa 34320
aagacagcat taagaaaatg aatagacaag ccacagaatg agttaaaaaa acagaaattc 34380
ccagcattta caagggatta aagatgtgta tcagaatata taaagaacct ctgaaggcca 34440
ggtgtggtgg tttacacctt taatcccagt gctctgggag gccaaggtgg gaggatcatt 34500
taaagctagg agttcaagac cagcctggta acatagtgaa acaagattct gtctttacaa 34560
aaaaaaaaaa aaaaaagtgt ttgggttttt ttttgtgttt tttttttttt gaagttagct 34620
aggcatggag gcatgtgcct atagtcccag ctattcagga gcttgaggct gtagtaagct 34680
atgatcatgc cactgcactc cagcctgggt gaccaagtgc gaccttgtct ctaaagatca 34740
aaaaaaaaaa aaaaaaaact cagaaattaa catttaaaaa attatgaact acttaatata 34800
aaaatgggca aaagactcga gcagacattt cacagaagat atacaaatgg ccaataagca 34860
catgaaaaga tttccaccat cattattagt catcagtaaa tgcaaattaa aaccatgata 34920
agataccact acaaattcaa accatcatga gatacccact agaatagctg aaataaaagt 34980
gactgatact actgaatagt tatgatatag accaactgga attctaactt attgctggtg 35040
ggaatataag aactatttct tataaagtta aacataacat ttacctaatg tgtcaggagg 35100
ttcccagaat catccctagg ttccatggtt cgctaggaca actcacagga ctcagcatga 35160
tgtcgtactc atggctctat cacttactac aatgaaaaga cacaaagcac agtcagcaaa 35220
gggaaaaggt gaatggggca aaatccaggg gagaccaggt acaagcttcc aacaatcctc 35280
ttccgtagag tctcacaaga cacacttaat tcccccagca aagagctgtg acaatacttg 35340
tgaaatctaa ccagccaggg aagttcgcta cagattcagt gcccagggct tttaccgggg 35400
tctgatcata ccctctgctc agcgcacacc caaattccag actcccaaag gaaagcaggt 35460
attaagcata aaccatattg ttatcataaa tgctttagac acatggagcc agtcttatca 35520
gatgggaatc agggtaggaa tcctcctaaa atccaagatc caagttccca gacaccaagc 35580
cagccttgca aacaggcttt tttaaggata agcataagaa tattaactct tttctgcaag 35640
tttacaacct agcattttgc taagtataac aaaaattgat gtaggaattt tgatagccga 35700
tgctggaaac agcccacata ttcaacaact ggaaattgta taaacaagct gtagtatatt 35760
ttggaatact acttaaaaag aactaaccac taatacatta aaacattgat gaatcccaac 35820
ctgttgcact cttctcattc tgtacctgac agtatgttaa ccaaaagaag ccaaatacaa 35880
gagtatacac tgtgattcaa tttatgtaaa gttaagactc agcaaaacta atctataatt 35940
acagaaacca aaatgtgatt gcctgggggc agagagagaa attaattgga aaagagcatg 36000
acagaatgtt ctaggataat agaaatgtat attatatatc ttgttttgtg cagtggttac 36060
gtgggtgtaa gaagttgtca aaagtcatca aacttaatgc ttaagatgtg cagagttcgt 36120
tgtatgttaa ctatagttca atttgaaaaa ttaactactg agaaacattg aaatccaatg 36180
acattcctat ccaaatacat atttggatag gaaaaacatc ttgtaaagat gtcagttctc 36240
cctgttctca aaataacaag aagttttgcc ttgatttttg tttttgaatt tagcaaaata 36300
ttcaaaagtt catctggaat tatcagccaa gtttaataag actgtgaagg gactttacag 36360
aagctacttg ggctgaattt aaaggatgag tatgattaaa atggcaataa atgtgaatat 36420
gaggtaaaag attatggagc atatttacaa aggcaaaaaa ctgtaaaggg aaaagattga 36480
tctagtaaga ttagagcttg gagtgtggga aaaataagag aagagcacag ttgtaatgtt 36540
tgaggcttga gtcaaggctg tattgcatag ttactagaga tccacaatat tgtcttaatt 36600
gagtaatggt gtaattagat atatgttttt agatagccaa ttctagtgac actgtagata 36660
atgaagtggg tggggagaaa ttggatactt tgtgctttca gggcctcttg tcttagttca 36720
tactgtctac ttaacctgtt gcactcttct cattctgtac ctgtcagaaa tcaggcccac 36780
tttctcctaa aattaccacg ttctgccttg tagattgtta gataataagg tcttttcaac 36840
ctcatttata tacttcattt atatacttgt atgagtgttt ttctcctcct ttcctttcca 36900
tcacccatcc ctttgcttca gctgctagtg tcttaataga aggtaattgc ttaatgaatg 36960
cttgttgaat tagagacaga tcagtcctgc atatgagaac tcttttaggg tctaatagtg 37020
atagagaaga ttgaaaaaaa aaggtgatga atttgagggt aatttaaggg gtggaagtga 37080
tgtcatgcaa gagaggagtt gaaagcacca aatgttttaa ccttggagat tgagaaagtg 37140
gtgatgtcat gaagaatgta ttccacattt gaataatgag cagagtaaga ggtaccaaca 37200
aatgaaacaa ttaaaggagg ccataaaaac aacagagatc atttcaacat tctattgagg 37260
aaatttgggg ggacacactt taattaaata ataacatcag tatttcttta cctttgtaac 37320
ttttaattaa tgaagatgtt ttaagatgaa atataaaatg tgaacctgag aactgtttaa 37380
catttaacat tatggatata catatccatg tttagaatgt tctctgtgta ttaatgcatg 37440
attttgtcat aaataccccca ctaggaagag aaaggtcgga gagagtgtgt gtgtctctat 37500
gtgtgtgtat ttgtgtgttt tgtcctggca aaaagacaaa ctgagagaac agaagaacaa 37560
aagagcagta ctgaaaatag ctagattaaa ggttgttttt ctgtcaccac acaccagata 37620
tggagagtag taaaagcaga cagatggaca gttctgttag ttttggagtg tgtgaataga 37680
gaaaagaaac attctgttcc ttttattcag aaaaggaatt tctagactaa attactggta 37740
tcagcaataa gtttcatatt ctgaccaaag aaacattatt tttttttac cctagggata 37800
atgactcatg ctgttctcag aattttgctt ttgtggaaac taaagtgcag tcataaatac 37860
ggcactgtta tttagatctt agtgctaatg atactattgt gagtagacta gtgatgggta 37920
agaacactag tattataaac ccagttgtaa caaagaaacc aagcacatct taattagctg 37980
attctagatg ggaaagtaga ttttttaaac aaattaacta attgttttaa ttctgtgaat 38040
tatgcaatag aaataggacc cataatttta ttttttttaat acttcattat tttgaggggt 38100
ttatgtcaga agttaaattt ctaacttcca atattgacag tggagataat taaacatatt 38160
ttctctgcct tttttcctta tgttcctcaa aattagtata agtctactaa atcatagtca 38220
catacaccat aaagcaccta tcaaaagagt atcagctagg tgaagttcaa agattatatt 38280

-continued

```
ctagttttat tttaaccttt aaagtcttgt aatttaagaa atagaggttt gaatgtcttc  38340
tttatatacc atagtactag atgctctcac tctgaatttt taccatgtca ggatactcca  38400
tcacatattt atctctgtaa ttataattat tgggcacata cacaaaagag ttgtccttta  38460
cggtatctct gtccaaccta aaaactttcc catttctctt cactttaatc tcttcagtcg  38520
ttccctttcc tgaattacct ctttactccc tagtgacggc ttaaagtttt agatcttaaa  38580
gttccctttt tcaaactttc ttacgtcttc ctctgtgcct ttattttaat gtcagcagaa  38640
gttagctcat gaatcataac atgtgaagca gttgtttgga ataattgaca gcttttaatg  38700
acttatgtta aatagccagt ttaaaagttt ttgtcagttg ataagcttta taaagaagca  38760
ttttaatgta ttaaatcatt gtaagtaatt tattgtttaa ctgcatgcct tgggtggtta  38820
actaatgtca tacagagcat cagtgaataa gagtggcagt attggctggg tgctatgact  38880
catgcctcta atcccagcac tttgaaagtc agaggcagaa agatcaccag agcccaggag  38940
ttcaagatca gcctgggcaa catggcgaga ccccatctct gcattaaaaa aaatttagct  39000
gggcatggta gcacacacag gtagtcctag ttcctagcta ctcgtgaagc tgaggcagga  39060
gaattgcttg agcctggggt tggggctgta gtgagccgtg ttcgtagcac tgtactccag  39120
cctggataac tgagagagac cctgtctcaa aaaaaaaggg taatattcta ctcactgatc  39180
atgtatgttg ctgcttttac acagttatac ccatttcagt ttgtcattct cattgcttgc  39240
tttttaaggt atagtaatta taatttccaa gatacttggt acattgaact gtacataagt  39300
ataaataaat agtaaatgct tgaaagggaa aataaagacc acttactaat atttctctcc  39360
caccattgaa gtattttggc tgtattgtat tatcgaaaag atggattttt tagaaatctg  39420
tgcttacatg acttcacatt gttgttgctt tcattcatag aacttgtctt cacatcttag  39480
ctaggtgaca cttgtgctga aattaagcta ccctctctct gattgcactt ctgggagatc  39540
tgagtttctt tgcttgccaa agttattact tcaagctttc ctgttgtgaa atagcccttt  39600
tgccagagat caaatactga aggatgataa atcactatta gtcaataatt gcttgcaatg  39660
gacattttca ttattactaa cataatacta ggatattttg ttattgccag aaaatggggc  39720
agatggcaac caattacatc aggatataaa gttattgttt ggtctttatc atggaaaaag  39780
cattgttatt taaatcaaat ttttactgta tatcatgtct ttcatccaat gtcgtaacat  39840
cccagataga cttggggtgt attcacttaa aaaaatacaa tatcttacgt tcattagagt  39900
atagttggaa gaaaatgtat tatttttgca agaagctgtt tatggattta tctgattaat  39960
ttatgtagag ccaggaaaaa gttgttttga ccaataaatt tggcatttga aatgagcagg  40020
ttaagaatag acattaagtg atcaccttaa gtgcaataaa atttcagtgc actatacatt  40080
ctgtgcttta tatctatttg taagaatacc aataatatat caatatggta taagaggaaa  40140
gaataagaga ttactataat agctcctaag aaaggaaatc agtccaagga cataggctga  40200
ggttgtgatg tggacaaaaa gataatagca aggatagata aataactaga caaaaatgtc  40260
agggacctaa gtatttatat ggcaaacaag gatactcagt acatctagag ccagactttt  40320
tccagtgtct aatccttgtt gtatattaaa tactttggga actaaaatat gttttatgac  40380
actgtgttaa ctgatgcata attatgtaat ggaagccatt agggcctgtg tcttggcagg  40440
aattaaacta aaagcaaggt ccttctagta tttttggtag aagattattg gctagtgcct  40500
attttcacag cacatactac taaaattagg aggacgacag aagacgagca ttgcccctcc  40560
ctgtgcaaaa ttgatagaca cattcaagaa gtattccata tttttaagct aatcttttta  40620
tttgattcac ttaccagcag gctgttttcc tgctgcaaag caaattggtg gagtccattt  40680
```

acaccttctc cttagcctat aagtattggc agaatcacca ccacgatcac agcagcacag 40740
tccagacagt gtcatttgat tttgaaaata ttgtccttgc aacagccagc taggacaatg 40800
acatactaat atctgctttg cttattattt gtgcctggga gtatgtaatc atagtcaaca 40860
gacaccatag ctacagtttt atgacacttg gtctcaggaa atagagaact ctacagaaga 40920
cagtagacca tgatgaagct ttatcattag tccctggttc tctcccctcc agatcacttt 40980
ggccttctga cagacagtac agataaatct gttaagtttg gaatgttgaa ttggtcaaaa 41040
atgaaaataa tagtccaaag caaaaagacc ttctgtgaaa catatgtgga tgcaattagg 41100
tgaatatatt gtatctgctg gtgtccccaa agttgatagc tttatttatt ggaccagcct 41160
agactgaaaa tcttctgttt aggcattttg gtggggattt tttcccctct gtggataccg 41220
actgttatat ttaaggaaga tagaacaatt ggttctacca agaaacctgt agctaaccca 41280
agtttcactt tatgatggca gcactttaaa agtttggtat gaaagactca tctcttcttc 41340
attctcaaga caatagggct aatcagtgag atgcaggcaa gttttaattt atctaaatac 41400
taaagagtat cactagaagg gatagtactt gaatacaagt ccctatggtg actaaattat 41460
gtcctcaccc catgatataa ggaaataagc tagccgttga tttttgatga agaaagactg 41520
tgggaacagt gtgtagcaac tgttttccaa gaagttatcc actctcaccc atagtagtgg 41580
aaagacttga aagaaagttg ttgaggtgtt cagagccaca gaaaggccta ttaagtcatt 41640
gagctatact agaaagaaac ataaaaacaa aagagcagaa gccatttgat aaacttcagg 41700
ggggagaagt tctaatccct gatgacttac agaaacatct tgccttcagc ttcttacaga 41760
tctttaaaag aatcaggtca agtgatttga aagacatatt gctaatatta cctttttcta 41820
gattctgtag aaataaacca tttttcctct gctctcacac tacaataatc aacacagaag 41880
acttctgtaa ctgctggtcg ccaagaagta tatggggatt tctccccacc aacaatcagt 41940
cagttgattc tgccgcagat tcttcaatag acagcagttg agtatcctgt aattcaattc 42000
agttctgaca ctatctgcct agagatagca tcagatccca tagattgagg gctcagtcac 42060
aagactgcca tccatttcca atggcagtca taagcttcag gttgttttac ttgtgcttct 42120
gactgactgg ctataaatca gcgttcccat gaccccctcc ttgggtttga ttaatttgat 42180
agagcagctc atagaactca gggaaataca tttctcggtt tattataaag aatactacaa 42240
aggatataga tgaagaagat gcatagggca gggcttgtgg gaaggggtgt ggagcttctg 42300
tgccctctgt ggacacacca ccttccagga acctccactt gttcagctat ccagaaggtc 42360
ctcgaactca gtccttttg gatttttatg gaaacttcat taagtagcat gattgattaa 42420
ataattggcc attggtgatc agcttaacct tcagcccctc tctcctctga ggaggtgggt 42480
agggggtgga ggtaggggta ggactaaaag ccccagttct ttaatcttgc cttggttttt 42540
ctggtgacca gccctcatcc tgaagcaacc taggggctgc cagccaccag tcaactcatt 42600
agcatacaga aagaccctta ccactttgga gattccaagg aatttaggag ctgtgtgcca 42660
ggagagagga cagagactaa atatgtattt cacaatatca catagatgtt cttaatttaa 42720
ttaagatgtt aatctagata ttcttaaact cttaatgaac tcaacaagct gagccctgga 42780
taatgtaccc ttttgtttct ttctttagct cacaagaagc caggaaacaa ctattttata 42840
agtcagccaa gtccagaatg gtgttagctt cattatggca agaaagagtg aagttacttt 42900
tcgtgaagcc ctgggctttt tgaagaaaaa gagaggagag gtggttttaa cattgacttt 42960
aagttgaaaa gtagagccct tttatacttt tttctttaat aaatccatca atcaagaatg 43020

-continued

```
gaacaatgtg tggttagcat catctttgaa gttccaagtc acaaagggat tttcttcctg  43080
aagtatgtgg gatgtgagtc atttgtaaat gggaattacg aaggacaatg agccctattt  43140
tttttggtta tcatcaatat aggtttggtt ataaacttgt tgtaaagagt taaaccatca  43200
ggaccttttc tcttagagtt ccacaggagc tgaaatgttt gcttagtagg aaatcgcagt  43260
aacatttcaa gaacccttcc gtattttgca tttcctttat attagaccat gattccttgc  43320
taagttggtc tcttcattga tctcattggt taaattttca ttgaggcaac caggtgcata  43380
gacttctatt ttcactgtct tcagtatata cagttggtcc tgaaatggat atacagctgg  43440
caaacttaaa taccttagga ttgtttctct ctttatgcaa aagatgctat tttttagtca  43500
ttttataagg gaagtgtttt ttttttccta atttaaaaaa ttaccctcta tatgataacc  43560
aaatttcctt taagtgttgc ttcagtgaac caaatagtgt tttactaagt gtaggagttc  43620
tagctagata atatctacca tctctttaca acaagcctga aacagtaagt tctgtttccc  43680
tttctggaca catgcattta gataacattg atccagtaga taagagaaag ggaggccggg  43740
tgcggtggct cacacctgta atcccagcac tttgggaggc cgaggtgggc ggatcacgag  43800
gtcaggagat cgagaccatc ctggctaaca cggtgaaacc ccgtctctac taaaaataca  43860
aaaaaattag ctgggcgtgg tggcgggcgc ctgtagtccc agctactcag gaggctgagg  43920
caggagaatt gcttgaaccc gggaggtgga ggttgcagtg agccgagatc gcgccactgc  43980
actccagcct gggcaacaga gcaagactcc gcctcaaaaa aaaaaaaaaa aaaaagagag  44040
aaacggatcc tttattgaat ttctgtgttc caagcactat gctgagaact ttacatatac  44100
catctcattt aattcttttg tttgtttttc tttgggatgg agtcttgctc tgtcgcccag  44160
ggtggagtgc agtggcacca tctcggctca ctgcaacctc cacctcccgg gttcaagcta  44220
ttctcctgcc tcagtcgccc gagtagctgg gactacaggc gcccgccacc atgcctggct  44280
aattttttgt atttttagta gagatggggt ttcaccatgt tggccaggct ggtctcgatc  44340
tcctgacctt gtgatccgcc cgcctcggcc tcccaaaatg ctgggattat aggcatgagc  44400
caccatgccc gaccctcatt taattcttat aacattactg tgagatagta actattttta  44460
ttcacctttt gcaaataagg aaactgcctt caaatgagcc tacaaagaag acttaagaat  44520
tggagagttc tccctagggt cagtggaatt caggatgatg gtgcactgat ctcaactaaa  44580
acgaaactac tggttggacc atttcttctc aggactagat tgtgttaata cacattcttc  44640
tctttgctac tatatgttaa ataatctgga gatttccata atgtttccag gttccttggt  44700
tactcatttg ctacaggtgt tgctaaagat gtgtaaaagc tcaagtcact agttaggctc  44760
tctttgtggt ttgattagct tttgtccttt tctttggcca ggagacactc taattctgtc  44820
cacctgtctt accagtgcat gccattggtc acaaggtggg ttggttaata taaaggaata  44880
aatgaattgg agaccaagta ttgtactact ggaaaaacaa aggcaaatgt tagtatattt  44940
ttttccattt ggaatagtag tcattctttt agttctgtat tttgaaatca ttatttacca  45000
atacagtctt cttgatgtga aaatgcaaac agagttttca gtgttacctg atttagggtc  45060
actggaactg agagtgatgg tttacttctg actgcctgct gctgctttta tgtgaaactg  45120
tgataatctg ccttgactcc cttcctccta ggaaagaaag aaataaaata attaaataag  45180
aaaaatattt agtagaaaac tctttatcac tgtggaatca tttgtatcct attaaatggt  45240
atattatgaa atatatatcg ttttccacat taagtacatt tgccttttct cataatccta  45300
tctcaccttc acctttatta atgtttagtc acattttgag cttatatttt aagaaacttt  45360
aatttgtcct tttgcatgct gaaatttgaa tttttaaaat tcaagtatgc tgggcacagt  45420
```

-continued

```
ggctcacacc tgtaatccca ggactttggg agaatgaggt gggcagatca cttgaggtca  45480
ggagttcaag accagcctgg ccaacatggc aaaaccccat ctctactaaa aatacaaaaa  45540
agttagctgg gcatggtagc acatgcttgt agtcccagct actcgggagg ctgaggcagg  45600
agaattgctc gaacctcgta aacagaggtt gcagtgagcc gaaatcatgc cactgcactc  45660
cagcctgcgt gacacagcaa gactccatct caaaaaaaaa gtaaaaataa aaaaataaaa  45720
ttcaaattga aaaagttcat tttcacgatt aaattcatat ttacagtgct gccaaactta  45780
aataccttag gattgtttct ctcttcatgt aaaagataca taaagtgact acacatttca  45840
gtatctggta tggtttctct ttataaaata caaaatttaa agttcatgct ttatctaata  45900
atctaagatc caagtattaa tctatacttc attaatggtt ctttaccaca tttgattctg  45960
ctattcaaac tggattcttt taacccaacc ttggtcacat ttactgataa tcagaagtcc  46020
acattgctat aaatactact cacctaagcc ttgattattt gtcattaaaa aaaaaatgtg  46080
ttagcacaga tcctctctaa acccattcat gggcctcata ttaggaaacc cttgtcttat  46140
ataatgcatt aaatctctga aatatatttt tataacatgt ttcttagcac tgtaaatatg  46200
aatttgataa tgaaaatgaa ttgcagttcc tcactaaagg aatttaaatt ttttgcatac  46260
tagtgatgag gacttgattt tccaccctga agttgtaaag gtctttcagt ctctctaaaa  46320
gtgtgagtta aatctgtttt ctcacggcca gcttttaaag gtcagtgaag gacggcactt  46380
tgaaagaaat ggataatatg catccttcca gagctagtat atattacagc tgtccctttg  46440
gactcactcc agaaacagct cagtgactct tagaggaaga gaattttaga ggccctaact  46500
ggggcccaga aaattgtact gaaggatact tgcttcctgt gcatctccac tatagtaaaa  46560
tttgtttaaa attacgcttc ttagccctca aatccaaatg gtctcttgag tgcttttgat  46620
ttttctttaa ccatccgttt cctactattt ctactgctac ctcgctttgt tcaggccctt  46680
gttacatttt cactagagta atttcaacaa tttagttttt ctacctgctc ttctatgctc  46740
taggattata gtgcataaaa aaaagtgcac tatatatata gtgcaccccc cccaccaccc  46800
ccagcataaa agaccctatc ctgaaaaagt tcatagccta ataggaggtc aaacatgact  46860
acagataatt ttaatgagta tgttgaggta cagttataga aatacatata aaaggctgtg  46920
gtaacattta aaaagggagt aactgactct agaaatattt aaagtaactt tcaactgcag  46980
taataagacc attgaattat taacccagat ttgaatcatg ttgtttctgt agcaaatgta  47040
gagggaagtt ttgttctcct gttccaaatc agactaaaga ttcatttggt aatttaaaaa  47100
tcagaaaagc tttttttttc tctctctctc tcgttaatgg gttgtagggg ggtgaaagaa  47160
ccgtctctgt ctcctctgga ggctcagtat ttgagtccaa gaaataaact tgacagtaga  47220
cagattaaca ggagaaaagg catgtaaatg tatcgtatgc atatgcatag gggtcctaca  47280
aagtatgaga ctcagataag ggccagacgg ctgaagctta aatagtactt ttagctacag  47340
aaacaaatat gggcttaagg ctcctggagg gtgaggggaa gaactgtact gtgaacgaaa  47400
attgtcttgc tctgcggata aagtctctca gatagtagcc ctcagaagaa taggtgaaaa  47460
gtctgtatgg gcctggtgtc ttgggtgtgc ggacctctag tctcctctcc tgtgatagga  47520
gttaatgtaa attccagaga tggggttcac aattccattc cttctggagg aacttccgtc  47580
ttgataaggg aaacttcaga gaaagccctt tcttcacttg aggagagaag atgaagagac  47640
agaggtacag gggaatgtca gaccttggtt ctgatgctgc ttttttagtt caaagaactc  47700
atcatgtcaa agtgtcatac tttggggtat agtttcctga cccctaacat gagcaaataa  47760
```

-continued

```
agagatgtaa ctgagttagc cacaaaacta ttttttctg ttggctctat ccaaaaatga  47820
gagtggaaaa tgttctgtga acatatatct aaaagtatgg gtaaaacttg ttttacaaac  47880
tgttggtcat tcagcaaaca tttaaacagc ttctatactt gtggaacata aataactaga  47940
aaatacaagc tgcttatttt agcaaattgt ggctgtttgc attgctcagg ctgccagttg  48000
tgccaattgt gctgaggtat gcttcaaaat aactttcttt cttattttta atgacttttt  48060
aatgcaggta caatatcgat gttttaaaaa cataagtatt tggtgttttg ttttgttttg  48120
ttttgttttt tgagatggag tttcgctctt gttgcccagg ctagagtgca atggcgcagt  48180
ctcggctcac tgcaacctct gcctcccagg ttcaaacaat tctcttgcct cagcctccca  48240
agtagctggg attacaggct cccgccacca gggcccagct aatttttgta tttttagtag  48300
agacggggtt tcaccatgtt agccaggctg gtctcaaact cttgacctca ggtgatctgc  48360
cctcctcagc ctcccaaagt gctaggatta caggcatgag ccaccacgcc tggcctaaaa  48420
acataagtat tttaaacata atacactttt gaaattgaaa cctgaactga aatatataaa  48480
atatactttc tgcatatttt aaagtagtta agccagaaaa catcttaggc tgtatttata  48540
gagactggta atccatagtc aagtaatagt tttctgtact ctgccttgga aatactgatt  48600
ccagaatatt gtagtagatt ttcattgcca cattttgaga tgaatattag caaaagggca  48660
tatccaatga tggcaaaaat gagatggtaa actatcttgc ctgaattatg gttgaaggaa  48720
ttggtggaaa aagacccagg ggaaattcta atagctttca agtatgtgat gagatagaga  48780
aagtggaact gagggaatga acaagataat ttaggagtaa ctatgtttag ggataacttc  48840
agaattactc cacaaaaagt tccctgtcag gcagtaagct cccagcaatg aaagtaccca  48900
cttaaatcac ttctgagata ctttcctatt tcaagatttt aacttaaggg cttaaagaac  48960
ttaggttgac actgtatagg actgtagttt gcagaggcag ggtttgggat aacttcttag  49020
ccactgggca cttatgcggt tgataccagg taattctaat acattacagg gatcagcaaa  49080
cttttttct gcaagatgcc agatagtaat attttaggct ttgcaggcca tatggtctct  49140
atagcatctg ctcaactctg ttgttgcagt gcaaaagtat tgttgacatt atgtaaacac  49200
agtttgttac ctgtgttcca ataaaacttt atttacaaaa gcaagtggtg agttggattt  49260
ggcctgtggg tcatgctttg acgacccttg ccttaactaa tgaaatctag aaatagagtt  49320
ctaatgtaaa tatagaaagg ctttcaatct agggattaaa aatcgaactg tcaagatgtc  49380
attgtcttct tggtctgaaa gagtacacat caagtgttca aaatagtgaa ttgcccaatg  49440
aattaagaaa ccttccagta taaaagtcaa atgacaatgg agaatctgat actgtttttt  49500
actctttatt tctgctactt aacgttgttc ttaaaggcgt cgttacttct gctgggtagt  49560
actgtctact cagttggact gctgatgcag acccagtcca taccaacaag ttaacacagg  49620
ttcaggcctt ctgagaacca aaagattttt aagtacttcc ttcctaaata cagtaacttt  49680
taacagtaat tttaacacca gaagcaagaa gtaaacaaaa atctctgatg atcgaggcat  49740
ctgttgtcat atattttgtg ctcctaaggt catacagcag agcctcttgt attatctttt  49800
ggtctgttgg cctttagttt atagtttgta aaatggtggt cacatgtcaa tgctgactag  49860
aagaaggaga tgctactgta atcaggcagg ttggccttcg ctgagaagtg accattgatt  49920
gctagaaaac aaagaaatgg gaggcattca gcaacctggg gttgttggtt ttaggaccag  49980
aaatgtaccc ccaagtctcc accaaatttc tcaataatcc tgaagagttt tgctgtttgt  50040
gttttaatat aacacagtaa ttggtgcttg taatgaggac tataattcat caaaaaggta  50100
aattgtgaat tgtgcacacg cacacacact cttctaagca aatgggactg ctctattttg  50160
```

aacagtcttc aaattgaaat aacttatttc gatatgtaga aaattaggat aagcaaaacc 50220
aatttattta ctcttaagag ttccagatag tagtgatttg tcagtatgca tatgaatctt 50280
tagtcctggc attctgaact caaaacctca atagagtggt ttcttgaccc ttaaagtgtt 50340
ttatttttag taaatacatt tttaattctg tgacctcaaa cctccaagct acattatgat 50400
ttcataattt tatagtgatt tatcccccca ttgctttaaa tttaataatc ccatcctctt 50460
tattggtatt taattttttc tgtagtctaa aggccctttt atttaaaatg ttatatattc 50520
tgatttctta attttaggga tttttctcta gacaattgag aatatgtaat ttttacactt 50580
taatgttcat ttgattataa cctacacttg aaaagcaatt tttaaagaaa tctgagagaa 50640
tttaaaaatc attttaaaag catcatgtca tttttagctc aaaatacttc agagaattta 50700
ttttatttta ttttttttgg agacagggtc ttgctctgtt gcccaggctg gaatgcagtg 50760
gtgccatcac ggcttgctgc agccttgacc tcccaggcta aaatgatcct cccacctcag 50820
cctcctgagt acctgggacc ataggcatgt gccaccacac ctagctaatt tgtttgtttt 50880
tttgtagaga tggggtcttg agcccaggct ggtctcgaac tcctcagctc aagggatcct 50940
gctgcctcag cctcccaaag tgctgggatt acaggtgtga gccacaaccc ccagcccaga 51000
gtctcctttt tactaacggt gtacaacata aaattcaaac tctaacatgg ttttacatct 51060
ggcccctacc taccttttgc ctctccttct ttgtcacata ctccacctgt tcccatgcac 51120
tttagactca agtaatgaaa aacagcttgt attgctagga acaggccgca ttctttcatg 51180
gtctgacttt atacacactc tcttgtggca acctagaaca cctgtctata ggctctctta 51240
catcaggcca taccctttct gtgaaatttt taatctgtaa tattctactg aaactttacc 51300
tctctgaagc cttccctaat ctcctcaggc ttttccattg ttcatattct gtcttgtaac 51360
agttatcaca ttgttaaagt cgttccccag taaactatga gacccttaac tgtggaaggg 51420
aaggcatctt tttaaccttt gtttttgtgc catacttagc ctagagcctg acattaagca 51480
ggtacttctc aaaaaaaaaa aaaaaaaaca cagggtagag acagataaca agggattcct 51540
gacacctacg ctgtagatag ctataacatt tcaataggaa tcttgggaat ctggggaact 51600
ggaagcagct gggaaagcac cggcatctga gccactcagt actcttccag gcttgtgtgt 51660
gagccttgcc accttcaggt attagcactt gaaatctaac ttctttatga agctccttat 51720
ttacttgcct tctcggtgaa aaaaaaaaac aacaacaaaa accgtttcct tccccatctg 51780
gtgccagcac tgtataattc ctaataagct tgaaaagata atgttggcaa tactttacaa 51840
gtttattgct aatgtttaac atttattagg tgcttgctgt gtgctgatct ctgtgcttac 51900
atatttttca tatatcactt catctatctt cacaacagtc cagtgaagta gatgccatta 51960
ttatcccaat ttcacaaatg ggaaaaatga gattcattga gataaattaa actacccaag 52020
gccatacaac tatagactaa gggggccaaa atttgaatct agtgtagatt caaattagag 52080
ctcattctct tattcactac tggggaatat tgcctggcca taactgaagt ccaaataaca 52140
gcatggttat aatatgggct ttaaaataat ctagacctgg attcaaaatc catttattgg 52200
aggcaagtga cttcacttct gatcttcagt tttctcatat gtaaaatgat aatatctacc 52260
tcaaaagtgt tactgcccac ccatgtacat ggtacatact aaaaaagcaa atgttagttc 52320
catttgccac ttctacactt tatgtgaacc ctgggggtaa tggtttgtac agaataaggc 52380
ctggcatgag aagacaaaaa ccatctgaca aataaaaaag ctgtcattct gtctaccaga 52440
atgtcaacca gtgcctgcct tccaggatca acaagtgttt tattaccata atcacattta 52500

-continued

```
ttctcttaat gaaaagggtg tgtcttgagt atttaatagt taattaccca taaatatact  52560
acagtagaat aaggaataaa accagtgatc tgtctactat agtaactagg tttctttctt  52620
ggtaatactt agggaacata tgagggttcc ctgtgggttg ttatttatta tataaaatag  52680
ttgctctggt agttccataa tagagacctg tcagtgccat tcagcagaga aaaatcataa  52740
acacagctgc tgtttttgtg tggcttgtgg ttttggtttt gttttcattt gaactttttt  52800
atgcaggcat gtcatcattt aaaagtagtc atttggcgtt ttcccttgca ttcttcagat  52860
tttttgtagg cttaaaaaaa tttaagtcac ttctataatt gttcatacag attgatccat  52920
ctggtctttt tactagccaa tgaaattttt gacatgtagg aaaaaggaca attattttaa  52980
attctataat ttcagtggat ctcttttata agtttgaaga aaaatagttt caactatcaa  53040
aaaatatttt tcttatattc ttcattgttt cctgttaatt tctgtatttt cgtgggggct  53100
aaaaaggcta ataatttctg ctattcctac tcttcacatc ctttgtgtgt tataactctg  53160
aagcatacca taattatttg tttgcaacca agaattggta cagcataaat gtctaatcaa  53220
attaggccct cttgctctct ttaagtcaca ctggctatga ggtggaggtg gattataggg  53280
ggcaggcatc aattcaggga gaccatttag gcctttgcag tggtccagac aagaaatatt  53340
gatggccggc ccaaggtact aagagtggta tttgaagaat gtagacagaa taaagagaga  53400
attaacgaag cttgttgatg ggttagatgt tgattggtgt gagatggaga gaggagtcag  53460
ggatggcagg tttcctctct tctttcttgt tgtgtttgtt caactcttgc ttatcttttt  53520
tttttctttg ttttttgatg gagtctcgct ctgtcgccca gactggagtg cagtggagcg  53580
atctcggctc actgcaacct ctgcctccca ggtttaagtg attctcctgc ttcagcctcc  53640
tgagtaggtg ggattacagg tgcatgccac cacgcccagc taacttttgt atttttagta  53700
gagacggggt ttcaccgtgt tggtcaggct ggtctcaaac tcctgacctc gtgatctgcc  53760
cacctcagcc tcccaaaatg ctaggattac aggtgtgagc caccatgccc agccacttat  53820
ctttaaagga ttaagtttat gtttcctact atgggaaacc atcccacccc aaacttgatg  53880
accgcattat gtgcttttat agaacctggc acttctccag gatagcattt attctgtttt  53940
gtaagtgtga atgtaattac cctacacaca gcatacacat aatcttcata ttctttgcct  54000
tgtcttgtga aggcaagggc catgtctatc ttattcgtca ttagattccc acatccaaca  54060
tagtcctggg gacagcacca atgcactttt ggtgcataag caaatagtgt catttatagc  54120
tcttacctac aatatctgat agactaatca aatatagtag gttatctggg ccttttttgat  54180
tcatgtctct agcttaactt tcattttttt cttatttggt atctctcact ttgccttttg  54240
atatactctt acagtttcgc tcactgagta aaagaaaata taaacagcaa gaagtaaact  54300
tgtgttttat ggattttgat aacatcttct aaaagacccc ccaagattgt tgatgtctaa  54360
aaaaattaag ggccttcaac tcataataat acttaatagt tcttaaaata ttacaaactg  54420
attggaacat tgcactaaca gagagagtca tggatcttat ttatgtgtag attcatttca  54480
gtcagaagta ttaggactgg tttatttgag aaagtaaata gatcattaca aattcatcgt  54540
catacttcaa ggaaaattca ttgatgacac tttctaatat tgtgactata tacctaaatc  54600
atactttaag aacagaatgt ctaagatatc acctagataa gaatcaatac aaaaagaaaa  54660
aggaaaatta caaagattga tttaagaaag acaaaagact aagccataaa atttctcatt  54720
attacaggtt gagggcaggg agtgaaaaag gaaaaggatt tgacttctct aggcatggtt  54780
ttacttattt taaaataaga gcagtggacc catgatctga aagattgttt ctggcctaaa  54840
ttctgttttt ccgtaagata gaagagaatg ataaaggtga tatgcaatgg gaattttggg  54900
```

ttgaattgca acttactttt cattcttccc atagcctcat ctctgtcttg atgaaacctt 54960
agagaatcca ctcaaatata gtgttttctt aaatgacttt attaaattta attaaataca 55020
aatggttttt ctaatctctg ctgaaataaa ttctttgtag cctaatttag agcaacagtc 55080
tagattagaa tacttaagat gaattattac tacttagcct aatcaagtca aactatggaa 55140
aatgagtttt tacattttag cagtgttata aatgtattct tctgtagttg tgtctctttt 55200
aacatatgtt ttccttcttt gatttaggtt tctgctttgg gacaaccata catctaattc 55260
cttaaagtag ttttatatgt aaaacttgca aagaatcaga acaatgcctc cacgaccatc 55320
atcaggtgaa ctgtggggca tccacttgat gcccccaaga atcctagtag aatgtttact 55380
accaaatgga atgatagtga ctttagaatg cctccgtgag gctacattaa taaccataaa 55440
gcatgaacta tttaaagaag caagaaaata ccccctccat caacttcttc aagatgaatc 55500
ttcttacatt ttcgtaagtg ttactcaaga agcagaaagg gaagaatttt ttgatgaaac 55560
aagacgactt tgtgaccttc ggctttttca accctttta aaagtaattg aaccagtagg 55620
caaccgtgaa gaaaagatcc tcaatcgaga aattggtatg atacaatatc ctattctaaa 55680
atgcaaataa ccataaagct taactgttgt ccctttctaa aatatttctg tctaaaccaa 55740
taccttcgta atcttaaata gctttctaaa taaaaatcat aaatctaaag tatgttttac 55800
tatcgaacta tggaactatt tttaacacct tgatattatt ccataaggtt ttatttaaga 55860
aatgtcattt gtgggatgac ttagatttgt tatatctcag tgttgttatt cttttaaaaa 55920
tgattgatag gaatgtttgc tgcctttgct ctaaattgct gaatatatta tttttttatat 55980 attaaaaata ttcaggactg tcaactttta atatatatgc attcatcaaa aatttgtttt 56040
aacctagcgg tactttttttt actttattgt gatcttccaa atctacagag ttccctgttt 56100
gcaaaaaaaa catgttcatg ctgtgtatgt aatagaatgt tatattcttt atgtaatttt 56160
attaaaggtt ttgctatcgg catgccagtg tgtgaatttg atatggttaa agatccagaa 56220
gtacaggact tccgaagaaa tattctgaac gtttgtaaag aagctgtgga tcttagggac 56280
ctcaattcac ctcatagtag agcaatgtat gtctatcctc caaatgtaga atcttcacca 56340
gaattgccaa agcacatata taataaatta gataaaggta agaaaatgac taatctactc 56400
taatcattac tatagtgcag tcttctacct gtgtctatat ctttgtatag tcttttttttt 56460 tttttccagc tagatagtaa gcttcttgaa ggcagggact gcttatactg acaagatata 56520
gttgagtgct aaatagaaat tatgtacaat caatatttat tggttgaatt tttgtgtgaa 56580
tatgatactg atttcttggt aaattgtcta taaaacggaa gaagtatgag tttgaaattt 56640
actatttttt aggattcaga attagagctg attatctttt cataaataaa aactataaat 56700
agaaacattt tatgaaattt tgggaaaact ttatacattc ttgttattat atatcataaa 56760
tacaccagaa aaaaataagt aattttctta agtattaaat gcagtaattc tgatcatggg 56820 tgataaatata tagggagatt tttgatattt aatatattag tttctagaat taagggaaca 56880
agaaactaaa ctatattgtt ttcaaaatgc atgtcattgt atcagataaa tatctatatt 56940
tttcagggta acagtaaaat tatcaatttg agttaactct cacacactat taaatatcaa 57000
attctgttag tagaataagt taagacatct tattactatt cgtatttttc aaagtagttt 57060
aatgcaacat aagatctttc aaaattcttt tctattctag catatatttt aatgctcttt 57120
tcattttccc gaacattctt tgtgaaaaat tttcaacata tagacaactt gaaagaaatg 57180
tactgtgaac aaccaaacct ctctaaatag tttgtcttcc cgttttcttc atctttctct 57240

```
tttcttcttt tttggactcc tggcttaatc ttaaaaggag aaaattagac aatgcatttc  57300
ctctcccctc gtaattttct tacctttcct ccctcacatt ttctgtcatt ctaattgaac  57360
atctttaaac ctccattggt tctttcttta cttcccatag ttaccaaaaa cttccacctt  57420
aggcactgtc aaacctttga gaccatcatg aatcactatt catagggggca gtacccatga  57480
agtatgtcat acagtttaga atggaaatta gcttggtctc aggtacttgt gacccacata  57540
tcacagtttt gtgtgcttgt cataaaacat gagatttggg aatgatctgg cagcccgctc  57600
agatataaac attttctgtt tctacctgat atttacctag ttttaattgg gctgattaaa  57660
aagcatttct gatatggata aagtaatgat agtgaatact tgttgaaatt tctcccttga  57720
aaaatgaaag agagatggtg attgcatcta atgttttcct gttatagggc aaataatagt  57780
ggtgatctgg gtaatagttt ctccaaataa tgacaagcag aagtatactc tgaaaatcaa  57840
ccatgactgt gtaccagaac aagtaattgc tgaagcaatc aggaaaaaaa ctcgaagtat  57900
gttgctatcc tctgaacaac taaaactctg tgttttagaa tatcagggca agtatatttt  57960
aaaagtgtgt ggatgtgatg aatacttcct agaaaaatat cctctgagtc agtataaggt  58020
gagtaacaag tttcaaaata ttaattttta atttaaaaag taatcacatt gaggatgagt  58080
atctgtattt tttttttttt tttgagacgg aatctcactc tcgcccaggc tggagtgcag  58140
tggcgcgatc tcggctcact gcaggctctg cctcctgggt tcatgccatt ctcctgcctc  58200
agcctcccga gcagctggga ctacaggcgc ccgccaccac acctggctaa tttttttgtat  58260
ttttagtaga gacaggtttt gcaccatgtt atctaggata gtcttgatct cctgacctcg  58320
tgatccactc tccgtggctt cccaaagtgc tgggattaca gacgtgagcc accacgccca  58380
gccaagtatc tatttttagg atatacttct tgataagtaa tattagtaaa tagcgtttgt  58440
aagcttattc ttttaattct gtgattaatt cgagaggctg aaaatgttgg cagttactcc  58500
agctcccaaa tatagatatt ccatggggtt gttgtttttg ttgttgtttg tttgtttttc  58560
gagacagggt ctcgctttgt ctctcaggct ggaatgcagt ggtatgatca tggcttactg  58620
cagcatcagc ctcccaggct caagcagtcc tctcacctca gcctcctaag tggctgggac  58680
cacatgcgtg tgccaccatg cccagctaat ttttgtttgt ttgtttgttt gtttagagac  58740
agagtctcat attgtccagg ttggtctcga attctgggca caaacaatcc tcctgccttg  58800
gcctcccaca gtgctgggat tacaggcgtg agccattgcg cccagcctat ttcgtgattt  58860
ttatcccctc caaccagtgg ctgtggaatg gaattgaaat agacatttca aaaaatccat  58920
gacctactgt taagatatac tattgatact ttcctactct ctttttctgt ttattaaata  58980
aatacctata agaagcaact acgtttgtgc caagcatatg tcgagtacta atttacataa  59040
ccaagtaaaa cctgggcctg gccttcaggt tgcttatttt ctagtggggc ttatgggtaa  59100
gaaaataatg tgtatatagt aacatttata ttaaaaatct cgtcttaact accatttcaa  59160
aattcagacc agtatatttt aacatttttt gtaaatatcc ataatgttac tggtctccac  59220
tatttgtggt tttttgtttt aattttagca aaactaatgt ttctcaggaa atgtttggac  59280
aaaaaagcaa gtgaacagca gcctttggat gggacatcag tatgacttaa tagattgaat  59340
gacagaggcg tcctaagtga tattactttt ctgttatcat atacaatgtt ttcataatga  59400
gtatcctgtg atccttgttt tttttttttt ttttttgaga cggagtcttg ctctgtcgcc  59460
caggctggag tgcagtggca ggatctcggc tcactgcaag ctccgcctcc cgggttcacg  59520
ccattctcct gcctcagcct cccaagtagc tgggactaca ggcgcccgcc actacgcccg  59580
gctaattttt tgtattttta gtagagacgg ggtttcaccg ttttagccag gatggtctcg  59640
```

-continued atctcctgac ctcgtgatcc gcccgcctcg gcctcccaaa gtgctgggat tacaggcgtg 59700
agccaccacg cccggccgtg atccttgttt ttaattcctt tttttgcctc cagttaaggg 59760
tagaactaca gtttcaaaag ttgaccttaa tttttttctt tcgtgcaatt tatattcaga 59820
agtgtttgat tgatcttgtg cttcaacgta aatcctaaat gttagtattt taaatgttat 59880
aggaactact agtaaatgtg gtctataatg tttaattttt tatcaccttt gcagattaat 59940
atgtagtcat aatactctga catgttactt ttaaaatgaa aaaccttaca ggaaatggct 60000
cgcccccttta atctcttaca gtatataaga agctgtataa tgcttgggag gatgcccaat 60060
ttgatgttga tggctaaaga aagcctttat tctcaactgc caatggactg ttttacaatg 60120
ccatcttatt ccagacgcat ttccacagct acaccatata tgaatggaga aacatctaca 60180
aaatcccttt gggttataaa tagtgcactc agaataaaaa ttctttgtgc aacctacgtg 60240
aatgtaaata ttcgagacat tgataaggta aagtcaaatg ctgatgctta ttattttata 60300
gaaattattt tagataacct ttttcttgca ctatacagta atctgttgac ctgtagtatg 60360
ttttcagatg gttaggagaa catccaaatc tccgaatgta aaaatatatc aagaatttta 60420
cttgagcttc catctacctt agctattata cagctcacag tcctttgtta ataattctaa 60480
tattcacaat tctagctctt aaaatcaaaa gttttacaga attcgtttgg cagaaagacc 60540
tgggccaacc ttaagtgagg gtttttataa tctttattaa ccccacttag tataaaattc 60600
cggtatctta ttaaagaaat attaatgtct ttatgaggta ctgcttcacc agctaaggaa 60660
gtagtattta gtaagtacgt gtaccaattt agctttctaa aatatggaaa aactctgaat 60720
tacatacctc ccttaagggg attgtgggcc tatatttatg ttttagtagt ctgatgtctc 60780
cattgttatt agtggatgaa ggcagcaact aattttggtg aagactctac atcagtatta 60840
acgtgttaca tatgtgaaaa aaaggagaac caagctatat ctgaacaaaa attccgtggt 60900
tttatatttg agtctatcga gtgtgtgcat atgtgtatgt tgagtgtata cattagtata 60960
tacctacttt tttcttttag atctatgttc gaacaggtat ctaccatgga ggagaaccct 61020
tatgtgacaa tgtgaacact caaagagtac cttgttccaa tcccaggtaa ggaagtatat 61080
agatttatat ttccaaaggt tatattagtg tttagcagta tgatccataa aagtagtata 61140
ttttttaga ccagcctggg caacaaagca agaccccatt tctacaaaaa gtttttctta 61200
aaaattagct aggcactggc caggcacggt ggctcatgcc tgtaatccca gcgctttggg 61260
aggctgaggc gggtggatca cgaagtcgga gtttgagacc agtctggcca agatggagaa 61320
accccatctc tactaaaaat aaaaaaacat tagccgggcg tggtggcggg cacctgtaat 61380
cccagctact tgggagactg aggcaggaga atcgcttgaa cctggaaggc tgaggttgca 61440
gtgagctgag attgtgccat tgcactccag cctgggcaac agagcgagac tccgtctcaa 61500
aaaaaaaaaa aaaaaaaaaa aaaaaaaaaa aaaattagct aggcacagtg gcatgtgcct 61560
gtagtcccag ccattaggga ggctgagaca ggagaatagg agaattgctt gatcctggaa 61620
gttccaggct gcagtcagct atgatcgtgc cactgcattc cagcattagt gagacctgat 61680
ctcaaaatat atatatattt tacatcatta gctttataca agctatatat taataaatta 61740
ccagaaatgt acatatagac cagcaagact ttctgtcaaa tgagtatcag tcacaggatt 61800
attttattga ttctgtctaa agttttatca gaatagtttc tgattgtctc ttttcattgt 61860
atcaaagaga gaacagagta tggttataat tttatgctaa tcattcccca cattagatta 61920
aaaacctagc attttattct tttcctgtct ccatcatcat tcacatgaag gagaagtaag 61980
agttggcaag caactccata accaaactac cctgaggcag tttccttcaa atcactccca 62040
agaatagata tttatggctt tcaaataaag ggtctttggt agcaaattaa tttgttagtg 62100
ggagagggag ttatggggaa cattttaaat tattactgcc tggatgtgat gaagaaataa 62160
aaagtagtat aatccaatag ctgactatcc tgcatttctt tgcttctctc tatacagtca 62220
tttgggaata agagtacccc tgaacgtaat agcagtaata tttcaagaga actcaaattg 62280
ttattggact ttatgataaa ataacaatag agctaactag tgactcctcc agaagtaaat 62340
ctcataatga atttagactg agttctaaga cattcaagaa aaagttctgg tcttgttgct 62400
aaagatggcc accctttag agcctaggta aggttaaaag agatggtagc cttgtctgcc 62460
acagggaagg aagatagttc ctcagcctac ctaaaccact gtaggtcaga aaacgtatca 62520
ttcaggtcag aaatgagatt gtgacaacaa acaacttcag gatctttttt tttttttttt 62580
tttttttgag ttgaagtctc accctgtggc ccaggctgga gtacagtcaa gtgtaagcga 62640
ttctcctgcc tcagcctccc tagtagctgg gactacaggc acatgccact gcgcccagct 62700
tattttttgt attttcagta gagggggggtt tcaccatgtt ggccaggctg gtcttgaact 62760
tctgacctca ggtgatccca cccaccttgg cctcccaaag tgctgggatt acaggcctga 62820
gccatcatgc ccggccagga tctttttaaa ttcttgctaa aacaagagtt tatatcccac 62880
tcatactggt atgcctcaca ctgattagtg gggtggttgt agcaggaaaa gaaaaacaac 62940
atttgaggaa ataatagcca gaatttttcc aaatttggta aaaactataa acccgtcaat 63000
ccaaggagtt caacaagccc caagcaaaga ccccaaaata atactggata gaattatcct 63060
agctagctgt ttcaagtacc acaagttaaa ctagctttat aaaagtaaaa ggctgggcgt 63120
ggtggctcac gcctataatc ccaacacttt gggaagccaa ggcagatgga tcatttgagc 63180
ccaggagttt gagaccaccc tgggctatat ggaaaaacac agtctctacc aaaaatacaa 63240
aaaattagcc tgggatggtg gtgtgtgtac ctatagtccc agctactcag gagggtgagg 63300
tgggaggatc acctgagccc agggaggttg agactgcagt gagccatgat cgtactactg 63360
cagtccagtc tagggggcag agtgagaccc cgactcaaaa aaaaaaaaaa aagtaaaaga 63420
taaacttatt taataatata tgattaaaat gttgaaatgt tagtaaaata gctatttaga 63480
aaggactata tttgtcttta agcattctgt agtctaaaag gtgaagtatt tatggtagtg 63540
tgaaaattta agtaaacttt ttaaactttt ctgtgcttac aaaaacaaaa atcagataaa 63600
tgaatatgaa gttattaaaa agatagaaaa gtagatttta aaaattctta ctaaatattt 63660
gtttcaaatc tgtgcttctt ttatgctaaa ttagatgctt tatgatttct ttgtaaatgt 63720
tacaagtatc tcccaaaatc agagtcaatt tggactgtat acacacacac aaccattttc 63780
tagaaataaa gaacttaatt gagcatgtgt atatgtgtgt gtgtctgtgt gttgtgggat 63840
ggatggactt tagaagaaaa gagaaacatg ctttattttg ttagcatagg gctgaacaag 63900
tagatttgta ggacatagct ctcttagagt atagaacact tcttattaat ttatgagcac 63960
ttctaaagat ttaggaataa taaaaagtct ggtacattaa agtaatatat ctttaatttt 64020
tcttttcttt tttttttttt tggaggcgga gtcttgctct gtcgcccagg ctggagtgca 64080
tggcacaaac tcgactcact gcaacctctg cctcagcctc ctgagtagct ggagttacag 64140
gcgcccacca ccacgcccag ctaatcttgg catttttagt agagatgggg ttttgccacg 64200
ttggccagac tggcttcgaa ctcctgacct caggtgatcc gtccaccttg gcctcccaaa 64260
gtgctgggat tacaggtgtg agccaccatg cccagcctaa tttttttttaa atcattgcgg 64320
acttaagtcc cataatattt ttctctatat gtttctacaa ttatatgtgt tactgggcat 64380

```
ggtagtatgc gcctgaaatc ccagcaactc aggaggctaa gggaggctga ggcaagagga  64440
tcacttgagc ccaggagttc gaagctataa tgcactttgg tcatgcctgt gactagccac  64500
tgcacttcag cctgggcaca tagcaatacc ctatctctaa aaaataataa taataataac  64560
atttgttttt tcttttacct ttagaattct tgccacattt ccccatttta aatgtgtctt  64620
gtttctataa atagaccata tttttaaaaa tctttatcca tacttgagca aaaatgctag  64680
aataaatgga acttatttta ctgatgaagt ttattactta gttggctaat taaaaataga  64740
attgttatac tattttattg ttgattaaga attattttat ttataatcaa gattagacca  64800
gaatgataag acatttgaaa agtttttaaa attactatct aacatatgag cttctatcat  64860
gggacaattg ctattctaat tcctttgctt gtgttatctc atttaatttt atgagatagt  64920
tatcaacctt atgagggtag gtactattat tagtcccatt tcatagagga ggcaaaagac  64980
aaagcaaggg tcacacactt agtgaaaaag gggaaataag attctactcc agtctgattt  65040
ctgagcccat actctttatc cattgttata atgttttttt aaaatacaaa actgtttatt  65100
gtatgtggtt ctttacaaat atgttcacca aagacagaca taatttcaca tgtagcaccc  65160
agtaaattga gggaatttat cattaaaatt caaataattt tttatcttgt tcacttttttg  65220
tagcagtgtt ttattcttcc cttatgaatg tgaagtttca ttacctttta taaaataatt  65280
attcttcaat tcaaatactt tatgtatcca tcattttatt tacctactga tttatttagt  65340
ggattccttt ggataaaact atattatgta taaaagtaac taaatgtaat cataatagga  65400
aatcttattt tacctttagt tttccttttg tttgactttt atgagcaaaa ttatatatat  65460
aaatatatag aaataataaa tatatattta tattatgtat atagtatatt atataatata  65520
tattataaat ataaataagt tttttagtga cgtatgtagc acacatgcat aaaagtatac  65580
aaatcataat tgtatagttc agtcacaaag taaataccca tgtcttctgc ttttaacaaa  65640
tgcacacatt tctgtggttt tattcctaca attggagctg ggtcacaggg aatacatatg  65700
ctcactttta ttagattatg ctttccaaat tggttgtaac aaattatacc ccaatactct  65760
tagtgtatga gatttcctat tactgcataa ccttaccacc ccttggcatc atcagtcttt  65820
atagtttagc cattcttatg tatagtgata tctccatgag attttaattt tcattttctg  65880
tatgactaat aatgactccc ttttcatgtt tattaactat ttgaatatga ccttataaag  65940
tgccttttcc aatcaatctc tttcctgttt ttcgtttggt tgatctttgt cttcgtgatt  66000
tgtaggagtc atttatatac tttgatgaag acttttcttg atgtattatt tttgctttaa  66060
aattttacat aggtggaatg aatggctgaa ttatgatata tacattcctg atcttcctcg  66120
tgctgctcga ctttgccttt ccatttgctc tgttaaaggc cgaaagggtg ctaaagaggt  66180
aaagtatttc agaaggaaca attatgttta cctttaaaaa ctcctgatta taccgctgat  66240
tgaatttttt cacaaattgg atgttatttt atatttaaga aaataataat aaacctattt  66300
ttaaaatttt aataaatgta tcatggaaga ataccttggg agagcttcag gaatttatga  66360
tgaatatgtt ttgagttctt attgatacca tttttaaaaa tgcaaagtga ctatataaca  66420
gggattgcat gcaaatatct catgcttgct ttggttcata ttttctattt ataattaaaa  66480
tacatgtaat ttcaaatggg gaaaaaggaa agaatgggct taaaccttga aaaatcaatt  66540
ttttttttt agatattccc attattatag agatgattgt tgaattttcc ttttggggaa  66600
gaaaagtgtt ttgaaatgtg ttttataatt tagactagtg aatatttttc tttgtttttt  66660
aaggaacact gtccattggc atggggaaat ataaacttgt ttgattacac agacactcta  66720
```

```
gtatctggaa aaatggcttt gaatctttgg ccagtacctc atggattaga agatttgctg  66780
aaccctattg gtgttactgg atcaaatcca aataaagtaa ggtttttatt gtcataaatt  66840
agatattttt tatggcagtc aaaccttctc tcttatgtat atataatagc ttttcttcca  66900
tctcttagga aactccatgc ttagagttgg agtttgactg gttcagcagt gtggtaaagt  66960
tcccagatat gtcagtgatt gaagagcatg ccaattggtc tgtatcccga gaagcaggat  67020
ttagctattc ccacgcagga ctggtaaggc aaatcactga gtttattaag tatcaattat  67080
aatctgtgga tttaggtaga tactttctct atggaaaagg atccatatat tttactggca  67140
tagatactat gaactctagg accaatattg caatagaatt aagttctcta tatgctaata  67200
tttttactgc acctctgctt ttttaaagcc ctagcttgcc ttcattcatt taacaaatat  67260
ttattgaatg ccgactatgt gtaaagcact gggaaaggca ctaggtaata aagtcatgaa  67320
ctaaacagac cttcattgag tatgcactct aactgtgaaa acagacatta agcagataaa  67380
agcagaaata taagattaca gttgaccctt gaacaacatg gatatgaact acactggtct  67440
acttatatgt ggattttttt caataaatat attggaaaat tttttggaga tttgtgacaa  67500
tttgaaaaaa acttggagat aaactacatt gtccagaagt atcaaaaaaa ttgaagttag  67560
gtatgtcatg aatccataaa atatgtatag atacaagtct attttatcat ttacgaccat  67620
aaaatataca caaatctatt ataaaaagtt aaaatttatc aaaacataca cacacaaaca  67680
cagaccatac atggtaccac tcatagtcaa gagaaatgca aacatatata aagatgcagt  67740
attaaattgt atctgcataa aattaactgt agtacatact gtactactgt aataatttca  67800
tagccacctc ctgttgctat tgtagtaagc tcaagcattg catatatcca cttaaaatgc  67860
tatgtaggct gggtgcagtg gctcatgcct gtaatcccag cactttggga ggccgaagcg  67920
ggtgaatcac ctgaggtcag agttcaaaac cagcctggca aacatggtga aatcccgtct  67980
ctactaaaaa tacaaaaagc cgggtgtggt ggcatgtgcc tgtaatccca gctactcggg  68040
aggctaagtt aggagaattg cttgaacccg ggaggcagag gttgcagtga gccgaggtca  68100
cgccattgca ctccagcctg ggcaacagag caagactccg tctcaaaaaa caaaacaaaa  68160
caaaatgcta tgtaatgctg atcatctcta catgagtact tcatcacttc agtaaattgt  68220
ttattgcagt gaaaagtgat ctctcacagt tcttggatat ttttcatcat gtttagtgca  68280
ataccgtgaa ccctgaataa cactatgagg gctgtaagga gtgcctctag tgatgctaga  68340
ggtactctca agaagcagag aaacgtcatg acgttacaag caaaagttga attgcttgat  68400
gtgtaccata tattgaggtc tgcagctgca gttgccctta tttcagacag acaactaatc  68460
ttgtaaacag acaacataaa ctttgtttgt ttttgttttt ttgagatggc gttttgctct  68520
tgttgctcag gctagagtgc aatggcacaa tcttggctca ctgcaacctc tgcctcccgg  68580
gttcaagtga tcctcctgcc tcagcctcct gagtagctgg gattacaggc atgcgccacc  68640
atgcccagct aatttttgta tttttaatag agacggggtg tctccatgtt ggtcaggctg  68700
gtcttgaact cctgacttca tgtgatccac ccgcctcggc ctcccaaagt gctgggatta  68760
caggcgtgag ccaccgcgcc cggccaaact tttttttttt aataagagat ggggtaggtg  68820
gatcacacct gtaatcctag cattttggga ggccgaggcg ggtggatcac gaggtcagga  68880
gttcaagacc agcccggcca atatggtgaa accccgtctc tactaaaaat accaaaatta  68940
gccaggcgtt gttgtacatg cctgttagct actcaggagg ctgaggcagg agaatcactt  69000
gaacctggga gatggaggtt gcagtgagcc gagattgcgc cgctgcactc cagcctgggc  69060
aacagagtga gactccgtct caaaaaaaca aaaaacaaga gagagatggg gtctcactgt  69120
```

-continued gttgcctggg ctggtctcga actcctgagc tcaagtgatc ctccctcccc tacctcccaa 69180
agtgctagga ttacaggtgt gagccatcat gcccggccaa aagacaaaat aaatgtatag 69240
tatcagtaaa tacagtacag tactgtaaat gaattttctc ttccttatga ttttcttaat 69300
aacattttat tttcactgtc ttactctatt gtaagaatat aatgtatagt acatatacca 69360
agtaagtgtt aatcaactgt ttatatttct gttaagactt ccaatctaca gtagtcattt 69420
gtagttaagt ttttggggag tcaaaattta cacatggatt ttcagttgta caggagatca 69480
gttgccccta tcccctatat tgtccaaggg tcagctgtat aaatcacatt aagtgccagg 69540
aaggaaaaaa caatagtgag ctaagaataa ctaactgagg atttgtgggg aaaaggcaaa 69600
tatatatata ttgggttcag gaaagacctc tctgagatga taaccttgaa gttgagactg 69660
aagtacagct atacctctga ggtattgtga gtggtctagt tctagaccac tgtactaaag 69720
cagaaatcac aatagagtca caaatgtttt ggtttcccag tgcatataaa agttctgttc 69780
acattatact gtcatctgta aagtgtgtaa tagtctgtca tctgtaaagt gtgtgatagc 69840
cttacgtcta acacaacaat gtacatactt taaaaatatt gctcaaaaat gctgatgatc 69900
atgcaaggct tcagcaagtt gtaatctttt tgctggtgga gggtcttgcc tcagtgttga 69960
tggctgctga cttaccaagc tggtggttgc tgaagtaacg ttagcgtggc tacagcagtt 70020
tctttaagac gacagtgaag tttgccacat tgattgaccc ttccttatgt gaaagatttc 70080
tctgcagcat gtgatgctat ttgatagcat tttgcccaca atagaacttc tttcagattt 70140
ggagtcagtc ctctcaaaac ctgacgttac agttaaccag ctgcattagc ccctaacaag 70200
agagtcagcc tgaagctttg aagccaggca ttaacttctc ttctctagct gtgaaagtcc 70260
tagatggcat cttcttccat tataagactg tttagtttac attgaaaatc tgttgcttag 70320
tgtagccacc ttcatcagtt atcttggcta gatcttctgg ataacttgca gcagcttctc 70380
catcagcact tgctgcttca cagcttcttt tttaaacctc ttataccaac ctctgctagc 70440
ttcaaacttt tcctctgaag catcttcgtc tctctcaata ttcatagaat tgaaaagagt 70500
tacggccttg ctctggatta ggctttgact taaggaaaag ttgtggctgg tttgatcttc 70560
tatctagacc actaaaactt tctccatttc agcattaagg ctgttttgtt ttcttatact 70620
tcattcactg aagtagcact tttaattttc ttcaggaact tttcctttgc attcacaact 70680
tagctgtttg gcaccagagg cctagccttg gcctgtatgg cttttgacat gcatttctca 70740
ctaaacttaa catttctagc ttttgatgtg aagcaagaga cgtggcactc ttcctgtcac 70800
ttgaacactt agaggccatt gtagggttat taattggcct aatttcaata ttgttgtgtc 70860
tcagggaata gggagtcctg agaggaggaa gaaagaggag caaaggttgg tcggtgaaga 70920
agtcagaaca tgcaacactt atcgaataag ttcaccatct taattggctc atggcacccc 70980
caactgcatc agagtaacat caaagatcac tgatctttga tcacagatca tcataatata 71040
taataataat gaaaagcttg aaatattata agaattacca aaatgtgaca cagagacaaa 71100
aaatgagcca tgcatttgga aaaatagtgc caggagactt cctttacata gggataccac 71160
cacaaacctt cagtttgttg gaaatgcaat atctgtgagg tatgataaag caaagcacaa 71220
taatacaggg tacacctgca caaatatatt gttagttgag cttggaagca gagaaaacag 71280
caggtcttca ccatgttatc ccaggttccc caggaaagag cgtatgtaag atggaattta 71340
aatattgatc tagttgtcta atcttggcca tagcttttga accacagtat aattatctag 71400
gttcaagaac cattaactct ccctgatttc tcaagggcaa agatgtcaat gccacgagaa 71460

-continued

```
gatgtttgtg ttcattggtg tttccaaata tattactttt tctttggctt tgttggctat  71520
agataaacca gccaatgaat tttgggccaa gaagtccaaa acacccctat cccattaaca  71580
gtaacagcag catcaagagg cagcctggta tattgcactt aggaaattta ttgattcata  71640
gctgtgttct cagtaaggcg tttaccacta cttttcggaa aacaaattat cttttctgca  71700
tatatatttt tctgcattta aaagatacga gtctcttttt tgagcagttc tctttgtaag  71760
aattgatatt tgatgactgt attctttctt aaaagaaatt ttatttcaaa gaaaagaaat  71820
ttgcttattt tatagcagaa taaaacttct atttttcagt tacaatttgt atctattgga  71880
aacttttgta aatctaagat acgacatgga atcttagttt ttctgtatct taaatatttt  71940
actatttcat catcctagaa attacttcat ccatattcat tatttccaac tatgctaaaa  72000
aagactaaaa taatatgaaa atataaaaga aggatagaat agcctagaag gacaataaaa  72060
tagtgaagta aatcatgatg ttacatcatc cttcagtttt cttattgcat tgcccagtgt  72120
cttgcatcat ctttccagaa gtatagaaga agtctgcaga cactgtcttt gtaatttttt  72180
tgtttggttg gttggtttct ttcaggcttt cattggacac ttgagaattc agaatttttc  72240
acttttcacc cagaatgatg acagatgaaa actgaccaag gaagatattt cacaagcatt  72300
agacaaatca taatatgaat gtagatagat agtagcagcc tagagcagag tttcccaacc  72360
tcagcactat tgacattttg cgccaaataa ttctttgttg taggagccat cctgtgtgtg  72420
caatccagga tgtttagcat ccctgtcctc taccctactg caggccagta gtgccatcct  72480
gctaagttat ggctatcaaa aatgtctcca gacattagcc aaggttcctg ggtggtcaag  72540
gggacacaaa atcaccctag ttgagaacca ctactctaaa ctctaatcat ggtgaagttt  72600
attatataaa tgaaatgtca gatgacaaca cctaaactgt ctctcagtta tcttaagtct  72660
tctcaaactc aggataatga tgagtaaaga atatatttct aacaacaaaa aggaaatttg  72720
atagtatttc taaagacaaa aaggaaattt gtattcacat tcagttagtc attccaccag  72780
aatgacttca tcacacaata ttttgtgaca agaacctgaa cagcctgttt tacagtattc  72840
ttttcatctt ttattatatg caccaaaatt tttttttaaa ttttcttgaa cctctaaatc  72900
tacgttaaaa atttacctga tacactttct aaatggacaa atgccgaagg tagctgtgta  72960
tacaaatgtg actagaagga aaaagatgat atagaaataa aataactcct tgagttgatc  73020
attctgattg gcatttatag agtagaaatg ttttgtaatt acagaggaaa aaagatggcc  73080
tttccttcaa cagttatgag ccgtcagaat tttcaaaaat actgcatttt gacaatgtag  73140
tttctagttt gacaatgata tatttatctt caaaaccagg aaaatgtaga taagaatttg  73200
gttttataat atttaaattc ttattaaaat gtctaataaa attgttttcc ccatcacttt  73260
attcttctgt aagttatttt atatttaaaa tgtaaacaaa taaaaataag taaataaaca  73320
gtagcagctt cttttcctga taaatcgagg attgagtatg tattatctct ttcctggact  73380
actggaataa cctctccctc cttccacaga gaagccataa taatctttat gaaatacaaa  73440
tcaaatcatg gtattcattc tttaaatagc tatcaataaa aataaaatcc caactttata  73500
ccctgttcgc aaattttacg tggtctgaat tcagcttaca tttcttcttt cccttgtcta  73560
ttgcccatca ggctcactgg ctttattcct tcacaccaaa ctagttattt ccggggtggg  73620
aggaaggctt gcagtgtttt ctccatctgc aatagtcttt cccaaatctt agtgtggata  73680
aaggttcctt cttgttactt gaatcacaaa tactatgttc tcagtcattc tctgttacat  73740
catccagagt acattatatc aattttccaa tatttttatt tatttgattt cccactataa  73800
cagaggctct gttagtgcag ggtcttttac tattttgtaa tcccaacagc aagaacaaaa  73860
```

caaggtacat agtacatatt taataaatac ttgttgaaca aatatgtgcc ggtaatattt 73920
cttcatgctg ctgaataagt taacagcata taaacacata caaaccaagt ggcatggatg 73980
tctgctttca tttttagcct tttaaaaata tatgtaaccc atcctaaggg gtttatattt 74040
gttttgcata atacattaat atgtactcat tattcattac acagttaata tatctatatt 74100
tgcagggaat atacattgct tggaattata caaaaaaata ttatttttcg ttttctaata 74160
ttcaggatac agtgttttaa tgggggtgtt tcttcattct ttttttctta ctggttttta 74220
ctttttaaat ttgaaagctt tgcagggatc ataaggatct gttcaggcaa agaacatgaa 74280
agggtttaca tttttatcat tttagtgttt cttattctct atatcaaaaa cattcacaga 74340
taagttaaca agatcctcat caggaggaaa agtaaattgt tcactaccat cctctagtat 74400
cctaatctgg tcttgttgtt ggctaacttc agcagttact attctgtgac tggtgtaata 74460
ttaaccaaat aaattactgg atttgttcta caaatattat gtcttagatt ggttctttcc 74520
tgtctctgaa aataaagtct tgcaatgaaa ataaattatt ttacaacagt taattagcaa 74580
tgtaaaattt attgaaaatg tatttgcttt ttctgtaaat catctgtgaa tccagagggg 74640
aaaaatatga caaagaaagc tatataagat attattttat tttacagagt aacagactag 74700
ctagagacaa tgaattaagg gaaaatgaca aagaacagct caaagcaatt tctacacgag 74760
atcctctctc tgaaatcact gagcaggaga aagattttct atggagtcac aggtaagtgc 74820
taaaatggag attctctgtt tctttttctt tattacagaa aaaataactg aatttggctg 74880
atctcagcat gtttttacca tacctattgg aataaataaa gcagaattta catgattttt 74940
aaactataaa cattgccttt ttaaaaacaa tggttgtaaa ttgatatttg tggaaaatca 75000
tactacattg gtagttggca cattaaatgc tttttcttac tctgaattcc tgatatgact 75060
ttctttagga ttgtttaaaa tattctagta gttttaggtc aatttagatg tgatttagtt 75120
ggtctagata ttataatttt taggggttcc ctttcatttt tctttttttct tacgtttctt 75180
caaatagtat aatgccttat tttcatttat gaagaaatta ccctgctgtt ggtgatacgg 75240
gtatatttaa ataaaccagt tgcagtgcat ttctgcagaa agtccattaa gacataaatt 75300
ttgtccagta actacagtag aagtggtgac tctatgattc attcatgttg cataagtagg 75360
tgaaaaatat gagctatatg aagagtggta taacatatat tcataatttt tcttaactgt 75420
taactaaatg taagtactta taatccattt gcattttcct tttgtgttct ttgccattat 75480
aactgtgcct aagtatatat gtaaatatat ttccaactat agtgttaaac actgatgtct 75540
tttgaatttt aaaaaagcta gtaatgtaag aagtttggga cttcttaaga agattcatat 75600
ggagaagtta gacatgtcaa ccttttgaac agcatgcaag aatgtttatg tttattttgt 75660
ttctcccaca cagacactat tgtgtaacta tccccgaaat tctacccaaa ttgcttctgt 75720
ctgttaaatg gaattctaga gatgaagtag cccaggtaaa tgtatgtttg agattactag 75780
ataactgttg tacaaattgg tatgtcactt aaattgtttt ctctcagaaa gtccacataa 75840
ataaatgaaa tagactaata gtaatatagt gtagaaaaaa acacccttaa cattatttcc 75900
atagataaaa ctaattagaa ctgtaaattc taaggagatt atttatctaa actaatttta 75960
aaatcagaag ttaaggcagt gttttagatg gctcattcac aactatcttt cccctttaaa 76020
tatgatttat tgtctttctc atacacagat gtattgcttg gtaaaagatt ggcctccaat 76080
caaacctgaa caggctatgg aacttctgga ctgtaattac ccagatccta tggttcgagg 76140
ttttgctgtt cggtgcttgg aaaaatattt aacagatgac aaactttctc agtatttaat 76200
tcagctagta caggtaaaat aatgtaaaat agtaaataat gtttaattac aataataatt 76260
tattctagat ccatacaact tccttttaaa aaacctactg cactaactag ttttatgctt 76320
aaaaaaaaaa attattacca gtaatatcca ctttctttct gaaaaaattt tctttagatc 76380
ggccatgcag aaactgaccc tgatttgttt ttttggaatc acctaggtcc taaaatatga 76440
acaatatttg gataacttgc ttgtgagatt tttactgaag aaagcattga ctaatcaaag 76500
gattgggcac tttttctttt ggcatttaaa gtaagtctaa ttattttccc attaaattct 76560
taaggtacat attacttgct ttcttaatag atttataaat atgtattact tatatacttt 76620
tgtttatgtt tggctggaag agttttccat actaaaagta ttttgtacca gtgatgagct 76680
tctcaacttt tgctctttga aatttaaaaa gcagtaaatt caaaactaaa ttttagtcat 76740
gaatgagagc ttaaatattt ttaaagattt ttgttctact taagtcaaat tttctaggtc 76800
cagatgaata ttgctgtagg tttcactgtg tgtatggatt acaatatccc caaacaaaga 76860
aaaaaatgtt ttaccttgaa attcagaaca atgtcaaact cccgtggttc ttactgaaaa 76920
acaagctaat taagaataaa aaatgttttg tagaatgtga tatatgtagt actcaaaagt 76980
tacaggtcat aaaccatata acttttcata aatttagaag cagatttata tctaatatga 77040
tattttaagt gttaaaattt aataatggaa cccagaagtt aagttgaaaa caagaagcat 77100
aggcgtgtgt cagaagagtc aaacagcatt cactgagcgc tttgttccct ccctcttcat 77160
ttgattattt ttgtgctcaa tttccttttt tcatgttttt atatcttgta ctgagattag 77220
tcaatgaaaa ctagttgaaa taaacctaaa aactagatgt ttatttaatc acatattcag 77280
gaactacctg aaactcatgg tggttttgtt tctaaattac aggttttgaa taattttatt 77340
attagtatga ttgtaacatt tattggattt caaaaatgag tgtttaaatt gtttagcaaa 77400
gattatttgt atactgattt aagactatat atatatattt ttaattttgc acgattcttt 77460
tagatctgag atgcacaata aaacagttag ccagaggttt ggcctgcttt tggagtccta 77520
ttgtcgtgca tgtgggatgt atttgaagca cctgaatagg caagtcgagg caatggaaaa 77580
gctcattaac ttaactgaca ttctcaaaca ggagaagaag gatgaaacac aaaaggtgtg 77640
tgactctagt ttgtgtttga gactcttttc actgcagtgg ggcagagttg tttagaagcc 77700
cagtgtatat acagatcatg gtccttggaa tcaagcagat taggatttgg aaccaagttc 77760
cactgcctct cagctgtgta gtgttagaca cgtcatgcag gctctcagga ctcattttct 77820
ttgtctgtaa aatggaaata atacctgctt cataaggcca ttgtgagaat taaattacac 77880
gagatatgca aagaacctat cacaatcctt ggaacataga aggtggccaa taaatgttag 77940
atccctttac tttcccttcc tttctcttat tcaggtccct aagtatttac agtgattatt 78000
tccttattct gtcatttatt gtctctcagt aatgaccctg aaaatgagtg gaaagaagtt 78060
agtttttaca tttccaagtt taaaatggat ttcgagtcac tcagtaaata tatcacactc 78120
tagtcatctg ctgtctagct tagtataact aagagtagga aatacaatgt aaactttttt 78180
tttttttttt tttttttttt tttgagacag ggtctggctc ttttgcctgg cctggaatgc 78240
agtggtgcaa tttcggctca ctgcagcctt gacctcctgg gttcaagcca tcctcccacc 78300
tcagcctcct gagtagctag gactatagga gcatgccacc acttccagct aatttttgta 78360
tttttagtag agacagtgtt tcgctttgtt gcccaggctg gtctccaatt cctgggctca 78420
agcagtctgc ccacctcggc ctcccaaagt gctggaatta caggcatgag ccactgtgcc 78480
tagcccaatg taaacttttt tatgaccttt tcctacaccc tattctttat tcaatccaat 78540
ccaccacatc ctaaattcac cacctcttac aattaaaagg aagctcattc ctcacctcta 78600

```
gtaaaaggaa aaaaaaaaga aaaatcgtat attagtgagt ccccaaagga cagagaatgt  78660
aagttagcag tactgaatga atttttccag catcttcatt actagtactt gaaggaaaaa  78720
aaaaaattaa aacaaagtta ttgtattaat gtaaatgtca tacagtgtga gttgatttta  78780
ttgaagtgtg atatataaat tcaaatatag gatggtagaa aataattgta ctctttctga  78840
tactggaatt tatgagcaag aagggtctag attgccctgg aagaacaaaa tttattgtat  78900
ttatatattg taactgagct gagaaaaaag aaactaaatt ttagatacat ttgtaaatac  78960
agatgttcct caacttataa cagggttata tcctgataaa cacatcataa gttgaaaata  79020
tcgtacaggc aaaaatgggc attttgtaga tgtgatggga tgcgaaaaca caaaacacag  79080
tatccaaaaa atgctggcca cacagtacgc tgtagactat tggtcgttta ccctcatgac  79140
tgcatggctg actgggagct gcggctcgct gctgctaccc agcatctcaa gaaaatactg  79200
tgttgcatat cactagccca ggaagagata aaagtttaaa atttgatgta tagtttctac  79260
tgaatgcatg taggaagaga taaaagttca aaatttgaca tataatttct gaatgcatgt  79320
tgctttcaca ccatcacaaa gttgaaaaat agtaagtcaa aaccattgta agttggagac  79380
catctgtgta ggcatttctt ctaagctgga gtttttatat cacaaattgg ctatgataca  79440
gtggattaat taggaacatg aaattcatta ctcagatcat tattggctta aatgagattt  79500
tgatagggaa ctaagattgc agtcatagaa acaagagcag ttactttgag tggctttgtg  79560
ttttgttgta acaatgagtg ataaaatata agaagcattg tgctaacatt agagttgtca  79620
gtgatagaaa tgcctttaca tgaacaagag ctatctagtc agtgatgatt agattttcta  79680
actattcatt tgtatataac aagaagaaaa aaacttattt aaattccagc atgaaaatta  79740
atttattata attcctagct cctaaccact ttttccccca ctcacatttt atattttcaa  79800
taggtgaaag tttcctaaaa taaaatccca gctattgcgt gataactcag cagtctgggc  79860
tctgatttga attgattaaa aagggatatt gttttgtagc cacatactaa aacctgaata  79920
tagtatgaga ctccatgtaa caaatgtttt tacaagtcct tttcccaaca atttctttta  79980
gcctcactag accactttca cccagcaaag agagtatgaa tgctgtgttt tcttaaaagc  80040
ctaaaagtaa ggttattaag ctaatgtaac atggtctcct tagtttttcc tctagaacac  80100
agatcagcaa gttttcttaa agggccagat agtaactgtt ttagactttg caggcccatg  80160
tggtctctgt cttaactatt caactctgct attctcgtaa aagcagccaa tatgtaatga  80220
atgggtgtag ctatattcta atacaactca atttacaaaa actggcagct gacctgccgg  80280
ttgactagcc ctgctctaca gccaaaagca ttgccactat caccaagcag atttcatctt  80340
cttacaggaa ggggtacaca gtgctgccag tcttgcttct gtctctgagt gttgctgctc  80400
tgtgttgtag aaaccctctt aattagaaag cagcagtcta ggatgtagat tcagagactg  80460
tacagtactg aggttctcat gtgagaaaga gattagcagt tagttttatc ttttattaag  80520
tcagtttctt actgtgacta tccttttttt ttaatcaggt acagatgaag tttttagttg  80580
agcaaatgag gcgaccagat ttcatggatg ctctacaggg ctttctgtct cctctaaacc  80640
ctgctcatca actaggaaac ctcaggtact ttcttggggg tttcattgat atatttaaat  80700
aaataccttt tctggataaa atcttgagaa aagtaaaaat gtctgttata attagaatgt  80760
tcaataattt atgcttctct ctctcattct cctaccctca aaataagagt agtatatctt  80820
aagttcagta ctgcctttat tcagaatgag tttttactac ttaaataata cagtttaaaa  80880
ccttctatgg ccagaatttc tgttaccata ggataagaaa tggaaatgta atatctgtaa  80940
```

-continued

```
aactaatgat atatctctat atatttgttg gaaattcata tgcaattata taacttttaa  81000
aacttttagt tttttttata ctctttagga atggattcct aaataaaaat tgaggtgaaa  81060
gttgtaaatc tttgtaacac ttcaaaaagc tatattgtat ttatatttta aaataaattt  81120
cagggtaaaa taataataaa gcaaaggtac ctagtaaagt ttttaactat tttaaaggct  81180
tgaagagtgt cgaattatgt cctctgcaaa aaggccactg tggttgaatt gggagaaccc  81240
agacatcatg tcagagttac tgtttcagaa caatgagatc atctttaaaa atggggatgg  81300
taaggaagag tattaatgag cttatgatgc atgaatttag ctatcttttt atacacagga  81360
tatttatgaa ccatgaaaac tactgaaagc catttaagga atatacacat gtgataaaat  81420
atgtaatatt tatcagatgt cttgaccttt gaaatatgca tgtataatca atgaaaagaa  81480
aagaagtact aggtttagat cagaagtcct gaaatcagtt ttttgttttt tctttttcct  81540
gttccctgcc tccaaccccc ctcccgtgga cctgtgtaga gaagtatttt ttgttgttgt  81600
tttggttttt tttttaatca gtttctaatt atcatttgct tagctgtgtg agtatccatt  81660
cattccataa atattctatg tgctaggccc tggggtttta gcagtgaaga aaacagaatc  81720
cctgccctct tggagcttac agcctaacag agaaaagagg gacattaaat gaataattac  81780
aaaaataaaa ttgcaagcat gttgcaaagg aagagtgtag tctgctcagg aaccatataa  81840
aagaaggtac ttatatggag gaaaaggcta tggggggagt gaaggaggat catggatggg  81900
ttttcaatag gaaatgacat ttcagcagtg aattctgttg atcccaatat tttaatataa  81960
acatgtgttc aaatttaagg attcagaaaa ataattacta taaatgcttt aattaaaaat  82020
ttttgtgaga tgcatgctca cttatcctac attgttattc aaatatgttt atgcaaagac  82080
tttaaaagtg gatttaagaa tcagaatatt aagagccatt tgtagtggtg catgcttgtg  82140
atcccagttg ctctggagga ttacttgagc ccaggagttt tagaccagcc tgggcaactt  82200
agcaagaccc catctcaaaa aattataaat acattaataa agctatgtaa aggctttgag  82260
tggacatata cactcattta taaatttttt gaaaagaaat cagaatattg ctttcctgaa  82320
gtttcttttg aagagtaaat atagctgtat ttgtttttca tttgaaaacc atgtgatggc  82380
gtgatcccca aatttgcatc tgtggcatta aatggtgata catattattt gaatttcaga  82440
tttacggcaa gatatgctaa cacttcaaat tattcgtatt atggaaaata tctggcaaaa  82500
tcaaggtctt gatcttcggt aggtaaccag taaggcaacc tgtatgttga aagttatcct  82560
gaaaaagtga actattaata attatagaag catatagagg catatgtcta aaaagaaatg  82620
tatgcagtaa ttatcagtag ttgattacac tatagtactt tgacatatcc tcctcttact  82680
tagaatagct aaattatatt cagctaagta aaaagagcta ataagctaat aaacactctg  82740
ctactgcctc tggagtgtca ccattaggaa caagacaaag gagacacaaa agacccctgt  82800
tttcattcag aaattaagag tttaaaagaa agtttcataa tgggaatttt ctaattctaa  82860
aactgtataa atcctcaaat attggaatca gttttgcagc aaaattatgc aaccagctat  82920
cttagagttt ttaccagtct gttggtttct acccaacttt ccacaatatc agtattatca  82980
ccaagttttc tgtcatgctt catcttctcc tagtcattgt tgcttctaaa atgttcttcc  83040
ttacctgact tgtctttttg caaatccata gtcattcagg caaagcccac tctgtccaaa  83100
gtattttggc ctataagtgg acatagagtc aagtctagct gtaacaacag ggtacattta  83160
gtaggaattg caggtaacac cagacaaggg cttatttgta tgcctcttat aaattttaag  83220
agtagctagt atacaaaaat gtgtcagtga caaatagttg taccctttta ttgcaaagaa  83280
gaaagtggac atttcaggtg acctgctaag gcacaaaatt gtcatcaact tcaaatttgt  83340
```

aactcctgat acgtagctta acccctgctg ctttccaaaa atggttaatg ttatatgaat 83400
caaatttcat tttttggtat aatttcctgt gtcatgagag atccacatgc cactactacc 83460
atgtccccca aaggaataga ctgtaaaaaa gattatagag ctaagaaaga gtaaaggaga 83520
taaccgtgta acgctggtta attacattgt ttaattataa agtaatgact ttgcaaaaaa 83580
gcatctgaag ttaagatgat tagaaatatt aatggttttt tagtcttgta ttttctgaat 83640
attttttaac ttaagtaaat ataagtaaaa attttatttc aagtttaact ttagattaaa 83700
attatttaag taaaatcata acagcatttt tatttatact tggcaaaact ataattcaga 83760
atcgggttta ttttaaccct gcttcttttt tttaataaca agacttagaa gacaattaaa 83820
ttctgtaaac tgtgagcatg ttcaacagtg ataaaaacat aaaataagaa agaatgagca 83880
ggagtacaac cttaagatat ttccctattt acgagggcag gtagaagaaa aggttgtgta 83940
agagaagtca tcaaaggaag ttggagtact agaggaagtg attgacaatt tgtagggcca 84000
gggcttcaag ggggttaaaa gaataaggcc tgtgaaaaag cacttggatt tagtgactca 84060
tcattagttt taagagttta ctcactagag tggtaggtgt agaagctagg ctacaaggaa 84120
ttaagtaaga aaatgaaaat aagtattgac cgtattagga atttaagaaa taaaggaaag 84180
gtggaaaata tggagagtag cttacgagaa gaacagagca aggaaaacca aactttggat 84240
acttacgtgt caatctgaat gttaggtgct ttttttcatt gtctctttaa atcctcacat 84300
ctgcaccctt gactaagtgt cctatttaat tttctatgtg aataaatgag aggtacccta 84360
aaaagcattt gtgccacatc ccaagtatta tggttgtatc aaagggaaac atttgtggga 84420
ttatttgagt tgtgagctga actagctgct gtttttatgg aacacgattt ttacttaaat 84480
aactagtagg caagctatgg ttattcagac atggatattt ggcagacatt ttcttgaaaa 84540
tgaacaatat gtgcctgtct ctttgaagaa aacaactgtg acagtatttg ttgccaatga 84600
taaaattcaa acttgcaaca aaaatttcat tagaaattca aaattagaat tttgaaaatt 84660
ctaattttca ttatctgccg ctgaacctaa tagagtccct aaacttaaca tctttctgat 84720
gagattcttg gtaatattaa caattgtggt tttttagtat ggtataatga aaagtatcaa 84780
catttggaac atctacaaat gaccatgcag gatactataa aatcatgtat gggtaagaga 84840
tccattaaaa ggcaagaaag acaaattgat tttaatgtaa ctgagtatga aaagtttatt 84900
gatacagttt tagattacat tttgcaactt aagaaactta tcttgtcagg ttttagaata 84960
gtaccaaaga aaaatatcac aattatctga aaagtctatt ataatactcc ttctttttct 85020
acctacctat ctttgtgagg ccagattttc tttttatact ttaattaaaa cattgcatta 85080
gattgcatac aaaagcatat atgagaatcc agctgggtac tatgaagcca gacatttaaa 85140
aattttttta aatgtgaaag aatttcactc ttctcactaa attttttaaa tgcatttttt 85200
gtttcatgaa atatgttact tatattaaca tgtcatagtt tgttgctttt aaatgaatta 85260
gtaaatattt aaaattttta ttttccctat ttcaatttct aatatcatta gatgtaattc 85320
acataactaa aagctctttg gagtcctcag taatttctac aagtgtaaag gagtcctgag 85380
accaaaattg agaacttctg ccctacagtt ttatttcgat gtcaattaaa catctttaaa 85440
ttaacacata tttttaaaat cataaatgtt tgtaaaattt taattgccac aataattttc 85500
ttaattcttt tctgataaaa atacagtgct ttctcagttg aaggttataa taaatgatga 85560
caggtaattt tgaggattat tccaggagta tgtttatcac accataaaaa agaaaattaa 85620
aattggggaa aggcagtaaa ggtcatgcat gacaaattta ctaataaaat actcatgttt 85680

-continued

```
tagcctgtta aaacatttgc tattttaaaa ttccatcatt taattgtaaa cgtgttactc  85740
ctctttcaga atgttacctt atggttgtct gtcaatcggt gactgtgtgg gacttattga  85800
ggtggtgcga aattctcaca ctattatgca aattcagtgc aaaggcggct tgaaaggtgc  85860
actgcagttc aacagccaca cactacatca gtggctcaaa gacaagaaca aaggagaaat  85920
gtgagttgta ttattctttc ttcctatgtt aatctaagtt tttgttagat gagtctgtcg  85980
gtgtttgtgt attcctctga gttagaacag agaaaacaat tgtactttct atggaaaaaa  86040
atatgctcaa cctttgaaat atttgatgtt aatggattta aatgattata attactttta  86100
atttggtaaa atcttaaaca ttcatcttat gtattatcta aaatgtattg ttattgctta  86160
ttctttttaa aacaaatgaa tattgcacat tcaaaatttt atttctaatt cattgttaaa  86220
atgattagaa aaaaataatt ttaatgacat gctaagtatt ttttcacatg aagaattatg  86280
ctttggtcag ggaacatctg gaaatttcct tagaaaccca tgaaaacttc acaatctcaa  86340
aatctttgga cataatttcc ttattcgttg tcagtgattg ttttcattgt ttaaatggaa  86400
acttgcaccc tgtttctctt tctcaagttg gcctgaatca ctatatttcc atactactca  86460
tgaggtgttt attctttgta gatatgatgc agccattgac ctgtttacac gttcatgtgc  86520
tggatactgt gtagctacct tcattttggg aattggagat cgtcacaata gtaacatcat  86580
ggtgaaagac gatggacaag taatggtttt ctctgtttaa aatgttttgg tgttcttaat  86640
ttattcaaga cattttgtat ctgcatatat caaactataa cataatttct tatttttgaa  86700
agctgtttca tatagatttt ggacactttt tggatcacaa gaagaaaaaa tttggttata  86760
aacgagaacg tgtgccattt gttttgacac aggatttctt aatagtgatt agtaaaggag  86820
cccaagaatg cacaaagaca agagaatttg agaggtgagc tcgagcaatt aaaaacacaa  86880
aataaagagt tctggctgct ctattagaaa caatcaatat ttttcaagca atttcaaaat  86940
aataaatgtt ggctgggtgt ggtggttcat gcctgtaatc ccaactcttt gggaggccga  87000
ggctggagga tcacttgagc tcaggaattg aaaccagcct gggtaacata gagagaattc  87060
atgtctacaa aaaaatttaa aaagtagcca ggcgtggtgg catgcactgt agtcccagct  87120
actcaggagg ctgagatggg aggatcactt gagcccagga ggttgaggtt gcagtgagcc  87180
attatcacgc cactgtactc caacctgggc aacagagtga gaccctgtat caaaataaat  87240
aaaatgaaat aatagaagtt cttttaccac ttcagcaaaa actatttttt gtttgttttt  87300
tattctatct tatttcaata gcttttgggg tacacgtggt ttttgattac atggatgaat  87360
taaatagtgg taaagtctga gattttagcg cacctgtaac ccaagtagtg tgctttgccc  87420
ccagtatata cttttttatc cctcactgtt cttcccaccg tctcccatct gagtctctgt  87480
agtccattat atcactctgt atgcctttgt gtacctatag cttagctccc acttacaagt  87540
gagaacatac tgtattttca ggttttccat tcctggcctc cagctccatc ccagttgctg  87600
caaaagacat tatttcattc ttttctgtgg tggagtagta ttctgtggtg tatatgtaca  87660
ctttctttat ccactcattg gtcagtgggt acttaacgtt ggtttcatat ctttgcaatt  87720
gtgaattgtg ctgcagtaaa catacgatat gcatgcagat gcctttttga tataatgact  87780
tcttttcctc tgggtagagg gattcctgga ccaaatggta gatctacttt tagttcttta  87840
agaaatctcc atactgtttt ccatagaggc tgtactaatt tacattccca ccaggagtgt  87900
ataagcattc tcatttcacc acatccatgt caacatctgt tgttttttga ctttttaatt  87960
atggccattc ttgcaggagt aaggtggtat ctcattgtgg ttttaatttg catttccctg  88020
atgattaatg atgttgagca ttttttcatg tttgttgacc atttatatat cttcttttga  88080
```

```
gaattgtcta ttcatgtcct tagcccactt tttttttttt tttttttttt ttttttgaga  88140
tggagtctca ctcttgttgc ccaggctgga gtacaatggc atgatctcag ctcaccgcaa  88200
cctccacctc ctgggttcaa agcaattctc ctgcctcagc ctcccaagta gctgggacta  88260
caggcacatg ccaccacaca cggctaattt ttgaattttt agtagagacg gggtttcacc  88320
atgttggtca ggctggtctt gaattcctga cctcaggtga tccacccgcc tcagcctccc  88380
taagtgctgg gattacaggc ttgagccact gcatcctgct ttaacccact ttttgatggg  88440
attctttgtt tcttgctgat ttgagttcct tatagattct ggatattagt cctttgtcag  88500
atgcatagtt tgggaatatt ttctcccatt ctacgggttg tctgttaact ttgatgattc  88560
tttcttttgt tatgcagagg ctttttagtt taattaggtc ccatttattt tgtttgtttt  88620
tgtcgcattt gcttttgggg tcttagtcat ttattatttg cctaggccag tgtttaaaag  88680
agtttttcct aagttatctt ctagaatttt tatggtttca ggtcttagat ttaagtcttc  88740
gatccatctt gagttgattt ttgtataagg tgagagacag ggatccagtt tcattctttt  88800
acatgtggct agctagtttt cccaccacca tttattaaac agaatgtcct ttctccaatt  88860
tatgttttta tatgtctaag atcagttcgt tgtaagtttt tggctttatt tctaggttct  88920
ccattctgtt ccattggtct gtgtgtctgc ttttgtgtgt atctgctgtt ttggtaatta  88980
tagtttcctg gtataatttg aagtccagta atgtgatgcc tccagatttg ttctttttgc  89040
ttagtcttgc tttggctatt cagactcttt ttggtcggtt ttatatgaat tttaggattt  89100
tttttctaa ttctgtgaaa aatgatggtg acagtgtttt gtagttttcc ttgaaaagat  89160
ctttcacccc cttggttaag tacattccta ggtatttttt tgaagctaaa agggcttgtg  89220
ttcttaattt gattctcagc ttggttgttg ttggtgtata gcaatgctgc tgatttgtgt  89280
acactgattt tgtaacctga gactttactg aattcattta tcaaatctag gagtcttttt  89340
ttttatcttt tttaagacag agtcttgctc tgtcccccag gctagagcgt agtggtgcga  89400
tctcagctca ctgcaacctc cacctcctgg gtttaagcaa ttctcctgcc tcagctttcc  89460
aagtagctgg gattacaggc atgcaccacc atgctcagct aatttttata tttttttagta  89520
gagatggggt ttcactttgt tggccaggct ggtcttgaac tcccaatctc gggtgatcct  89580
cctgcctcgg cttcccaaag tgctgggatt atagaaatga gccaccacac ctggctgaaa  89640
tctaggaatt ttttggagaa ctcttgggtt ttctaggtat atgattatgt cattggtaaa  89700
cagctatagt ttgacttcct cttttccaat ttggatgcca atgtgggctt ccttgtcttg  89760
ttctagttct caggggggagt gctttcagct tttccccatt cagtatgata ttggccgtgg  89820
gtttgtcaca tgacttttat tattttgagg taagtccctt ctatgcctag tttgttgagt  89880
gaaaaactat tttaattttt tttttttgta tttatttgtg tgatgctgtg aaggaaaatg  89940
gaaagggaat acaatttaat ttgttgagct aattaaggcc taaaaagaaa gtaatcctta  90000
aacttcataa cacattaaag gtttttattt actgagcttt aaatagttgg actccacctc  90060
tatattgaca aataatgtat agtgcttaat acgacatttt ttggtcatac actttgagga  90120
aagtcagtca accataatca ccttgtttat tcataacttt tttaccacct tatggtatct  90180
cattagacta tatcagactt taaagtactt tttacaatct tctataaaat tctgctttgt  90240
ctacaacaca gtcctgactc tagcttaagc acaaaaggat ttagtatgaa ccaattcata  90300
catttaatac ttattaaact cctgacatgc caggcattgt tgtaggtgct ggtaataaag  90360
cagtttttaa aaagtcctta ttctcttgaa gtttacattc tagtggggta aagggaatca  90420
```

aaagatgttg gtaagagaag tgagagagga atgctatttt tttatagctt tgtctacgaa 90480
agcctctcta attttgtgac atttgagcaa agacctgaag gtattaacat catttgctcc 90540
aaactgacca aactgttctt attacttata ggtttcagga gatgtgttac aaggcttatc 90600
tagctattcg acagcatgcc aatctcttca taaatctttt ctcaatgatg cttggctctg 90660
gaatgccaga actacaatct tttgatgaca ttgcatacat tcgaaagacc ctagccttag 90720
ataaaactga gcaagaggct ttggagtatt tcatgaaaca aatgaatgat gcacatcatg 90780
gtggctggac aacaaaaatg gattggatct tccacacaat taaacagcat gcattgaact 90840
gaaaagataa ctgagaaaat gaaagctcac tctggattcc acactgcact gttaataact 90900
ctcagcaggc aaagaccgat tgcataggaa ttgcacaatc catgaacagc attagaattt 90960
acagcaagaa cagaaataaa atactatata atttaaataa tgtaaacgca aacagggttt 91020
gatagcactt aaactagttc atttcaaaat taagctttag aataatgcgc aatttcatgt 91080
tatgccttaa gtccaaaaag gtaaactttg aagattgttt gtatcttttt ttaaaaaaca 91140
aaacaaaaca aaaatcccca aaatatatag aaatgatgga gaaggaaaaa gtgatggttt 91200
tttttgtctt gcaaatgttc tatgttttga aatgtggaca caacaaaggc tgttattgca 91260
ttaggtgtaa gtaaactgga gtttatgtta aattacattg attggaaaag aatgaaaatt 91320
tcttattttt ccattgctgt tcaatttata gtttgaagtg ggtttttgac tgcttgttta 91380
atgaagaaaa atgcttgggg tggaagggac tcttgagatt tcaccagaga ctttttcttt 91440
ttaataaatc aaaccttttg atgatttgag gttttatctg cagttttgga agcagtcaca 91500
aatgagacct gttataaggt ggtatttttt tttttcttct ggacagtatt taaaggatct 91560
tattcttatt tcccagggaa attctgggct cccacaaagt aaaaaaaaaa aaaaatcata 91620
gaaaaagaat gagcaggaat agttcttatt ccagaattgt acagtattca ccttaagttg 91680
atttttttc tccttctgca attgaactga atacattttt catgcatgtt ttccagaaaa 91740
tagaagtatt aatgttatta aaaagattat ttttttatt aaaggctatt tatattatag 91800
aaactatcat taatatatat tctttattta catgatctgt cccatagtca tgcattgttt 91860
tgcaccccaa atttttatt gttcatagca gcatggtcag ctttcttctt gatctataga 91920
tgaggctcag gcactatccc atttatacca ataaccagtg tataactact taaggaaaac 91980
ataaaaactt catcttcttt ccttttattt cttatgtgaa tctcccgtct tccattctct 92040
tttataattg agaatgtctc aatcatatga aattagttac cagaattaac acaatttaga 92100
ctatcttcct gattccttaa accccttac tgaagtatac tcatgaataa tactttaaaa 92160
tatgggggaa tagaaaccat gaacttttta cctttttaaa ctatttatcc atatctccaa 92220
agtagaacat taaaccattt taagatatgt ctcattccca agtagtcaga gctcactctc 92280
caactttatt aaatactatt tgagcacagg acacattctt aaacattttg aaaaacatta 92340
acccaagatg tagaggctac tgctagtcgt cattctagaa tctgatattt tactctgtat 92400
ttgaaatgaa tgattaatgt cctaggaaat tagctttagc agatgtccag gtgccacatc 92460
aaaaaagtgc aataattatt gacagttttt tagattaggc atattattgg aaaacaactt 92520
tataaagagt gaacattgta tactctagta aaacagcatc actttaaaaa tattcattta 92580
tgaaatctgt tacctatagt tgaagtcttg agtagtgaac aagggactct aataccaata 92640
ctcttaatat ctggctattt tagatccctt aaagggcata attattggaa atttaggtat 92700
ttcactaaag catgtatata atattgccaa caagaaaagt aaatttgaag attaagggaa 92760
cttacttctg caaactgtct tgcgatagtt aagcagaatt taaactctgt tttaagcagg 92820

```
aaaccagaaa gattattttg cagttgtaga agatttcata acttattaaa acttattaac  92880

attttgtgtt gtttagatat aggcagttga tacatactaa catcccagcc ttttcaatat  92940

cagggttaaa ttataggaaa actcagtaaa atggtacaaa tctgaaagtt tgatggtaga  93000

aactgaagat ttaacagaga actgtgtttt acccgagtgc caaaaatgct gtgagcctcc  93060

ttgcacaaaa tttataccac ttttgcattt ttatctatca gtccagatag ttgtctcccc  93120

tccttctccc aggacctctc caccattaaa atgcacaaac cacatggccg atttcaccat  93180

ttacatttat                                                         93190


<210> SEQ ID NO 2
<211> LENGTH: 1068
<212> TYPE: PRT
<213> ORGANISM: Homo sapiens

<400> SEQUENCE: 2

Met Pro Pro Arg Pro Ser Ser Gly Glu Leu Trp Gly Ile His Leu Met
1               5                   10                  15

Pro Pro Arg Ile Leu Val Glu Cys Leu Leu Pro Asn Gly Met Ile Val
            20                  25                  30

Thr Leu Glu Cys Leu Arg Glu Ala Thr Leu Ile Thr Ile Lys His Glu
        35                  40                  45

Leu Phe Lys Glu Ala Arg Lys Tyr Pro Leu His Gln Leu Leu Gln Asp
    50                  55                  60

Glu Ser Ser Tyr Ile Phe Val Ser Val Thr Gln Glu Ala Glu Arg Glu
65                  70                  75                  80

Glu Phe Phe Asp Glu Thr Arg Arg Leu Cys Asp Leu Arg Leu Phe Gln
                85                  90                  95

Pro Phe Leu Lys Val Ile Glu Pro Val Gly Asn Arg Glu Glu Lys Ile
            100                 105                 110

Leu Asn Arg Glu Ile Gly Phe Ala Ile Gly Met Pro Val Cys Glu Phe
        115                 120                 125

Asp Met Val Lys Asp Pro Glu Val Gln Asp Phe Arg Arg Asn Ile Leu
    130                 135                 140

Asn Val Cys Lys Glu Ala Val Asp Leu Arg Asp Leu Asn Ser Pro His
145                 150                 155                 160

Ser Arg Ala Met Tyr Val Tyr Pro Pro Asn Val Glu Ser Ser Pro Glu
                165                 170                 175

Leu Pro Lys His Ile Tyr Asn Lys Leu Asp Lys Gly Gln Ile Ile Val
            180                 185                 190

Val Ile Trp Val Ile Val Ser Pro Asn Asn Asp Lys Gln Lys Tyr Thr
        195                 200                 205

Leu Lys Ile Asn His Asp Cys Val Pro Glu Gln Val Ile Ala Glu Ala
    210                 215                 220

Ile Arg Lys Lys Thr Arg Ser Met Leu Leu Ser Ser Glu Gln Leu Lys
225                 230                 235                 240

Leu Cys Val Leu Glu Tyr Gln Gly Lys Tyr Ile Leu Lys Val Cys Gly
                245                 250                 255

Cys Asp Glu Tyr Phe Leu Glu Lys Tyr Pro Leu Ser Gln Tyr Lys Tyr
            260                 265                 270

Ile Arg Ser Cys Ile Met Leu Gly Arg Met Pro Asn Leu Met Leu Met
        275                 280                 285

Ala Lys Glu Ser Leu Tyr Ser Gln Leu Pro Met Asp Cys Phe Thr Met
    290                 295                 300
```

-continued

```
Pro Ser Tyr Ser Arg Arg Ile Ser Thr Ala Thr Pro Tyr Met Asn Gly
305                 310                 315                 320

Glu Thr Ser Thr Lys Ser Leu Trp Val Ile Asn Ser Ala Leu Arg Ile
                325                 330                 335

Lys Ile Leu Cys Ala Thr Tyr Val Asn Val Asn Ile Arg Asp Ile Asp
            340                 345                 350

Lys Ile Tyr Val Arg Thr Gly Ile Tyr His Gly Gly Glu Pro Leu Cys
        355                 360                 365

Asp Asn Val Asn Thr Gln Arg Val Pro Cys Ser Asn Pro Arg Trp Asn
    370                 375                 380

Glu Trp Leu Asn Tyr Asp Ile Tyr Ile Pro Asp Leu Pro Arg Ala Ala
385                 390                 395                 400

Arg Leu Cys Leu Ser Ile Cys Ser Val Lys Gly Arg Lys Gly Ala Lys
                405                 410                 415

Glu Glu His Cys Pro Leu Ala Trp Gly Asn Ile Asn Leu Phe Asp Tyr
            420                 425                 430

Thr Asp Thr Leu Val Ser Gly Lys Met Ala Leu Asn Leu Trp Pro Val
        435                 440                 445

Pro His Gly Leu Glu Asp Leu Leu Asn Pro Ile Gly Val Thr Gly Ser
    450                 455                 460

Asn Pro Asn Lys Glu Thr Pro Cys Leu Glu Leu Glu Phe Asp Trp Phe
465                 470                 475                 480

Ser Ser Val Val Lys Phe Pro Asp Met Ser Val Ile Glu Glu His Ala
                485                 490                 495

Asn Trp Ser Val Ser Arg Glu Ala Gly Phe Ser Tyr Ser His Ala Gly
            500                 505                 510

Leu Ser Asn Arg Leu Ala Arg Asp Asn Glu Leu Arg Glu Asn Asp Lys
        515                 520                 525

Glu Gln Leu Lys Ala Ile Ser Thr Arg Asp Pro Leu Ser Glu Ile Thr
    530                 535                 540

Glu Gln Glu Lys Asp Phe Leu Trp Ser His Arg His Tyr Cys Val Thr
545                 550                 555                 560

Ile Pro Glu Ile Leu Pro Lys Leu Leu Leu Ser Val Lys Trp Asn Ser
                565                 570                 575

Arg Asp Glu Val Ala Gln Met Tyr Cys Leu Val Lys Asp Trp Pro Pro
            580                 585                 590

Ile Lys Pro Glu Gln Ala Met Glu Leu Leu Asp Cys Asn Tyr Pro Asp
        595                 600                 605

Pro Met Val Arg Gly Phe Ala Val Arg Cys Leu Glu Lys Tyr Leu Thr
    610                 615                 620

Asp Asp Lys Leu Ser Gln Tyr Leu Ile Gln Leu Val Gln Val Leu Lys
625                 630                 635                 640

Tyr Glu Gln Tyr Leu Asp Asn Leu Leu Val Arg Phe Leu Leu Lys Lys
                645                 650                 655

Ala Leu Thr Asn Gln Arg Ile Gly His Phe Phe Phe Trp His Leu Lys
            660                 665                 670

Ser Glu Met His Asn Lys Thr Val Ser Gln Arg Phe Gly Leu Leu Leu
        675                 680                 685

Glu Ser Tyr Cys Arg Ala Cys Gly Met Tyr Leu Lys His Leu Asn Arg
    690                 695                 700

Gln Val Glu Ala Met Glu Lys Leu Ile Asn Leu Thr Asp Ile Leu Lys
705                 710                 715                 720
```

```
Gln Glu Lys Lys Asp Glu Thr Gln Lys Val Gln Met Lys Phe Leu Val
                725                 730                 735

Glu Gln Met Arg Arg Pro Asp Phe Met Asp Ala Leu Gln Gly Phe Leu
            740                 745                 750

Ser Pro Leu Asn Pro Ala His Gln Leu Gly Asn Leu Arg Leu Glu Glu
        755                 760                 765

Cys Arg Ile Met Ser Ser Ala Lys Arg Pro Leu Trp Leu Asn Trp Glu
    770                 775                 780

Asn Pro Asp Ile Met Ser Glu Leu Leu Phe Gln Asn Asn Glu Ile Ile
785                 790                 795                 800

Phe Lys Asn Gly Asp Asp Leu Arg Gln Asp Met Leu Thr Leu Gln Ile
                805                 810                 815

Ile Arg Ile Met Glu Asn Ile Trp Gln Asn Gln Gly Leu Asp Leu Arg
            820                 825                 830

Met Leu Pro Tyr Gly Cys Leu Ser Ile Gly Asp Cys Val Gly Leu Ile
        835                 840                 845

Glu Val Val Arg Asn Ser His Thr Ile Met Gln Ile Gln Cys Lys Gly
    850                 855                 860

Gly Leu Lys Gly Ala Leu Gln Phe Asn Ser His Thr Leu His Gln Trp
865                 870                 875                 880

Leu Lys Asp Lys Asn Lys Gly Glu Ile Tyr Asp Ala Ala Ile Asp Leu
                885                 890                 895

Phe Thr Arg Ser Cys Ala Gly Tyr Cys Val Ala Thr Phe Ile Leu Gly
            900                 905                 910

Ile Gly Asp Arg His Asn Ser Asn Ile Met Val Lys Asp Asp Gly Gln
        915                 920                 925

Leu Phe His Ile Asp Phe Gly His Phe Leu Asp His Lys Lys Lys Lys
    930                 935                 940

Phe Gly Tyr Lys Arg Glu Arg Val Pro Phe Val Leu Thr Gln Asp Phe
945                 950                 955                 960

Leu Ile Val Ile Ser Lys Gly Ala Gln Glu Cys Thr Lys Thr Arg Glu
                965                 970                 975

Phe Glu Arg Phe Gln Glu Met Cys Tyr Lys Ala Tyr Leu Ala Ile Arg
            980                 985                 990

Gln His Ala Asn Leu Phe Ile Asn  Leu Phe Ser Met Met  Leu Gly Ser
        995                 1000                1005

Gly Met  Pro Glu Leu Gln Ser  Phe Asp Asp Ile Ala  Tyr Ile Arg
    1010                1015                1020

Lys Thr  Leu Ala Leu Asp Lys  Thr Glu Gln Glu Ala  Leu Glu Tyr
    1025                1030                1035

Phe Met  Lys Gln Met Asn Asp  Ala His His Gly Gly  Trp Thr Thr
    1040                1045                1050

Lys Met  Asp Trp Ile Phe His  Thr Ile Lys Gln His  Ala Leu Asn
    1055                1060                1065
```

<210> SEQ ID NO 3
<211> LENGTH: 125
<212> TYPE: DNA
<213> ORGANISM: Homo sapiens

<400> SEQUENCE: 3

```
agtaacagac tagctagaga caatgaatta agggaaaatg acaaagaaca gctcaaagca     60

atttctacac gagatcctct ctctgaaatc actgagcagg agaaagattt tctatggagt    120

cacag                                                                125
```

<210> SEQ ID NO 4
<211> LENGTH: 42
<212> TYPE: PRT
<213> ORGANISM: Homo sapiens

<400> SEQUENCE: 4

```
Glu His Ala Asn Trp Ser Val Ser Arg Glu Ala Gly Phe Ser Tyr Ser
1               5                   10                  15

His Ala Gly Leu Ser Asn Arg Leu Ala Arg Asp Asn Glu Leu Arg Glu
            20                  25                  30

Asn Asp Lys Glu Gln Leu Lys Ala Ile Ser
        35                  40
```

<210> SEQ ID NO 5
<211> LENGTH: 107
<212> TYPE: PRT
<213> ORGANISM: Mus musculus

<400> SEQUENCE: 5

```
Asp Thr Val Met Thr Gln Ser His Lys Ile Met Ser Thr Ser Val Gly
1               5                   10                  15

Asp Arg Val Ser Ile Thr Cys Lys Ala Ser Gln Asp Val Ser Ile Gly
            20                  25                  30

Val Ala Trp Tyr Gln Gln Arg Pro Gly Gln Ser Pro Lys Leu Leu Ile
        35                  40                  45

Tyr Ser Ala Ser Tyr Arg Tyr Thr Gly Val Pro Asp Arg Phe Thr Gly
    50                  55                  60

Ser Gly Ser Gly Thr Asp Phe Thr Phe Thr Ile Ser Ser Val Gln Ala
65                  70                  75                  80

Glu Asp Leu Ala Val Tyr Tyr Cys Gln Gln Tyr Tyr Ile Tyr Pro Tyr
                85                  90                  95

Thr Phe Gly Gly Gly Thr Lys Leu Glu Ile Lys
            100                 105
```

<210> SEQ ID NO 6
<211> LENGTH: 119
<212> TYPE: PRT
<213> ORGANISM: Mus musculus

<400> SEQUENCE: 6

```
Glu Val Gln Leu Gln Gln Ser Gly Pro Glu Leu Val Lys Pro Gly Thr
1               5                   10                  15

Ser Val Lys Ile Ser Cys Lys Ala Ser Gly Phe Thr Phe Thr Asp Tyr
            20                  25                  30

Thr Met Asp Trp Val Lys Gln Ser His Gly Lys Ser Leu Glu Trp Ile
        35                  40                  45

Gly Asp Val Asn Pro Asn Ser Gly Gly Ser Ile Tyr Asn Gln Arg Phe
    50                  55                  60

Lys Gly Lys Ala Ser Leu Thr Val Asp Arg Ser Ser Arg Ile Val Tyr
65                  70                  75                  80

Met Glu Leu Arg Ser Leu Thr Phe Glu Asp Thr Ala Val Tyr Tyr Cys
                85                  90                  95

Ala Arg Asn Leu Gly Pro Ser Phe Tyr Phe Asp Tyr Trp Gly Gln Gly
            100                 105                 110

Thr Thr Leu Thr Val Ser Ser
        115
```

<210> SEQ ID NO 7
<211> LENGTH: 107
<212> TYPE: PRT
<213> ORGANISM: Artificial Sequence
<220> FEATURE:
<223> OTHER INFORMATION: Description of Artificial Sequence: Synthetic humanized 574 variable light chain polypeptide

<400> SEQUENCE: 7

```
Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Asp Val Ser Ile Gly
            20                  25                  30

Val Ala Trp Tyr Gln Gln Lys Pro Gly Lys Ala Pro Lys Leu Leu Ile
        35                  40                  45

Tyr Ser Ala Ser Tyr Arg Tyr Thr Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Tyr Ile Tyr Pro Tyr
                85                  90                  95

Thr Phe Gly Gln Gly Thr Lys Val Glu Ile Lys
            100                 105
```

<210> SEQ ID NO 8
<211> LENGTH: 119
<212> TYPE: PRT
<213> ORGANISM: Artificial Sequence
<220> FEATURE:
<223> OTHER INFORMATION: Description of Artificial Sequence: Synthetic humanized 574 variable heavy chain polypeptide

<400> SEQUENCE: 8

```
Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Thr Asp Tyr
            20                  25                  30

Thr Met Asp Trp Val Arg Gln Ala Pro Gly Lys Gly Leu Glu Trp Val
        35                  40                  45

Ala Asp Val Asn Pro Asn Ser Gly Gly Ser Ile Tyr Asn Gln Arg Phe
    50                  55                  60

Lys Gly Arg Phe Thr Leu Ser Val Asp Arg Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Asn Leu Gly Pro Ser Phe Tyr Phe Asp Tyr Trp Gly Gln Gly
            100                 105                 110

Thr Leu Val Thr Val Ser Ser
        115
```

<210> SEQ ID NO 9
<211> LENGTH: 107
<212> TYPE: PRT
<213> ORGANISM: Artificial Sequence
<220> FEATURE:
<223> OTHER INFORMATION: Description of Artificial Sequence: Synthetic consensus framework hum kappa1 variable light chain polypeptide

<400> SEQUENCE: 9

-continued

Asp Ile Gln Met Thr Gln Ser Pro Ser Ser Leu Ser Ala Ser Val Gly
1 5 10 15

Asp Arg Val Thr Ile Thr Cys Arg Ala Ser Gln Ser Ile Ser Asn Tyr
20 25 30

Leu Ala Trp Tyr Gln Gln Lys Pro Gly Lys Ala Pro Lys Leu Leu Ile
35 40 45

Tyr Ala Ala Ser Ser Leu Glu Ser Gly Val Pro Ser Arg Phe Ser Gly
50 55 60

Ser Gly Ser Gly Thr Asp Phe Thr Leu Thr Ile Ser Ser Leu Gln Pro
65 70 75 80

Glu Asp Phe Ala Thr Tyr Tyr Cys Gln Gln Tyr Asn Ser Leu Pro Trp
85 90 95

Thr Phe Gly Gln Gly Thr Lys Val Glu Ile Lys
100 105

<210> SEQ ID NO 10
<211> LENGTH: 119
<212> TYPE: PRT
<213> ORGANISM: Artificial Sequence
<220> FEATURE:
<223> OTHER INFORMATION: Description of Artificial Sequence: Synthetic consensus framework hum kappa1 variable heavy chain polypeptide

<400> SEQUENCE: 10

Glu Val Gln Leu Val Glu Ser Gly Gly Gly Leu Val Gln Pro Gly Gly
1 5 10 15

Ser Leu Arg Leu Ser Cys Ala Ala Ser Gly Phe Thr Phe Ser Ser Tyr
20 25 30

Ala Met Ser Trp Val Arg Gln Ala Pro Gly Lys Gly Leu Glu Trp Val
35 40 45

Ala Val Ile Ser Gly Asp Gly Gly Ser Thr Tyr Tyr Ala Asp Ser Val
50 55 60

Lys Gly Arg Phe Thr Ile Ser Arg Asp Asn Ser Lys Asn Thr Leu Tyr
65 70 75 80

Leu Gln Met Asn Ser Leu Arg Ala Glu Asp Thr Ala Val Tyr Tyr Cys
85 90 95

Ala Arg Gly Arg Val Gly Tyr Ser Leu Tyr Asp Tyr Trp Gly Gln Gly
100 105 110

Thr Leu Val Thr Val Ser Ser
115

<210> SEQ ID NO 11
<211> LENGTH: 214
<212> TYPE: PRT
<213> ORGANISM: Artificial Sequence
<220> FEATURE:
<223> OTHER INFORMATION: Description of Artificial Sequence: Synthetic pertuzumab light chain polypeptide

<400> SEQUENCE: 11

Asp Ile Gln Met Thr Gln Ser Pro Ser Ser Leu Ser Ala Ser Val Gly
1 5 10 15

Asp Arg Val Thr Ile Thr Cys Lys Ala Ser Gln Asp Val Ser Ile Gly
20 25 30

Val Ala Trp Tyr Gln Gln Lys Pro Gly Lys Ala Pro Lys Leu Leu Ile
35 40 45

Tyr Ser Ala Ser Tyr Arg Tyr Thr Gly Val Pro Ser Arg Phe Ser Gly
50 55 60

Ser Gly Ser Gly Thr Asp Phe Thr Leu Thr Ile Ser Ser Leu Gln Pro
65 70 75 80

Glu Asp Phe Ala Thr Tyr Tyr Cys Gln Gln Tyr Tyr Ile Tyr Pro Tyr
85 90 95

Thr Phe Gly Gln Gly Thr Lys Val Glu Ile Lys Arg Thr Val Ala Ala
100 105 110

Pro Ser Val Phe Ile Phe Pro Pro Ser Asp Glu Gln Leu Lys Ser Gly
115 120 125

Thr Ala Ser Val Val Cys Leu Leu Asn Asn Phe Tyr Pro Arg Glu Ala
130 135 140

Lys Val Gln Trp Lys Val Asp Asn Ala Leu Gln Ser Gly Asn Ser Gln
145 150 155 160

Glu Ser Val Thr Glu Gln Asp Ser Lys Asp Ser Thr Tyr Ser Leu Ser
165 170 175

Ser Thr Leu Thr Leu Ser Lys Ala Asp Tyr Glu Lys His Lys Val Tyr
180 185 190

Ala Cys Glu Val Thr His Gln Gly Leu Ser Ser Pro Val Thr Lys Ser
195 200 205

Phe Asn Arg Gly Glu Cys
210

<210> SEQ ID NO 12
<211> LENGTH: 448
<212> TYPE: PRT
<213> ORGANISM: Artificial Sequence
<220> FEATURE:
<223> OTHER INFORMATION: Description of Artificial Sequence: Synthetic pertuzumab heavy chain polypeptide

<400> SEQUENCE: 12

Glu Val Gln Leu Val Glu Ser Gly Gly Gly Leu Val Gln Pro Gly Gly
1 5 10 15

Ser Leu Arg Leu Ser Cys Ala Ala Ser Gly Phe Thr Phe Thr Asp Tyr
20 25 30

Thr Met Asp Trp Val Arg Gln Ala Pro Gly Lys Gly Leu Glu Trp Val
35 40 45

Ala Asp Val Asn Pro Asn Ser Gly Gly Ser Ile Tyr Asn Gln Arg Phe
50 55 60

Lys Gly Arg Phe Thr Leu Ser Val Asp Arg Ser Lys Asn Thr Leu Tyr
65 70 75 80

Leu Gln Met Asn Ser Leu Arg Ala Glu Asp Thr Ala Val Tyr Tyr Cys
85 90 95

Ala Arg Asn Leu Gly Pro Ser Phe Tyr Phe Asp Tyr Trp Gly Gln Gly
100 105 110

Thr Leu Val Thr Val Ser Ser Ala Ser Thr Lys Gly Pro Ser Val Phe
115 120 125

Pro Leu Ala Pro Ser Ser Lys Ser Thr Ser Gly Gly Thr Ala Ala Leu
130 135 140

Gly Cys Leu Val Lys Asp Tyr Phe Pro Glu Pro Val Thr Val Ser Trp
145 150 155 160

Asn Ser Gly Ala Leu Thr Ser Gly Val His Thr Phe Pro Ala Val Leu
165 170 175

Gln Ser Ser Gly Leu Tyr Ser Leu Ser Ser Val Val Thr Val Pro Ser
180 185 190

Ser Ser Leu Gly Thr Gln Thr Tyr Ile Cys Asn Val Asn His Lys Pro

-continued

```
        195                 200                 205

Ser Asn Thr Lys Val Asp Lys Lys Val Glu Pro Lys Ser Cys Asp Lys
    210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Asn Ser Thr Tyr Arg Val
    290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Arg Glu Glu Met Thr Lys Asn Gln Val Ser Leu Thr
        355                 360                 365

Cys Leu Val Lys Gly Phe Tyr Pro Ser Asp Ile Ala Val Glu Trp Glu
    370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
            420                 425                 430

Ala Leu His Asn His Tyr Thr Gln Lys Ser Leu Ser Leu Ser Pro Gly
        435                 440                 445


<210> SEQ ID NO 13
<211> LENGTH: 214
<212> TYPE: PRT
<213> ORGANISM: Artificial Sequence
<220> FEATURE:
<223> OTHER INFORMATION: Description of Artificial Sequence: Synthetic
      trastuzumab light chain polypeptide

<400> SEQUENCE: 13

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Asn Thr Ala
            20                  25                  30

Val Ala Trp Tyr Gln Gln Lys Pro Gly Lys Ala Pro Lys Leu Leu Ile
        35                  40                  45

Tyr Ser Ala Ser Phe Leu Tyr Ser Gly Val Pro Ser Arg Phe Ser Gly
    50                  55                  60

Ser Arg Ser Gly Thr Asp Phe Thr Leu Thr Ile Ser Ser Leu Gln Pro
65                  70                  75                  80

Glu Asp Phe Ala Thr Tyr Tyr Cys Gln Gln His Tyr Thr Thr Pro Pro
                85                  90                  95

Thr Phe Gly Gln Gly Thr Lys Val Glu Ile Lys Arg Thr Val Ala Ala
            100                 105                 110
```

-continued

```
Pro Ser Val Phe Ile Phe Pro Pro Ser Asp Glu Gln Leu Lys Ser Gly
        115                 120                 125

Thr Ala Ser Val Val Cys Leu Leu Asn Asn Phe Tyr Pro Arg Glu Ala
    130                 135                 140

Lys Val Gln Trp Lys Val Asp Asn Ala Leu Gln Ser Gly Asn Ser Gln
145                 150                 155                 160

Glu Ser Val Thr Glu Gln Asp Ser Lys Asp Ser Thr Tyr Ser Leu Ser
                165                 170                 175

Ser Thr Leu Thr Leu Ser Lys Ala Asp Tyr Glu Lys His Lys Val Tyr
            180                 185                 190

Ala Cys Glu Val Thr His Gln Gly Leu Ser Ser Pro Val Thr Lys Ser
        195                 200                 205

Phe Asn Arg Gly Glu Cys
    210


<210> SEQ ID NO 14
<211> LENGTH: 449
<212> TYPE: PRT
<213> ORGANISM: Artificial Sequence
<220> FEATURE:
<223> OTHER INFORMATION: Description of Artificial Sequence: Synthetic
      trastuzumab heavy chain polypeptide

<400> SEQUENCE: 14

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Asn Ile Lys Asp Thr
            20                  25                  30

Tyr Ile His Trp Val Arg Gln Ala Pro Gly Lys Gly Leu Glu Trp Val
        35                  40                  45

Ala Arg Ile Tyr Pro Thr Asn Gly Tyr Thr Arg Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ser Arg Trp Gly Gly Asp Gly Phe Tyr Ala Met Asp Tyr Trp Gly Gln
            100                 105                 110

Gly Thr Leu Val Thr Val Ser Ser Ala Ser Thr Lys Gly Pro Ser Val
        115                 120                 125

Phe Pro Leu Ala Pro Ser Ser Lys Ser Thr Ser Gly Gly Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Gln Thr Tyr Ile Cys Asn Val Asn His Lys
        195                 200                 205

Pro Ser Asn Thr Lys Val Asp Lys Lys Val Glu Pro Lys Ser Cys Asp
    210                 215                 220

Lys Thr His Thr Cys Pro Pro Cys Pro Ala Pro Glu Leu Leu Gly Gly
225                 230                 235                 240

Pro Ser Val Phe Leu Phe Pro Pro Lys Pro Lys Asp Thr Leu Met Ile
                245                 250                 255
```

```
Ser Arg Thr Pro Glu Val Thr Cys Val Val Val Asp Val Ser His Glu
            260                 265                 270

Asp Pro Glu Val Lys Phe Asn Trp Tyr Val Asp Gly Val Glu Val His
        275                 280                 285

Asn Ala Lys Thr Lys Pro Arg Glu Glu Gln Tyr Asn Ser Thr Tyr Arg
    290                 295                 300

Val Val Ser Val Leu Thr Val Leu His Gln Asp Trp Leu Asn Gly Lys
305                 310                 315                 320

Glu Tyr Lys Cys Lys Val Ser Asn Lys Ala Leu Pro Ala Pro Ile Glu
                325                 330                 335

Lys Thr Ile Ser Lys Ala Lys Gly Gln Pro Arg Glu Pro Gln Val Tyr
            340                 345                 350

Thr Leu Pro Pro Ser Arg Glu Glu Met Thr Lys Asn Gln Val Ser Leu
        355                 360                 365

Thr Cys Leu Val Lys Gly Phe Tyr Pro Ser Asp Ile Ala Val Glu Trp
    370                 375                 380

Glu Ser Asn Gly Gln Pro Glu Asn Asn Tyr Lys Thr Thr Pro Pro Val
385                 390                 395                 400

Leu Asp Ser Asp Gly Ser Phe Phe Leu Tyr Ser Lys Leu Thr Val Asp
                405                 410                 415

Lys Ser Arg Trp Gln Gln Gly Asn Val Phe Ser Cys Ser Val Met His
            420                 425                 430

Glu Ala Leu His Asn His Tyr Thr Gln Lys Ser Leu Ser Leu Ser Pro
        435                 440                 445

Gly


<210> SEQ ID NO 15
<211> LENGTH: 217
<212> TYPE: PRT
<213> ORGANISM: Artificial Sequence
<220> FEATURE:
<223> OTHER INFORMATION: Description of Artificial Sequence: Synthetic
      variant pertuzumab light chain polypeptide

<400> SEQUENCE: 15

Val His Ser Asp Ile Gln Met Thr Gln Ser Pro Ser Ser Leu Ser Ala
1               5                   10                  15

Ser Val Gly Asp Arg Val Thr Ile Thr Cys Lys Ala Ser Gln Asp Val
            20                  25                  30

Ser Ile Gly Val Ala Trp Tyr Gln Gln Lys Pro Gly Lys Ala Pro Lys
        35                  40                  45

Leu Leu Ile Tyr Ser Ala Ser Tyr Arg Tyr Thr Gly Val Pro Ser Arg
    50                  55                  60

Phe Ser Gly Ser Gly Ser Gly Thr Asp Phe Thr Leu Thr Ile Ser Ser
65                  70                  75                  80

Leu Gln Pro Glu Asp Phe Ala Thr Tyr Tyr Cys Gln Gln Tyr Tyr Ile
                85                  90                  95

Tyr Pro Tyr Thr Phe Gly Gln Gly Thr Lys Val Glu Ile Lys Arg Thr
            100                 105                 110

Val Ala Ala Pro Ser Val Phe Ile Phe Pro Pro Ser Asp Glu Gln Leu
        115                 120                 125

Lys Ser Gly Thr Ala Ser Val Val Cys Leu Leu Asn Asn Phe Tyr Pro
    130                 135                 140

Arg Glu Ala Lys Val Gln Trp Lys Val Asp Asn Ala Leu Gln Ser Gly
145                 150                 155                 160
```

```
Asn Ser Gln Glu Ser Val Thr Glu Gln Asp Ser Lys Asp Ser Thr Tyr
                165                 170                 175

Ser Leu Ser Ser Thr Leu Thr Leu Ser Lys Ala Asp Tyr Glu Lys His
            180                 185                 190

Lys Val Tyr Ala Cys Glu Val Thr His Gln Gly Leu Ser Ser Pro Val
        195                 200                 205

Thr Lys Ser Phe Asn Arg Gly Glu Cys
    210                 215


<210> SEQ ID NO 16
<211> LENGTH: 449
<212> TYPE: PRT
<213> ORGANISM: Artificial Sequence
<220> FEATURE:
<223> OTHER INFORMATION: Description of Artificial Sequence: Synthetic
      variant pertuzumab heavy chain polypeptide

<400> SEQUENCE: 16

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Thr Asp Tyr
            20                  25                  30

Thr Met Asp Trp Val Arg Gln Ala Pro Gly Lys Gly Leu Glu Trp Val
        35                  40                  45

Ala Asp Val Asn Pro Asn Ser Gly Gly Ser Ile Tyr Asn Gln Arg Phe
    50                  55                  60

Lys Gly Arg Phe Thr Leu Ser Val Asp Arg Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Asn Leu Gly Pro Ser Phe Tyr Phe Asp Tyr Trp Gly Gln Gly
            100                 105                 110

Thr Leu Val Thr Val Ser Ser Ala Ser Thr Lys Gly Pro Ser Val Phe
        115                 120                 125

Pro Leu Ala Pro Ser Ser Lys Ser Thr Ser Gly Gly Thr Ala Ala Leu
    130                 135                 140

Gly Cys Leu Val Lys Asp Tyr Phe Pro Glu Pro Val Thr Val Ser Trp
145                 150                 155                 160

Asn Ser Gly Ala Leu Thr Ser Gly Val His Thr Phe Pro Ala Val Leu
                165                 170                 175

Gln Ser Ser Gly Leu Tyr Ser Leu Ser Ser Val Val Thr Val Pro Ser
            180                 185                 190

Ser Ser Leu Gly Thr Gln Thr Tyr Ile Cys Asn Val Asn His Lys Pro
        195                 200                 205

Ser Asn Thr Lys Val Asp Lys Lys Val Glu Pro Lys Ser Cys Asp Lys
    210                 215                 220

Thr His Thr Cys Pro Pro Cys Pro Ala Pro Glu Leu Leu Gly Gly Pro
225                 230                 235                 240

Ser Val Phe Leu Phe Pro Pro Lys Pro Lys Asp Thr Leu Met Ile Ser
                245                 250                 255

Arg Thr Pro Glu Val Thr Cys Val Val Val Asp Val Ser His Glu Asp
            260                 265                 270

Pro Glu Val Lys Phe Asn Trp Tyr Val Asp Gly Val Glu Val His Asn
        275                 280                 285

Ala Lys Thr Lys Pro Arg Glu Glu Gln Tyr Asn Ser Thr Tyr Arg Val
```

```
    290                 295                 300

Val Ser Val Leu Thr Val Leu His Gln Asp Trp Leu Asn Gly Lys Glu
305                 310                 315                 320

Tyr Lys Cys Lys Val Ser Asn Lys Ala Leu Pro Ala Pro Ile Glu Lys
                325                 330                 335

Thr Ile Ser Lys Ala Lys Gly Gln Pro Arg Glu Pro Gln Val Tyr Thr
            340                 345                 350

Leu Pro Pro Ser Arg Glu Glu Met Thr Lys Asn Gln Val Ser Leu Thr
        355                 360                 365

Cys Leu Val Lys Gly Phe Tyr Pro Ser Asp Ile Ala Val Glu Trp Glu
    370                 375                 380

Ser Asn Gly Gln Pro Glu Asn Asn Tyr Lys Thr Thr Pro Pro Val Leu
385                 390                 395                 400

Asp Ser Asp Gly Ser Phe Phe Leu Tyr Ser Lys Leu Thr Val Asp Lys
                405                 410                 415

Ser Arg Trp Gln Gln Gly Asn Val Phe Ser Cys Ser Val Met His Glu
            420                 425                 430

Ala Leu His Asn His Tyr Thr Gln Lys Ser Leu Ser Leu Ser Pro Gly
        435                 440                 445

Lys


<210> SEQ ID NO 17
<211> LENGTH: 125
<212> TYPE: DNA
<213> ORGANISM: Homo sapiens

<400> SEQUENCE: 17

agtaacagac tagctagaga caatgaatta agggaaaatg acaaagaaca gctcaaagca     60

atttctacac gagatcctct ctctaaaatc actgagcagg agaaagattt tctatggagt    120

cacag                                                                125


<210> SEQ ID NO 18
<211> LENGTH: 1068
<212> TYPE: PRT
<213> ORGANISM: Homo sapiens

<400> SEQUENCE: 18

Met Pro Pro Arg Pro Ser Ser Gly Glu Leu Trp Gly Ile His Leu Met
1               5                   10                  15

Pro Pro Arg Ile Leu Val Glu Cys Leu Leu Pro Asn Gly Met Ile Val
            20                  25                  30

Thr Leu Glu Cys Leu Arg Glu Ala Thr Leu Ile Thr Ile Lys His Glu
        35                  40                  45

Leu Phe Lys Glu Ala Arg Lys Tyr Pro Leu His Gln Leu Leu Gln Asp
    50                  55                  60

Glu Ser Ser Tyr Ile Phe Val Ser Val Thr Gln Glu Ala Glu Arg Glu
65                  70                  75                  80

Glu Phe Phe Asp Glu Thr Arg Arg Leu Cys Asp Leu Arg Leu Phe Gln
                85                  90                  95

Pro Phe Leu Lys Val Ile Glu Pro Val Gly Asn Arg Glu Glu Lys Ile
            100                 105                 110

Leu Asn Arg Glu Ile Gly Phe Ala Ile Gly Met Pro Val Cys Glu Phe
        115                 120                 125

Asp Met Val Lys Asp Pro Glu Val Gln Asp Phe Arg Arg Asn Ile Leu
    130                 135                 140
```

-continued

```
Asn Val Cys Lys Glu Ala Val Asp Leu Arg Asp Leu Asn Ser Pro His
145                 150                 155                 160

Ser Arg Ala Met Tyr Val Tyr Pro Pro Asn Val Glu Ser Ser Pro Glu
                165                 170                 175

Leu Pro Lys His Ile Tyr Asn Lys Leu Asp Lys Gly Gln Ile Ile Val
            180                 185                 190

Val Ile Trp Val Ile Val Ser Pro Asn Asn Asp Lys Gln Lys Tyr Thr
        195                 200                 205

Leu Lys Ile Asn His Asp Cys Val Pro Glu Gln Val Ile Ala Glu Ala
    210                 215                 220

Ile Arg Lys Lys Thr Arg Ser Met Leu Leu Ser Ser Glu Gln Leu Lys
225                 230                 235                 240

Leu Cys Val Leu Glu Tyr Gln Gly Lys Tyr Ile Leu Lys Val Cys Gly
                245                 250                 255

Cys Asp Glu Tyr Phe Leu Glu Lys Tyr Pro Leu Ser Gln Tyr Lys Tyr
            260                 265                 270

Ile Arg Ser Cys Ile Met Leu Gly Arg Met Pro Asn Leu Met Leu Met
        275                 280                 285

Ala Lys Glu Ser Leu Tyr Ser Gln Leu Pro Met Asp Cys Phe Thr Met
    290                 295                 300

Pro Ser Tyr Ser Arg Arg Ile Ser Thr Ala Thr Pro Tyr Met Asn Gly
305                 310                 315                 320

Glu Thr Ser Thr Lys Ser Leu Trp Val Ile Asn Ser Ala Leu Arg Ile
                325                 330                 335

Lys Ile Leu Cys Ala Thr Tyr Val Asn Val Asn Ile Arg Asp Ile Asp
            340                 345                 350

Lys Ile Tyr Val Arg Thr Gly Ile Tyr His Gly Gly Glu Pro Leu Cys
        355                 360                 365

Asp Asn Val Asn Thr Gln Arg Val Pro Cys Ser Asn Pro Arg Trp Asn
    370                 375                 380

Glu Trp Leu Asn Tyr Asp Ile Tyr Ile Pro Asp Leu Pro Arg Ala Ala
385                 390                 395                 400

Arg Leu Cys Leu Ser Ile Cys Ser Val Lys Gly Arg Lys Gly Ala Lys
                405                 410                 415

Glu Glu His Cys Pro Leu Ala Trp Gly Asn Ile Asn Leu Phe Asp Tyr
            420                 425                 430

Thr Asp Thr Leu Val Ser Gly Lys Met Ala Leu Asn Leu Trp Pro Val
        435                 440                 445

Pro His Gly Leu Glu Asp Leu Leu Asn Pro Ile Gly Val Thr Gly Ser
    450                 455                 460

Asn Pro Asn Lys Glu Thr Pro Cys Leu Glu Leu Glu Phe Asp Trp Phe
465                 470                 475                 480

Ser Ser Val Val Lys Phe Pro Asp Met Ser Val Ile Glu Glu His Ala
                485                 490                 495

Asn Trp Ser Val Ser Arg Glu Ala Gly Phe Ser Tyr Ser His Ala Gly
            500                 505                 510

Leu Ser Asn Arg Leu Ala Arg Asp Asn Glu Leu Arg Glu Asn Asp Lys
        515                 520                 525

Glu Gln Leu Lys Ala Ile Ser Thr Arg Asp Pro Leu Ser Lys Ile Thr
    530                 535                 540

Glu Gln Glu Lys Asp Phe Leu Trp Ser His Arg His Tyr Cys Val Thr
545                 550                 555                 560
```

-continued

```
Ile Pro Glu Ile Leu Pro Lys Leu Leu Leu Ser Val Lys Trp Asn Ser
                565                 570                 575

Arg Asp Glu Val Ala Gln Met Tyr Cys Leu Val Lys Asp Trp Pro Pro
            580                 585                 590

Ile Lys Pro Glu Gln Ala Met Glu Leu Leu Asp Cys Asn Tyr Pro Asp
        595                 600                 605

Pro Met Val Arg Gly Phe Ala Val Arg Cys Leu Glu Lys Tyr Leu Thr
    610                 615                 620

Asp Asp Lys Leu Ser Gln Tyr Leu Ile Gln Leu Val Gln Val Leu Lys
625                 630                 635                 640

Tyr Glu Gln Tyr Leu Asp Asn Leu Leu Val Arg Phe Leu Leu Lys Lys
                645                 650                 655

Ala Leu Thr Asn Gln Arg Ile Gly His Phe Phe Phe Trp His Leu Lys
            660                 665                 670

Ser Glu Met His Asn Lys Thr Val Ser Gln Arg Phe Gly Leu Leu Leu
        675                 680                 685

Glu Ser Tyr Cys Arg Ala Cys Gly Met Tyr Leu Lys His Leu Asn Arg
    690                 695                 700

Gln Val Glu Ala Met Glu Lys Leu Ile Asn Leu Thr Asp Ile Leu Lys
705                 710                 715                 720

Gln Glu Lys Lys Asp Glu Thr Gln Lys Val Gln Met Lys Phe Leu Val
                725                 730                 735

Glu Gln Met Arg Arg Pro Asp Phe Met Asp Ala Leu Gln Gly Phe Leu
            740                 745                 750

Ser Pro Leu Asn Pro Ala His Gln Leu Gly Asn Leu Arg Leu Glu Glu
        755                 760                 765

Cys Arg Ile Met Ser Ser Ala Lys Arg Pro Leu Trp Leu Asn Trp Glu
    770                 775                 780

Asn Pro Asp Ile Met Ser Glu Leu Leu Phe Gln Asn Asn Glu Ile Ile
785                 790                 795                 800

Phe Lys Asn Gly Asp Asp Leu Arg Gln Asp Met Leu Thr Leu Gln Ile
                805                 810                 815

Ile Arg Ile Met Glu Asn Ile Trp Gln Asn Gln Gly Leu Asp Leu Arg
            820                 825                 830

Met Leu Pro Tyr Gly Cys Leu Ser Ile Gly Asp Cys Val Gly Leu Ile
        835                 840                 845

Glu Val Val Arg Asn Ser His Thr Ile Met Gln Ile Gln Cys Lys Gly
    850                 855                 860

Gly Leu Lys Gly Ala Leu Gln Phe Asn Ser His Thr Leu His Gln Trp
865                 870                 875                 880

Leu Lys Asp Lys Asn Lys Gly Glu Ile Tyr Asp Ala Ala Ile Asp Leu
                885                 890                 895

Phe Thr Arg Ser Cys Ala Gly Tyr Cys Val Ala Thr Phe Ile Leu Gly
            900                 905                 910

Ile Gly Asp Arg His Asn Ser Asn Ile Met Val Lys Asp Asp Gly Gln
        915                 920                 925

Leu Phe His Ile Asp Phe Gly His Phe Leu Asp His Lys Lys Lys Lys
    930                 935                 940

Phe Gly Tyr Lys Arg Glu Arg Val Pro Phe Val Leu Thr Gln Asp Phe
945                 950                 955                 960

Leu Ile Val Ile Ser Lys Gly Ala Gln Glu Cys Thr Lys Thr Arg Glu
                965                 970                 975

Phe Glu Arg Phe Gln Glu Met Cys Tyr Lys Ala Tyr Leu Ala Ile Arg
```

-continued

```
        980                 985                 990

Gln His Ala Asn Leu Phe Ile Asn  Leu Phe Ser Met Met  Leu Gly Ser
        995                 1000                1005

Gly Met  Pro Glu Leu Gln Ser  Phe Asp Asp Ile Ala  Tyr Ile Arg
    1010                 1015                1020

Lys Thr  Leu Ala Leu Asp Lys  Thr Glu Gln Glu Ala  Leu Glu Tyr
    1025                 1030                1035

Phe Met  Lys Gln Met Asn Asp  Ala His His Gly Gly  Trp Thr Thr
    1040                 1045                1050

Lys Met  Asp Trp Ile Phe His  Thr Ile Lys Gln His  Ala Leu Asn
    1055                 1060                1065
```

<210> SEQ ID NO 19
<211> LENGTH: 125
<212> TYPE: DNA
<213> ORGANISM: Homo sapiens

<400> SEQUENCE: 19

```
agtaacagac tagctagaga caatgaatta agggaaaatg acaaagaaca gctcaaagca     60

atttctacac gagatcctct ctctgaaatc actaagcagg agaaagattt tctatggagt    120

cacag                                                                125
```

<210> SEQ ID NO 20
<211> LENGTH: 1068
<212> TYPE: PRT
<213> ORGANISM: Homo sapiens

<400> SEQUENCE: 20

```
Met Pro Pro Arg Pro Ser Ser Gly Glu Leu Trp Gly Ile His Leu Met
1               5                   10                  15

Pro Pro Arg Ile Leu Val Glu Cys Leu Leu Pro Asn Gly Met Ile Val
            20                  25                  30

Thr Leu Glu Cys Leu Arg Glu Ala Thr Leu Ile Thr Ile Lys His Glu
        35                  40                  45

Leu Phe Lys Glu Ala Arg Lys Tyr Pro Leu His Gln Leu Leu Gln Asp
    50                  55                  60

Glu Ser Ser Tyr Ile Phe Val Ser Val Thr Gln Glu Ala Glu Arg Glu
65                  70                  75                  80

Glu Phe Phe Asp Glu Thr Arg Arg Leu Cys Asp Leu Arg Leu Phe Gln
                85                  90                  95

Pro Phe Leu Lys Val Ile Glu Pro Val Gly Asn Arg Glu Glu Lys Ile
            100                 105                 110

Leu Asn Arg Glu Ile Gly Phe Ala Ile Gly Met Pro Val Cys Glu Phe
        115                 120                 125

Asp Met Val Lys Asp Pro Glu Val Gln Asp Phe Arg Arg Asn Ile Leu
    130                 135                 140

Asn Val Cys Lys Glu Ala Val Asp Leu Arg Asp Leu Asn Ser Pro His
145                 150                 155                 160

Ser Arg Ala Met Tyr Val Tyr Pro Pro Asn Val Glu Ser Ser Pro Glu
                165                 170                 175

Leu Pro Lys His Ile Tyr Asn Lys Leu Asp Lys Gly Gln Ile Ile Val
            180                 185                 190

Val Ile Trp Val Ile Val Ser Pro Asn Asn Asp Lys Gln Lys Tyr Thr
        195                 200                 205

Leu Lys Ile Asn His Asp Cys Val Pro Glu Gln Val Ile Ala Glu Ala
```

```
    210                 215                 220

Ile Arg Lys Lys Thr Arg Ser Met Leu Leu Ser Ser Glu Gln Leu Lys
225                 230                 235                 240

Leu Cys Val Leu Glu Tyr Gln Gly Lys Tyr Ile Leu Lys Val Cys Gly
                245                 250                 255

Cys Asp Glu Tyr Phe Leu Glu Lys Tyr Pro Leu Ser Gln Tyr Lys Tyr
            260                 265                 270

Ile Arg Ser Cys Ile Met Leu Gly Arg Met Pro Asn Leu Met Leu Met
        275                 280                 285

Ala Lys Glu Ser Leu Tyr Ser Gln Leu Pro Met Asp Cys Phe Thr Met
    290                 295                 300

Pro Ser Tyr Ser Arg Arg Ile Ser Thr Ala Thr Pro Tyr Met Asn Gly
305                 310                 315                 320

Glu Thr Ser Thr Lys Ser Leu Trp Val Ile Asn Ser Ala Leu Arg Ile
                325                 330                 335

Lys Ile Leu Cys Ala Thr Tyr Val Asn Val Asn Ile Arg Asp Ile Asp
            340                 345                 350

Lys Ile Tyr Val Arg Thr Gly Ile Tyr His Gly Gly Glu Pro Leu Cys
        355                 360                 365

Asp Asn Val Asn Thr Gln Arg Val Pro Cys Ser Asn Pro Arg Trp Asn
    370                 375                 380

Glu Trp Leu Asn Tyr Asp Ile Tyr Ile Pro Asp Leu Pro Arg Ala Ala
385                 390                 395                 400

Arg Leu Cys Leu Ser Ile Cys Ser Val Lys Gly Arg Lys Gly Ala Lys
                405                 410                 415

Glu Glu His Cys Pro Leu Ala Trp Gly Asn Ile Asn Leu Phe Asp Tyr
            420                 425                 430

Thr Asp Thr Leu Val Ser Gly Lys Met Ala Leu Asn Leu Trp Pro Val
        435                 440                 445

Pro His Gly Leu Glu Asp Leu Leu Asn Pro Ile Gly Val Thr Gly Ser
    450                 455                 460

Asn Pro Asn Lys Glu Thr Pro Cys Leu Glu Leu Glu Phe Asp Trp Phe
465                 470                 475                 480

Ser Ser Val Val Lys Phe Pro Asp Met Ser Val Ile Glu Glu His Ala
                485                 490                 495

Asn Trp Ser Val Ser Arg Glu Ala Gly Phe Ser Tyr Ser His Ala Gly
            500                 505                 510

Leu Ser Asn Arg Leu Ala Arg Asp Asn Glu Leu Arg Glu Asn Asp Lys
        515                 520                 525

Glu Gln Leu Lys Ala Ile Ser Thr Arg Asp Pro Leu Ser Glu Ile Thr
    530                 535                 540

Lys Gln Glu Lys Asp Phe Leu Trp Ser His Arg His Tyr Cys Val Thr
545                 550                 555                 560

Ile Pro Glu Ile Leu Pro Lys Leu Leu Leu Ser Val Lys Trp Asn Ser
                565                 570                 575

Arg Asp Glu Val Ala Gln Met Tyr Cys Leu Val Lys Asp Trp Pro Pro
            580                 585                 590

Ile Lys Pro Glu Gln Ala Met Glu Leu Leu Asp Cys Asn Tyr Pro Asp
        595                 600                 605

Pro Met Val Arg Gly Phe Ala Val Arg Cys Leu Glu Lys Tyr Leu Thr
    610                 615                 620

Asp Asp Lys Leu Ser Gln Tyr Leu Ile Gln Leu Val Gln Val Leu Lys
625                 630                 635                 640
```

```
Tyr Glu Gln Tyr Leu Asp Asn Leu Leu Val Arg Phe Leu Leu Lys Lys
                645                 650                 655

Ala Leu Thr Asn Gln Arg Ile Gly His Phe Phe Phe Trp His Leu Lys
            660                 665                 670

Ser Glu Met His Asn Lys Thr Val Ser Gln Arg Phe Gly Leu Leu Leu
        675                 680                 685

Glu Ser Tyr Cys Arg Ala Cys Gly Met Tyr Leu Lys His Leu Asn Arg
    690                 695                 700

Gln Val Glu Ala Met Glu Lys Leu Ile Asn Leu Thr Asp Ile Leu Lys
705                 710                 715                 720

Gln Glu Lys Lys Asp Glu Thr Gln Lys Val Gln Met Lys Phe Leu Val
                725                 730                 735

Glu Gln Met Arg Arg Pro Asp Phe Met Asp Ala Leu Gln Gly Phe Leu
            740                 745                 750

Ser Pro Leu Asn Pro Ala His Gln Leu Gly Asn Leu Arg Leu Glu Glu
        755                 760                 765

Cys Arg Ile Met Ser Ser Ala Lys Arg Pro Leu Trp Leu Asn Trp Glu
    770                 775                 780

Asn Pro Asp Ile Met Ser Glu Leu Leu Phe Gln Asn Asn Glu Ile Ile
785                 790                 795                 800

Phe Lys Asn Gly Asp Asp Leu Arg Gln Asp Met Leu Thr Leu Gln Ile
                805                 810                 815

Ile Arg Ile Met Glu Asn Ile Trp Gln Asn Gln Gly Leu Asp Leu Arg
            820                 825                 830

Met Leu Pro Tyr Gly Cys Leu Ser Ile Gly Asp Cys Val Gly Leu Ile
        835                 840                 845

Glu Val Val Arg Asn Ser His Thr Ile Met Gln Ile Gln Cys Lys Gly
    850                 855                 860

Gly Leu Lys Gly Ala Leu Gln Phe Asn Ser His Thr Leu His Gln Trp
865                 870                 875                 880

Leu Lys Asp Lys Asn Lys Gly Glu Ile Tyr Asp Ala Ala Ile Asp Leu
                885                 890                 895

Phe Thr Arg Ser Cys Ala Gly Tyr Cys Val Ala Thr Phe Ile Leu Gly
            900                 905                 910

Ile Gly Asp Arg His Asn Ser Asn Ile Met Val Lys Asp Asp Gly Gln
        915                 920                 925

Leu Phe His Ile Asp Phe Gly His Phe Leu Asp His Lys Lys Lys Lys
    930                 935                 940

Phe Gly Tyr Lys Arg Glu Arg Val Pro Phe Val Leu Thr Gln Asp Phe
945                 950                 955                 960

Leu Ile Val Ile Ser Lys Gly Ala Gln Glu Cys Thr Lys Thr Arg Glu
                965                 970                 975

Phe Glu Arg Phe Gln Glu Met Cys Tyr Lys Ala Tyr Leu Ala Ile Arg
            980                 985                 990

Gln His Ala Asn Leu Phe Ile Asn  Leu Phe Ser Met Met  Leu Gly Ser
        995                 1000                 1005

Gly Met  Pro Glu Leu Gln Ser  Phe Asp Asp Ile Ala  Tyr Ile Arg
    1010                 1015                 1020

Lys Thr  Leu Ala Leu Asp Lys  Thr Glu Gln Glu Ala  Leu Glu Tyr
    1025                 1030                 1035

Phe Met  Lys Gln Met Asn Asp  Ala His His Gly Gly  Trp Thr Thr
    1040                 1045                 1050
```

-continued

```
Lys Met  Asp Trp Ile Phe His  Thr Ile Lys Gln His  Ala Leu Asn
    1055                1060                1065


<210> SEQ ID NO 21
<211> LENGTH: 125
<212> TYPE: DNA
<213> ORGANISM: Homo sapiens

<400> SEQUENCE: 21

agtaacagac tagctagaga caatgaatta agggaaaatg acaaagaaca gctcaaagca      60

atttctacac gagatcctct ctctgaaatc actgcgcagg agaaagattt tctatggagt     120

cacag                                                                 125


<210> SEQ ID NO 22
<211> LENGTH: 1068
<212> TYPE: PRT
<213> ORGANISM: Homo sapiens

<400> SEQUENCE: 22

Met Pro Pro Arg Pro Ser Ser Gly Glu Leu Trp Gly Ile His Leu Met
1               5                   10                  15

Pro Pro Arg Ile Leu Val Glu Cys Leu Leu Pro Asn Gly Met Ile Val
            20                  25                  30

Thr Leu Glu Cys Leu Arg Glu Ala Thr Leu Ile Thr Ile Lys His Glu
        35                  40                  45

Leu Phe Lys Glu Ala Arg Lys Tyr Pro Leu His Gln Leu Leu Gln Asp
    50                  55                  60

Glu Ser Ser Tyr Ile Phe Val Ser Val Thr Gln Glu Ala Glu Arg Glu
65                  70                  75                  80

Glu Phe Phe Asp Glu Thr Arg Arg Leu Cys Asp Leu Arg Leu Phe Gln
                85                  90                  95

Pro Phe Leu Lys Val Ile Glu Pro Val Gly Asn Arg Glu Glu Lys Ile
            100                 105                 110

Leu Asn Arg Glu Ile Gly Phe Ala Ile Gly Met Pro Val Cys Glu Phe
        115                 120                 125

Asp Met Val Lys Asp Pro Glu Val Gln Asp Phe Arg Arg Asn Ile Leu
    130                 135                 140

Asn Val Cys Lys Glu Ala Val Asp Leu Arg Asp Leu Asn Ser Pro His
145                 150                 155                 160

Ser Arg Ala Met Tyr Val Tyr Pro Pro Asn Val Glu Ser Ser Pro Glu
                165                 170                 175

Leu Pro Lys His Ile Tyr Asn Lys Leu Asp Lys Gly Gln Ile Ile Val
            180                 185                 190

Val Ile Trp Val Ile Val Ser Pro Asn Asn Asp Lys Gln Lys Tyr Thr
        195                 200                 205

Leu Lys Ile Asn His Asp Cys Val Pro Glu Gln Val Ile Ala Glu Ala
    210                 215                 220

Ile Arg Lys Lys Thr Arg Ser Met Leu Leu Ser Ser Glu Gln Leu Lys
225                 230                 235                 240

Leu Cys Val Leu Glu Tyr Gln Gly Lys Tyr Ile Leu Lys Val Cys Gly
                245                 250                 255

Cys Asp Glu Tyr Phe Leu Glu Lys Tyr Pro Leu Ser Gln Tyr Lys Tyr
            260                 265                 270

Ile Arg Ser Cys Ile Met Leu Gly Arg Met Pro Asn Leu Met Leu Met
        275                 280                 285
```

-continued

```
Ala Lys Glu Ser Leu Tyr Ser Gln Leu Pro Met Asp Cys Phe Thr Met
    290                 295                 300

Pro Ser Tyr Ser Arg Arg Ile Ser Thr Ala Thr Pro Tyr Met Asn Gly
305                 310                 315                 320

Glu Thr Ser Thr Lys Ser Leu Trp Val Ile Asn Ser Ala Leu Arg Ile
                325                 330                 335

Lys Ile Leu Cys Ala Thr Tyr Val Asn Val Asn Ile Arg Asp Ile Asp
            340                 345                 350

Lys Ile Tyr Val Arg Thr Gly Ile Tyr His Gly Gly Glu Pro Leu Cys
        355                 360                 365

Asp Asn Val Asn Thr Gln Arg Val Pro Cys Ser Asn Pro Arg Trp Asn
    370                 375                 380

Glu Trp Leu Asn Tyr Asp Ile Tyr Ile Pro Asp Leu Pro Arg Ala Ala
385                 390                 395                 400

Arg Leu Cys Leu Ser Ile Cys Ser Val Lys Gly Arg Lys Gly Ala Lys
                405                 410                 415

Glu Glu His Cys Pro Leu Ala Trp Gly Asn Ile Asn Leu Phe Asp Tyr
            420                 425                 430

Thr Asp Thr Leu Val Ser Gly Lys Met Ala Leu Asn Leu Trp Pro Val
        435                 440                 445

Pro His Gly Leu Glu Asp Leu Leu Asn Pro Ile Gly Val Thr Gly Ser
    450                 455                 460

Asn Pro Asn Lys Glu Thr Pro Cys Leu Glu Leu Glu Phe Asp Trp Phe
465                 470                 475                 480

Ser Ser Val Val Lys Phe Pro Asp Met Ser Val Ile Glu Glu His Ala
                485                 490                 495

Asn Trp Ser Val Ser Arg Glu Ala Gly Phe Ser Tyr Ser His Ala Gly
            500                 505                 510

Leu Ser Asn Arg Leu Ala Arg Asp Asn Glu Leu Arg Glu Asn Asp Lys
        515                 520                 525

Glu Gln Leu Lys Ala Ile Ser Thr Arg Asp Pro Leu Ser Glu Ile Thr
    530                 535                 540

Ala Gln Glu Lys Asp Phe Leu Trp Ser His Arg His Tyr Cys Val Thr
545                 550                 555                 560

Ile Pro Glu Ile Leu Pro Lys Leu Leu Leu Ser Val Lys Trp Asn Ser
                565                 570                 575

Arg Asp Glu Val Ala Gln Met Tyr Cys Leu Val Lys Asp Trp Pro Pro
            580                 585                 590

Ile Lys Pro Glu Gln Ala Met Glu Leu Leu Asp Cys Asn Tyr Pro Asp
        595                 600                 605

Pro Met Val Arg Gly Phe Ala Val Arg Cys Leu Glu Lys Tyr Leu Thr
    610                 615                 620

Asp Asp Lys Leu Ser Gln Tyr Leu Ile Gln Leu Val Gln Val Leu Lys
625                 630                 635                 640

Tyr Glu Gln Tyr Leu Asp Asn Leu Leu Val Arg Phe Leu Leu Lys Lys
                645                 650                 655

Ala Leu Thr Asn Gln Arg Ile Gly His Phe Phe Phe Trp His Leu Lys
            660                 665                 670

Ser Glu Met His Asn Lys Thr Val Ser Gln Arg Phe Gly Leu Leu Leu
        675                 680                 685

Glu Ser Tyr Cys Arg Ala Cys Gly Met Tyr Leu Lys His Leu Asn Arg
    690                 695                 700

Gln Val Glu Ala Met Glu Lys Leu Ile Asn Leu Thr Asp Ile Leu Lys
```

-continued

```
705                 710                 715                 720

Gln Glu Lys Lys Asp Glu Thr Gln Lys Val Gln Met Lys Phe Leu Val
                725                 730                 735

Glu Gln Met Arg Arg Pro Asp Phe Met Asp Ala Leu Gln Gly Phe Leu
            740                 745                 750

Ser Pro Leu Asn Pro Ala His Gln Leu Gly Asn Leu Arg Leu Glu Glu
        755                 760                 765

Cys Arg Ile Met Ser Ser Ala Lys Arg Pro Leu Trp Leu Asn Trp Glu
    770                 775                 780

Asn Pro Asp Ile Met Ser Glu Leu Leu Phe Gln Asn Asn Glu Ile Ile
785                 790                 795                 800

Phe Lys Asn Gly Asp Asp Leu Arg Gln Asp Met Leu Thr Leu Gln Ile
                805                 810                 815

Ile Arg Ile Met Glu Asn Ile Trp Gln Asn Gln Gly Leu Asp Leu Arg
            820                 825                 830

Met Leu Pro Tyr Gly Cys Leu Ser Ile Gly Asp Cys Val Gly Leu Ile
        835                 840                 845

Glu Val Val Arg Asn Ser His Thr Ile Met Gln Ile Gln Cys Lys Gly
    850                 855                 860

Gly Leu Lys Gly Ala Leu Gln Phe Asn Ser His Thr Leu His Gln Trp
865                 870                 875                 880

Leu Lys Asp Lys Asn Lys Gly Glu Ile Tyr Asp Ala Ala Ile Asp Leu
                885                 890                 895

Phe Thr Arg Ser Cys Ala Gly Tyr Cys Val Ala Thr Phe Ile Leu Gly
            900                 905                 910

Ile Gly Asp Arg His Asn Ser Asn Ile Met Val Lys Asp Asp Gly Gln
        915                 920                 925

Leu Phe His Ile Asp Phe Gly His Phe Leu Asp His Lys Lys Lys Lys
    930                 935                 940

Phe Gly Tyr Lys Arg Glu Arg Val Pro Phe Val Leu Thr Gln Asp Phe
945                 950                 955                 960

Leu Ile Val Ile Ser Lys Gly Ala Gln Glu Cys Thr Lys Thr Arg Glu
                965                 970                 975

Phe Glu Arg Phe Gln Glu Met Cys Tyr Lys Ala Tyr Leu Ala Ile Arg
            980                 985                 990

Gln His Ala Asn Leu Phe Ile Asn  Leu Phe Ser Met Met  Leu Gly Ser
        995                 1000                1005

Gly Met  Pro Glu Leu Gln Ser  Phe Asp Asp Ile Ala  Tyr Ile Arg
    1010                1015                1020

Lys Thr  Leu Ala Leu Asp Lys  Thr Glu Gln Glu Ala  Leu Glu Tyr
    1025                1030                1035

Phe Met  Lys Gln Met Asn Asp  Ala His His Gly Gly  Trp Thr Thr
    1040                1045                1050

Lys Met  Asp Trp Ile Phe His  Thr Ile Lys Gln His  Ala Leu Asn
    1055                1060                1065
```

<210> SEQ ID NO 23
<211> LENGTH: 125
<212> TYPE: DNA
<213> ORGANISM: Homo sapiens

<400> SEQUENCE: 23

```
agtaacagac tagctagaga caatgaatta agggaaaatg acaaagaaca gctcaaagca     60

atttctacac gagatcctct ctctgaaatc actgggcagg agaaagattt tctatggagt    120
```

```
cacag                                                                 125

<210> SEQ ID NO 24
<211> LENGTH: 1068
<212> TYPE: PRT
<213> ORGANISM: Homo sapiens

<400> SEQUENCE: 24

Met Pro Pro Arg Pro Ser Ser Gly Glu Leu Trp Gly Ile His Leu Met
1               5                   10                  15

Pro Pro Arg Ile Leu Val Glu Cys Leu Leu Pro Asn Gly Met Ile Val
            20                  25                  30

Thr Leu Glu Cys Leu Arg Glu Ala Thr Leu Ile Thr Ile Lys His Glu
        35                  40                  45

Leu Phe Lys Glu Ala Arg Lys Tyr Pro Leu His Gln Leu Leu Gln Asp
    50                  55                  60

Glu Ser Ser Tyr Ile Phe Val Ser Val Thr Gln Glu Ala Glu Arg Glu
65                  70                  75                  80

Glu Phe Phe Asp Glu Thr Arg Arg Leu Cys Asp Leu Arg Leu Phe Gln
                85                  90                  95

Pro Phe Leu Lys Val Ile Glu Pro Val Gly Asn Arg Glu Glu Lys Ile
            100                 105                 110

Leu Asn Arg Glu Ile Gly Phe Ala Ile Gly Met Pro Val Cys Glu Phe
        115                 120                 125

Asp Met Val Lys Asp Pro Glu Val Gln Asp Phe Arg Arg Asn Ile Leu
    130                 135                 140

Asn Val Cys Lys Glu Ala Val Asp Leu Arg Asp Leu Asn Ser Pro His
145                 150                 155                 160

Ser Arg Ala Met Tyr Val Tyr Pro Pro Asn Val Glu Ser Ser Pro Glu
                165                 170                 175

Leu Pro Lys His Ile Tyr Asn Lys Leu Asp Lys Gly Gln Ile Ile Val
            180                 185                 190

Val Ile Trp Val Ile Val Ser Pro Asn Asn Asp Lys Gln Lys Tyr Thr
        195                 200                 205

Leu Lys Ile Asn His Asp Cys Val Pro Glu Gln Val Ile Ala Glu Ala
    210                 215                 220

Ile Arg Lys Lys Thr Arg Ser Met Leu Leu Ser Ser Glu Gln Leu Lys
225                 230                 235                 240

Leu Cys Val Leu Glu Tyr Gln Gly Lys Tyr Ile Leu Lys Val Cys Gly
                245                 250                 255

Cys Asp Glu Tyr Phe Leu Glu Lys Tyr Pro Leu Ser Gln Tyr Lys Tyr
            260                 265                 270

Ile Arg Ser Cys Ile Met Leu Gly Arg Met Pro Asn Leu Met Leu Met
        275                 280                 285

Ala Lys Glu Ser Leu Tyr Ser Gln Leu Pro Met Asp Cys Phe Thr Met
    290                 295                 300

Pro Ser Tyr Ser Arg Arg Ile Ser Thr Ala Thr Pro Tyr Met Asn Gly
305                 310                 315                 320

Glu Thr Ser Thr Lys Ser Leu Trp Val Ile Asn Ser Ala Leu Arg Ile
                325                 330                 335

Lys Ile Leu Cys Ala Thr Tyr Val Asn Val Asn Ile Arg Asp Ile Asp
            340                 345                 350

Lys Ile Tyr Val Arg Thr Gly Ile Tyr His Gly Gly Glu Pro Leu Cys
        355                 360                 365
```

```
Asp Asn Val Asn Thr Gln Arg Val Pro Cys Ser Asn Pro Arg Trp Asn
    370                 375                 380

Glu Trp Leu Asn Tyr Asp Ile Tyr Ile Pro Asp Leu Pro Arg Ala Ala
385                 390                 395                 400

Arg Leu Cys Leu Ser Ile Cys Ser Val Lys Gly Arg Lys Gly Ala Lys
                405                 410                 415

Glu Glu His Cys Pro Leu Ala Trp Gly Asn Ile Asn Leu Phe Asp Tyr
            420                 425                 430

Thr Asp Thr Leu Val Ser Gly Lys Met Ala Leu Asn Leu Trp Pro Val
        435                 440                 445

Pro His Gly Leu Glu Asp Leu Leu Asn Pro Ile Gly Val Thr Gly Ser
    450                 455                 460

Asn Pro Asn Lys Glu Thr Pro Cys Leu Glu Leu Glu Phe Asp Trp Phe
465                 470                 475                 480

Ser Ser Val Val Lys Phe Pro Asp Met Ser Val Ile Glu Glu His Ala
                485                 490                 495

Asn Trp Ser Val Ser Arg Glu Ala Gly Phe Ser Tyr Ser His Ala Gly
            500                 505                 510

Leu Ser Asn Arg Leu Ala Arg Asp Asn Glu Leu Arg Glu Asn Asp Lys
        515                 520                 525

Glu Gln Leu Lys Ala Ile Ser Thr Arg Asp Pro Leu Ser Glu Ile Thr
    530                 535                 540

Gly Gln Glu Lys Asp Phe Leu Trp Ser His Arg His Tyr Cys Val Thr
545                 550                 555                 560

Ile Pro Glu Ile Leu Pro Lys Leu Leu Leu Ser Val Lys Trp Asn Ser
                565                 570                 575

Arg Asp Glu Val Ala Gln Met Tyr Cys Leu Val Lys Asp Trp Pro Pro
            580                 585                 590

Ile Lys Pro Glu Gln Ala Met Glu Leu Leu Asp Cys Asn Tyr Pro Asp
        595                 600                 605

Pro Met Val Arg Gly Phe Ala Val Arg Cys Leu Glu Lys Tyr Leu Thr
    610                 615                 620

Asp Asp Lys Leu Ser Gln Tyr Leu Ile Gln Leu Val Gln Val Leu Lys
625                 630                 635                 640

Tyr Glu Gln Tyr Leu Asp Asn Leu Leu Val Arg Phe Leu Leu Lys Lys
                645                 650                 655

Ala Leu Thr Asn Gln Arg Ile Gly His Phe Phe Phe Trp His Leu Lys
            660                 665                 670

Ser Glu Met His Asn Lys Thr Val Ser Gln Arg Phe Gly Leu Leu Leu
        675                 680                 685

Glu Ser Tyr Cys Arg Ala Cys Gly Met Tyr Leu Lys His Leu Asn Arg
    690                 695                 700

Gln Val Glu Ala Met Glu Lys Leu Ile Asn Leu Thr Asp Ile Leu Lys
705                 710                 715                 720

Gln Glu Lys Lys Asp Glu Thr Gln Lys Val Gln Met Lys Phe Leu Val
                725                 730                 735

Glu Gln Met Arg Arg Pro Asp Phe Met Asp Ala Leu Gln Gly Phe Leu
            740                 745                 750

Ser Pro Leu Asn Pro Ala His Gln Leu Gly Asn Leu Arg Leu Glu Glu
        755                 760                 765

Cys Arg Ile Met Ser Ser Ala Lys Arg Pro Leu Trp Leu Asn Trp Glu
    770                 775                 780
```

```
Asn Pro Asp Ile Met Ser Glu Leu Leu Phe Gln Asn Asn Glu Ile Ile
785                 790                 795                 800

Phe Lys Asn Gly Asp Asp Leu Arg Gln Asp Met Leu Thr Leu Gln Ile
                805                 810                 815

Ile Arg Ile Met Glu Asn Ile Trp Gln Asn Gln Gly Leu Asp Leu Arg
            820                 825                 830

Met Leu Pro Tyr Gly Cys Leu Ser Ile Gly Asp Cys Val Gly Leu Ile
        835                 840                 845

Glu Val Val Arg Asn Ser His Thr Ile Met Gln Ile Gln Cys Lys Gly
    850                 855                 860

Gly Leu Lys Gly Ala Leu Gln Phe Asn Ser His Thr Leu His Gln Trp
865                 870                 875                 880

Leu Lys Asp Lys Asn Lys Gly Glu Ile Tyr Asp Ala Ala Ile Asp Leu
                885                 890                 895

Phe Thr Arg Ser Cys Ala Gly Tyr Cys Val Ala Thr Phe Ile Leu Gly
            900                 905                 910

Ile Gly Asp Arg His Asn Ser Asn Ile Met Val Lys Asp Asp Gly Gln
        915                 920                 925

Leu Phe His Ile Asp Phe Gly His Phe Leu Asp His Lys Lys Lys Lys
    930                 935                 940

Phe Gly Tyr Lys Arg Glu Arg Val Pro Phe Val Leu Thr Gln Asp Phe
945                 950                 955                 960

Leu Ile Val Ile Ser Lys Gly Ala Gln Glu Cys Thr Lys Thr Arg Glu
                965                 970                 975

Phe Glu Arg Phe Gln Glu Met Cys Tyr Lys Ala Tyr Leu Ala Ile Arg
            980                 985                 990

Gln His Ala Asn Leu Phe Ile Asn  Leu Phe Ser Met Met  Leu Gly Ser
        995                 1000                 1005

Gly Met  Pro Glu Leu Gln Ser  Phe Asp Asp Ile Ala  Tyr Ile Arg
    1010                 1015                 1020

Lys Thr  Leu Ala Leu Asp Lys  Thr Glu Gln Glu Ala  Leu Glu Tyr
    1025                 1030                 1035

Phe Met  Lys Gln Met Asn Asp  Ala His His Gly Gly  Trp Thr Thr
    1040                 1045                 1050

Lys Met  Asp Trp Ile Phe His  Thr Ile Lys Gln His  Ala Leu Asn
    1055                 1060                 1065
```

<210> SEQ ID NO 25
<211> LENGTH: 31
<212> TYPE: DNA
<213> ORGANISM: Artificial Sequence
<220> FEATURE:
<223> OTHER INFORMATION: Description of Artificial Sequence: Synthetic
542/545 forward primer PIK3CA-9F13T
<220> FEATURE:
<223> OTHER INFORMATION: Description of Combined DNA/RNA Molecule:
Synthetic 542/545 forward primer PIK3CA-9F13T
<220> FEATURE:
<221> NAME/KEY: modified_base
<222> LOCATION: (1)..(1)
<223> OTHER INFORMATION: 5-propynyl dU
<220> FEATURE:
<221> NAME/KEY: modified_base
<222> LOCATION: (6)..(8)
<223> OTHER INFORMATION: 5-propynyl dU
<220> FEATURE:
<221> NAME/KEY: modified_base
<222> LOCATION: (10)..(11)
<223> OTHER INFORMATION: 5-propynyl dU
<220> FEATURE:
<221> NAME/KEY: modified_base
<222> LOCATION: (17)..(17)
<223> OTHER INFORMATION: 5-propynyl dU
<220> FEATURE:
<221> NAME/KEY: modified_base
<222> LOCATION: (19)..(19)
<223> OTHER INFORMATION: 5-propynyl dU
<220> FEATURE:
<221> NAME/KEY: modified_base
<222> LOCATION: (21)..(23)
<223> OTHER INFORMATION: 5-propynyl dU

<400> SEQUENCE: 25
uaaaauuuau ugagaaugua uuugcttttt c 31

<210> SEQ ID NO 26
<211> LENGTH: 24
<212> TYPE: DNA
<213> ORGANISM: Artificial Sequence
<220> FEATURE:
<223> OTHER INFORMATION: Description of Artificial Sequence: Synthetic
542/545 reverse primer PIK3CA-9R01

<400> SEQUENCE: 26
tccattttag cacttacctg tgac 24

<210> SEQ ID NO 27
<211> LENGTH: 30
<212> TYPE: DNA
<213> ORGANISM: Artificial Sequence
<220> FEATURE:
<223> OTHER INFORMATION: Description of Artificial Sequence: Synthetic
542 WT probe
<220> FEATURE:
<223> OTHER INFORMATION: Description of Combined DNA/RNA Molecule:
Synthetic 542 WT probe
<220> FEATURE:
<223> OTHER INFORMATION: 5'-FAM reporter dye
<220> FEATURE:
<221> NAME/KEY: misc_feature
<222> LOCATION: (5)..(6)
<223> OTHER INFORMATION: BHQ2 quencher dye between positions
<220> FEATURE:
<221> NAME/KEY: modified_base
<222> LOCATION: (14)..(14)
<223> OTHER INFORMATION: 5-propynyl dU
<220> FEATURE:
<221> NAME/KEY: modified_base
<222> LOCATION: (15)..(15)
<223> OTHER INFORMATION: 5-methyl dC
<220> FEATURE:
<221> NAME/KEY: modified_base
<222> LOCATION: (16)..(16)
<223> OTHER INFORMATION: 5-propynyl dU
<220> FEATURE:
<221> NAME/KEY: modified_base
<222> LOCATION: (17)..(17)
<223> OTHER INFORMATION: 5-methyl dC
<220> FEATURE:
<221> NAME/KEY: modified_base
<222> LOCATION: (19)..(19)
<223> OTHER INFORMATION: 5-propynyl dU
<220> FEATURE:
<221> NAME/KEY: modified_base
<222> LOCATION: (21)..(21)
<223> OTHER INFORMATION: 5-propynyl dU
<220> FEATURE:
<221> NAME/KEY: modified_base
<222> LOCATION: (27)..(28)
<223> OTHER INFORMATION: 5-propynyl dU
<220> FEATURE:
<221> NAME/KEY: modified_base
<222> LOCATION: (30)..(30)
<223> OTHER INFORMATION: 5-methyl dC
<220> FEATURE:
<223> OTHER INFORMATION: 3'-phosphate

<400> SEQUENCE: 27
tttcaagaga ggaucucgug uagaaauugc 30

<210> SEQ ID NO 28
<211> LENGTH: 33
<212> TYPE: DNA
<213> ORGANISM: Artificial Sequence
<220> FEATURE:
<223> OTHER INFORMATION: Description of Artificial Sequence: Synthetic
542 542K mutation probe
<220> FEATURE:
<223> OTHER INFORMATION: Description of Combined DNA/RNA Molecule:
Synthetic 542 542K mutation probe
<220> FEATURE:
<223> OTHER INFORMATION: 5'-HEX reporter dye
<220> FEATURE:
<221> NAME/KEY: misc_feature
<222> LOCATION: (5)..(6)
<223> OTHER INFORMATION: BHQ2 quencher dye between positions
<220> FEATURE:
<221> NAME/KEY: modified_base
<222> LOCATION: (15)..(15)
<223> OTHER INFORMATION: 5-propynyl dU
<220> FEATURE:
<221> NAME/KEY: modified_base
<222> LOCATION: (16)..(16)
<223> OTHER INFORMATION: 5-methyl dC
<220> FEATURE:
<221> NAME/KEY: modified_base
<222> LOCATION: (17)..(17)
<223> OTHER INFORMATION: 5-propynyl dU
<220> FEATURE:
<221> NAME/KEY: modified_base
<222> LOCATION: (18)..(18)
<223> OTHER INFORMATION: 5-methyl dC
<220> FEATURE:
<221> NAME/KEY: modified_base
<222> LOCATION: (20)..(20)
<223> OTHER INFORMATION: 5-propynyl dU
<220> FEATURE:
<221> NAME/KEY: modified_base
<222> LOCATION: (22)..(22)
<223> OTHER INFORMATION: 5-propynyl dU
<220> FEATURE:
<221> NAME/KEY: modified_base
<222> LOCATION: (28)..(29)
<223> OTHER INFORMATION: 5-propynyl dU
<220> FEATURE:
<221> NAME/KEY: modified_base
<222> LOCATION: (31)..(31)
<223> OTHER INFORMATION: 5-methyl dC
<220> FEATURE:
<221> NAME/KEY: modified_base
<222> LOCATION: (32)..(33)
<223> OTHER INFORMATION: 5-propynyl dU
<220> FEATURE:
<223> OTHER INFORMATION: 3'-phosphate

<400> SEQUENCE: 28
attttgagag aggaucucgu guagaaauug cuu 33

<210> SEQ ID NO 29
<211> LENGTH: 32
<212> TYPE: DNA
<213> ORGANISM: Artificial Sequence
<220> FEATURE:
<223> OTHER INFORMATION: Description of Artificial Sequence: Synthetic
545 WT probe
<220> FEATURE:
<223> OTHER INFORMATION: Description of Combined DNA/RNA Molecule:
Synthetic 545 WT probe
<220> FEATURE:
<223> OTHER INFORMATION: 5'-CY5.5 reporter dye
<220> FEATURE:

<221> NAME/KEY: misc_feature
<222> LOCATION: (9)..(10)
<223> OTHER INFORMATION: BHQ2 quencher dye between positions
<220> FEATURE:
<221> NAME/KEY: modified_base
<222> LOCATION: (11)..(13)
<223> OTHER INFORMATION: 5-propynyl dU
<220> FEATURE:
<221> NAME/KEY: modified_base
<222> LOCATION: (14)..(14)
<223> OTHER INFORMATION: deoxyinosine
<220> FEATURE:
<223> OTHER INFORMATION: 3'-phosphate

<400> SEQUENCE: 29
ctgctcagta uuunagagag aggatctcgt gt 32

<210> SEQ ID NO 30
<211> LENGTH: 34
<212> TYPE: DNA
<213> ORGANISM: Artificial Sequence
<220> FEATURE:
<223> OTHER INFORMATION: Description of Artificial Sequence: Synthetic
545 545K mutation probe
<220> FEATURE:
<223> OTHER INFORMATION: Description of Combined DNA/RNA Molecule:
Synthetic 545 545K mutation probe
<220> FEATURE:
<223> OTHER INFORMATION: 5'-JA270 reporter dye
<220> FEATURE:
<221> NAME/KEY: misc_feature
<222> LOCATION: (10)..(11)
<223> OTHER INFORMATION: BHQ2 quencher dye between positions
<220> FEATURE:
<221> NAME/KEY: modified_base
<222> LOCATION: (21)..(24)
<223> OTHER INFORMATION: 5-propynyl dU
<220> FEATURE:
<221> NAME/KEY: modified_base
<222> LOCATION: (25)..(25)
<223> OTHER INFORMATION: 5-methyl dC
<220> FEATURE:
<221> NAME/KEY: modified_base
<222> LOCATION: (26)..(26)
<223> OTHER INFORMATION: 5-propynyl dU
<220> FEATURE:
<221> NAME/KEY: modified_base
<222> LOCATION: (28)..(28)
<223> OTHER INFORMATION: 5-propynyl dU
<220> FEATURE:
<221> NAME/KEY: modified_base
<222> LOCATION: (33)..(33)
<223> OTHER INFORMATION: 5-propynyl dU
<220> FEATURE:
<221> NAME/KEY: modified_base
<222> LOCATION: (34)..(34)
<223> OTHER INFORMATION: 5-methyl dC
<220> FEATURE:
<223> OTHER INFORMATION: 3'-phosphate

<400> SEQUENCE: 30
aatcactaag aggagaaaga uuuucuaugg aguc 34

<210> SEQ ID NO 31
<211> LENGTH: 30
<212> TYPE: DNA
<213> ORGANISM: Artificial Sequence
<220> FEATURE:
<223> OTHER INFORMATION: Description of Artificial Sequence: Synthetic
545 545A mutation probe
<220> FEATURE:
<223> OTHER INFORMATION: Description of Combined DNA/RNA Molecule:
Synthetic 545 545A mutation probe
<220> FEATURE:
<223> OTHER INFORMATION: 5'-FAM reporter dye
<220> FEATURE:
<221> NAME/KEY: misc_feature
<222> LOCATION: (6)..(7)
<223> OTHER INFORMATION: BHQ2 quencher dye between positions
<220> FEATURE:
<221> NAME/KEY: modified_base
<222> LOCATION: (16)..(19)
<223> OTHER INFORMATION: 5-propynyl dU
<220> FEATURE:
<221> NAME/KEY: modified_base
<222> LOCATION: (20)..(20)
<223> OTHER INFORMATION: 5-methyl dC
<220> FEATURE:
<221> NAME/KEY: modified_base
<222> LOCATION: (21)..(21)
<223> OTHER INFORMATION: 5-propynyl dU
<220> FEATURE:
<221> NAME/KEY: modified_base
<222> LOCATION: (23)..(23)
<223> OTHER INFORMATION: 5-propynyl dU
<220> FEATURE:
<221> NAME/KEY: modified_base
<222> LOCATION: (28)..(28)
<223> OTHER INFORMATION: 5-propynyl dU
<220> FEATURE:
<221> NAME/KEY: modified_base
<222> LOCATION: (29)..(29)
<223> OTHER INFORMATION: 5-methyl dC
<220> FEATURE:
<223> OTHER INFORMATION: 3'-phosphate

<400> SEQUENCE: 31
ctgcgcggag aaagauuuuc uauggaguca 30

<210> SEQ ID NO 32
<211> LENGTH: 30
<212> TYPE: DNA
<213> ORGANISM: Artificial Sequence
<220> FEATURE:
<223> OTHER INFORMATION: Description of Artificial Sequence: Synthetic
545 545G mutation probe
<220> FEATURE:
<223> OTHER INFORMATION: Description of Combined DNA/RNA Molecule:
Synthetic 545 545G mutation probe
<220> FEATURE:
<223> OTHER INFORMATION: 5'-HEX reporter dye
<220> FEATURE:
<221> NAME/KEY: misc_feature
<222> LOCATION: (7)..(8)
<223> OTHER INFORMATION: BHQ2 quencher dye between positions
<220> FEATURE:
<221> NAME/KEY: modified_base
<222> LOCATION: (12)..(14)
<223> OTHER INFORMATION: 5-propynyl dU
<220> FEATURE:
<221> NAME/KEY: modified_base
<222> LOCATION: (15)..(15)
<223> OTHER INFORMATION: deoxyinosine
<220> FEATURE:
<223> OTHER INFORMATION: 3'-phosphate

<400> SEQUENCE: 32
cctgcccgtg auuunagaga gaggatctcg 30

<210> SEQ ID NO 33
<211> LENGTH: 25
<212> TYPE: DNA
<213> ORGANISM: Artificial Sequence
<220> FEATURE:
<223> OTHER INFORMATION: Description of Artificial Sequence: Synthetic
codon 420 forward primer PIK3CA-7F03
<220> FEATURE:
<221> NAME/KEY: modified_base
<222> LOCATION: (1)..(4)
<223> OTHER INFORMATION: 5-propynyl dU
<220> FEATURE:
<221> NAME/KEY: modified_base
<222> LOCATION: (17)..(17)
<223> OTHER INFORMATION: 5-propynyl dU
<220> FEATURE:
<221> NAME/KEY: modified_base
<222> LOCATION: (19)..(22)
<223> OTHER INFORMATION: 5-propynyl dU

<400> SEQUENCE: 33
uuuuggggaa gaaaaguguu uugaa 25

<210> SEQ ID NO 34
<211> LENGTH: 29
<212> TYPE: DNA
<213> ORGANISM: Artificial Sequence
<220> FEATURE:
<223> OTHER INFORMATION: Description of Artificial Sequence: Synthetic
codon 420 reverse primer PIK3CA-7R04

<400> SEQUENCE: 34
gattcaaagc catttttcca gatactaga 29

<210> SEQ ID NO 35
<211> LENGTH: 23
<212> TYPE: DNA
<213> ORGANISM: Artificial Sequence
<220> FEATURE:
<223> OTHER INFORMATION: Description of Artificial Sequence: Synthetic
codon 1047 forward primer PIK3CA-20F01

<400> SEQUENCE: 35
gaggctttgg agtatttcat gaa 23

<210> SEQ ID NO 36
<211> LENGTH: 21
<212> TYPE: DNA
<213> ORGANISM: Artificial Sequence
<220> FEATURE:
<223> OTHER INFORMATION: Description of Artificial Sequence: Synthetic
codon 1047 reverse primer PIK3CA-20R01

<400> SEQUENCE: 36
ccaatccatt tttgttgtcc a 21

<210> SEQ ID NO 37
<211> LENGTH: 37
<212> TYPE: DNA
<213> ORGANISM: Artificial Sequence
<220> FEATURE:
<223> OTHER INFORMATION: Description of Artificial Sequence: Synthetic
codon 420 WT probe
<220> FEATURE:
<223> OTHER INFORMATION: Description of Combined DNA/RNA Molecule:
Synthetic codon 420 WT probe
<220> FEATURE:
<223> OTHER INFORMATION: 5'-JA270 Reporter dye
<220> FEATURE:
<221> NAME/KEY: misc_feature
<222> LOCATION: (10)..(11)
<223> OTHER INFORMATION: BHQ2 quencher dye between positions
<220> FEATURE:
<221> NAME/KEY: modified_base
<222> LOCATION: (12)..(13)
<223> OTHER INFORMATION: 5-propynyl dU
<220> FEATURE:
<221> NAME/KEY: modified_base
<222> LOCATION: (14)..(15)
<223> OTHER INFORMATION: 5-methyl dC
<220> FEATURE:
<221> NAME/KEY: modified_base
<222> LOCATION: (16)..(17)
<223> OTHER INFORMATION: 5-propynyl dU
<220> FEATURE:
<221> NAME/KEY: modified_base
<222> LOCATION: (24)..(24)
<223> OTHER INFORMATION: 5-methyl dC
<220> FEATURE:
<221> NAME/KEY: modified_base
<222> LOCATION: (34)..(34)
<223> OTHER INFORMATION: 5-propynyl dU
<220> FEATURE:
<221> NAME/KEY: modified_base
<222> LOCATION: (36)..(37)
<223> OTHER INFORMATION: 5-propynyl dU
<220> FEATURE:
<223> OTHER INFORMATION: 3'-phosphate

<400> SEQUENCE: 37
caatggacag guuccuuaaa aaacaaagaa aaauauu 37

<210> SEQ ID NO 38
<211> LENGTH: 31
<212> TYPE: DNA
<213> ORGANISM: Artificial Sequence
<220> FEATURE:
<223> OTHER INFORMATION: Description of Artificial Sequence: Synthetic
codon 420 420R mutation probe
<220> FEATURE:
<223> OTHER INFORMATION: Description of Combined DNA/RNA Molecule:
Synthetic codon 420 420R mutation probe
<220> FEATURE:
<223> OTHER INFORMATION: 5'-CY5.5 Reporter dye
<220> FEATURE:
<221> NAME/KEY: misc_feature
<222> LOCATION: (7)..(8)
<223> OTHER INFORMATION: BHQ2 quencher dye between positions
<220> FEATURE:
<221> NAME/KEY: modified_base
<222> LOCATION: (12)..(13)
<223> OTHER INFORMATION: 5-propynyl dU
<220> FEATURE:
<221> NAME/KEY: modified_base
<222> LOCATION: (16)..(16)
<223> OTHER INFORMATION: 5-methyl dC
<220> FEATURE:
<221> NAME/KEY: modified_base
<222> LOCATION: (18)..(18)
<223> OTHER INFORMATION: 5-propynyl dU
<220> FEATURE:
<221> NAME/KEY: modified_base
<222> LOCATION: (26)..(26)
<223> OTHER INFORMATION: 5-propynyl dU
<220> FEATURE:
<221> NAME/KEY: modified_base
<222> LOCATION: (28)..(28)
<223> OTHER INFORMATION: 5-propynyl dU
<220> FEATURE:
<223> OTHER INFORMATION: 3'-phosphate

<400> SEQUENCE: 38
gaacacctcc auuggcaugg ggaaauauaa a 31

<210> SEQ ID NO 39
<211> LENGTH: 25
<212> TYPE: DNA
<213> ORGANISM: Artificial Sequence
<220> FEATURE:
<223> OTHER INFORMATION: Description of Artificial Sequence: Synthetic
codon 1047 WT probe
<220> FEATURE:
<223> OTHER INFORMATION: 5'-FAM Reporter dye
<220> FEATURE:
<221> NAME/KEY: modified_base
<222> LOCATION: (2)..(2)
<223> OTHER INFORMATION: 7-deaza dG

```
<220> FEATURE:
<221> NAME/KEY: misc_feature
<222> LOCATION: (8)..(9)
<223> OTHER INFORMATION: BHQ2 quencher dye between positions
<220> FEATURE:
<221> NAME/KEY: modified_base
<222> LOCATION: (10)..(11)
<223> OTHER INFORMATION: 7-deaza dG
<220> FEATURE:
<221> NAME/KEY: modified_base
<222> LOCATION: (13)..(14)
<223> OTHER INFORMATION: 7-deaza dG
<220> FEATURE:
<221> NAME/KEY: modified_base
<222> LOCATION: (17)..(18)
<223> OTHER INFORMATION: 7-deaza dG
<220> FEATURE:
<223> OTHER INFORMATION: 3'-phosphate

<400> SEQUENCE: 39

tgcacatctg gtggctggac aacaa                                             25


<210> SEQ ID NO 40
<211> LENGTH: 25
<212> TYPE: DNA
<213> ORGANISM: Artificial Sequence
<220> FEATURE:
<223> OTHER INFORMATION: Description of Artificial Sequence: Synthetic
      codon 1047 1047R mutation probe
<220> FEATURE:
<223> OTHER INFORMATION: Description of Combined DNA/RNA Molecule:
      Synthetic codon 1047 1047R mutation probe
<220> FEATURE:
<223> OTHER INFORMATION: 5'-HEX Reporter dye
<220> FEATURE:
<221> NAME/KEY: misc_feature
<222> LOCATION: (5)..(6)
<223> OTHER INFORMATION: BHQ2 quencher dye between positions
<220> FEATURE:
<221> NAME/KEY: modified_base
<222> LOCATION: (8)..(8)
<223> OTHER INFORMATION: 5-propynyl dU
<220> FEATURE:
<221> NAME/KEY: modified_base
<222> LOCATION: (9)..(9)
<223> OTHER INFORMATION: 5-methyl dC
<220> FEATURE:
<221> NAME/KEY: modified_base
<222> LOCATION: (11)..(12)
<223> OTHER INFORMATION: 5-propynyl dU
<220> FEATURE:
<221> NAME/KEY: modified_base
<222> LOCATION: (13)..(13)
<223> OTHER INFORMATION: 5-methyl dC
<220> FEATURE:
<221> NAME/KEY: modified_base
<222> LOCATION: (15)..(17)
<223> OTHER INFORMATION: 5-propynyl dU
<220> FEATURE:
<221> NAME/KEY: modified_base
<222> LOCATION: (19)..(21)
<223> OTHER INFORMATION: 5-propynyl dU
<220> FEATURE:
<221> NAME/KEY: modified_base
<222> LOCATION: (22)..(22)
<223> OTHER INFORMATION: 5-methyl dC
<220> FEATURE:
<221> NAME/KEY: modified_base
<222> LOCATION: (24)..(24)
<223> OTHER INFORMATION: 5-propynyl dU
<220> FEATURE:
<223> OTHER INFORMATION: 3'-phosphate

<400> SEQUENCE: 40

gacgtcauca uucauuuguu ucaug                                             25
```

<210> SEQ ID NO 41
<211> LENGTH: 27
<212> TYPE: DNA
<213> ORGANISM: Artificial Sequence
<220> FEATURE:
<223> OTHER INFORMATION: Description of Artificial Sequence: Synthetic
      codon 1047 1047L mutation probe
<220> FEATURE:
<223> OTHER INFORMATION: 5'-JA270 Reporter dye
<220> FEATURE:
<221> NAME/KEY: misc_feature
<222> LOCATION: (10)..(11)
<223> OTHER INFORMATION: BHQ2 quencher dye between positions
<220> FEATURE:
<223> OTHER INFORMATION: 3'-phosphate

<400> SEQUENCE: 41
gcacttcatg tggctggaca acaaaaa 27

<210> SEQ ID NO 42
<211> LENGTH: 27
<212> TYPE: DNA
<213> ORGANISM: Artificial Sequence
<220> FEATURE:
<223> OTHER INFORMATION: Description of Artificial Sequence: Synthetic
      codon 1047 1047Y mutation probe
<220> FEATURE:
<223> OTHER INFORMATION: Description of Combined DNA/RNA Molecule:
      Synthetic codon 1047 1047Y mutation probe
<220> FEATURE:
<223> OTHER INFORMATION: 5'-CY5.5 Reporter dye
<220> FEATURE:
<221> NAME/KEY: misc_feature
<222> LOCATION: (10)..(11)
<223> OTHER INFORMATION: BHQ2 quencher dye between positions
<220> FEATURE:
<221> NAME/KEY: modified_base
<222> LOCATION: (13)..(13)
<223> OTHER INFORMATION: 5-propynyl dU
<220> FEATURE:
<221> NAME/KEY: modified_base
<222> LOCATION: (14)..(14)
<223> OTHER INFORMATION: 5-methyl dC
<220> FEATURE:
<221> NAME/KEY: modified_base
<222> LOCATION: (16)..(17)
<223> OTHER INFORMATION: 5-propynyl dU
<220> FEATURE:
<221> NAME/KEY: modified_base
<222> LOCATION: (18)..(18)
<223> OTHER INFORMATION: 5-methyl dC
<220> FEATURE:
<221> NAME/KEY: modified_base
<222> LOCATION: (20)..(22)
<223> OTHER INFORMATION: 5-propynyl dU
<220> FEATURE:
<221> NAME/KEY: modified_base
<222> LOCATION: (24)..(26)
<223> OTHER INFORMATION: 5-propynyl dU
<220> FEATURE:
<221> NAME/KEY: modified_base
<222> LOCATION: (27)..(27)
<223> OTHER INFORMATION: 5-methyl dC
<220> FEATURE:
<223> OTHER INFORMATION: 3'-phosphate

<400> SEQUENCE: 42
accatgatat caucauucau uuguuuc 27

<210> SEQ ID NO 43
<211> LENGTH: 195
<212> TYPE: PRT
<213> ORGANISM: Homo sapiens

<400> SEQUENCE: 43

Thr Gln Val Cys Thr Gly Thr Asp Met Lys Leu Arg Leu Pro Ala Ser
1 5 10 15

Pro Glu Thr His Leu Asp Met Leu Arg His Leu Tyr Gln Gly Cys Gln
20 25 30

Val Val Gln Gly Asn Leu Glu Leu Thr Tyr Leu Pro Thr Asn Ala Ser
35 40 45

Leu Ser Phe Leu Gln Asp Ile Gln Glu Val Gln Gly Tyr Val Leu Ile
50 55 60

Ala His Asn Gln Val Arg Gln Val Pro Leu Gln Arg Leu Arg Ile Val
65 70 75 80

Arg Gly Thr Gln Leu Phe Glu Asp Asn Tyr Ala Leu Ala Val Leu Asp
85 90 95

Asn Gly Asp Pro Leu Asn Asn Thr Thr Pro Val Thr Gly Ala Ser Pro
100 105 110

Gly Gly Leu Arg Glu Leu Gln Leu Arg Ser Leu Thr Glu Ile Leu Lys
115 120 125

Gly Gly Val Leu Ile Gln Arg Asn Pro Gln Leu Cys Tyr Gln Asp Thr
130 135 140

Ile Leu Trp Lys Asp Ile Phe His Lys Asn Asn Gln Leu Ala Leu Thr
145 150 155 160

Leu Ile Asp Thr Asn Arg Ser Arg Ala Cys His Pro Cys Ser Pro Met
165 170 175

Cys Lys Gly Ser Arg Cys Trp Gly Glu Ser Ser Glu Asp Cys Gln Ser
180 185 190

Leu Thr Arg
195

<210> SEQ ID NO 44
<211> LENGTH: 124
<212> TYPE: PRT
<213> ORGANISM: Homo sapiens

<400> SEQUENCE: 44

Thr Val Cys Ala Gly Gly Cys Ala Arg Cys Lys Gly Pro Leu Pro Thr
1 5 10 15

Asp Cys Cys His Glu Gln Cys Ala Ala Gly Cys Thr Gly Pro Lys His
20 25 30

Ser Asp Cys Leu Ala Cys Leu His Phe Asn His Ser Gly Ile Cys Glu
35 40 45

Leu His Cys Pro Ala Leu Val Thr Tyr Asn Thr Asp Thr Phe Glu Ser
50 55 60

Met Pro Asn Pro Glu Gly Arg Tyr Thr Phe Gly Ala Ser Cys Val Thr
65 70 75 80

Ala Cys Pro Tyr Asn Tyr Leu Ser Thr Asp Val Gly Ser Cys Thr Leu
85 90 95

Val Cys Pro Leu His Asn Gln Glu Val Thr Ala Glu Asp Gly Thr Gln
100 105 110

Arg Cys Glu Lys Cys Ser Lys Pro Cys Ala Arg Val
115 120

<210> SEQ ID NO 45
<211> LENGTH: 169
<212> TYPE: PRT
<213> ORGANISM: Homo sapiens

<400> SEQUENCE: 45

```
Cys Tyr Gly Leu Gly Met Glu His Leu Arg Glu Val Arg Ala Val Thr
1               5                   10                  15

Ser Ala Asn Ile Gln Glu Phe Ala Gly Cys Lys Lys Ile Phe Gly Ser
            20                  25                  30

Leu Ala Phe Leu Pro Glu Ser Phe Asp Gly Asp Pro Ala Ser Asn Thr
        35                  40                  45

Ala Pro Leu Gln Pro Glu Gln Leu Gln Val Phe Glu Thr Leu Glu Glu
    50                  55                  60

Ile Thr Gly Tyr Leu Tyr Ile Ser Ala Trp Pro Asp Ser Leu Pro Asp
65                  70                  75                  80

Leu Ser Val Phe Gln Asn Leu Gln Val Ile Arg Gly Arg Ile Leu His
                85                  90                  95

Asn Gly Ala Tyr Ser Leu Thr Leu Gln Gly Leu Gly Ile Ser Trp Leu
            100                 105                 110

Gly Leu Arg Ser Leu Arg Glu Leu Gly Ser Gly Leu Ala Leu Ile His
        115                 120                 125

His Asn Thr His Leu Cys Phe Val His Thr Val Pro Trp Asp Gln Leu
    130                 135                 140

Phe Arg Asn Pro His Gln Ala Leu Leu His Thr Ala Asn Arg Pro Glu
145                 150                 155                 160

Asp Glu Cys Val Gly Glu Gly Leu Ala
                165
```

<210> SEQ ID NO 46
<211> LENGTH: 142
<212> TYPE: PRT
<213> ORGANISM: Homo sapiens

<400> SEQUENCE: 46

```
Cys His Gln Leu Cys Ala Arg Gly His Cys Trp Gly Pro Gly Pro Thr
1               5                   10                  15

Gln Cys Val Asn Cys Ser Gln Phe Leu Arg Gly Gln Glu Cys Val Glu
            20                  25                  30

Glu Cys Arg Val Leu Gln Gly Leu Pro Arg Glu Tyr Val Asn Ala Arg
        35                  40                  45

His Cys Leu Pro Cys His Pro Glu Cys Gln Pro Gln Asn Gly Ser Val
    50                  55                  60

Thr Cys Phe Gly Pro Glu Ala Asp Gln Cys Val Ala Cys Ala His Tyr
65                  70                  75                  80

Lys Asp Pro Pro Phe Cys Val Ala Arg Cys Pro Ser Gly Val Lys Pro
                85                  90                  95

Asp Leu Ser Tyr Met Pro Ile Trp Lys Phe Pro Asp Glu Glu Gly Ala
            100                 105                 110

Cys Gln Pro Cys Pro Ile Asn Cys Thr His Ser Cys Val Asp Leu Asp
        115                 120                 125

Asp Lys Gly Cys Pro Ala Glu Gln Arg Ala Ser Pro Leu Thr
    130                 135                 140
```

<210> SEQ ID NO 47
<211> LENGTH: 3724
<212> TYPE: DNA
<213> ORGANISM: Homo sapiens

<400> SEQUENCE: 47

```
tctccctcgg cgccgccgcc gccgcccgcg gggctgggac ccgatgcggt tagagccgcg     60
```

```
gagcctggaa gagccccgag cgtttctgct ttgggacaac catacatcta attccttaaa    120
gtagttttat atgtaaaact tgcaaagaat cagaacaatg cctccacgac catcatcagg    180
tgaactgtgg ggcatccact tgatgccccc aagaatccta gtagaatgtt tactaccaaa    240
tggaatgata gtgactttag aatgcctccg tgaggctaca ttaataacca taaagcatga    300
actatttaaa gaagcaagaa aatacccccct ccatcaactt cttcaagatg aatcttctta    360
cattttcgta agtgttactc aagaagcaga aagggaagaa ttttttgatg aaacaagacg    420
actttgtgac cttcggcttt ttcaaccctt tttaaaagta attgaaccag taggcaaccg    480
tgaagaaaag atcctcaatc gagaaattgg ttttgctatc ggcatgccag tgtgtgaatt    540
tgatatggtt aaagatccag aagtacagga cttccgaaga aatattctga acgtttgtaa    600
agaagctgtg gatcttaggg acctcaattc acctcatagt agagcaatgt atgtctatcc    660
tccaaatgta gaatcttcac cagaattgcc aaagcacata tataataaat tagataaagg    720
gcaaataata gtggtgatct gggtaatagt ttctccaaat aatgacaagc agaagtatac    780
tctgaaaatc aaccatgact gtgtaccaga acaagtaatt gctgaagcaa tcaggaaaaa    840
aactcgaagt atgttgctat cctctgaaca actaaaactc tgtgttttag aatatcaggg    900
caagtatatt ttaaaagtgt gtggatgtga tgaatacttc ctagaaaaat atcctctgag    960
tcagtataag tatataagaa gctgtataat gcttgggagg atgcccaatt tgatgttgat   1020
ggctaaagaa agcctttatt ctcaactgcc aatggactgt tttacaatgc catcttattc   1080
cagacgcatt tccacagcta caccatatat gaatggagaa acatctacaa aatccctttg   1140
ggttataaat agtgcactca gaataaaaat tctttgtgca acctacgtga atgtaaatat   1200
tcgagacatt gataagatct atgttcgaac aggtatctac catggaggag aacccttatg   1260
tgacaatgtg aacactcaaa gagtaccttg ttccaatccc aggtggaatg aatggctgaa   1320
ttatgatata tacattcctg atcttcctcg tgctgctcga ctttgccttt ccatttgctc   1380
tgttaaaggc cgaaagggtg ctaaagagga acactgtcca ttggcatggg gaaatataaa   1440
cttgtttgat tacacagaca ctctagtatc tggaaaaatg gctttgaatc tttggccagt   1500
acctcatgga ttagaagatt tgctgaaccc tattggtgtt actggatcaa atccaaataa   1560
agaaactcca tgcttagagt tggagtttga ctggttcagc agtgtggtaa agttcccaga   1620
tatgtcagtg attgaagagc atgccaattg gtctgtatcc cgagaagcag gatttagcta   1680
ttcccacgca ggactgagta acagactagc tagagacaat gaattaaggg aaaatgacaa   1740
agaacagctc aaagcaattt ctacacgaga tcctctctct gaaatcactg agcaggagaa   1800
agattttcta tggagtcaca gacactattg tgtaactatc cccgaaattc tacccaaatt   1860
gcttctgtct gttaaatgga attctagaga tgaagtagcc cagatgtatt gcttggtaaa   1920
agattggcct ccaatcaaac ctgaacaggc tatggaactt ctggactgta attacccaga   1980
tcctatggtt cgaggttttg ctgttcggtg cttggaaaaa tatttaacag atgacaaact   2040
ttctcagtat ttaattcagc tagtacaggt cctaaaatat gaacaatatt tggataactt   2100
gcttgtgaga tttttactga agaaagcatt gactaatcaa aggattgggc actttttctt   2160
ttggcattta aaatctgaga tgcacaataa aacagttagc cagaggtttg gcctgctttt   2220
ggagtcctat tgtcgtgcat gtgggatgta tttgaagcac ctgaataggc aagtcgaggc   2280
aatggaaaag ctcattaact taactgacat tctcaaacag gagaagaagg atgaaacaca   2340
aaaggtacag atgaagtttt tagttgagca aatgaggcga ccagatttca tggatgctct   2400
```

-continued

```
acagggcttt ctgtctcctc taaaccctgc tcatcaacta ggaaacctca ggcttgaaga   2460

gtgtcgaatt atgtcctctg caaaaaggcc actgtggttg aattgggaga acccagacat   2520

catgtcagag ttactgtttc agaacaatga gatcatcttt aaaaatgggg atgatttacg   2580

gcaagatatg ctaacacttc aaattattcg tattatggaa aatatctggc aaaatcaagg   2640

tcttgatctt cgaatgttac cttatggttg tctgtcaatc ggtgactgtg tgggacttat   2700

tgaggtggtg cgaaattctc acactattat gcaaattcag tgcaaaggcg gcttgaaagg   2760

tgcactgcag ttcaacagcc acacactaca tcagtggctc aaagacaaga acaaaggaga   2820

aatatatgat gcagccattg acctgtttac acgttcatgt gctggatact gtgtagctac   2880

cttcattttg ggaattggag atcgtcacaa tagtaacatc atggtgaaag acgatggaca   2940

actgtttcat atagattttg gacacttttt ggatcacaag aagaaaaaat ttggttataa   3000

acgagaacgt gtgccatttg ttttgacaca ggatttctta atagtgatta gtaaaggagc   3060

ccaagaatgc acaaagacaa gagaatttga gaggtttcag gagatgtgtt acaaggctta   3120

tctagctatt cgacagcatg ccaatctctt cataaatctt ttctcaatga tgcttggctc   3180

tggaatgcca gaactacaat cttttgatga cattgcatac attcgaaaga ccctagcctt   3240

agataaaact gagcaagagg ctttggagta tttcatgaaa caaatgaatg atgcacatca   3300

tggtggctgg acaacaaaaa tggattggat cttccacaca attaaacagc atgcattgaa   3360

ctgaaaagat aactgagaaa atgaaagctc actctggatt ccacactgca ctgttaataa   3420

ctctcagcag gcaaagaccg attgcatagg aattgcacaa tccatgaaca gcattagaat   3480

ttacagcaag aacagaaata aaatactata taatttaaat aatgtaaacg caaacagggt   3540

ttgatagcac ttaaactagt tcatttcaaa attaagcttt agaataatgc gcaatttcat   3600

gttatgcctt aagtccaaaa aggtaaactt tgaagattgt ttgtatcttt ttttaaaaaa   3660

caaaacaaaa caaaaatccc caaaatatat agaaatgatg gagaaggaaa aaaaaaaaaa   3720

aaaa                                                                3724
```